US012180290B2

(12) United States Patent
Bammert et al.

(10) Patent No.: US 12,180,290 B2
(45) Date of Patent: Dec. 31, 2024

(54) ANTIBODIES TO CANINE AND FELINE ONCOSTATIN M RECEPTOR BETA AND USES THEREOF

(71) Applicant: Zoetis Services LLC, Parsippany, NJ (US)

(72) Inventors: Gary Francis Bammert, Portage, MI (US); Andrea Joy Gonzales, Portage, MI (US)

(73) Assignee: Zoetis Services LLC, Parsippany, NJ (US)

(*) Notice: Subject to any disclaimer, the term of this patent is extended or adjusted under 35 U.S.C. 154(b) by 13 days.

(21) Appl. No.: 17/503,592

(22) Filed: Oct. 18, 2021

(65) Prior Publication Data

US 2022/0177594 A1 Jun. 9, 2022

Related U.S. Application Data

(60) Provisional application No. 63/093,607, filed on Oct. 19, 2020.

(51) Int. Cl.

| | |
|---|---|
| ***C07K 16/00*** | (2006.01) |
| ***A61P 17/00*** | (2006.01) |
| ***C07K 16/28*** | (2006.01) |
| ***C07K 16/46*** | (2006.01) |
| ***G01N 33/68*** | (2006.01) |
| *A61K 39/00* | (2006.01) |

(52) U.S. Cl.

CPC .......... *C07K 16/2866* (2013.01); *A61P 17/00* (2018.01); *G01N 33/6863* (2013.01); *A61K 2039/505* (2013.01); *C07K 2317/24* (2013.01); *C07K 2317/76* (2013.01); *C07K 2317/92* (2013.01); *G01N 2333/7155* (2013.01)

(58) Field of Classification Search

None

See application file for complete search history.

(56) References Cited

U.S. PATENT DOCUMENTS

| | | | | |
|---|---|---|---|---|
| 5,428,012 | A | 6/1995 | Shoyab et al. | |
| 5,451,506 | A | 9/1995 | Shoyab et al. | |
| 5,618,715 | A | 4/1997 | Shoyab et al. | |
| 5,681,930 | A | 10/1997 | Radka et al. | |
| 5,707,624 | A | 1/1998 | Nickoloff et al. | |
| 5,736,378 | A * | 4/1998 | Elder | C07K 14/005 435/235.1 |
| 5,907,033 | A | 5/1999 | Radka et al. | |
| 7,572,896 | B2 | 8/2009 | Mather et al. | |
| 7,858,753 | B2 | 12/2010 | Ellis et al. | |
| 8,309,688 | B2 | 11/2012 | Cotty et al. | |
| 8,790,651 | B2 | 7/2014 | Bammert et al. | |
| 8,916,695 | B2 | 12/2014 | Bembridge et al. | |
| 9,475,876 | B2 | 10/2016 | Morikawa et al. | |
| 9,550,828 | B2 | 1/2017 | Jorcyk et al. | |
| 9,663,571 | B2 | 5/2017 | Arnett et al. | |
| 10,421,813 | B2 | 9/2019 | Arnett et al. | |
| 2018/0022800 | A1 | 1/2018 | West et al. | |
| 2018/0333489 | A1 | 11/2018 | Manning et al. | |
| 2019/0284272 | A1 * | 9/2019 | Bammert | A61P 17/00 |

FOREIGN PATENT DOCUMENTS

| | | | |
|---|---|---|---|
| CR | 20150083 | A | 4/2015 |
| EP | 0 290 948 | A3 | 11/1988 |
| EP | 0 450 472 | B1 | 10/1991 |
| EP | 0 451 612 | B1 | 1/1997 |
| WO | WO 93/10151 | A1 | 5/1993 |
| WO | WO 95/33059 | A2 | 12/1995 |
| WO | WO 99/48523 | A2 | 9/1999 |
| WO | WO 00/18932 | A2 | 4/2000 |
| WO | WO 03/039455 | A2 | 5/2003 |
| WO | WO 2004/039951 | A2 | 5/2004 |
| WO | WO 2005/005638 | A2 | 1/2005 |
| WO | WO 2005/058956 | A1 | 6/2005 |
| WO | WO 2005/095457 | A2 | 10/2005 |
| WO | WO 2006/063864 | A2 | 6/2006 |
| WO | WO 2006/063865 | A1 | 6/2006 |
| WO | WO 2006/084092 | A2 | 8/2006 |
| WO | WO 2006/088855 | A1 | 8/2006 |
| WO | WO 2010/040882 | A1 | 4/2010 |
| WO | WO 2010/139742 | A1 | 12/2010 |
| WO | WO 2012/018687 | A1 | 2/2012 |
| WO | WO 2012/051111 | A2 | 4/2012 |
| WO | WO 2012/069433 | A2 | 5/2012 |
| WO | WO 2012/093172 | A1 | 7/2012 |
| WO | WO 2013/168829 | A1 | 11/2013 |
| WO | WO 2014/194274 | A2 | 12/2014 |
| WO | WO 2015/095895 | A1 | 6/2015 |
| WO | WO 2016/046738 | A1 | 3/2016 |

(Continued)

OTHER PUBLICATIONS

Campbell A, General properties and applications of monoclonal antibodies, Elsevier Science Publishers, section 1.1, pp. 1-32, 1984. (Year: 1984).*

Harlow E, Lane D.. Antibodies a laboratory manual. Cold Spring Harbor, New York: Cold Spring Harbor Laboratory Press, pp. 141-155, 1989. (Year: 1989).*

Arita et al. Oncostatin M Receptor-β Mutations Underlie Familial Primary Localized Cutaneous Amyloidosis. Am J Hum Genet. Jan. 2008;82(1):73-80. (Year: 2008).*

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Lloyd et al., Modelling the human immune response: performance of a 1011 human antibody repertoire against a broad panel of therapeutically relevant antigens. Protein Eng Des Sel. Mar. 2009;22(3): 159-68. (Year: 2009).*

(Continued)

*Primary Examiner* — Maher M Haddad

(74) *Attorney, Agent, or Firm* — Gloria K. Szakiel

(57) ABSTRACT

The invention provides an isolated antibody, or antigen-binding portion thereof that specifically binds to canine or feline Oncostatin M receptor Beta (OSMR-β) or both, wherein the antibody antagonizes IL-31-mediated signaling or OSM-mediated signaling or both in a canine and/or feline cell.

9 Claims, 16 Drawing Sheets

Specification includes a Sequence Listing.

(56) References Cited

FOREIGN PATENT DOCUMENTS

| | | | |
|---|---|---|---|
| WO | WO 2016/120625 | A1 | 8/2016 |
| WO | WO 2016/164502 | A1 | 10/2016 |
| WO | WO 2016/179605 | A1 | 11/2016 |
| WO | WO 2018/041823 | A2 | 3/2018 |
| WO | WO 2018/042018 | A2 | 3/2018 |
| WO | WO 2018/183908 | A1 | 10/2018 |
| WO | WO 2018/191414 | A1 | 10/2018 |
| WO | WO 2019/177697 | A2 | 9/2019 |
| WO | WO 2019/229525 | A2 | 12/2019 |

OTHER PUBLICATIONS

Goel et al., Plasticity within the antigen-combining site may manifest as molecular mimicry in the humoral immune response. J Immunol. Dec. 15, 2004; 173(12):7358-67. (Year: 2004).*

Kanyavuz et al., Breaking the law: unconventional strategies for antibody diversification. Nat Rev Immunol. Jun. 2019; 19(6):355-368. (Year: 2019).*

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*

Vajdos et al. Comprehensive functional maps of the antigen-binding site of an anti-ErbB2 antibody obtained with shotgun scanning mutagenesis. J. Mol. Biol. 2002, Jul. 5, 320(2):415-28. (Year: 2002).*

Rabia et al. Understanding and overcoming trade-offs between antibody affinity, specificity, stability and solubility. Biochem Eng J. Sep. 15, 2018; 137: 365-374. (Year: 2018).*

Stacey R. Dillon, et al., "Interleukin 31, a cytokine produced by activated T cells, induces dermatitis in mice," Nature Immunology, vol. 5, No. 7, Jul. 2004, pp. 752-760.

Mark M. Neis, MD, et al., "Enhanced expression levels of IL-31 correlate with IL-4 and IL-13 in atopic and allergic contact dermatitis," J Allergy Clin Immunol vol. 118, No. 4, pp. 930-937.

Anja Rabenhorst, et al., "Interleukin-31: a Novel Diagnostic Marker of Allergic Diseases," Current Allergy and Asthma Reports, (2014) 14:423.

Christian Cornelissen, et al., "Signaling by IL-31 and functional consequences," European Journal of Cell Biology 91 (2012), pp. 552-566.

A. Takaoka, et al., "Involvement of IL-31 on scratching behavior in NC/Nga mice with atopic-like dermatitis," Experimental Dermatology 2006: 15, pp. 161-167.

Eniko Sonkoly, MD, et al., "IL-31: a new link between T cells and pruritus in atopic skin inflammation," J Allergy Clin Immunol, Feb. 2006, pp. 411-417.

K.E. Lewis, et al., "Interleukin (IL) 31 induces in cynomolgus monkeys a rapid and intense itch response that can be inhibited by an IL-31 neutralizing antibody," European Academy of Dermatology and Venereology, 2017, 31, pp. 142-150.

Ulrike Raap, MD, et al., "Correlation of IL-31 serum levels with severity of atopic dermatitis," J Allergy Clin Immunol vol. 122, No. 2, Aug. 2008, pp. 421-423.

Mhm Ezzat, et al., "Serum measurement of interleukin-31 (IL-31) in paediatric atopic dermatitis: elevated levels correlate with severity scoring," Journal of the European Academy of Dermatology and Venereology, 2011, 25, pp. 334-339.

Eleni Pantazi, et al., "The atopic dermatitis market," Nature Reviews Drug Discovery, vol. 17, Apr. 2018, pp. 237-238.

O. Nemoto, et al., "The first trial of CIM331, a humanized antihuman interleukin-31 receptor A antibody, in healthy volunteers and patients with atopic dermatitis to evaluate safety, tolerability and pharmacokinetics of a single dose in a randomized, double-blind, placebo-controlled study," British Journal of Dermatology (2016) 174, pp. 296-304.

Gina M. Michels, et al., "A blinded, randomized, placebo-controlled, dose determination trial of lokivetmab (ZTS-00103289), a caninized, anti-canine IL-31 monoclonal antibody in client owned dogs with atopic dermatitis," Vet Dermatol 2016; 27, pp. 478-e129.

Sabine Le Saux, et al., "Molecular Dissection of Human Interleukin-31-mediated Signal Transduction through Site-directed Mutagenesis," The Journal of Biological Chemistry, vol. 285, No. 5, pp. 3470-3477, Jan. 29, 2010.

Caroline Diveu, et al., "Predominant expression of the long isoform of GP130-like (GPL) receptor is required for interleukin-31 signaling," Eur. Cytokine Netw., vol. 15 No 4, Dec. 2004, pp. 291-302.

Qing Zhang, et al., "Structures and biological functions of IL-31 and IL-31 receptors," Cytokine and Growth Factor Reviews 19 (2008) pp. 347-356.

Caroline Diveu, et al., "GPL, a Novel Cytokine Receptor Related to GP130 and Leukemia Inhibitory Factor Receptor," the Journal of Biological Chemistry, vol. 278, No. 50, Issue of Dec. 12, pp. 49850-49859, 2003.

Julia Dambacher, et al., "Interleukin 31 mediates MAP kinase and STAT1/3 activation in intestinal epithelial cells and its expression is upregulated in inflammatory bowel disease," Gut 2007; 56, pp. 1257-1265.

Alexandra Dreuw, et al., Characterization of the Signaling Capacities of the Novel gp130-like Cytokine Receptor, the Journal of Biological Chemistry, vol. 279, No. 34, Issue of Aug. 20, pp. 36112-36120, 2004.

Martin J. Boulanger, et al., "Hexameric Structure and Assembly of the Interleukin-6/ IL-6 α-Receptor/gp130 Complex," Science vol. 300, Jun. 27, 2003, pp. 2101-2104.

Angelica V. Medina-Cucurella, et al., "Feline Interleukin-31 Shares Overlapping Epitopes with the Oncostatin M Receptor and IL-31RA," Biochemistry 2020, 59, 23, pp. 2171-2181.

Angelica V. Medina-Cucurella, et al., "Characterizing Protein-Protein Interactions Using Deep Sequencing Coupled to Yeast Surface Display," Methods in Molecular Biology, 2018, vol. 1764, pp. 101-121.

Ginger Chao, et al., "Isolating and engineering human antibodies using yeast surface display," Nature Protocols, vol. 1, No. 2, 2006, pp. 755-768.

Emily E Wrenbeck, et al., "Plasmid-based one-pot saturation mutagenesis," Nature Methods, vol. 13, No. 11, Nov. 2016, pp. 928-930.

Carlos L. Araya, et al., "Deep mutational scanning: assessing protein function on a massive scale," Trends in Biotechnology, Sep. 2011, vol. 29, No. 9, pp. 435-442.

Zamaneh Mikhak, et al., "First-In-Human Study of KPL-716, Anti-Oncostatin M Receptor Beta Monoclonal Antibody, in Healthy Volunteers and Subjects with Atopic Dermatitis," Presented at: the 27th Congress of the European Academy of Dermatology and Venereology; Sep. 12-16, 2018; Paris, France, pp. 1-18.

Heike M. Hermanns, "Oncostatin M and interleukin-31: Cytokines, receptors, signal transduction and physiology," Cytokine & Growth Factor Reviews 26 (2015) pp. 545-558.

Katia Boniface, et al., "Oncostatin M Secreted by Skin Infiltrating T Lymphocytes Is a Potent Keratinocyte Activator Involved in Skin Inflammation," the Journal of Immunology 2007; 178, pp. 4615-4622.

C. E. Older, et al., Abstract SOS-2, entitled "Cytokine expression in feline allergic dermatitis and feline asthma," Lloyd D. The 9th World Congress of Veterinary Dermatology First published: Oct. 21, 2020. Veterinary Dermatology, 2020, 31(5):343, pp. 15-16.

* cited by examiner

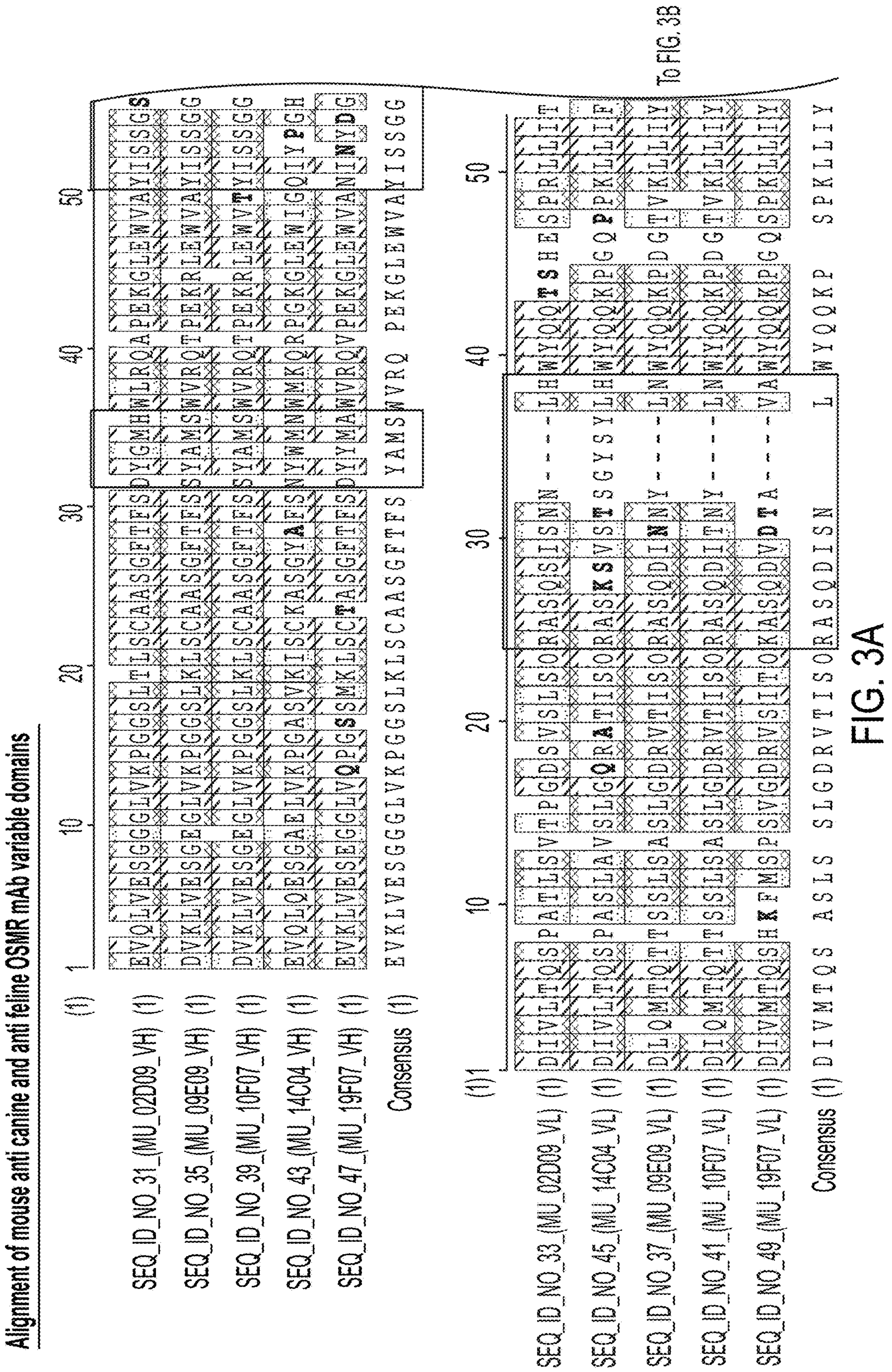

FIG. 3A

Alignment of mouse anti canine and anti feline OSMR mAb variable domains

```
                                1         10         20         30         40         50
SEQ_ID_NO_31_(MU_02D09_VH) (1)  EVQLVESGGGLVKPGGSLTLSCAASGFTFSDYGMHWLRQAPEKGLEWVAYISSGS
SEQ_ID_NO_35_(MU_09E09_VH) (1)  DVKLVESGEGLVKPGGSLKLSCAASGFTFSSYAMSWVRQTPEKRLEWVAYISGG
SEQ_ID_NO_39_(MU_10F07_VH) (1)  DVKLVESGEGLVKPGGSLKLSCAASGFTFSSYAMSWVRQTPEKRLEWVATISGG
SEQ_ID_NO_43_(MU_14C04_VH) (1)  EVQLQESGAELVKPGASVKISCKASGYKISCKTASGETFSGYAFSNWMKQRPGKGLEWIGQIYPGH
SEQ_ID_NO_47_(MU_19F07_VH) (1)  EVKLVESEGGLVQPGSSMKLSCTASGFTFSDIYMAWVRQVPEKGLEWVANIYDG
Consensus (1)                   EVKLVESGGGLVKPGGSLKLSCAASGFTFS   YAMS WVRQ PEKGLEWVAYISSGG

                                1         10         20         30         40         50
SEQ_ID_NO_33_(MU_02D09_VL) (1)  DIVLTIQSPATLSVTPGDSVSLSCRASIQRATTISNNLHWYQQTSHESPRLLIT
SEQ_ID_NO_45_(MU_14C04_VL) (1)  DIVLTIQSPASLAVSLGQRATTISCKASQSISNN         LHWYQQKPGQPPKLLIF
SEQ_ID_NO_37_(MU_09E09_VL) (1)  DLQMTQTTSSLSASLGDRVTISCRASQDINNY         LNWYQQKPDGTVKLLIY
SEQ_ID_NO_41_(MU_10F07_VL) (1)  DIQMTQTTSSLSASLGDRVTISCRASQDITNY         LNWYQQKPDGTVKLLIY
SEQ_ID_NO_49_(MU_19F07_VL) (1)  DIVMTQSHKFMSPSSVGDRVSITCKASQDVDTA         VAWYQQKPGQSPKLLIY
Consensus (1)                   DIVMTQS ASLS SLGDRVTISCRASQDISN          L   WYQQKP SPKLLIY
```

From FIG. 3A

Pairwise comparison of the CDR structures from 5 mouse anti-OSMR antibodies

CDRH2

RMSD = 1.890 A

| | 1 | 2 | 3 | 4 | 5 |
|---|---|---|---|---|---|
| 1: MU_02D09_VH_SI_31 | 0.00 | 0.72 | 0.71 | 2.37 | 1.63 |
| 2: MU_09E09_VH_SI_35 | 0.72 | 0.00 | 0.20 | 2.66 | 1.62 |
| 3: MU_10F07_VH_SI_39 | 0.71 | 0.20 | 0.00 | 2.66 | 1.55 |
| 4: MU_14C04_VH_SI_43 | 2.37 | 2.66 | 2.66 | 0.00 | 2.69 |
| 5: MU_19F07_VH_SI_47 | 1.63 | 1.62 | 1.55 | 2.69 | 0.00 |

4.0 3.5 3.0 2.5 2.0 1.5 1.0 0.5 0.0

CDRL2

RMSD = 1.557 A

| | 9 | 10 | 11 | 12 | 13 |
|---|---|---|---|---|---|
| 9: MU_02D09_VL_SI_3 | 0.00 | 1.94 | 1.82 | 2.28 | 1.40 |
| 10: MU_09E09_VL_SI_3 | 1.94 | 0.00 | 0.31 | 1.29 | 1.30 |
| 11: MU_10F07_VL_SI_4 | 1.82 | 0.31 | 0.00 | 1.29 | 1.18 |
| 12: MU_14C04_VL_SI_4 | 2.28 | 1.29 | 1.29 | 0.00 | 1.87 |
| 13: MU_19F07_VL_SI_4 | 1.40 | 1.30 | 1.18 | 1.87 | 0.00 |

Pairwise comparison of the CDR structures from 5 mouse anti-OSMR antibodies

CDRH3

RMSD = 2.915 A

| | 1 | 2 | 3 | 4 | 5 |
|---|---|---|---|---|---|
| 1: MU_02D09_VH_SI_31 | 0.00 | 4.06 | 3.87 | 3.90 | 3.93 |
| 2: MU_09E09_VH_SI_35 | 4.06 | 0.00 | 0.80 | 2.26 | 1.94 |
| 3: MU_10F07_VH_SI_39 | 3.87 | 0.80 | 0.00 | 2.49 | 2.09 |
| 4: MU_14C04_VH_SI_43 | 3.90 | 2.26 | 2.49 | 0.00 | 1.66 |
| 5: MU_19F07_VH_SI_47 | 3.93 | 1.94 | 2.09 | 1.66 | 0.00 |

4.0 3.5 3.0 2.5 2.0 1.5 1.0 0.5 0.0

CDRL3

RMSD = 1.454 A

| | 9 | 10 | 11 | 12 | 13 |
|---|---|---|---|---|---|
| 9: MU_02D09_VL_SI_3 | 0.00 | 1.27 | 1.84 | 2.27 | 1.41 |
| 10: MU_09E09_VL_SI_3 | 1.27 | 0.00 | 0.79 | 1.72 | 0.62 |
| 11: MU_10F07_VL_SI_4 | 1.84 | 0.79 | 0.00 | 1.33 | 0.81 |
| 12: MU_14C04_VL_SI_4 | 2.27 | 1.72 | 1.33 | 0.00 | 1.61 |
| 13: MU_19F07_VL_SI_4 | 1.41 | 0.62 | 0.81 | 1.61 | 0.00 |

Expression of OSMR protein in control (normal) and diseased (allergic) cat skin biopsies using IHC

A

Evaluation of Anti-Canine OSMR Chimeric Antibodies in a Canine Model of IL-31-Induced Pruritus

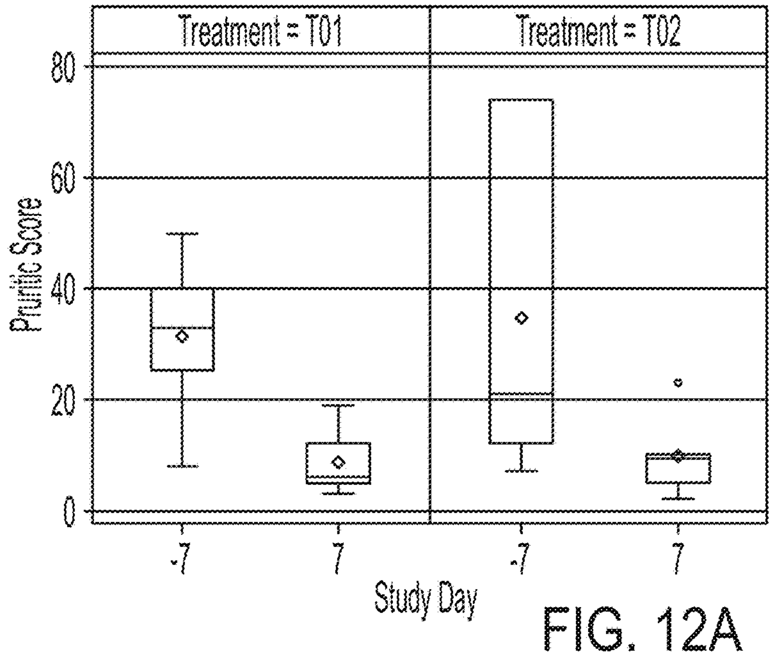

T01 - anti OSMr 19F07 (mouse:canine chimera)
T02 - anti OSMr 10F07 (mouse:canine chimera)

Mean and 90% confidence limits

| treatment number | number of animals | paired difference mean | standard error | 90% confidence lower limit | 90% confidence upper limit | t-value | df | p-value | range | significant at alpha=0.10 (1) |
|---|---|---|---|---|---|---|---|---|---|---|
| T01 | 6 | 23.0 | 8.81 | 5.2 | 40.8 | 2.61 | 5 | 0.0477 | 2 to 38 | * |
| T02 | 6 | 25.0 | 8.81 | 7.2 | 42.8 | 2.84 | 5 | 0.0364 | 2 to 64 | * |

FIG. 12B

ANTIBODIES TO CANINE AND FELINE ONCOSTATIN M RECEPTOR BETA AND USES THEREOF

CROSS-REFERENCE TO RELATED APPLICATIONS

This application claims the benefit of U.S. Provisional Application No. 63/093,607, filed Oct. 19, 2020, the entire contents of which are incorporated herein by reference in their entirety.

FIELD OF THE INVENTION

The present invention is in the field of immunotherapy. More specifically, it concerns a receptor for Oncostatin M (OSM), and its modulators such as monoclonal antibodies that bind to the canine and/or feline Oncostatin M receptor Beta subunit (OSMR-β). The invention also concerns the diagnosis and/or treatment of diseases in canines and felines associated with OSM and IL-31 using anti-OSMR-β antibodies.

BACKGROUND OF THE INVENTION

Cytokines comprise a large family of small proteins that play a critical role in the development and control of the immune response. Certain cytokines are associated with the initiation and the persistence of pathological pain behavior including nerve and skin injuries. A more recently discovered cytokine, interleukin-31 (IL-31), has been linked to the induction of chronic skin inflammation (Dillon et al. (2004) *Nat. Immunol.* 5, 752-760). Human and murine data have shown high expression of IL-31 associated with severe inflammatory skin disorders including pruritis, alopecia, skin lesion, and atopic dermatitis (AD) and with other regulated allergic diseases such as asthma (Dillon et al. (2004) supra; Neis et al. (2006) *J. Allergy Clin. Immunol.* 118, 930-937; Rabenhorst et al. (2014) *Curr. Allergy Asthma Rep.* 14, 423; Cornelissen et al. (2012) *Eur. J. Cell Biol.* 91, 552-566; Takaoka et al. (2006) *Exp. Dermatol.* 15, 161-167; Sonkoly et al. (2006) *J. Allergy Clin. Immunol.* 117, 411-417; Lewis et al. (2017) *J. Eur. Acad. Dermatology Venereol.* 31, 142-150).

An experimental animal model for human AD reported a strong correlation between itch-associated scratching behavior in NC/Nga mice and expression of IL-31 mRNA (Takaoka et al. supra). Elevated IL-31 serum levels were found in adult patients with AD compare to healthy control subjects (Raap et al. (2008) *J. Allergy Clin. Immunol.* 122, 421-423) and in pediatric patients during AD flare and quiescence (Ezzat et al. (2011) *J. Eur. Acad. Dermatology Venereol.* 25, 334-339).

Together, these data suggest that IL-31 represents an important target for the development of treatments against such skin inflammatory diseases in humans. Antagonist anti-IL-31 monoclonal antibodies (mAbs) are currently in development for human health (Pantazi et al. (2017) *Nat. Rev. Drug Discov.* 17, 237-238; Nemoto et al. (2016) *Br. J. Dermatol.* 174, 296-304). Also, ant-IL-31 mAbs have already been developed in animal health (U.S. Pat. No. 8,790,651B2 to Bammert et al.; Michels et al. (2016) *Vet. Dermatol.* 27, 478-e129). For example, an anti-hIL-31RA mAb, CIM331, binds to IL-31RA, inhibits IL-31 signaling, and reduces severe pruritus (Nemoto et al. (2016) supra). In veterinary medicine a "caninized" anti-IL-31 mAb, Lokivetmab, showed efficacy in clinical trials for canine pruritis and is currently approved as an AD therapy for dogs (Michels et al. (2016) supra).

IL-31 is a member of the IL-6 cytokine superfamily produced preferentially by T helper type 2 cells (Dillon et al. (2004) supra). Mature human IL-31 (hIL-31) is composed of 141 amino acids (Dillon et al. (2004) supra) with a predicted topology of four antiparallel helices (Le Saux et al. (2010) *J. Biol. Chem.* 285, 3470-3477). The IL-31 signaling pathway is thought to be mediated through a gp130-like type 1 cytokine receptor (IL-31RA, also known as GPL) and Oncostatin M receptor (OSMR) (Dillon et al. supra; Le Saux et al. (2010) supra; Diveu et al. (2004) *Eur. Cytokine Netw.* 15, 291-302; Zhang et al. (2008) *Cytokine Growth Factor Rev.* 19, 347-356). Both receptors belong to the type I cytokine receptor family which share a common cytokine binding domain (CBD) formed by two fibronectin type III-like domains (Diveu et al. (2003) *J. Biol. Chem.* 278, 49850-49859).

Previous studies supplied immunoprecipitation evidence that human IL-31RA (hIL-31RA) binds directly to hIL-31. In these same studies, immunoprecipitation results failed to detect direct human OSMR (hOSMR) binding to hIL-31 (Le Saux et al. (2010) Molecular dissection of human interleukin-31-mediated signal transduction through site-directed mutagenesis. *J. Biol. Chem.* 285, 3470-3477; Diveu et al. (2004) supra). However, an increase in binding was distinguished when hIL-31RA and hOSMR were combined, suggesting that hIL-31 binds first to hIL-31RA, at which time hOSMR is recruited to form the ternary complex (Le Saux et al. (2010) supra; Diveu et al. (2004) supra). In this model, the ternary complex activates numerous downstream signaling pathways (Dillon et al. (2004) supra; Le Saux et al. (2010) supra, Diveu et al. (2004) supra; Dambacher et al. (2007) Gut 56, 1257-1265; Dreuw et al. (2004) *J. Biol. Chem.* 279, 36112-36120).

Based on the structure of IL-6/IL-6 α-Receptor/gp130 complex (Boulanger et al. (2003) *Science.* 300, 2101-2104), the IL-6 cytokine superfamily is thought to interact with their receptors through three different contact binding sites (sites I, II, and III). Le Saux et al. used computational analysis and sparse alanine scanning to delineate sites II and III only as critical binding sites for the interaction between hIL-31 and its receptors (Le Saux et al. (2010) supra). In particular, Glu44, Glu106, and His110 were identified as critical residues for binding site II while Lys134 was identified within the binding site III.

Applicant initiated a study to gain insights into the interactions between feline IL-31 (fIL-31) and its feline receptors fOSMR and fIL-31 RA and to map the conformational epitope for an anti-fIL-31 mAb termed mAb #1 or 15H05 (Medina-Cucurella AV et al; Feline Interleukin-31 Shares Overlapping Epitopes with the Oncostatin M Receptor and IL-31 RA. Biochemistry. 2020 Jun. 16; 59(23):2171-2181); WO2019/177697A2 (Zoetis Services LLC). In contrast to previous studies conducted with human homologs, which showed that OSMR cannot interact with IL-31 in the absence of IL-31RA, Applicant discovered through multiple biophysical methods that fOSMR directly binds fIL-31 and partially interferes with fIL-31RA binding. Applicant identified the potential fIL-31 binding sites for fOSMR, fIL31-RA, and an anti-fIL-31 mAb using a predicted structural model combined with fine epitope mapping (Medina-Cucurella (2019) *Methods Mol. Biol.* 1764, 101-121), using yeast surface display (Chao et al. (2006) *Nat. Protoc.* 1, 755-768), nicking mutagenesis (Wrenbeck et al. (2016) *Nat. Methods* 13, 928-930), and deep sequencing (Araya and Fowler (2011) *Trends Biotechnol.* 29, 435-442). The constructed binding sites agreed with the sites previously found by Le Saux et al. supra and showed an additional overlapping site between both receptors which Applicant termed the "shared site". Specifically, the binding site for IL31-RA contains fIL-31 positions E20 and K82, while the binding site for OSMR comprises the "PADNFERK" motif (P103-K110) and positions G39 and K100, which agreed with previous studies on the human homolog. However, Applicant's results also revealed a new overlapping site, composed of positions R69, R72, P73, D76, D81, and E97, between both feline receptors which was not previously reported for human. The conformational epitope of an anti-feline IL-31 mAb that inhibits both OSMR and IL-31RA also mapped to this shared site. Combined, Applicant's results show that fIL-31 binds IL-31RA and OSMR independently through a partially shared epitope. These results suggest that the mechanisms for IL-31 signaling in companion animals such as cats may be different from the mechanisms for IL-31 signaling in humans. This in turn implies that efficient therapeutic strategies to antagonize IL-31-mediated signaling in companion animals may be different from therapeutic strategies to antagonize IL-31-mediated signaling in higher animals.

It would be desirable to provide therapeutic monoclonal antibodies that bind to the canine and/or feline Oncostatin M receptor Beta subunit (OSMR-β) and antagonize OSM-mediated and/or IL-31-mediated signaling in canines and/or felines. Such antibodies would preferably be useful for the diagnosis and/or treatment of diseases in canines and felines associated with OSM and IL-31, including severe inflammatory skin disorders, such as allergic dermatitis and atopic dermatitis and fibrotic conditions, such as dermal or renal fibrosis, in dogs and cats.

Cellular models describe the role of OSM in modulating human keratinocyte function by influencing the expression of genes encoding proteins involved in support structure/metabolism, inflammation/innate immunity, and tissue remodeling. (Boniface K et al; Oncostatin M secreted by skin infiltrating T lymphocytes is a potent keratinocyte activator involved in skin inflammation. J Immunol. 2007 Apr. 1; 178(7):4615-22). These investigators provide compelling evidence for the role of OSM-mediated OSMR activation in cutaneous inflammation resulting from keratinocyte activation in a cell models using primary keratinocytes in a reconstituted epidermis. OSM-mediated OSMR activation in these keratinocyte cultures upregulates gene expression patterns consistent with psoriatic and atopic disease in skin. These data were supported by increased expression of both OSM and OSMR in patients with inflammatory skin disorders (psoriatic or atopic dermatitic (AD). By targeting OSMR-β with a blocking monoclonal antibody, the function of both IL-31 and OSM cytokines will be blocked. By blocking the function of IL-31, it is anticipated that anti-pruritic and anti-inflammatory properties, similar to Lokivetmab will be achieved, but additional anti-inflammatory and anti-fibrotic activity beyond Lokivetmab may be achieved due to inhibition of OSM.

SUMMARY OF THE INVENTION

The present invention provides an isolated antibody, or antigen-binding portion thereof that specifically binds to canine or feline Oncostatin M receptor Beta (OSMR-β) or both, wherein the antibody antagonizes IL-31-mediated signaling or OSM-mediated signaling or both in a canine and/or feline cell. In one embodiment, the antibody, or antigen-binding portion thereof antagonizes both IL-31-mediated signaling and OSM-mediated signaling in a canine and/or feline cell. In one embodiment, the IL-31-mediated signaling is pSTAT signaling, such as, but not limited to, pSTAT3 signaling. In another embodiment, the OSM-mediated signaling is pSTAT signaling, such as, but not limited to, pSTAT3 signaling.

In one embodiment, the antibody, or antigen-binding portion thereof of the present invention includes a combination of complementary determining region (CDR) sequences selected from the following:

```
1) 02D09:
variable heavy (VH)-CDR1 of SEQ ID NO: 1
(DYGMH),

VH-CDR2 of SEQ ID NO: 2
(YISSGSRAVFFADTVKG),

VH-CDR3 of SEQ ID NO: 3
(DRYDGRGFAY),

variable light (VL)-CDR1 of SEQ ID NO: 4
(RASQSISNNLH),

VL-CDR2 of SEQ NO: 5
(YASQSIS),
and

VL-CDR3 of SEQ ID NO: 6
(QQSNSWPLT);

2) 09E09:
VH-CDR1 of SEQ ID NO: 7
(SYAMS),

VH-CDR2 of SEQ ID NO: 8
(YISSGGDYIYYADTVKG),

VH-CDR3 of SEQ ID NO: 9
(DPITGTFAY),

VL-CDR1 of SEQ ID NO: 10
(RASQDINNYLN),

VL-CDR2 of SEQ ID NO: 11
(YTSTLHS),
and

VL-CDR3 of SEQ ID NO: 12
(QQGNTLPWT);

3) 10F07:
VH-CDR1 of SEQ ID NO: 13
(SYAMS),

VH-CDR2 of SEQ ID NO: 14
(YISSGGDYFYYADTVKG),

VH-CDR3 of SEQ ID NO: 15
(DPITGTFAY),

VL-CDR1 of SEQ ID NO: 16
(RASQDITNYLN),

VL-CDR2 of SEQ ID NO: 17
(YTSTLHS),
and

VL-CDR3 of SEQ ID NO: 18
(QQGHMLPWT);

4) 14004:
VH-CDR1 of SEQ ID NO: 19
(NYWMN),

VH-CDR2 of SEQ ID NO: 20
(QIYPGHVNTNYNGNFKD),
```

-continued

VH-CDR3 of SEQ ID NO: 21
(SADNSGFVLFAY),

VL-CDR1 of SEQ ID NO: 22
(RASKSVSTSGYSYLH),

VL-CDR2 of SEQ ID NO: 23
(LASNLES),
and

VL-CDR3 of SEQ ID NO: 24
(QHSRELPLT);

5) 19F07:
VH-CDR1 of SEQ ID NO: 25
(DYYMA),

VH-CDR2 of SEQ ID NO: 26
(NINYDGSSTYYLDSLKS),

VH-CDR3 of SEQ ID NO: 27
(GLTWDFDV),

VL-CDR1 of SEQ ID NO: 28
(KASQDVDTAVA),

-continued

VL-CDR2 of SEQ ID NO: 29
(LASTRHT),
and

VL-CDR3 of SEQ ID NO: 30
(QQYSRFPLT);
or

6) CDR variants of 1, 2, 3, 4, or 5.

In some embodiments of the CDR variants of the parent antibodies, amino acid residues located in parent antibodies 02D09, 09E09, 10F07, and 19F07 at the mutation positions denoted in Table A of the example section are conserved in the CDR variants of the respective parent antibody.

In other embodiments, CDR variants of the 19F07 parent antibody are provided in Table B of the example section. Specifically, Table B provides a generic description for each CDR of the 19F07 antibody and shows allowable amino acid substitutions for each CDR of 19F07.

In another embodiment, an antibody according to the present invention includes at least one of the following variable heavy chains and variable light chains:

(a) a variable heavy chain comprising
(MU_02D09_VH)
SEQ ID NO: 31
EVQLVESGGGLVKPGGSLTLSCAASGFTFSDYGMHWLRQAPEKGLEWVAYISSGSRAVFFAD

TVKGRFTISRDNAKNTLFLQMTSLRSDDTAMYYCARDRYDGRGFAYWGQGTLVTVSA, (MU_09E09_VH)
SEQ ID NO: 35
DVKLVESGEGLVKPGGSLKLSCAASGFTFSSYAMSWVRQTPEKRLEWVAYISSGGDYIYYADT

VKGRFTISRDNARNTLYLQMSSLKSEDTAMYYCTRDPITGTFAYWGQGTLVTVSA, (MU_10F07_VH)
SEQ ID NO: 39
DVKLVESGEGLVKPGGSLKLSCAASGFTFSSYAMSWVRQTPEKRLEWVTYISSGGDYFYYAD

TVKGRFTISRDNARNTLYLQMSSLKSEDTAMYYCTRDPITGTFAYWGQGTLVTVSA, (MU_14004_VH)
SEQ ID NO: 43
EVQLQESGAELVKPGASVKISCKASGYAFSNYWMNWMKQRPGKGLEWIGQIYPGHVNTNYN

GNFKDKATLTADK

SSSTAYMQLSSLTSEDSAVYFCARSADNSGFVLFAYWGQGTLVTVS, (MU_19F07_VH)
SEQ ID NO: 47
EVKLVESEGGLVQPGSSMKLSCTASGFTFSDYYMAWVRQVPEKGLEWVANINYDGSSTYYLD

SLKSRFIISRDNAKNILYLQMSSLKSEDTATYYCARGLTWDFDVWGTGTTVTVSS, (FEL_02D09_VH1)
SEQ ID NO: 51
DVQLVESGGDLVKPGGSLRLTCVASGFTYSDYGMHWVRQAPGKGLQWVAYISSGSRAVFFA

DTVKGRFTISRDNAKNTLYLQMNSLKTEDTATYYCVRDRYDGRGFAYWGQGTLVTVSS, (FEL_02D09_VH2)
SEQ ID NO: 53
DVQLVESGGDLVKPGGSLRLTCVASGFTFSDYGMHWVRQAPGKGLQWVAYISSGSRAVFFA

DTVKGRFTISRDNAKNTLYLQMNGLRTEDTATYYCARDRYDGRGFAYWGQGTLVTVSS, (CAN_09E09_VH1)
SEQ ID NO: 59
EVQLVESGGDLVKPGGSLRLSCVASGFTFSSYAMSWVRQAPGKGLQWVAYISSGGDYIYYAD

-continued

TVKGRFTISRDNAKNTLYLQMNSLRAEDTAMYYCVRDPITGTFAYWGQGTLVTVSS, (CAN_09E09_VH2)
SEQ ID NO: 61
EVQLVESGGDLVKPAGSLTLSCLASGFTFSSYAMSWVRQTPEKGLQWVAYISSGGDYIYYADT

VKGRFTISRDNAKNTLYLQMNSLRDEDTAVYYCARDPITGTFAYWGQGTLVTVSS, (FEL_09E09_VH1)
SEQ ID NO: 67
DVQLVESGGDLVKPGGSLRLTCVASGFTYSSYAMSWVRQAPGKGLQWVAYISSGGDYIYYAD

TVKGRFTISRDNAKNTLYLQMNSLKTEDTATYYCVRDPITGTFAYWGQGTLVTVSS, (FEL_09E09_VH2)
SEQ ID NO: 69
DVQLVESGGNLVKPGGSLRLTCVASGFTFSSYAMSWVRQAPGKGLQWVAYISSGGDYIYYAD

TVKGRFTISKDNAKNTLYLQMNSLKTEDTATYYCARDPITGTFAYWGQGTLVTVSS, (CAN_10F07_VH1)
SEQ ID NO: 75
EVQLVESGGDLVKPGGSLRLSCVASGFTFSSYAMSWVRQAPGKGLQWVAYISSGGDYFYYA

DTVKGRFTISRDNAKNTLYLQMNSLRAEDTAMYYCVRDPITGTFAYWGQGTLVTVSS, (CAN_10F07_VH2)
SEQ ID NO: 79
EVQLVESGGDLVKPAGSLTLSCLASGFTFSSYAMSWVRQTPEKGLQWVAYISSGGDYFYYAD

TVKGRFTISRDNAKNTLYLQMNSLRDEDTAVYYCARDPITGTFAYWGQGTLVTVSS, (FEL_10F07_VH1)
SEQ ID NO: 83
DVQLVESGGDLVKPGGSLRLTCVASGFTYSSYAMSWVRQAPGKGLQWVAYISSGGDYFYYA

DTVKGRFTISRDNAKNTLYLQMNSLKTEDTATYYCVRDPITGTFAYWGQGTLVTVSS, (FEL_10F07_VH2)
SEQ ID NO: 87
DVQLVESGGDLVKPGGSLRLTCVASGFTFSSYAMSWVRQAPGKGLQWVAYISSGGDYFYYA

DTVKGRFTISRDDAKNTLYLQMSSLKTEDTATYYCTGDPITGTFAYWGQGTLVTVSS, (CAN_19F07_VH1)
SEQ ID NO: 91
EVQLVESGGDLVKPGGSLRLSCVASGFTFSDYYMAWVRQAPGKGLQWVANINYDGSSTYYLD

SLKSRFTISRDNAKNTLYLQMNSLRAEDTAMYYCVRGLTWDFDVWGQGTLVTVSS, (CAN_19F07_VH2)
SEQ ID NO: 95
EVQLVESGGDLVKPAGSLTLSCLASGFTFSDYYMAWVRQTPEKGLQWVANINYDGSSTYYLD

SLKSRFTISRDNAKNTLYLQMNSLRDEDTAVYYCARGLTWDFDVWGQGTLVTVSS, (FEL_19F07_VH1)
SEQ ID NO: 99
DVQLVESGGDLVKPGGSLRLTCVASGFTYSDYYMAWVRQAPGKGLQWVANINYDGSSTYYL

DSLKSRFTISRDNAKNTLYLQMNSLKTEDTATYYCVRGLTWDFDVWGQGTLVTVSS, (FEL_19F07_VH2)
SEQ ID NO: 103
DVQLVESGGNLVKPGGSLRLTCVASGFTFSDYYMAWVRQAPGKGLQWVANINYDGSSTYYLD

SLKSRFTISRDNAKNTLYLQMNSLKTEDTATYYCARGLTWDFDVWGQGTLVTVSS,

.(CAN_14C04_VH1)
SEQ ID NO: 127
EVQLVESGGDLVKPGGSLRLSCVASGFTFSNYWMNWVRQAPGKGLQWVAQIYPGHVNTNYN

GNFKDRFTISRDNARNTVYLQMNSLRAEDTAVYYCARSADNSGFVLFAYWGQGTLVTVSS,
or

.(CAN_14C04_VH2)
SEQ ID NO: 129
EVQLVESGGDLVKPGGSLRLSCVASGFTFSNYWMNWVRQSPGKGLQWVAQIYPGHVNTNYN

GNFKDRFTISRDNAKNTLYLQMSLRAEDTAVYFCARSADNSGFVLFAYWGQGTLVTVSS,

-continued and (b) a variable light chain comprising
(MU_02D09_VL)
SEQ ID NO: 33
DIVLTQSPATLSVTPGDSVSLSCRASQSISNNLHWYQQTSHESPRLLITYASQSISGIPSRFSGS

GSGTDFTLSINSVETEDFGMYFCQQSNSWPLTFGAGTKLELK, (MU_09E09_VL)
SEQ ID NO: 37
DLQMTQTTSSLSASLGDRVTISCRASQDINNYLNWYQQKPDGTVKLLIYYTSTLHSGVPSRFSG

SGSGTDYSLTISNLEQEDIATYFCQQGNTLPWTFGGGTKLEIK, (MU_10F07_VL)
SEQ ID NO: 41
DIQMTQTTSSLSASLGDRVTISCRASQDITNYLNWYQQKPDGTVKLLIYYTSTLHSGVPSRFSG

SGSGTDFSLTISNLEQEDIATYFCQQGHMLPWTFGGGTKLEIK, (MU_14004_VL)
SEQ ID NO: 45
DIVLTQSPASLAVSLGQRATISCRASKSVSTSGYSYLHWYQQKPGQPPKLLIFLASNLESGVPA

RFSGSGSGTDFTLNIHPVEEEDAATYYCQHSRELPLTFGAGTKLELK, (MU_19F07_VL)
SEQ ID NO: 49
DIVMTQSHKFMSPSVGDRVSITCKASQDVDTAVAWYQQKPGQSPKLLIYLASTRHTGVPDRFT

GSGSGTDFTLTISNVQSEDLADYFCQQYSRFPLTFGAGTKLELK, (FEL_02D09_VL1)
SEQ ID NO: 55
EIQMTQSPSSLSASPGDRVTITCRASQSISNNLHWYQQKPGKVPKLLIYYASQSISGVPSRFSG

SGSGTDFTLTISSLEPEDAATYYCQQSNSWPLTFGQGT, (FEL_02D09_VL2)
SEQ ID NO: 57
DIVMTQTPLSLSVTPGESASISCRASQSISNNLHWYLQKSGQSPRRLIYYASQSISGVPDRFSG

SGSGTDFTLRISRVEADDVGVYYCQQSNSWPLTFGQGT, (CAN_09E09_VL1)
SEQ ID NO: 63
EIVMTQSPASLSLSQEEKVTITCRASQDINNYLNWYQQKPGQAPKLLIYYTSTLHSGVPSRFSG

SGSGTDFSFTISSLEPEDVAVYYCQQGNTLPWTFGQGT, (CAN_09E09_VL2)
SEQ ID NO: 65
DIVLTQPTSVSGSLGQRVTISCRASQDINNYLNWYQQLPGKAPKLLVYYTSTLHSGVPDRFSGS

NSGSSATLTITGLQAEDEADYYCQQGNTLPWTFGQGT, (FEL_09E09_VL1)
SEQ ID NO: 71
EIQMTQSPSSLSASPGDRVTITCRASQDINNYLNWYQQKPGKVPKLLIYYTSTLHSGVPSRFSG

SGSGTDFTLTISSLEPEDAATYYCQQGNTLPWTFGQGT, (FEL_09E09_VL2)
SEQ ID NO: 73
DITMTQSPGSLAGSPGQQVTMNCRASQDINNYLNWYQQKPGQHPKLLIYYTSTLHSGVPDRF

SGSGSGTDFTLTISNLQAEDVASYYCQQGNTLPWTFGQGT, (CAN_10F07_VL1)
SEQ ID NO: 77
EIVMTQSPASLSLSQEEKVTITCRASQDITNYLNWYQQKPGQAPKLLIYYTSTLHSGVPSRFSG

SGSGTDFSFTISSLEPEDVAVYYCQQGHMLPWTFGQGT, (CAN_10F07_VL2)
SEQ ID NO: 81
DIVLTQPTSVSGSLGQRVTISCRASQDITNYLNWYQQLPGKAPKLLVYYTSTLHSGVPDRFSGS

NSGSSATLTITGLQAEDEADYYCQQGHMLPWTFGQGT,

-continued (FEL_10F07_VL1)
SEQ ID NO: 85
EIQMTQSPSSLSASPGDRVTITCRASQDITNYLNWYQQKPGKVPKLLIYYTSTLHSGVPSRFSG

SGSGTDFTLTISSLEPEDAATYYCQQGHMLPWTFGQGT, (FEL_10F07_VL2)
SEQ ID NO: 89
DITMTQSPGSLAGSPGQQVTMNCRASQDITNYLNWYQQKPGQHPKLLIYYTSTLHSGVPDRFS

GSGSGTDFTLTISNLQAEDVASYYCQQGHMLPWTFGQGT, (CAN_19F07_VL1)
SEQ ID NO: 93
EIVMTQSPASLSLSQEEKVTITCKASQDVDTAVAWYQQKPGQAPKWYLASTRHTGVPSRFSG

SGSGTDFSFTISSLEPEDVAVYYCQQYSRFPLTFGQGT, (CAN_19F07_VL2)
SEQ ID NO: 97
DIVMTQTPLSLSVSPGETASISCKASQDVDTAVAWFRQKPGQSPQRLIYLASTRHTGVPDRFS

GSGSGTDFTLRISRVEADDTGVYYCQQYSRFPLTFGQGT, (FEL_19F07_VL1)
SEQ ID NO: 101
EIQMTQSPSSLSASPGDRVTITCKASQDVDTAVAWYQQKPGKVPKLLIYLASTRHTGVPSRFS

GSGSGTDFTLTISSLEPEDAATYYCQQYSRFPLTFGQGT, (FEL_19F07_VL2)
SEQ ID NO: 105
DITMTQSPGSLAGSPGQQVTMNCKASQDVDTAVAWYQQKPGQHPKLLIYLASTRHTGVPDRF

SGSGSGTDFTLTISNLQAEDVASYYCQQYSRFPLTFGQGT,

.(CAN_14004_VL1)
SEQ ID NO: 131
EIVMTQSPASLSLSQEEKVTITCRASKSVSTSGYSYLHWYQQKPGQAPKLLIYLASNLESGVPS

RFSGSGSGTDFSFTISSLEPEDVAVYYCQHSRELPLTFGQGT,
or

.(CAN_14004_VL2)
SEQ ID NO: 133
DIVMTQTPLSLSVSPGETASISCRASKSVSTSGYSYLHWYLQKPGQSPQLLIYLASNLESGVSK

RFSGSGSGTDFTLRISRVEADDTGIYYCQHSRELPLTFGQGT.

In one embodiment, the antibody is chimeric. In another embodiment, the antibody is caninized or felinized.

In one embodiment, the antibody inhibits or neutralizes an IL-31-mediated or OSM-mediated pruritic or allergic condition in a dog or cat. In one aspect, the IL-31-mediated or OSM-mediated pruritic condition is selected from atopic dermatitis, eczema, psoriasis, scleroderma, and pruritis.

In another aspect, the IL-31-mediated or OSM-mediated allergic condition is selected from allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity.

In one embodiment, the antibody inhibits an IL-31-mediated or OSM-mediated fibrotic or inflammatory disorder. In one aspect, the IL-31-mediated or OSM-mediated fibrotic disorder is selected from renal fibrosis, pulmonary fibrosis, and dermal fibrosis. In another aspect, the IL-31-mediated or OSM-mediated inflammatory disorder is selected from inflammatory processes resulting from autoimmunity, inflammation in the skin or joint of animals affected by osteoarthritis, immune-mediated polyarthritis, chronic bronchitis, allergic asthma, atopic dermatitis, allergic dermatitis, pyotraumatic dermatitis, atherosclerosis, and cardiovascular disease.

In a further embodiment, the antibody reduces IL-31-mediated or OSM-mediated inflammatory pain. In one aspect, the IL-31-mediated or OSM-mediated inflammatory pain is osteoarthritis pain.

The present invention also provides a veterinary composition comprising a therapeutically effective amount of an antibody as described above.

This invention also provides a method of treating an IL-31-mediated or OSM-mediated disorder in a subject, comprising administering an antibody according to the invention to the subject. In one embodiment of this method, the IL-31-mediated or OSM-mediated disorder is selected from a pruritic condition, an allergic condition, a fibrotic disorder, an inflammatory disorder, or inflammatory pain.

In another embodiment of the method of treating, the IL-31-mediated or OSM-mediated pruritic condition is selected from the group consisting of atopic dermatitis, eczema, psoriasis, scleroderma, and pruritis. In yet another embodiment of the method, the IL-31-mediated or OSM-mediated allergic condition is selected from allergic dermatitis, summer eczema, urticaria, heaves, inflammatory airway disease, recurrent airway obstruction, airway hyper-responsiveness, chronic obstruction pulmonary disease, or inflammatory processes resulting from autoimmunity.

In further embodiments of the method of treating, the IL-31-mediated or OSM-mediated fibrotic disorder is selected from renal fibrosis, pulmonary fibrosis, or dermal fibrosis. In another embodiment of the method, the IL-31-mediated or OSM-mediated inflammatory disorder is selected from inflammatory processes resulting from autoimmunity, inflammation in the skin or joint of animals affected by osteoarthritis, immune-mediated polyarthritis, chronic bronchitis, allergic asthma, atopic dermatitis, allergic dermatitis, pyotraumatic dermatitis, atherosclerosis, or cardiovascular disease.

In a still further embodiment of the method of treating, the IL-31-mediated or OSM-mediated inflammatory pain is osteoarthritis pain.

In one embodiment of the method of treating, the subject is a dog or a cat.

The present invention further provides a method of inhibiting IL-31 and/or OSM activity in a dog or cat comprising administering an antibody as described above to the dog or cat.

Also provided is a method of detecting OSMR Beta in a sample. This method includes incubating a sample comprising OSMR Beta in the presence of an antibody as described above; and detecting the antibody which is bound to OSMR Beta in the sample. In one embodiment of this method, the antibody comprises a label. In one embodiment, the detection method further includes quantitating the OSMR Beta in the sample.

The present invention also provides host cells and nucleic acids that can be used to produce the antibodies or antigen-binding portions thereof of this invention. In one embodiment, the invention provides a host cell that produces an isolated antibody or antigen-binding portion thereof which includes at least one of the following combinations of complementary determining region (CDR) sequences:

```
1) 02D09:
variable heavy (VH)-CDR1 of SEQ ID NO: 1
(DYGMH),

VH-CDR2 of SEQ ID NO: 2
(YISSGSRAVFFADTVKG),

VH-CDR3 of SEQ ID NO: 3
(DRYDGRGFAY),

variable light (VL)-CDR1 of SEQ ID NO: 4
(RASQSISNNLH),

VL-CDR2 of SEQ NO: 5
(YASQSIS),
and

VL-CDR3 of SEQ ID NO: 6
(QQSNSWPLT);

2) 09E09:
VH-CDR1 of SEQ ID NO: 7
(SYAMS),

VH-CDR2 of SEQ ID NO: 8
(YISSGGDYIYYADTVKG),

VH-CDR3 of SEQ ID NO: 9
(DPITGTFAY),

VL-CDR1 of SEQ ID NO: 10
(RASQDINNYLN),

VL-CDR2 of SEQ ID NO: 11
(YTSTLHS),
and
```

-continued

```
VL-CDR3 of SEQ ID NO: 12
(QQGNTLPWT);

3) 10F07:
VH-CDR1 of SEQ ID NO: 13
(SYAMS),

VH-CDR2 of SEQ ID NO: 14
(YISSGGDYFYYADTVKG),

VH-CDR3 of SEQ ID NO: 15
(DPITGTFAY),

VL-CDR1 of SEQ ID NO: 16
(RASQDITNYLN),

VL-CDR2 of SEQ ID NO: 17
(YTSTLHS),
and

VL-CDR3 of SEQ ID NO: 18
(QQGHMLPWT);

4) 14004:
VH-CDR1 of SEQ ID NO: 19
(NYWMN),

VH-CDR2 of SEQ ID NO: 20
(QIYPGHVNTNYNGNFKD),

VH-CDR3 of SEQ ID NO: 21
(SADNSGFVLFAY),

VL-CDR1 of SEQ ID NO: 22
(RASKSVSTSGYSYLH),

VL-CDR2 of SEQ ID NO: 23
(LASNLES),
and

VL-CDR3 of SEQ ID NO: 24
(QHSRELPLT);

5) 19F07:
VH-CDR1 of SEQ ID NO: 25
(DYYMA),

VH-CDR2 of SEQ ID NO: 26
(NINYDGSSTYYLDSLKS),

VH-CDR3 of SEQ ID NO: 27
(GLTWDFDV),

VL-CDR1 of SEQ ID NO: 28
(KASQDVDTAVA),

VL-CDR2 of SEQ ID NO: 29
(LASTRHT),
and

VL-CDR3 of SEQ ID NO: 30
(QQYSRFPLT);
or

6) CDR variants of 1, 2, 3, 4, or 5.
```

The present invention also provides an isolated nucleic acid including a nucleic acid sequence encoding at least one of the following combinations of variable heavy complementary determining region (CDR) sequences:

```
1) 02D09: variable heavy (VH)-CDR1 of
SEQ ID NO: 1 (DYGMH),
VH-CDR2 of SEQ ID NO: 2 (YISSGSRAVFFADTVKG), and
VH-CDR3 of SEQ ID NO: 3 (DRYDGRGFAY);
```

-continued

```
2) 09E09: VH-CDR1 of SEQ ID NO: 7 (SYAMS),
VH-CDR2 of SEQ ID NO: 8 (YISSGGDYIYYADTVKG), and
VH-CDR3 of SEQ ID NO: 9 (DPITGTFAY);

3) 10F07: VH-CDR1 of SEQ ID NO: 13 (SYAMS),
VH-CDR2 of SEQ ID NO: 14 (YISSGGDYFYYADTVKG), and
VH-CDR3 of SEQ ID NO: 15 (DPITGTFAY);

4) 14C04: VH-CDR1 of SEQ ID NO: 19 (NYWMN),
VH-CDR2 of SEQ ID NO: 20 (QIYPGHVNTNYNGNFKD), and
VH-CDR3 of SEQ ID NO: 21 (SADNSGFVLFAY);

5) 19F07: VH-CDR1 of SEQ ID NO: 25 (DYYMA),
VH-CDR2 of SEQ ID NO: 26 (NINYDGSSTYYLDSLKS), and
VH-CDR3 of SEQ ID NO: 27 (GLTWDFDV);
or

6) CDR variants of 1, 2, 3, 4, or 5.
```

In one embodiment, the nucleic acid described above further includes a nucleic acid sequence encoding at least one of the following combinations of variable light CDR sequences:

```
1) 02D09: variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

2) 09E09: VL-CDR1 of VL-CDR1 of SEQ ID NO: 10
(RASQDINNYLN),
VL-CDR2 of SEQ ID NO: 11 (YTSTLHS), and
VL-CDR3 of SEQ ID NO: 12 (QQGNTLPWT);

3) 10F07: VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

4) 14C04: VL-CDR1 of SEQ ID NO: 22
(RASKSVSTSGYSYLH),
VL-CDR2 of SEQ ID NO: 23 (LASNLES), and
VL-CDR3 of SEQ ID NO: 24 (QHSRELPLT);

5) 19F07: VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or

6) CDR variants of 1, 2, 3, 4, or 5.
```

In another embodiment, a nucleic acid sequence according to the invention encodes at least one of the following combinations of variable light CDR sequences:

```
1) 02D09: variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

2) 09E09: VL-CDR1 of VL-CDR1 of SEQ ID NO: 10
(RASQDINNYLN),
VL-CDR2 of SEQ ID NO: 11 (YTSTLHS), and
VL-CDR3 of SEQ ID NO: 12 (QQGNTLPWT);

3) 10F07: VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

4) 14C04: VL-CDR1 of SEQ ID NO: 22
(RASKSVSTSGYSYLH),
VL-CDR2 of SEQ ID NO: 23 (LASNLES), and
VL-CDR3 of SEQ ID NO: 24 (QHSRELPLT);
```

-continued

```
5) 19F07: VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or

6) CDR variants of 1, 2, 3, 4, or 5.
```

The present invention further provides a vector that includes a nucleic acid as described above.

Furthermore, the present invention provides a method of producing an antibody. This method includes culturing the host cell described above under conditions that result in production of the antibody and isolating the antibody from the host cell or culture medium of the host cell.

BRIEF DESCRIPTION OF THE DRAWINGS

FIGS. 3A and 3B are an alignment of the variable heavy and variable light chain sequences of the anti-OSMR antibodies described in this application.

FIG. 12A shows the pre and post dosing pruritic scores in a canine model of IL-31 induced pruritus comparing the anti-OSMR mouse:canine chimera 19F07 (T01) and 10F07 (T02), both dosed subcutaneously to six animals per group on day zero with a dose of 12.0 mg/kg.

FIG. 12B shows the summary statistics for post-challenge scores by treatment group and paired t-test with mean and 90% confidence limits.

BRIEF DESCRIPTION OF THE SEQUENCES

Figure 1A:
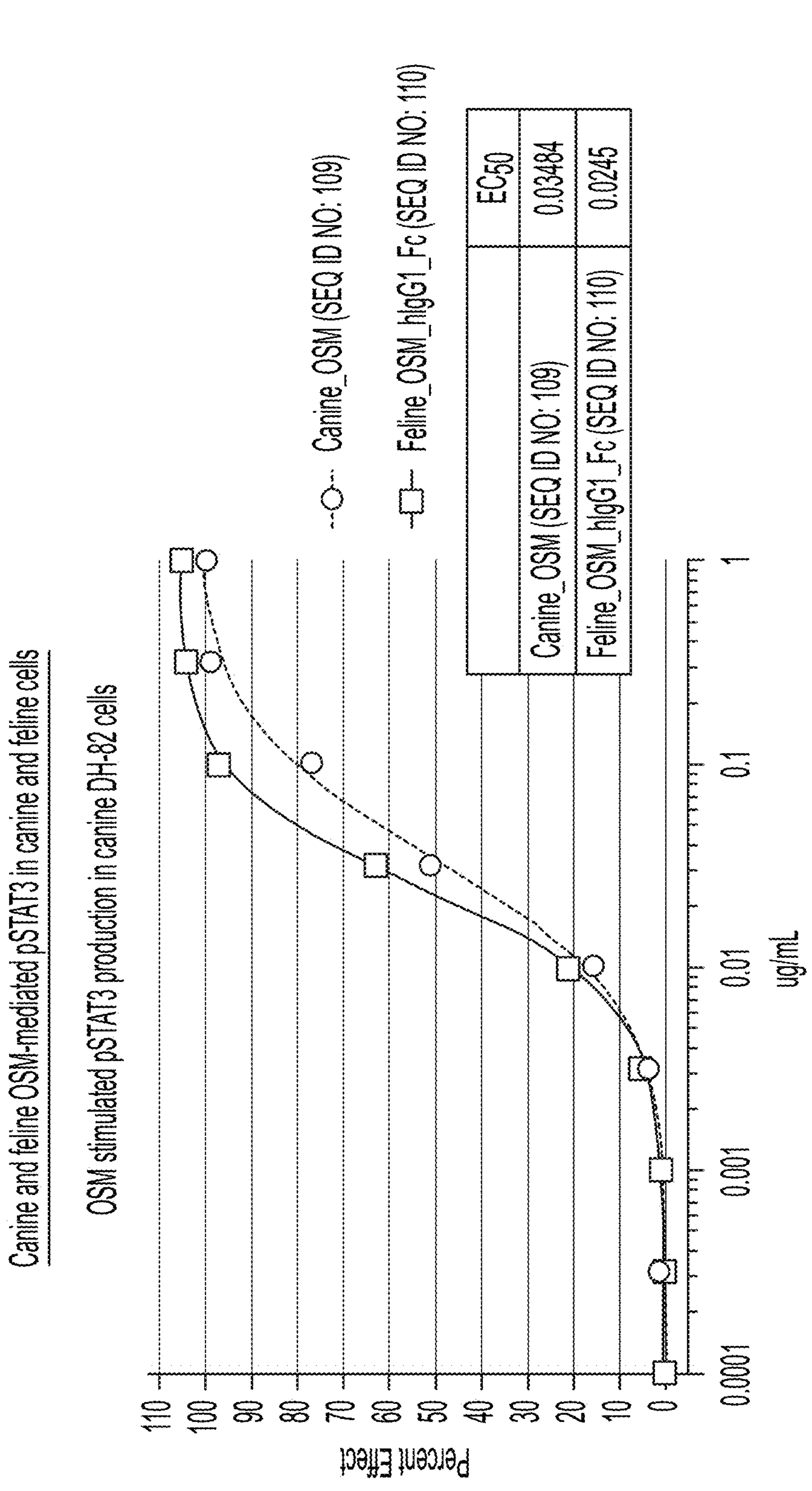
FIGS. 1A and 1B are graphs showing the pSTAT3 dose-response produced by treatment of canine and feline OSM in canine DH82 cells and in feline Fcwf4 cells, respectively.

SEQ ID NO: 1 is a variable heavy chain CDR1 referred to herein as 02D09-VH-CDR1;

SEQ ID NO: 2 is a variable heavy chain CDR2 referred to herein as 02D09-VH-CDR2;

SEQ ID NO: 3 is a variable heavy chain CDR3 referred to herein as 02D09-VH-CDR3;

SEQ ID NO: 4 is a variable light chain CDR1 referred to herein as 02D09-VL-CDR1;

SEQ ID NO: 5 is a variable light chain CDR2 referred to herein as 02D09-VL-CDR2;

SEQ ID NO: 6 is a variable light chain CDR3 referred to herein as 02D09-VL-CDR3;

SEQ ID NO: 7 is a variable heavy chain CDR1 referred to herein as 09E09-VH-CDR1;

SEQ ID NO: 8 is a variable heavy chain CDR2 referred to herein as 09E09-VH-CDR2;

SEQ ID NO: 9 is a variable heavy chain CDR3 referred to herein as 09E09-VH-CDR3;

SEQ ID NO: 10 is a variable light chain CDR1 referred to herein as 09E09-VL-CDR1;

SEQ ID NO: 11 is a variable light chain CDR2 referred to herein as 09E09-VL-CDR2;

SEQ ID NO: 12 is a variable light chain CDR3 referred to herein as 09E09-VL-CDR3;

SEQ ID NO: 13 is a variable heavy chain CDR1 referred to herein as 10F07-VH-CDR1;

SEQ ID NO: 14 is a variable heavy chain CDR2 referred to herein as 10F07-VH-CDR2;

SEQ ID NO: 15 is a variable heavy chain CDR3 referred to herein as 10F07-VH-CDR3;

SEQ ID NO: 16 is a variable light chain CDR1 referred to herein as 10F07-VL-CDR1;

SEQ ID NO: 17 is a variable light chain CDR2 referred to herein as 10F07-VL-CDR2;

SEQ ID NO: 18 is a variable light chain CDR3 referred to herein as 10F07-VL-CDR3;

SEQ ID NO: 19 is a variable heavy chain CDR1 referred to herein as 14C04-VH-CDR1;

SEQ ID NO: 20 is a variable heavy chain CDR2 referred to herein as 14C04-VH-CDR2;

SEQ ID NO: 21 is a variable heavy chain CDR3 referred to herein as 14C04-VH-CDR3;

SEQ ID NO: 22 is a variable light chain CDR1 referred to herein as 14C04-VL-CDR1;

SEQ ID NO: 23 is a variable light chain CDR2 referred to herein as 14C04-VL-CDR2;

SEQ ID NO: 24 is a variable light chain CDR3 referred to herein as 14C04-VL-CDR3;

SEQ ID NO: 25 is a variable heavy chain CDR1 referred to herein as 19F07-VH-CDR1;

SEQ ID NO: 26 is a variable heavy chain CDR2 referred to herein as 19F07-VH-CDR2;

SEQ ID NO: 27 is a variable heavy chain CDR3 referred to herein as 19F07-VH-CDR3;

SEQ ID NO: 28 is a variable light chain CDR1 referred to herein as 19F07-VL-CDR1;

SEQ ID NO: 29 is a variable light chain CDR2 referred to herein as 19F07-VL-CDR2;

SEQ ID NO: 30 is a variable light chain CDR3 referred to herein as 19F07-VL-CDR3;

SEQ ID NO: 31 is a variable heavy chain sequence referred to herein as MU_02D09_VH;

SEQ ID NO: 32 is the nucleotide sequence encoding the variable heavy chain sequence referred to herein as MU_02D09_VH;

SEQ ID NO: 33 is a variable light chain sequence referred to herein as MU_02D09_VL;

SEQ ID NO: 34 is the nucleotide sequence encoding the variable light chain sequence referred to herein as MU_02D09_VL;

SEQ ID NO: 35 is a variable heavy chain sequence referred to herein as MU_09E09_VH;

SEQ ID NO: 36 is the nucleotide sequence encoding the variable heavy chain sequence referred to herein as MU_09E09_VH;

SEQ ID NO: 37 is a variable light chain sequence referred to herein as MU_09E09_VL;

SEQ ID NO: 38 is the nucleotide sequence encoding the variable light chain sequence referred to herein as MU_09E09_VL;

SEQ ID NO: 39 is a variable heavy chain sequence referred to herein as MU_10F07_VH;

SEQ ID NO: 40 is the nucleotide sequence encoding the variable heavy chain sequence referred to herein as MU_10F07_VH;

SEQ ID NO: 41 is a variable light chain sequence referred to herein as MU_10F07_VL;

SEQ ID NO: 42 is the nucleotide sequence encoding the variable light chain sequence referred to herein as MU_10F07_VL;

SEQ ID NO: 43 is a variable heavy chain sequence referred to herein as MU_14C04_VH;

SEQ ID NO: 44 is the nucleotide sequence encoding the variable heavy chain sequence referred to herein as MU_14C04_VH;

SEQ ID NO: 45 is a variable light chain sequence referred to herein as MU_14C04_VL;

SEQ ID NO: 46 is the nucleotide sequence encoding the variable light chain sequence referred to herein as MU_14C04_VL;

SEQ ID NO: 47 is a variable heavy chain sequence referred to herein as MU_19F07_VH;

SEQ ID NO: 48 is the nucleotide sequence encoding the variable heavy chain sequence referred to herein as MU_19F07_VH;

SEQ ID NO: 49 is a variable light chain sequence referred to herein as MU_19F07_VL;

SEQ ID NO: 50 is the nucleotide sequence encoding the variable light chain sequence referred to herein as MU_19F07_VL;

SEQ ID NO: 51 is a variable heavy chain sequence referred to herein as FEL_02D09_VH1;

SEQ ID NO: 52 is the nucleotide sequence encoding the variable heavy chain sequence referred to herein as FEL_02D09_VH1;

SEQ ID NO: 53 is a variable heavy chain sequence referred to herein as FEL_02D09_VH2;

SEQ ID NO: 54 is the nucleotide sequence encoding the variable heavy chain sequence referred to herein as FEL_02D09_VH2;

SEQ ID NO: 55 is a variable light chain sequence referred to herein as FEL_02D09_VL1;

SEQ ID NO: 56 is the nucleotide sequence encoding the variable light chain sequence referred to herein as FEL_02D09_VL1;

SEQ ID NO: 57 is a variable light chain sequence referred to herein as FEL_02D09_VL2;

SEQ ID NO: 58 is the nucleotide sequence encoding the variable light chain sequence referred to herein as FEL_02D09_VL2;

SEQ ID NO: 59 is a variable heavy chain sequence referred to herein as CAN_09E09_VH1;

SEQ ID NO: 60 is the nucleotide sequence encoding the variable heavy chain sequence referred to herein as CAN_09E09_VH1;

SEQ ID NO: 61 is a variable heavy chain sequence referred to herein as CAN_09E09_VH2;

SEQ ID NO: 62 is the nucleotide sequence encoding the variable heavy chain sequence referred to herein as CAN_09E09_VH2;

SEQ ID NO: 63 is a variable light chain sequence referred to herein as CAN_09E09_VL1;

SEQ ID NO: 64 is the nucleotide sequence encoding the variable light chain sequence referred to herein as CAN_09E09_VL1;

SEQ ID NO: 65 is a variable light chain sequence referred to herein as CAN_09E09_VL2;

SEQ ID NO: 66 is the nucleotide sequence encoding the variable light chain sequence referred to herein as CAN_09E09_VL2;

SEQ ID NO: 67 is a variable heavy chain sequence referred to herein as FEL_09E09_VH1;

SEQ ID NO: 68 is the nucleotide sequence encoding the variable heavy chain sequence referred to herein as FEL_09E09_VH1;

SEQ ID NO: 69 is a variable heavy chain sequence referred to herein as FEL_09E09_VH2;

SEQ ID NO: 70 is the nucleotide sequence encoding the variable heavy chain sequence referred to herein as FEL_09E09_VH2;

SEQ ID NO: 71 is a variable light chain sequence referred to herein as FEL_09E09_VL1;

SEQ ID NO: 72 is the nucleotide sequence encoding the variable light chain sequence referred to herein as FEL_09E09_VL1;

SEQ ID NO: 73 is a variable light chain sequence referred to herein as FEL_09E09_VL2;

SEQ ID NO: 74 is the nucleotide sequence encoding the variable light chain sequence referred to herein as FEL_09E09_VL2;

SEQ ID NO: 75 is a variable heavy chain sequence referred to herein as CAN_10F07_VH1;

SEQ ID NO: 76 is the nucleotide sequence encoding the variable heavy chain sequence referred to herein as CAN_10F07_VH1;

SEQ ID NO: 77 is a variable light chain sequence referred to herein as CAN_10F07_VL1;

SEQ ID NO: 78 is the nucleotide sequence encoding the variable light chain sequence referred to herein as CAN_10F07_VL1;

SEQ ID NO: 79 is a variable heavy chain sequence referred to herein as CAN_10F07_VH2;

SEQ ID NO: 80 is the nucleotide sequence encoding the variable heavy chain sequence referred to herein as CAN_10F07_VH2;

SEQ ID NO: 81 is a variable light chain sequence referred to herein as CAN_10F07_VL2;

SEQ ID NO: 82 is the nucleotide sequence encoding the variable light chain sequence referred to herein as CAN_10F07_VL2;

SEQ ID NO: 83 is a variable heavy chain sequence referred to herein as FEL_10F07_VH1;

SEQ ID NO: 84 is the nucleotide sequence encoding the variable heavy chain sequence referred to herein as FEL_10F07_VH1;

SEQ ID NO: 85 is a variable light chain sequence referred to herein as FEL_10F07_VL1;

SEQ ID NO: 86 is the nucleotide sequence encoding the variable light chain sequence referred to herein as FEL_10F07_VL1;

SEQ ID NO: 87 is a variable heavy chain sequence referred to herein as FEL_10F07_VH2;

SEQ ID NO: 88 is the nucleotide sequence encoding the variable heavy chain sequence referred to herein as FEL_10F07_VH2;

SEQ ID NO: 89 is a variable light chain sequence referred to herein as FEL_10F07_VL2;

SEQ ID NO: 90 is the nucleotide sequence encoding the variable light chain sequence referred to herein as FEL_10F07_VL2;

SEQ ID NO: 91 is a variable heavy chain sequence referred to herein as CAN_19F07_VH1;

SEQ ID NO: 92 is the nucleotide sequence encoding the variable heavy chain sequence referred to herein as CAN_19F07_VH1;

SEQ ID NO: 93 is a variable light chain sequence referred to herein as CAN_19F07_VL1;

SEQ ID NO: 94 is the nucleotide sequence encoding the variable light chain sequence referred to herein as CAN_19F07_VL1;

SEQ ID NO: 95 is a variable heavy chain sequence referred to herein as CAN_19F07_VH2;

SEQ ID NO: 96 is the nucleotide sequence encoding the variable heavy chain sequence referred to herein as CAN_19F07_VH2;

SEQ ID NO: 97 is a variable light chain sequence referred to herein as CAN_19F07_VL2;

SEQ ID NO: 98 is the nucleotide sequence encoding the variable light chain sequence referred to herein as CAN_19F07_VL2;

SEQ ID NO: 99 is a variable heavy chain sequence referred to herein as FEL_19F07_VH1;

SEQ ID NO: 100 is the nucleotide sequence encoding the variable heavy chain sequence referred to herein as FEL_19F07_VH1;

SEQ ID NO: 101 is a variable light chain sequence referred to herein as FEL_19F07_VL1;

SEQ ID NO: 102 is the nucleotide sequence encoding the variable light chain sequence referred to herein as FEL_19F07_VL1;

SEQ ID NO: 103 is a variable heavy chain sequence referred to herein as FEL_19F07_VH2;

SEQ ID NO: 104 is the nucleotide sequence encoding the variable heavy chain sequence referred to herein as FEL_19F07_VH2;

SEQ ID NO: 105 is a variable light chain sequence referred to herein as FEL_19F07_VL2;

SEQ ID NO: 106 is the nucleotide sequence encoding the variable light chain sequence referred to herein as FEL_19F07_VL2;

SEQ ID NO: 107 is the amino acid sequence of a canine OSMR-Fc fusion protein designated herein as Canine_OSMR_hlgG1_Fc;

SEQ ID NO: 108 is the nucleotide sequence encoding the canine OSMR-Fc fusion protein designated herein as Canine_OSMR_hlgG1_Fc;

SEQ ID NO: 109 is the amino acid sequence corresponding to canine OSM, which is referred to herein as Canine_OSM;

SEQ ID NO: 110 is the amino acid sequence corresponding to feline OSM-Fc fusion protein, which is referred to herein as Feline_OSM_hlgG1_Fc;

SEQ ID NO: 111 is the nucleotide sequence corresponding to feline OSM-Fc fusion protein, which is referred to herein as Feline_OSM_hlgG1_Fc;

SEQ ID NO: 112 is the amino acid sequence of a feline OSMR-Fc fusion protein designated herein as Feline_OSMR_hlgG1_Fc;

SEQ ID NO: 113 is the nucleotide sequence encoding the feline OSMR-Fc fusion protein designated herein as Feline_OSMR_hlgG1_Fc;

SEQ ID NO: 114 is the amino acid sequence for the canine heavy chain constant region referred to herein as Canine_HC_65_1;

SEQ ID NO: 115 is the nucleotide sequence encoding the canine heavy chain constant region referred to herein as Canine_HC_65_1;

SEQ ID NO: 116 is the amino acid sequence for the canine light chain constant region referred to herein as Canine_LC_Kappa;

SEQ ID NO: 117 is the nucleotide sequence encoding the canine light chain constant region referred to herein as Canine_LC_Kappa;

SEQ ID NO: 118 is the amino acid sequence for the feline heavy chain constant region referred to herein as Feline_HC_AlleleA_1;

SEQ ID NO: 119 is the nucleotide sequence encoding the feline heavy chain constant region referred to herein as Feline_HC_AlleleA_1;

SEQ ID NO: 120 is the amino acid sequence for the feline light chain constant region referred to herein as Feline_LC_Kappa_G_minus;

SEQ ID NO: 121 is the nucleotide sequence encoding the amino acid sequence for the feline light chain constant region referred to herein as Feline_LC_Kappa_G_minus;

SEQ ID NO: 122 is the amino acid sequence for the human OSMR protein referred to herein as Human_OSMR;

SEQ ID NO: 123 is the amino acid sequence for the canine IL31 protein referred to herein as Canine_IL31;

SEQ ID NO: 124 is the nucleotide sequence encoding canine IL31 protein referred to herein as Canine_IL31;

SEQ ID NO: 125 is the amino acid sequence for the feline IL31 protein referred to herein as Feline_IL31;

SEQ ID NO: 126 is the nucleotide sequence encoding feline IL31 protein referred to herein as Feline_IL31;

SEQ ID NO: 127 is a variable heavy chain sequence referred to herein as CAN_14C04_VH1;

SEQ ID NO: 128 is the nucleotide sequence encoding the variable heavy chain sequence referred to herein as CAN_14C04_VH1;

SEQ ID NO: 129 is a variable heavy chain sequence referred to herein as CAN_14C04_VH2;

SEQ ID NO: 130 is the nucleotide sequence encoding the variable heavy chain sequence referred to herein as CAN_14C04_VH2;

SEQ ID NO: 131 is a variable heavy chain sequence referred to herein as CAN_14C04_VL1;

SEQ ID NO: 132 is the nucleotide sequence encoding the variable heavy chain sequence referred to herein as CAN_14C04_VL2;

SEQ ID NO: 133 is a variable heavy chain sequence referred to herein as CAN_14C04_VL1;

SEQ ID NO: 134 is the nucleotide sequence encoding the variable heavy chain sequence referred to herein as CAN_14C04_VL2;

SEQ ID NO: 135; is the amino acid sequence of the human LIFR protein designated herein as Human_LIFR;

SEQ ID NO: 136; is the amino acid sequence of the human LIF protein designated herein as Human_LIF;

Definitions

Before describing the present invention in detail, several terms used in the context of the present invention will be defined. In addition to these terms, others are defined elsewhere in the specification, as necessary. Unless otherwise expressly defined herein, terms of art used in this specification will have their art-recognized meanings.

As used in the specification and claims, the singular form "a", "an" and "the" include plural references unless the context clearly dictates otherwise. For example, reference to "an antibody" includes a plurality of such antibodies.

As used herein, the term "comprising" is intended to mean that the compositions and methods include the recited elements, but not excluding others.

Epitope, as used herein, refers to the antigenic determinant recognized by the CDRs of the antibody. In other words, epitope refers to that portion of any molecule capable of being recognized by, and bound by, an antibody. Unless indicated otherwise, the term "epitope" as used herein, refers to the region of OSMR Beta to which an anti-OSMR Beta agent is reactive to.

An "antigen" is a molecule or a portion of a molecule capable of being bound by an antibody which is additionally capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

The term "specifically" in the context of antibody binding, refers to high avidity and/or high affinity binding of an antibody to a specific antigen, i.e., a polypeptide, or epitope. In many embodiments, the specific antigen is an antigen (or a fragment or subfraction of an antigen) used to immunize the animal host from which the antibody-producing cells were isolated. Antibody specifically binding an antigen is stronger than binding of the same antibody to other antigens. Antibodies which bind specifically to a polypeptide may be capable of binding other polypeptides at a weak, yet detectable level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_D$ of $10^{-7}$ M or less, e.g., $10^{-8}$ M or less (e.g., $10^{-9}$ M or less, $10^{-10}$ or less, $10^{-11}$ or less, $10^{-12}$ or less, or $10^{-13}$ or less, etc.).

As used herein, the term "antibody" refers to an intact immunoglobulin having two light and two heavy chains. Thus, a single isolated antibody or fragment may be a polyclonal antibody, a monoclonal antibody, a synthetic antibody, a recombinant antibody, a chimeric antibody, a heterochimeric antibody, a caninized antibody, or a felinized antibody. The term "antibody" preferably refers to monoclonal antibodies and fragments thereof, and immunologic binding equivalents thereof that can bind to the OSMR Beta protein and fragments thereof. The term antibody is used both to refer to a homogeneous molecular, or a mixture such as a serum product made up of a plurality of different molecular entities.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise multiple FRs, largely adopting a β-sheet configuration, connected by three hypervariable regions, which form loops connecting, and in some cases forming part of, the α-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (Kabat, et al. (1991), above) and/or those residues from a "hypervariable loop" (Chothia and Lesk J. Mol. Biol. 196:901-917 (1987). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) can recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2 (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

"Monoclonal antibody" as defined herein is an antibody produced by a single clone of cells (specifically, a single clone of hybridoma cells) and therefore a single pure homogeneous type of antibody. All monoclonal antibodies produced from the same clone are identical and have the same antigen specificity. The term "monoclonal" pertains to a single clone of cells, a single cell, and the progeny of that cell.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. In this embodiment, the antigen binding site is derived from mouse while the $F_c$ portion is canine.

"Caninized" forms of non-canine (e.g., murine) antibodies are genetically engineered antibodies that contain minimal sequence derived from non-canine immunoglobulin. Caninized antibodies are canine immunoglobulin sequences (recipient antibody) in which hypervariable region residues of the recipient are replaced by hypervariable region residues from a non-canine species (donor antibody) such as mouse having the desired specificity, affinity, and capacity. In some instances, framework region (FR) residues of the canine immunoglobulin sequences are replaced by corresponding non-canine residues. Furthermore, caninized antibodies may include residues that are not found in the recipient antibody or in the donor antibody. These modifications are made to further refine antibody performance. In general, the caninized antibody will include substantially all of at least one, and typically two, variable domains, in which all or substantially all of the hypervariable regions correspond to those of a non-canine immunoglobulin sequence and all or substantially all of the FRs are those of a canine immunoglobulin sequence. The caninized antibody optionally also will comprise a complete, or at least a portion of an immunoglobulin constant region (Fc), typically that of a canine immunoglobulin sequence. In one embodiment, mouse CDRs are grafted onto canine frameworks.

"Felinized" forms of non-feline (e.g., murine) antibodies are genetically engineered antibodies that contain minimal sequence derived from non-feline immunoglobulin. Felinized antibodies are feline immunoglobulin sequences (recipient antibody) in which hypervariable region residues of the recipient are replaced by hypervariable region residues from a non-feline species (donor antibody) such as mouse having the desired specificity, affinity, and capacity. In some instances, framework region (FR) residues of the feline immunoglobulin sequences are replaced by corresponding non-feline residues. Furthermore, felinized antibodies may include residues that are not found in the recipient antibody or in the donor antibody. These modifications are made to further refine antibody performance. In general, the felinized antibody will include substantially all of at least one, and typically two, variable domains, in which all or substantially all of the hypervariable regions correspond to those of a non-feline immunoglobulin sequence and all or substantially all of the FRs are those of a feline immunoglobulin sequence. The felinized antibody optionally also will comprise a complete, or at least a portion of an immunoglobulin constant region (Fc), typically that of a feline immunoglobulin sequence.

The term "heterochimeric" as defined herein, refers to an antibody in which one of the antibody chains (heavy or light) is caninized while the other is chimeric. In one embodiment, a caninized variable heavy chain (where all of the CDRs are mouse and all FRs are canine) is paired with a chimeric variable light chain (where all of the CDRs are mouse and all FRs are mouse. In this embodiment, both the variable heavy and variable light chains are fused to a canine constant region.

A "variant" anti-OSMR Beta antibody, refers herein to a molecule which differs in amino acid sequence from a "parent" anti-OSMR Beta antibody amino acid sequence by virtue of addition, deletion, and/or substitution of one or more amino acid residue(s) in the parent antibody sequence and retains at least one desired activity of the parent anti-OSMR Beta-antibody. Desired activities can include the ability to bind the antigen specifically, the ability to reduce, inhibit or neutralize OSM activity and/or IL-31 activity in an animal, and the ability to inhibit OSM-mediated and/or IL-31-mediated pSTAT signaling (STAT phosphorylation) in a cell-based assay. In one embodiment, the variant comprises one or more amino acid substitution(s) in one or more hypervariable (CDR) and/or framework region(s) of the parent antibody. For example, the variant may comprise at least one, e.g. from about one to about fifteen, and preferably from about two to about five, or from two to about ten substitutions in one or more hypervariable (CDR) and/or framework regions of the parent antibody. In one embodiment, the variant can include at least about the following number of amino acid substitutions in one or more of the CDR regions of the parent antibody: 1, 2, 3, 4, 5, 6, 7, 8, 9, 10, 11, 12, 13, 14, or 15. In another embodiment, the variant can include up to about the following number of amino acid substitutions in one or more of the CDR regions of the parent antibody: 1, 2, 3, 4, 5, 6, 7, 8, 9, 10, 11, 12, 13, 14, or 15. Regarding a variant antibody, it is to be understood that the number of amino acid substitutions in any given CDR of the parent antibody can be different from the number of substitutions in other CDRs of the parent antibody. In one embodiment, the variant will have variable heavy CDR1, variable heavy CDR2, and variable heavy CDR3 amino acid sequences which can each independently have at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% amino acid sequence identity with the variable heavy CDR1, variable heavy CDR2, and variable heavy CDR3 amino acid sequences of the parent antibody. In another embodiment, the variant will have variable light CDR1, variable light CDR2, and variable light CDR3 amino acid sequences which can each independently have at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% amino acid sequence identity with the variable light CDR1, variable light CDR2, and variable light CDR3 amino acid sequences of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind an OSMR Beta and preferably has desired activities which are superior to those of the parent antibody. For example, the variant may have a stronger binding affinity, enhanced ability to reduce, inhibit or neutralize OSM and/or IL-31 activity in an animal, and/or enhanced ability to inhibit OSM and/or IL-31-mediated pSTAT signaling in a cell-based assay.

A "variant" nucleic acid refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The "parent" antibody herein is one that is encoded by an amino acid sequence used for the preparation of the variant. Preferably, the parent antibody has a canine framework region and, if present, has canine antibody constant region (s). For example, the parent antibody may be a caninized or canine antibody. As another example, the parent antibody may be a felinized or feline antibody. As yet another example, the parent antibody is a murine monoclonal antibody.

The term "isolated" means that the material (e.g., antibody or nucleic acid) is separated and/or recovered from a component of its natural environment. Contaminant components of its natural environment are materials that would interfere with diagnostic or therapeutic uses for the material, and may include enzymes, hormones, and other proteinaceous or nonproteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

The word "label" when used herein refers to a detectable compound or composition that is conjugated directly or indirectly to the antibody or nucleic acid. The label may itself be detectable by itself (e.g., radioisotope labels or fluorescent labels) or, in the case of an enzymatic label, may catalyze chemical alteration of a substrate compound or composition that is detectable.

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included.

A "subject" or "patient" refers to an animal in need of treatment that can be affected by molecules of the invention. Animals that can be treated in accordance with the invention include vertebrates, with mammals such as canine, feline, and equine animals being particularly preferred examples.

A "therapeutically effective amount" (or "effective amount") refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with treatment of a pruritic condition or an allergic condition including clinical improvement in symptoms. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

"Treatment", "treating", and the like refers to both therapeutic treatment and prophylactic or preventative measures. Animals in need of treatment include those already with the disorder as well as those in which the disorder is to be prevented. The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "allergic condition" is defined herein as a disorder or disease caused by an interaction between the immune system and a substance foreign to the body. This foreign substance is termed "an allergen". Common allergens include aeroallergens, such as pollens, dust, molds, dust mite proteins, injected saliva from insect bites, etc. Examples of allergic conditions include, but are not limited to, the following: allergic dermatitis, summer eczema, urticaria, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

The term "pruritic condition" is defined herein as a disease or disorder characterized by an intense itching sensation that produces the urge to rub or scratch the skin to obtain relief. Examples of pruritic conditions include, but are not limited to, the following: atopic dermatitis, eczema, psoriasis, scleroderma, and pruritus.

The term "fibrotic disorder" is defined herein as a disease or disorder characterized by fibrosis, which is the accumulation of extracellular matrix components in organs or tissues, changing their structure and leading to a disruption of normal function. Fibrosis can occur in almost any organ or tissue and is associated with a wide variety of diseases. Examples of types of fibrotic disorders include, but are not limited to, renal fibrosis, pulmonary fibrosis, and dermal fibrosis.

The term "inflammatory disorder" includes a vast array of disorders and conditions that are characterized by inflammation. Examples include, but are not limited to, inflammatory processes resulting from autoimmunity, inflammation in the skin or joint of animals affected by osteoarthritis, immune-mediated polyarthritis, chronic bronchitis, allergic asthma, atopic dermatitis, allergic dermatitis, pyotraumatic dermatitis, atherosclerosis, and cardiovascular disease.

The term "inflammatory pain" as used herein is the spontaneous hypersensitivity to pain that occurs in response to tissue damage and inflammation (e.g., postoperative pain, trauma, arthritis). In one non-limiting example, the inflammatory pain is pain associated with osteoarthritis.

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

A "composition" is intended to mean a combination of active agent and another compound or composition which can be inert (e.g., a label), or active, such as an adjuvant.

As defined herein, pharmaceutically acceptable carriers suitable for use in the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-HCl, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be any one that occurs within one of the following six groups 1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gln; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gln (Asn); Glu (Asp); Gly (Pro); His (Asn; Gln); Ile (Leu; Val); Leu (Ile; Val); Lys (Arg; Gln; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

DETAILED DESCRIPTION OF THE INVENTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification, See e.g., Sambrook et al. MOLECULAR CLONING: LAB. MANUAL (3rd ed., Cold Spring Harbor Lab. Press, Cold Spring Harbor, N.Y., 2001) and Ausubel et al. Current Protocols in Molecular Biology (New York: Greene Publishing Association/Wiley Interscience), 1993. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

The present invention provides for recombinant monoclonal antibodies and peptides and their uses in clinical and scientific procedures, including diagnostic procedures. With the advent of methods of molecular biology and recombinant technology, it is possible to produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion or portions of any molecule capable of being recognized by, and bound by, an antibody (the corresponding antibody binding region may be referred to as a paratope).

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The term "antibody" is meant to include both intact immunoglobulin molecules as well as portions, fragments, peptides and derivatives thereof such as, for example, Fab, Fab', $F(ab')_2$, Fv, Fse, CDR regions, paratopes, or any portion or peptide sequence of the antibody that is capable of binding an antigen or epitope. An antibody is said to be "capable of binding" a molecule if it is capable of specifically reacting with the molecule to thereby bind the molecule to the antibody.

Antibody also includes chimeric antibodies, heterochimeric antibodies, caninized antibodies, or felinized antibodies, as well as fragments, portions, regions, peptides or derivatives thereof, provided by any known technique, such as, but not limited to, enzymatic cleavage, peptide synthesis, or recombinant techniques. Such antibodies of the present invention are capable of specifically binding at least one of canine OSMR Beta or feline OSMR Beta. Antibody fragments or portions may lack the Fc fragment of intact antibody, clear more rapidly from the circulation, and may have less non-specific tissue binding than an intact antibody. Examples of antibody fragments may be produced from intact antibodies using methods well known in the art, for example by proteolytic cleavage with enzymes such as papain (to produce Fab fragments) or pepsin (to produce $F(ab')._2$ fragments). See, e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

Clones 02D09, 09E09, 10F07, 14C04, and 19F07 Nucleotide and Amino Acid Sequences In some embodiments, the present invention provides for novel monoclonal antibodies that specifically bind to at least one of canine OSMR Beta or feline OSMR Beta. In one embodiment, a monoclonal antibody of the invention binds to canine OSMR beta or feline OSMR Beta and prevents or inhibits activation of the IL-31 co-receptor complex comprising IL-31 receptor A (IL-31Ra) and Oncostatin-M-specific receptor (OsmR or OSMR Beta). The monoclonal antibodies of the present invention are identified herein as "02D09", "09E09, "10F07", "14C04", and "19F07" _which refers to the number assigned to its hybridoma clone. Herein, "02D09", "09E09", "10F07", "14C04", and "19F07" also refers to the portion of the monoclonal antibody, the paratope or CDRs, that bind specifically with an OSMR Beta epitope identified as 02D09, 09E09, 10F07, 14C04, and 19F07 because of its ability to bind the 02D09, 09E09, 10F07, 14C04, and 19F07 antibodies, respectively. The several recombinant, chimeric, heterochimeric, caninized and/or felinized forms of 02D09, 09E09, 10F07, 14C04, and 19F07 described herein may be referred to by the same name.

In one embodiment, the antibody, or antigen-binding portion thereof of the present invention includes a combination of complementary determining region (CDR) sequences selected from the following:

```
1) 02D09: variable heavy (VH)-CDR1 of SEQ ID NO: 1
(DYGMH),
VH-CDR2 of SEQ ID NO: 2 (YISSGSRAVFFADTVKG),
VH-CDR3 of SEQ ID NO: 3 (DRYDGRGFAY),
variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

2) 09E09: VH-CDR1 of SEQ ID NO: 7 (SYAMS),
VH-CDR2 of SEQ ID NO: 8 (YISSGGDYIYYADTVKG),
VH-CDR3 of SEQ ID NO: 9 (DPITGTFAY),
VL-CDR1 of SEQ ID NO: 10 (RASQDINNYLN),
VL-CDR2 of SEQ ID NO: 11 (YTSTLHS), and
VL-CDR3 of SEQ ID NO: 12 (QQGNTLPWT);

3) 10F07: VH-CDR1 of SEQ ID NO: 13 (SYAMS),
VH-CDR2 of SEQ ID NO: 14 (YISSGGDYFYYADTVKG),
VH-CDR3 of SEQ ID NO: 15 (DPITGTFAY),
VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

4) 14C04: VH-CDR1 of SEQ ID NO: 19 (NYWMN),
VH-CDR2 of SEQ ID NO: 20 (QIYPGHVNTNYNGNFKD),
VH-CDR3 of SEQ ID NO: 21 (SADNSGFVLFAY),
VL-CDR1 of SEQ ID NO: 22 (RASKSVSTSGYSYLH),
VL-CDR2 of SEQ ID NO: 23 (LASNLES), and
VL-CDR3 of SEQ ID NO: 24 (QHSRELPLT);

5) 19F07: VH-CDR1 of SEQ ID NO: 25 (DYYMA),
VH-CDR2 of SEQ ID NO: 26 (NINYDGSSTYYLDSLKS),
```

-continued

```
VH-CDR3 of SEQ ID NO: 27 (GLTWDFDV),
VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or

6) CDR variants of 1, 2, 3, 4, or 5.
```

In some embodiments, amino acid residues located in parent antibodies 02D09, 09E09, 10F07, and 19F07 at the mutation positions denoted in Table A of the example section are conserved in the CDR variants of the respective parent antibody. For example, based on the information in Table A and the sequence listing, in some embodiments the underlined amino acid residues shown below are conserved in CDR variants of parent antibodies 02D09, 09E09, 10F07, and 19F07.

```
02D09: variable heavy (VH)-CDR1 of SEQ ID NO: 1
(DYGMH),
VH-CDR2 of SEQ ID NO: 2 (YISSGSRAVFFADTVKG),
VH-CDR3 of SEQ ID NO: 3 (DRYDGRGFAY),
variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

09E09: VH-CDR1 of SEQ ID NO: 7 (SYAMS),
VH-CDR2 of SEQ ID NO: 8 (YISSGGDYIYYADTVKG),
VH-CDR3 of SEQ ID NO: 9 (DPITGTFAY),
VL-CDR1 of SEQ ID NO: 10 (RASQDINNYLN),
VL-CDR2 of SEQ ID NO: 11 (YTSTLHS), and
VL-CDR3 of SEQ ID NO: 12 (QQGNTLPWT);

10F07: VH-CDR1 of SEQ ID NO: 13 (SYAMS),
VH-CDR2 of SEQ ID NO: 14 (YISSGGDYFYYADTVKG),
VH-CDR3 of SEQ ID NO: 15 (DPITGTFAY),
VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

19F07: VH-CDR1 of SEQ ID NO: 25 (DYYMA),
VH-CDR2 of SEQ ID NO: 26 (NINYDGSSTYYLDSLKS),
VH-CDR3 of SEQ ID NO: 27 (GLTWDFDV),
VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT).
```

Based on the results described in Example 19, Alanine replacement mutations at the underlined positions negatively impacted binding of the antibody to the OSMR target. By inference, the residues which are not underlined can be substituted in the CDR variants since Alanine mutations at those positions did not negatively impact binding of the antibody to the OSMR target.

Furthermore, the information in Table B of the example section supports that in some embodiments CDR variants of the 19F07 parent antibody are those which can have the allowed substitutions specified in the sequence definitions in that table, which is reproduced below.

| SEQ ID NO: | SEQUENCE DEFINITION WITH ALLOWED SUBSTITUTIONS | DESCRIPTION WITH (BINDING TARGET PROTEIN) |
|---|---|---|
| 25 | $D_1Y_2Y_3M_4A_5$<br>wherein $Y_3$ is Y | CDR-H1 (canine OSMR) |

-continued

| SEQ ID NO: | SEQUENCE DEFINITION WITH ALLOWED SUBSTITUTIONS | DESCRIPTION WITH (BINDING TARGET PROTEIN) |
|---|---|---|
| 26 | $N_1I_2N_3Y_4D_5G_6S_7S_8T_9Y_{10}Y_{11}L_{12}D_{13}S_{14}L_{15}K_{16}S_{17}$<br>wherein $Y_{10}$ is Y, C, F, H, T, or W | CDR-H2 (canine OSMR) |
| 27 | $G_1L_2T_3W_4D_5F_6D_7V_8W_9$<br>wherein $W_4$ is W, G, or C | CDR-H3 (canine OSMR) |
| 27 | $G_1L_2T_3W_4D_5F_6D_7V_8W_9$<br>wherein $W_4$ is W, G, or F | CDR-H3 (feline OSMR) |
| 28 | $K_1A_2S_3Q_4D_5V_6D_7T_8A_9V_{10}A_{11}$<br>wherein $V_6$ is V, L, M, A, N, S, E, I, H, or C; $D_7$ is D, G, Y, N, or E; $A_9$ is A, S, or G; $V_{10}$ is V, L, L, A, D, T, M, or C; $A_{11}$ is A, S, T, G, or C | CDR-L1 (canine OSMR) |
| 28 | $K_1A_2S_3Q_4D_5V_6D_7T_8A_9V_{10}A_{11}$<br>wherein $V_6$ is V, L, M, A, G, N, T, S, P, I, F, or H; $D_7$ is D, G, Y, N, E, S, R, A, L, M, H, T, Q, I, or W; $A_9$ is A, S, V, T, or G; $V_{10}$ is V, L, F, I, A, S, G, T, M, Q, N, or C; $A_{11}$ is A, S, T, V, G, C, N, or D | CDR-L1 (feline OSMR) |
| 29 | $L_1A_2S_3T_4R_5H_6T_7$<br>wherein $L_1$ is L, S, F, M, A, G, or Q; $A_2$ is A, S, V, G, D, P, T, L, E, or C | CDR-L2 (canine OSMR) |
| 29 | $L_1A_2S_3T_4R_5H_6T_7$<br>wherein $A_2$ is A, S, V, G, D, T, L, E, R, C, Y | CDR-L2 (feline OSMR) |
| 30 | $Q_1Q_2Y_3S_4R_5F_6P_7L_8T_9F_{10}$<br>wherein $Q_1$ is Q, S, H, K, E, G, M, A, N, F, or Y; $Q_2$ is Q or H; $Y_3$ is Y or F; $S_4$ is S, I, N, A, or T; $F_6$ is F, L, I, V, Y, M, E, W, or D; $P_7$ is P, S, C, A, G, or D; $L_8$ is L, R, P, M, S, V, I, W, F, or E; $F_{10}$ is F, L, M, I, Y, or W | CDR-L3 (canine OSMR) |
| 30 | $Q_1Q_2Y_3S_4R_5F_6P_7L_8T_9F_{10}$<br>wherein $Q_1$ is Q, L, S, H, K, V, E, G, M, A, T, N, F, Y, or C; $Q_2$ is Q, M, H, S, Y, T, N, F, E, C, or A; $Y_3$ is Y, L, R, M, F, W, H, I, or N; $P_7$ is P, S, H, T, R, C, A, G, or D | CDR-L3 (feline OSMR) |

In another embodiment, an antibody according to the present invention includes at least one of the following variable heavy chains and variable light chains:

```
(a) a variable heavy chain comprising
(MU_02D09_VH)
                                                      SEQ ID NO: 31
EVQLVESGGGLVKPGGSLTLSCAASGFTFSDYGMHWLRQAPEKGLEWVAYISSGSRAVFFAD

TVKGRFTISRDNAKNTLFLQMTSLRSDDTAMYYCARDRYDGRGFAYWGQGTLVTVSA,

(MU_09E09_VH)
                                                      SEQ ID NO: 35
DVKLVESGEGLVKPGGSLKLSCAASGFTFSSYAMSWVRQTPEKRLEWVAYISSGGDYIYYADT

VKGRFTISRDNARNTLYLQMSSLKSEDTAMYYCTRDPITGTFAYWGQGTLVTVSA,

(MU_10F07_VH)
                                                      SEQ ID NO: 39
DVKLVESGEGLVKPGGSLKLSCAASGFTFSSYAMSWVRQTPEKRLEWVTYISSGGDYFYYAD

TVKGRFTISRDNARNTLYLQMSSLKSEDTAMYYCTRDPITGTFAYWGQGTLVTVSA,

(MU_14C04_VH)
                                                      SEQ ID NO: 43
EVQLQESGAELVKPGASVKISCKASGYAFSNYWMNWMKQRPGKGLEWIGQIYPGHVNTNYN

GNFKDKATLTADKSSSTAYMQLSSLTSEDSAVYFCARSADNSGFVLFAYWGQGTLVTVS,

(MU_19F07_VH)
                                                      SEQ ID NO: 47
EVKLVESEGGLVQPGSSMKLSCTASGFTFSDYYMAWVRQVPEKGLEWVANINYDGSSTYYLD

SLKSRFIISRDNAKNILYLQMSSLKSEDTATYYCARGLTWDFDVWGTGTTVTVSS,

(FEL_02D09_VH1)
                                                      SEQ ID NO: 51
DVQLVESGGDLVKPGGSLRLTCVASGFTYSDYGMHWVRQAPGKGLQWVAYISSGSRAVFFA

DTVKGRFTISRDNAKNTLYLQMNSLKTEDTATYYCVRDRYDGRGFAYWGQGTLVTVSS,

(FEL_02D09_VH2)
                                                      SEQ ID NO: 53
DVQLVESGGDLVKPGGSLRLTCVASGFTFSDYGMHWVRQAPGKGLQWVAYISSGSRAVFFA
```

-continued

DTVKGRFTISRDNAKNTLYLQMNGLRTEDTATYYCARDRYDGRGFAYWGQGTLVTVSS, (CAN_09E09_VH1)
SEQ ID NO: 59
EVQLVESGGDLVKPGGSLRLSCVASGFTFSSYAMSWVRQAPGKGLQWVAYISSGGDYIYYAD

TVKGRFTISRDNAKNTLYLQMNSLRAEDTAMYYCVRDPITGTFAYWGQGTLVTVSS, (CAN_09E09_VH2)
SEQ ID NO: 61
EVQLVESGGDLVKPAGSLTLSCLASGFTFSSYAMSWVRQTPEKGLQWVAYISSGGDYIYYADT

VKGRFTISRDNAKNTLYLQMNSLRDEDTAVYYCARDPITGTFAYWGQGTLVTVSS, (FEL_09E09_VH1)
SEQ ID NO: 67
DVQLVESGGDLVKPGGSLRLTCVASGFTYSSYAMSWVRQAPGKGLQWVAYISSGGDYIYYAD

TVKGRFTISRDNAKNTLYLQMNSLKTEDTATYYCVRDPITGTFAYWGQGTLVTVSS, (FEL_09E09_VH2)
SEQ ID NO: 69
DVQLVESGGNLVKPGGSLRLTCVASGFTFSSYAMSWVRQAPGKGLQWVAYISSGGDYIYYAD

TVKGRFTISKDNAKNTLYLQMNSLKTEDTATYYCARDPITGTFAYWGQGTLVTVSS, (CAN_10F07_VH1)
SEQ ID NO: 75
EVQLVESGGDLVKPGGSLRLSCVASGFTFSSYAMSWVRQAPGKGLQWVAYISSGGDYFYYA

DTVKGRFTISRDNAKNTLYLQMNSLRAEDTAMYYCVRDPITGTFAYWGQGTLVTVSS, (CAN_10F07_VH2)
SEQ ID NO: 79
EVQLVESGGDLVKPAGSLTLSCLASGFTFSSYAMSWVRQTPEKGLQWVAYISSGGDYFYYAD

TVKGRFTISRDNAKNTLYLQMNSLRDEDTAVYYCARDPITGTFAYWGQGTLVTVSS, (FEL_10F07_VH1)
SEQ ID NO: 83
DVQLVESGGDLVKPGGSLRLTCVASGFTYSSYAMSWVRQAPGKGLQWVAYISSGGDYFYYA

DTVKGRFTISRDNAKNTLYLQMNSLKTEDTATYYCVRDPITGTFAYWGQGTLVTVSS, (FEL_10F07_VH2)
SEQ ID NO: 87
DVQLVESGGDLVKPGGSLRLTCVASGFTFSSYAMSWVRQAPGKGLQWVAYISSGGDYFYYA

DTVKGRFTISRDDAKNTLYLQMSSLKTEDTATYYCTGDPITGTFAYWGQGTLVTVSS, (CAN_19F07_VH1)
SEQ ID NO: 91
EVQLVESGGDLVKPGGSLRLSCVASGFTFSDYYMAWVRQAPGKGLQWVANINYDGSSTYYLD

SLKSRFTISRDNAKNTLYLQMNSLRAEDTAMYYCVRGLTWDFDVWGQGTLVTVSS, (CAN_19F07_VH2)
SEQ ID NO: 95
EVQLVESGGDLVKPAGSLTLSCLASGFTFSDYYMAWVRQTPEKGLQWVANINYDGSSTYYLD

SLKSRFTISRDNAKNTLYLQMNSLRDEDTAVYYCARGLTWDFDVWGQGTLVTVSS, (FEL_19F07_VH1)
SEQ ID NO: 99
DVQLVESGGDLVKPGGSLRLTCVASGFTYSDYYMAWVRQAPGKGLQWVANINYDGSSTYYL

DSLKSRFTISRDNAKNTLYLQMNSLKTEDTATYYCVRGLTWDFDVWGQGTLVTVSS, (FEL_19F07_VH2)
SEQ ID NO: 103
DVQLVESGGNLVKPGGSLRLTCVASGFTFSDYYMAWVRQAPGKGLQWVANINYDGSSTYYLD

SLKSRFTISRDNAKNTLYLQMNSLKTEDTATYYCARGLTWDFDVWGQGTLVTVSS, (CAN_14C04_VH1)
SEQ ID NO: 127
EVQLVESGGDLVKPGGSLRLSCVASGFTFSNYWMNWVRQAPGKGLQWVAQIYPGHVNTNYN

GNFKDRFTISRDNARNTVYLQMNSLRAEDTAVYYCARSADNSGFVLFAYWGQGTLVTVSS,
or

-continued (CAN_14C04_VH2)

SEQ ID NO: 129

EVQLVESGGDLVKPGGSLRLSCVASGFTFSNYWMNWVRQSPGKGLQWVAQIYPGHVNTNYN

GNFKDRFTISRDNAKNTLYLQMNSLRAEDTAVYFCARSADNSGFVLFAYWGQGTLVTVSS;

and (b) a variable light chain comprising (MU_02D09_VL)

SEQ ID NO: 33

DIVLTQSPATLSVTPGDSVSLSCRASQSISNNLHWYQQTSHESPRLLITYASQSISGIPSRFSGS

GSGTDFTLSINSVETEDFGMYFCQQSNSWPLTFGAGTKLELK, (MU_09E09_VL)

SEQ ID NO: 37

DLQMTQTTSSLSASLGDRVTISCRASQDINNYLNWYQQKPDGTVKLLIYYTSTLHSGVPSRFSG

SGSGTDYSLTISNLEQEDIATYFCQQGNTLPWTFGGGTKLEIK, (MU_10F07_VL)

SEQ ID NO: 41

DIQMTQTTSSLSASLGDRVTISCRASQDITNYLNWYQQKPDGTVKLLIYYTSTLHSGVPSRFSG

SGSGTDFSLTISNLEQEDIATYFCQQGHMLPWTFGGGTKLEIK, (MU_14C04_VL)

SEQ ID NO: 45

DIVLTQSPASLAVSLGQRATISCRASKSVSTSGYSYLHWYQQKPGQPPKLLIFLASNLESGVPA

RFSGSGSGTDFTLNIHPVEEEDAATYYCQHSRELPLTFGAGTKLELK, (MU_19F07_VL)

SEQ ID NO: 49

DIVMTQSHKFMSPSVGDRVSITCKASQDVDTAVAWYQQKPGQSPKWYLASTRHTGVPDRFT

GSGSGTDFTLTISNVQSEDLADYFCQQYSRFPLTFGAGTKLELK, (FEL_02D09_VL1)

SEQ ID NO: 55

EIQMTQSPSSLSASPGDRVTITCRASQSISNNLHWYQQKPGKVPKLLIYYASQSISGVPSRFSG

SGSGTDFTLTISSLEPEDAATYYCQQSNSWPLTFGQGT, (FEL_02D09_VL2)

SEQ ID NO: 57

DIVMTQTPLSLSVTPGESASISCRASQSISNNLHWYLQKSGQSPRRLIYYASQSISGVPDRFSG

SGSGTDFTLRISRVEADDVGVYYCQQSNSWPLTFGQGT, (CAN_09E09_VL1)

SEQ ID NO: 63

EIVMTQSPASLSLSQEEKVTITCRASQDINNYLNWYQQKPGQAPKLLIYYTSTLHSGVPSRFSG

SGSGTDFSFTISSLEPEDVAVYYCQQGNTLPWTFGQGT, (CAN_09E09_VL2)

SEQ ID NO: 65

DIVLTQPTSVSGSLGQRVTISCRASQDINNYLNWYQQLPGKAPKLLVYYTSTLHSGVPDRFSGS

NSGSSATLTITGLQAEDEADYYCQQGNTLPWTFGQGT, (FEL_09E09_VL1)

SEQ ID NO: 71

EIQMTQSPSSLSASPGDRVTITCRASQDINNYLNWYQQKPGKVPKLLIYYTSTLHSGVPSRFSG

SGSGTDFTLTISSLEPEDAATYYCQQGNTLPWTFGQGT, (FEL_09E09_VL2)

SEQ ID NO: 73

DITMTQSPGSLAGSPGQQVTMNCRASQDINNYLNWYQQKPGQHPKLLIYYTSTLHSGVPDRF

SGSGSGTDFTLTISNLQAEDVASYYCQQGNTLPWTFGQGT, (CAN_10F07_VL1)

SEQ ID NO: 77

EIVMTQSPASLSLSQEEKVTITCRASQDITNYLNWYQQKPGQAPKLLIYYTSTLHSGVPSRFSG

SGSGTDFSFTISSLEPEDVAVYYCQQGHMLPWTFGQGT,

-continued (CAN_10F07_VL2)
SEQ ID NO: 81
DIVLTQPTSVSGSLGQRVTISCRASQDITNYLNWYQQLPGKAPKLLVYYTSTLHSGVPDRFSGS

NSGSSATLTITGLQAEDEADYYCQQGHMLPWTFGQGT, (FEL_10F07_VL1)
SEQ ID NO: 85
EIQMTQSPSSLSASPGDRVTITCRASQDITNYLNWYQQKPGKVPKLLIYYTSTLHSGVPSRFSG

SGSGTDFTLTISSLEPEDAATYYCQQGHMLPWTFGQGT, (FEL_10F07_VL2)
SEQ ID NO: 89
DITMTQSPGSLAGSPGQQVTMNCRASQDITNYLNWYQQKPGQHPKLLIYYTSTLHSGVPDRFS

GSGSGTDFTLTISNLQAEDVASYYCQQGHMLPWTFGQGT, (CAN_19F07_VL1)
SEQ ID NO: 93
EIVMTQSPASLSLSQEEKVTITCKASQDVDTAVAWYQQKPGQAPKWYLASTRHTGVPSRFSG

SGSGTDFSFTISSLEPEDVAVYYCQQYSRFPLTFGQGT, (CAN_19F07_VL2)
SEQ ID NO: 97
DIVMTQTPLSLSVSPGETASISCKASQDVDTAVAWFRQKPGQSPQRLIYLASTRHTGVPDRFS

GSGSGTDFTLRISRVEADDTGVYYCQQYSRFPLTFGQGT, (FEL_19F07_VL1)
SEQ ID NO: 101
EIQMTQSPSSLSASPGDRVTITCKASQDVDTAVAWYQQKPGKVPKLLIYLASTRHTGVPSRFS

GSGSGTDFTLTISSLEPEDAATYYCQQYSRFPLTFGQGT, (FEL_19F07_VL2)
SEQ ID NO: 105
DITMTQSPGSLAGSPGQQVTMNCKASQDVDTAVAWYQQKPGQHPKLLIYLASTRHTGVPDRF

SGSGSGTDFTLTISNLQAEDVASYYCQQYSRFPLTFGQGT, (CAN_14C04_VL1)
SEQ ID NO: 131
EIVMTQSPASLSLSQEEKVTITCRASKSVSTSGYSYLHWYQQKPGQAPKLLIYLASNLESGVPS

RFSGSGSGTDFSFTISSLEPEDVAVYYCQHSRELPLTFGQGT,
or (CAN_14C04_VL2)
SEQ ID NO: 133
DIVMTQTPLSLSVSPGETASISCRASKSVSTSGYSYLHWYLQKPGQSPQLLIYLASNLESGVSK

RFSGSGSGTDFTLRISRVEADDTGIYYCQHSRELPLTFGQGT.

In other embodiments, the invention provides a host cell that produces an antibody described above.

The present invention also includes, within its scope, nucleotide sequences encoding the variable regions of the light and heavy chains of the anti-OSMR Beta antibody of the present invention. Included also within the scope of the invention is any nucleotide sequence that encodes the amino acid sequence of the 02D09, 09E09, 10F07, 14C04, and 19F07 antibodies or antigen-binding portions thereof.

The present invention also provides an isolated nucleic acid including a nucleic acid sequence encoding at least one of the following combinations of variable heavy complementary determining region (CDR) sequences:

1) 02D09: variable heavy (VH)-CDR1 of SEQ ID NO: 1 (DYGMH),
VH-CDR2 of SEQ ID NO: 2 (YISSGSRAVFFADTVKG), and
VH-CDR3 of SEQ ID NO: 3 (DRYDGRGFAY);

-continued 2) 09E09: VH-CDR1 of SEQ ID NO: 7 (SYAMS),
VH-CDR2 of SEQ ID NO: 8 (YISSGGDYIYYADTVKG), and
VH-CDR3 of SEQ ID NO: 9 (DPITGTFAY);

3) 10F07: VH-CDR1 of SEQ ID NO: 13 (SYAMS),
VH-CDR2 of SEQ ID NO: 14 (YISSGGDYFYYADTVKG), and
VH-CDR3 of SEQ ID NO: 15 (DPITGTFAY);

4) 14C04: VH-CDR1 of SEQ ID NO: 19 (NYWMN),
VH-CDR2 of SEQ ID NO: 20 (QIYPGHVNTNYNGNFKD), and
VH-CDR3 of SEQ ID NO: 21 (SADNSGFVLFAY);

5) 19F07: VH-CDR1 of SEQ ID NO: 25 (DYYMA),
VH-CDR2 of SEQ ID NO: 26 (NINYDGSSTYYLDSLKS), and
VH-CDR3 of SEQ ID NO: 27 (GLTWDFDV);
or 6) CDR variants of 1, 2, 3, 4, or 5.

In one embodiment, the nucleic acid described above further includes a nucleic acid sequence encoding at least one of the following combinations of variable light CDR sequences:

```
1) 02D09: variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

2) 09E09: VL-CDR1 of VL-CDR1 of SEQ ID NO: 10
(RASQDINNYLN),
VL-CDR2 of SEQ ID NO: 11 (YTSTLHS), and
VL-CDR3 of SEQ ID NO: 12 (QQGNTLPWT);

3) 10F07: VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

4) 14C04: VL-CDR1 of SEQ ID NO: 22
(RASKSVSTSGYSYLH),
VL-CDR2 of SEQ ID NO: 23 (LASNLES), and
VL-CDR3 of SEQ ID NO: 24 (QHSRELPLT);

5) 19F07: VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or

6) CDR variants of 1, 2, 3, 4, or 5.
```

In another embodiment, a nucleic acid sequence according to the invention encodes at least one of the following combinations of variable light CDR sequences:

```
1) 02D09: variable light (VL)-CDR1 of SEQ ID NO: 4
(RASQSISNNLH),
VL-CDR2 of SEQ NO: 5 (YASQSIS), and
VL-CDR3 of SEQ ID NO: 6 (QQSNSWPLT);

2) 09E09: VL-CDR1 of VL-CDR1 of SEQ ID NO: 10
(RASQDINNYLN),
VL-CDR2 of SEQ ID NO: 11 (YTSTLHS), and
VL-CDR3 of SEQ ID NO: 12 (QQGNTLPWT);

3) 10F07: VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

4) 14C04: VL-CDR1 of SEQ ID NO: 22
(RASKSVSTSGYSYLH),
VL-CDR2 of SEQ ID NO: 23 (LASNLES), and
VL-CDR3 of SEQ ID NO: 24 (QHSRELPLT);

5) 19F07: VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or

6) CDR variants of 1, 2, 3, 4, or 5.
```

The present invention further provides a vector that includes a nucleic acid as described above. A single expression vector can carry the nucleic acid sequence encoding the variable light CDR sequences as well as the nucleic acid sequence encoding the variable heavy CDR sequences. Alternatively, the nucleic acid sequence encoding the variable light CDRs may be carried by one vector whereas the nucleic acid sequence encoding the variable heavy CDRs may be carried by a separate vector.

Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-OSMR Beta antibody or portion thereof. Such "codon usage rules" are disclosed by Lathe, et al., 183 J. Molec. Biol. 1-12 (1985). Using the "codon usage rules" of Lathe, a single nucleotide sequence, or a set of nucleotide sequences, that contains a theoretical "most probable" nucleotide sequence capable of encoding anti-OSMR Beta sequences can be identified.

It is also intended that the antibody coding regions for use in the present invention could also be provided by altering existing antibody genes using standard molecular biological techniques that result in variants (agonists) of the antibodies and antigen-binding portions described herein. Such variants include, but are not limited to, deletions, additions and substitutions in the amino acid sequence of the anti-OSMR Beta antibodies or antigen-binding portions thereof.

For example, one class of substitutions is conservative amino acid substitutions. Such substitutions are those that substitute a given amino acid in an anti-OSMR Beta antibody sequence by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-OSMR Beta antibodies or antigen-binding portions thereof may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W.H. Freeman & Co., NY, 1993). Many detailed reviews are available on this subject, such as by Wold, Posttranslational Covalent Modification of proteins, 1-12 (Johnson, ed., Academic Press, NY, 1983); Seifter et al. 182 Meth. Enzymol. 626-46 (1990); and Rattan et al. 663 Ann. NY Acad. Sci. 48-62 (1992).

Accordingly, the antibodies and antigen-binding portions thereof of the present invention also encompass derivatives or analogs in which a substituted amino acid residue is not one encoded by the genetic code.

Similarly, the additions and substitutions in the amino acid sequence as well as variations, and modifications just described may be equally applicable to the amino acid sequence of the OSM Beta antigen and/or epitopes thereof, and are thus encompassed by the present invention. As mentioned above, the genes encoding a monoclonal antibody according to the present invention is specifically effective in the recognition of OSMR Beta.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine ($^{125}I$, $^{131}I$), carbon ($^{14}C$), sulfur ($^{35}S$), indium ($^{111}In$), tritium ($^{3}H$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. No. 20030031671.

Recombinant Expression of Antibodies

In some embodiments, the nucleic acids encoding a subject monoclonal antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing.

Traditionally, monoclonal antibodies have been produced as native molecules in murine hybridoma lines. In addition to that technology, the present invention provides for recombinant DNA expression of monoclonal antibodies. This allows the production of caninized and felinized antibodies, as well as a spectrum of antibody derivatives and fusion proteins in a host species of choice.

A nucleic acid sequence encoding at least one anti-OSMR Beta antibody, or antigen-binding portion thereof of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, NY, 1982 and 1989), and Ausubel et al. 1993 supra, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-OSMR beta polypeptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an anti-OSMR Beta antibody or antigen-binding portion thereof, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli (such as, for example, pBR322, ColE1, pSC101, pACYC 184, .pi.VX). Such plasmids are, for example, disclosed by Maniatis et al., 1989 supra; Ausubel et al, 1993 supra. *Bacillus* plasmids include pC194, pC221, pT127, etc. Such plasmids are disclosed by Gryczan, in THE MOLEC. BIO. OF THE BACILLI 307-329 (Academic Press, N Y, 1982). Suitable Streptomyces plasmids include pIJ101 (Kendall et al., 169 J. Bacteriol. 4177-83 (1987)), and Streptomyces bacteriophages such as .phi.C31 (Chater et al., in SIXTH INT'L SYMPOSIUM ON ACTINOMYCETALES BIO. 45-54 (Akademiai Kaido, Budapest, Hungary 1986). Pseudomonas plasmids are reviewed in John et al., 8 Rev. Infect. Dis. 693-704 (1986); Izaki, 33 Jpn. J. Bacteriol. 729-42 (1978); and Ausubel et al., 1993 supra.

Alternatively, gene expression elements useful for the expression of cDNA encoding anti-OSMR Beta antibodies or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 Proc. Natl. Acad. Sci., USA 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with a gene encoding an anti-OSMR Beta immunoglobulin chain or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-OSMR Beta immunoglobulin H and L chains or chimeric H and L chains, or portions thereof are assembled in separate expression vectors that are then used to co-transfect a recipient cell. Alternatively, the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric, caninized or felinized antibody construct or anti-OSMR Beta immunoglobulin gene construct of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988).

Yeast can provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of anti-OSMR Beta antibody sequences, antibody and assembled murine and chimeric, heterochimeric, caninized, or felinized antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.) IRL Press, Oxford, UK 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized or felinized antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, NY (1994-2001); Colligan et al., eds. Current Protocols in Protein Science, John Wiley & Sons, NY, NY (1997-2001).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells.

Many vector systems are available for the expression of cloned anti-OSMR Beta H and L chain genes in mammalian cells (see Glover, 1985 supra). Different approaches can be followed to obtain complete $H_2L_2$ antibodies. It is possible to co-express H and L chains in the same cells to achieve intracellular association and linkage of H and L chains into complete tetrameric $H_2L_2$ antibodies and/or anti-OSMR Beta fragments (e.g., antigen-binding portion thereof). The co-expression can occur by using either the same or different plasmids in the same host. Genes for both H and L chains and/or anti-OSMR Beta fragments can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-OSMR Beta amino acids sequences and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical Applications

The anti-OSMR Beta antibodies or antigen-binding portions thereof of the present invention can be used for example in the treatment of various conditions in companion animals, such as dogs and cats. These conditions include pruritic conditions, allergic conditions, inflammatory conditions, fibrotic conditions, and pain associated with inflammation. Specific but non-limiting examples of these types of conditions are disclosed herein. It is to be understood that in some cases, a particular disorder may be considered to fall under more than only one category. For example, certain allergic conditions can be considered inflammatory conditions as well. More specifically, the invention further provides for a pharmaceutical composition comprising a pharmaceutically acceptable carrier or diluent and, as active ingredient, an antibody or peptide according to the invention. The antibody can be a chimeric, heterochimeric, caninized, or felinized antibody according to the present invention. Intact immunoglobulins or their binding fragments, such as Fab, are also envisioned. The antibody and pharmaceutical compositions thereof of this invention are useful for parenteral administration, e.g., subcutaneously, intramuscularly or intravenously.

Anti-OSMR Beta antibodies and/or antigen-binding portions thereof of the present invention can be administered either as individual therapeutic agents or in combination with other therapeutic agents. They can be administered alone, but are generally administered with a pharmaceutical carrier selected on the basis of the chosen route of administration and standard pharmaceutical practice.

Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be, for example, in the form of an ingestible liquid or solid formulation.

In some desired embodiments, the antibodies are administered by parenteral injection. For parenteral administration, anti-OSMR Beta antibodies or antigen-binding portions thereof can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The compositions containing the present antibodies, or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art.

In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system, but generally range from about 0.1 mg antibody per kg body weight to about 10 mg antibody per kg body weight, preferably about 0.3 mg antibody per kg of body weight to about 5 mg of antibody per kg of body weight. In view of the minimization of extraneous substances and the lower probability of "foreign substance" rejections which are achieved by the present canine-like and feline-like antibodies of this invention, it may be possible to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of IL-31-related or OSM-related pathologies in dogs or cats can be provided as a biweekly or monthly dosage of anti-OSMR Beta antibodies of the present invention in the dosage range described above.

Example antibodies for canine or feline therapeutic use are high affinity (these may also be high avidity) antibodies, and fragments, regions and derivatives thereof having potent in vivo anti-OSMR Beta activity, according to the present invention.

Single or multiple administrations of the compositions can be carried out with dose levels and pattern being selected by the treating veterinarian. In any event, the pharmaceutical formulations should provide a quantity of the antibody(ies) of this invention sufficient to effectively treat the subject.

Diagnostic Applications

The present invention also provides the above anti-OSMR Beta antibodies and antigen-binding portions thereof for use in diagnostic methods for detecting OSMR Beta in companion animals known to be or suspected of having an OSM and/or IL-31-mediated condition, such as a pruritic condition, an allergic condition, an inflammatory condition, a fibrotic condition, or pain associated with inflammation.

Anti-OSMR Beta antibodies and/or antigen-binding portions thereof of the present invention are useful for immunoassays which detect or quantitate OSMR Beta, or anti-OSMR Beta antibodies, in a sample. An immunoassay for OSMR Beta typically comprises incubating a clinical or biological sample in the presence of a detectably labeled high affinity (or high avidity) anti-OSMR Beta antibody of the present invention capable of selectively binding to OSMR Beta, and detecting the labeled antibody which is bound in a sample. Various clinical assay procedures are well known in the art. See, e.g., IMMUNOASSAYS FOR THE 80'S (Voller et al., eds., Univ. Park, 1981). Such samples include tissue biopsy, blood, serum, and fecal samples, or liquids collected from animal subjects and subjected to ELISA analysis as described below.

In some embodiments, the binding of antigen to antibody is detected without the use of a solid support. For example, the binding of antigen to antibody can be detected in a liquid format.

In other embodiments, an anti-OSMR Beta antibody can, for example, be fixed to nitrocellulose, or another solid support which is capable of immobilizing cells, cell particles or soluble proteins. The support can then be washed with suitable buffers followed by treatment with the detectably labeled OSMR Beta-specific antibody. The solid phase support can then be washed with the buffer a second time to remove unbound labeled antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to OSMR Beta or an anti-OSMR Beta antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation.

Well known method steps can determine binding activity of a given lot of anti-OSMR Beta antibody. Those skilled in the art can determine operative and optimal assay conditions by routine experimentation.

Detectably labeling an OSMR Beta-specific antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the OSMR Beta-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the OSMR Beta-specific antibodies, it is possible to detect OSMR beta through the use of a radioimmunoassay (RIA). See Work et al., LAB. TECHNIQUES & BIOCHEM. 1N MOLEC. Bio. (No. Holland Pub. Co., NY, 1978). The radioactive isotope can be detected by such means as the use of a gamma counter or a scintillation counter or by autoradiography. Isotopes which are particularly useful for the purpose of the present invention include: $^{3}H$, $^{125}I$, $^{131}I$, $^{35}S$, $^{14}C$, and $^{125}I$. It is also possible to label the OSMR Beta-specific antibodies with a fluorescent compound.

When the fluorescent labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The OSMR Beta-specific antibodies can also be delectably labeled using fluorescence-emitting metals such a $^{125}Eu$, or others of the lanthanide series. These metals can be attached to the OSMR Beta-specific antibody using such metal chelating groups as diethylenetriaminepentaacetic acid (DTPA) or ethylenediamine-tetraacetic acid (EDTA).

The OSMR Beta-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the OSMR Beta-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the OSMR Beta-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

For the purposes of the present invention, the OSMR Beta which is detected by the above assays can be present in a biological sample. Any sample containing OSMR Beta may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of OSMR Beta but also the distribution of OSMR Beta in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid-phase antibody, antigen, and labeled antibody.

The antibodies may be used to quantitatively or qualitatively detect the OSMR Beta in a sample or to detect presence of cells that express the OSMR Beta. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine or feline immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

In one embodiment, the diagnostic method for detecting OSMR Beta is a lateral flow immunoassay test. This is also known as the immunochromatographic assay, Rapid ImmunoMigration (RIM™) or strip test. Lateral flow immunoassays are essentially immunoassays adapted to operate along a single axis to suit the test strip format. A number of variations of the technology have been developed into commercial products, but they all operate according to the same basic principle. A typical test strip consists of the following components: (1) sample pad—an absorbent pad onto which the test sample is applied; (2) conjugate or reagent pad—this contains antibodies specific to the target analyte conjugated to colored particles (usually colloidal gold particles, or latex microspheres); (3) reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and (4) wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones.

There are two main types of lateral flow immunoassay used in microbiological testing: double antibody sandwich assays and competitive assays. In the double antibody sandwich format, the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Competitive assays differ from the double antibody sandwich format in that the conjugate pad contains antibodies that are already bound to the target analyte, or to an analogue of it. If the target analyte is present in the sample it will therefore not bind with the conjugate and will remain unlabeled. As the sample migrates along the membrane and reaches the capture zone an excess of unlabeled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabeled target analyte is not present, a weak line may be produced in the capture zone, indicating an inconclusive result. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed.

Importantly, the antibodies of the present invention may be helpful in diagnosing a pruritic condition, an allergic condition, an inflammatory disorder, a fibrotic disorder, pain associated with inflammation, or combinations thereof in dogs or cats. More specifically, the antibody of the present invention may identify the overexpression of OSMR Beta in companion animals. Thus, the antibody of the present invention may provide an important immunohistochemistry tool. The antibodies of the present invention may be used on antibody arrays, highly suitable for measuring gene expression profiles.

Kits

Also included within the scope of the present invention are kits for practicing the subject methods. The kits at least include one or more of the antibodies of the present invention, a nucleic acid encoding the same, or a cell containing the same. In one embodiment, an antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

In one embodiment, a kit according to the present invention is a test strip kit (lateral flow immunoassay kit) useful for detecting canine or feline OSMR Beta protein in a sample. Such a test strip will typically include a sample pad onto which the test sample is applied; a conjugate or reagent pad containing an antibody specific to canine or feline OSMR Beta, wherein the antibody is conjugated to colored particles (usually colloidal gold particles); a reaction membrane onto which anti-OSMR Beta antibodies are immobilized in a line across the membrane as a capture zone or test line (a control zone may also be present, containing antibodies specific for the conjugate antibodies); and a further absorbent pad designed to draw the sample across the reaction membrane by capillary action and collect it. The test strip kit will generally also include directions for use.

Cell-Based Assays for Assessing Functional Activity of Canine or Feline OSMR Beta Inhibitor Candidates The present invention also provides a cell-based assay for assessing the functional activity of a canine or feline OSMR Beta inhibitor candidate. This method includes: providing cells that endogenously express receptors for and are responsive to canine or feline OSM; incubating canine or feline OSM in the presence of a composition comprising an OSMR Beta inhibitor candidate or a vehicle control; treating the cells with the incubated canine or feline OSM; measuring the direct phosphorylation of a protein induced by the canine or feline OSM treatment; and determining whether the composition comprising the canine or feline OSMR Beta inhibitor candidate inhibited the canine or feline OSM induced direct protein phosphorylation relative to the vehicle control.

In one embodiment, the measuring step comprises measuring direct phosphorylation of a STAT protein. In one specific embodiment, the STAT protein is STAT3.

In another embodiment of the cell-based assay, the cells are monocytes and/or macrophages. For example, in one embodiment, the cells are canine DH82 cells. DH82 cells are a macrophage-monocyte cell line from a dog with malignant histiocytosis.

In one embodiment, the direct protein phosphorylation induced by the canine or feline OSM treatment results in an increase in signal. In another embodiment, the inhibition of the direct protein phosphorylation induced by the canine or feline OSMR Beta inhibitor candidate results in a decrease in signal.

In one embodiment, the canine or feline OSMR Beta inhibitor candidate is a recombinant canine or feline anti-OSMR Beta antibody. In one specific embodiment, the recombinant canine or feline anti-OSMR Beta antibody is contained in a hybridoma culture supernatant. In other embodiments, the canine or feline OSMR Beta inhibitor candidate is a small molecule pharmaceutical compound.

In one embodiment, the canine or feline OSM is co-incubated with the canine or feline OSMR Beta inhibitor candidate prior to treating the cells with the canine or feline OSM. In another embodiment, the cells are preincubated with a gamma interferon prior to the canine or feline OSM treatment for a period of time sufficient to increase OSM Beta receptor expression. In one embodiment, the cells are preincubated with canine gamma interferon. In some embodiments, following the preincubation with canine gamma interferon, the cells are subsequently serum starved prior to the canine or feline OSM treatment.

In some embodiments, a canine or feline OSMR Beta inhibitor candidate that inhibits greater than 50% of the direct protein phosphorylation relative to the vehicle control is selected for further purification and/or characterization. In one embodiment, the method can further include identifying the $IC_{50}$ values of the canine or feline OSMR Beta inhibitor candidate via the cell-based assay for any that candidates that inhibited greater than 50% of the direct protein phosphorylation relative to the vehicle control, for example.

In one embodiment, inhibition of the canine or feline OSM induced direct protein phosphorylation observed in the assay correlates with inhibition of an IL-31-mediated or OSM-mediated condition in dogs or cats. Such disorders include, but are not limited to, the IL-31-mediated or OSM-mediated pruritic, allergic, inflammatory, and fibrotic disorders described herein, as well as OSM-mediated inflammatory pain, such as osteoarthritis pain.

In one specific embodiment, the present invention provides a cell-based assay for assessing the functional activity of a canine or feline IL-31 inhibitor candidate, including: providing canine DH82 cells that endogenously express receptors for and are responsive to canine or feline OSM; incubating canine or feline OSM in the presence of a composition comprising an OSMR Beta inhibitor candidate or a vehicle control; treating the DH82 cells with the incubated canine or feline OSM; measuring a biological activity in the DH82 cells induced by the canine or feline OSM treatment; and determining whether the composition comprising the canine or feline OSMR Beta inhibitor candidate inhibited the canine or feline OSM induced biological activity relative to the vehicle control. This cell-based assay is referred to as the DH82 assay below.

In one embodiment of the DH82 assay, the biological activity is direct phosphorylation of a protein induced by the canine or feline OSM treatment. In one embodiment of the DH82 assay, the protein is a STAT protein, such as STAT3. In another embodiment of the DH82 assay, the direct protein phosphorylation induced by canine or feline OSM treatment results in an increase in signal. In another embodiment of the DH82 assay, the inhibition of the direct protein phosphorylation induced by the canine or feline OSMR Beta inhibitor candidate results in a decrease in signal.

In a further embodiment of the DH82 assay, the canine or feline OSMR Beta inhibitor candidate is a recombinant canine or feline anti-OSMR Beta antibody. Such a recombinant canine or feline anti-OSMR Beta antibody may be contained in a hybridoma culture supernatant, for example. In other embodiments of the DH82 assay, the canine or feline OSMR Beta inhibitor candidate is a small molecule pharmaceutical compound.

In another embodiment of the DH82 assay, the canine or feline OSM is co-incubated with the canine or feline OSMR Beta inhibitor candidate prior to treating the DH82 cells with the canine or feline OSM. In a further embodiment of the DH82 assay, the DH82 cells are preincubated with a gamma interferon, such as, but not limited to, canine gamma interferon prior to the canine or feline OSM treatment for a period of time sufficient to increase OSMR Beta receptor expression. In one embodiment, the DH82 cells are subsequently serum starved prior to the canine or feline OSM treatment.

In one specific embodiment of the DH82 assay, a canine or feline OSMR Beta inhibitor candidate that inhibits greater than 50% of the direct protein phosphorylation relative to the vehicle control is selected for further purification and/or characterization. In one embodiment, for example, the method can include identifying the IC50 values of the canine or feline OSMR Beta inhibitor candidate via the DH82 cell-based assay.

In one embodiment of the DH82 assay, inhibition of the canine or feline OSM induced direct protein phosphorylation observed in the assay correlates with inhibition of an IL-31-mediated or OSM-mediated condition in dogs or cats. Such disorders include, but are not limited to, the IL-31-mediated or OSM-mediated pruritic, allergic, inflammatory, and fibrotic disorders described herein, as well as OSM-mediated inflammatory pain, such as osteoarthritis pain.

The invention will now be described further by the non-limiting examples below.

EXAMPLES

Example 1. Generation of Recombinant Proteins Used for this Work

Recombinant proteins were generated for the purpose of generating antibodies and to assess the affinity and potency of the antibody candidates. By homology to the human homologs, the cytokine binding, Ig-like, and fibronectin III domains were identified for canine and feline OSMR. Synthetic DNA constructs were designed for optimal expression of canine (SEQ ID NO: 107; Canine_OSMR_hlgG1_Fc) the corresponding nucleotide sequence for which is (SEQ ID NO: 108; Canine_OSMR_hlgG1_Fc) and feline (SEQ ID NO: 112; Feline_OSMR_hlgG1_Fc) the corresponding nucleotide sequence for which is (SEQ ID NO: 113; Feline_OSMR_hlgG1_Fc) OSMR proteins as human IgG1 Fc fusions. A synthetic DNA construct was also designed for optimal expression of the feline OSM gene (SEQ ID NO: 110; Feline_OSM_hlgG1_Fc) the corresponding nucleotide sequence for which is (SEQ ID NO: 111; Feline_OSM_hlgG1_Fc). Canine OSM was purchased from Kingfisher Biotech, Inc. (Saint Paul, MN) and the protein sequence is (SEQ ID NO: 109; Canine_OSM). All synthetic cassettes were cloned into pcDNA3.1 using standard molecular biology methods and expressed in one of two mammalian suspension cell systems, Freestyle 293F (Human Embryonic Kidney) cells or EXPICHO-S (Chinese Hamster Ovary) cells.

Suspension cells were maintained in Freestyle 293 expression medium (Gibco) between 0.15 and approximately 2.5x10e6 cells/ml. On transfection day the cells were diluted to 1.0x10e6 cells/ml and transfected with a mixture of plasmid DNA and FectoPRO (Polyplus Transfection) reagent described in the FectoPro Protocol following condition C. Approximately 24 hours later, deviating from the FectoPro protocol, a feed consisting of 20% w/v Tryptone, diluted in Freestyle 293 medium, was added to each culture. Following 7 days of incubation, the cultures were harvested and clarified. For suspension EXPICHO-S, cells were maintained in EXPICHO expression medium (Gibco) between 0.14 and 8.0×10e6 cells/ml. Cells are diluted following the ExpiCHO protocol user manual on Day −1 and transfection day. Diluted cells were transfected as described in the protocol using reagents sourced from ExpiFectamine CHO Transfection Kit (Gibco) following Max Titer conditions. Following 12-14 days of incubation, the cultures were harvested and clarified.

For purification of hexahistidine tagged proteins, conditioned media was adjusted to 500 mM sodium chloride, 5 mM imidazole, and pH 7.4, and loaded onto IMAC resin (either Ni Sepharose Excel (GE Healthcare) or HisPur Cobalt (Thermo Scientific)) which had been pre-equilibrated with buffer A (5 mM imidazole, 20 mM sodium phosphate, 500 mM sodium chloride, pH 7.4). Following load, IMAC resin was washed extensively with Buffer A and then eluted via increasing concentrations of imidazole from 5 to 500 mM, in the same buffer. Fractions were evaluated by SDS-PAGE. Pools were made and dialyzed out of imidazole into the final buffer. Fc fusion proteins and antibodies were purified using Protein A chromatography. Conditioned media was loaded onto MabSelect Sure LX (GE Healthcare) or AmMag Protein A Magnetic beads (Genscript) which had been pre-equilibrated with PBS. Following sample load, the resin was washed with PBS and then with 20 mM sodium acetate, pH 5.5. In the cases where magnetic beads were used, 0.05% tween-20 was added to the equilibration and wash buffers. Using either method, the samples were eluted from the column with 20 mM acetic acid, pH 3.5. Following elution, pools were made and neutralized with the addition of 1 M sodium acetate to 4%. Depending on available volume and intended use, samples were sometimes exchanged into a final buffer (e.g. PBS, other). Final protein concentration was measured by absorbance at 280 nm or by BCA protein assay.

Synthesis and characterization of the canine IL-31 protein (SEQ ID NO: 123; Canine_IL31) the corresponding nucleotide sequence for which is (SEQ ID NO: 124; Canine_IL31) was described previously (U.S. Pat. No. 8,790,651 to Bammert, et al). Synthesis and characterization of the feline IL-31 protein (SEQ ID NO: 125; Feline_IL31) the corresponding nucleotide sequence for which is (SEQ ID NO: 126; Feline_IL31) was described previously (US Patent Application No. 20190284272 to Bammert, et al).

Example 2. Identification of Mouse Monoclonal Antibodies Recognizing Canine and/or Feline OSMR A mixture of recombinant canine and feline OSMR proteins represented by (SEQ ID NO: 107; Canine_OSMR_hlgG1_Fc), the corresponding nucleotide sequence for which is (SEQ ID NO: 108; Canine_OSMR_hlgG1_Fc) and (SEQ ID NO: 112; Feline_OSMR_hlgG1_Fc), the corresponding nucleotide sequence for which is (SEQ ID NO: 113; Feline_OSMR_hlgG1_Fc) respectively, were used to immunize female AJ and CD1 mice for the purpose of generating monoclonal antibodies. Mice were immunized using a 28 Day Rapid Immunization Protocol (RIMMS) which includes a series of low-dosage immunizations administered over a two-week period. Serum antibody titers from immunized mice were determined using an enzyme linked immunosorbent assay (ELISA). Canine or feline OSMR (50 ng/well) was immobilized to polystyrene mi-croplates and used as a capture antigen. A separate ELISA was performed to determine the antibody response to an unrelated human IgG Fc fusion protein. Prior to assay, each plate was blocked using casein and serum from immunized mice was diluted in phosphate buffered saline with 0.05% tween-20 (PBST). The presence of anti-OSMR (or anti human IgG Fc) antibodies was detected with an anti-mouse HRP labeled secondary antibody. Following addition of a chromogenic substrate (SureBlue Reserve TMB 1-Component Microwell Peroxidase Substrate, KPL, Inc., Gaithersburg, MD) and after a 10-minute incubation at room temperature (RT) the reaction was stopped with the addition of 100 μL of 0.1 N HCl. The absorbance of each well was determined at an optical density (OD) of 450 nm.

Test bleeds were taken on Day 20 and antisera samples were assessed to determine whether a fusion-ready titer, as defined by an OD>0.1 above background at 1:31K serum dilution, has been reached. In addition, a human IgG absorption assay was utilized to evaluate anti-OSMR specificity. Serum samples were spiked with pooled/purified human IgG prior to application on the ELISA plate. Antibodies that recognize the "irrelevant" human IgG Fc component of the fusion proteins were absorbed from the system; antibodies that are OSMR-specific bound OSMR on the ELISA plate. Post-absorption anti-OSMR signal was indicative of target-specific responses. A single responsive CD-1 mouse was selected having a high specific titer to both canine and feline OSMR following absorption of the anti-human IgGs. This mouse received a pre-fusion boost and donor splenocytes were used for fusion on day 28.

Hybridoma supernatants were screened for antibodies that bind to canine and/or feline OSMR proteins but do not bind to the irrelevant human IgG Fc by ELISA. Candidate mouse anti OSMR hybridomas that selectively bound canine and/or feline OSMR were further subcloned to generate a hybridomas producing homogeneous antibody and for sequencing of the variable heavy and light chains. Cells producing antibodies with these desired properties were chosen for sequence analysis of RNA transcripts of the variable heavy (VH) and variable light (VL) IgG chains.

Example 3. Method to Determine Affinity of Anti-OSMR Antibodies for OSMR Using Surface Plasmon Resonance The affinity with which candidate mAbs bind canine, feline, and human (SEQ ID NO: 122; Human_OSMR) (R&D Systems, Minneapolis, MN) OSMR was determined using surface plasmon resonance (SPR) on a Biacore system (Biacore Life Sciences (GE Healthcare), Uppsala, Sweden). To avoid affinity differences associated with differential surface preparation that can occur when immobilizing antibodies to surfaces; OSMR from each species was directly conjugated to individual surfaces. Immobilization was obtained by amine coupling 5 μg/mL OSMR using N-hydroxysuccinimide (NHS)/1-Ethyl-3-(3-dimethylaminopropyl) carbodiimide (EDC) chemistry. Chips were quenched with ethanolamine and the affinity with which all candidate mAbs bound to the immobilized OSMR was evaluated. All curves were fit to a 1:1 model. Affinity constants (KD) less than $1\times10^{-11}$ M (1E-11 M) are below the lower limit of quantitation of detection for the instrument. Results for affinity measurements are described herein.

Example 4. Method to Determine Potency of Anti-OSMR Antibodies Assessed by Inhibition of Canine and Feline IL-31 Induced PSTAT3 Signaling in Canine and Feline Macrophage Cells To identify candidates with inhibitory activity, antibodies were assessed for their ability to affect IL-31-mediated STAT3 phosphorylation in either a canine or feline cell-based assay. STAT3 phosphorylation was determined in canine DH-82 (ATCC® CRL-10389™) or feline Fcwf-4 macrophage-like cells (ATCC CRL-2787). DH82 and Fcwf-4 cells were primed with canine interferon gamma (R&D Systems, Minneapolis, MN) at 10 ng/mL for 24 hours or feline interferon gamma (R&D Systems, Minneapolis, MN) at 125 ng/mL for 96 hours, respectively, to increase receptor expression. Both cell types were serum starved for 2 hours prior to IL-31 and mAb treatment. Using two independent methods, all candidate mAbs were evaluated for their ability to inhibit either 1 μg/mL canine or 42 ng/mL feline IL-31 induced STAT3 phosphorylation. Assays were also run to demonstrate cross-reactivity of canine and feline cytokines and cross-functionality of the antibodies ability to inhibit signaling in both species. To ensure complex formation, a one-hour co-incubation of mAb and IL-31 cytokine prior to cell stimulation was completed. IL-31 cell stimulation was carried out for five minutes. STAT3 phosphorylation was measured using AlphaLISA SureFire ULTRA™ technology (Perkin Elmer, Waltham, MA). In the case where antibody concentration and purity are unknown, hybridoma supernatants were qualitatively measured for their ability to inhibit STAT3 phosphorylation following a one-hour co-incubation with 1 μg/ml canine or 42 ng/ml feline IL-31. The potency of individual monoclonal antibodies defined by their ability to inhibit IL-31 mediated STAT3 phosphorylation in these assays was considered the key selection criteria for further advancement of select antibodies. The term potency refers to the $IC_{50}$ value calculated from these assays and is the concentration of the antibody where signaling induced by IL-31 is reduced to one half its maximal value. Increased potency described herein correlates to a lower $IC_{50}$ value.

Figure 1B:
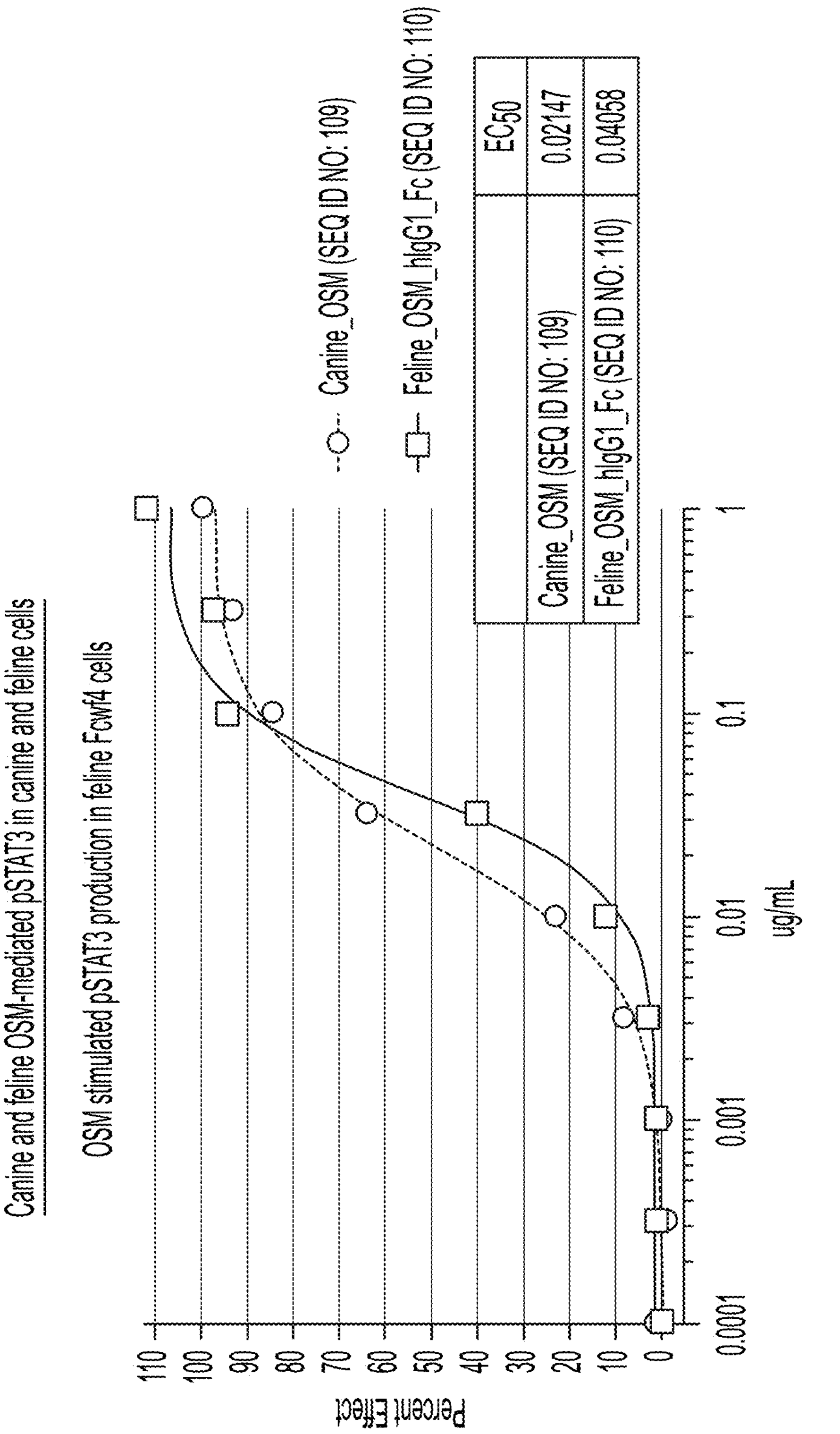

Example 5. Method to Determine Potency of Anti-OSMR Antibodies Assessed by Inhibition of Canine and Feline OSM Induced pSTAT3 Signaling in Canine and Feline Macrophage Cells To identify candidates with inhibitory activity, antibodies were assessed for their ability to affect OSM-mediated STAT3 phosphorylation in either a canine or feline cell-based assay. STAT3 phosphorylation was determined in canine DH-82 (ATCC CRL-10389™) or feline Fcwf-4 macrophage-like cells (ATCC CRL-2787). To assess the dynamic range of these assays, a dose response curve using canine and feline OSM was assessed in both cell types. Cells were serum starved for 2 hours followed by treatment for 10 minutes with a nine point, half log curve from 1 μg/mL to 0.0001 μg/mL canine or feline OSM to induced STAT3 phosphorylation. Reactions were quenched with lysis buffer and STAT3 phosphorylation was measured using AlphaLISA SureFire ULTRA™ technology (Perkin Elmer, Waltham, MA). $EC_{50}$ values were determined as the concentration of OSM protein which induces a 50 percent maximal signal. FIGS. 1A and 1B show the dose-response curves and $EC_{50}$ values for canine and feline OSM in canine DH-82 and feline Fcwf-4 cells respectively.

To determine the potency of candidate antibodies by assaying their ability to inhibit OSM-mediated STAT3 phosphorylation, both canine and feline assays were performed. Cells were serum starved for 2 hours prior to OSM and mAb treatment. Using two independent methods, all candidate mAbs were evaluated for their ability to inhibit 0.02 μg/mL canine OSM induced STAT3 phosphorylation. Assays were conducted allowing 30-minute incubation for DH-82 or 20-minute incubation for Fcwf-4 cells of the anti-OSMR mAb with the serum starved cells. At this time the supernatant was removed and media containing 0.02 μg/mL canine OSM added for cell stimulation for ten minutes. The reaction was quenched with lysis buffer and STAT3 phosphorylation was measured. In the case where antibody concentration and purity are unknown, hybridoma supernatants were qualitatively measured for their ability to inhibit STAT3 phosphorylation following a 30 minute or 20-minute incubation on cells as above, followed by a 0.02 μg/mL stimulation with canine OSM. The potency of individual monoclonal antibodies defined by their ability to inhibit OSM mediated STAT3 phosphorylation in these assays was considered the key selection criteria for further advancement of select antibodies. The term potency refers to the $IC_{50}$ value calculated from these assays and is the concentration of the antibody where signaling induced by OSM is reduced to one half its maximal value. Increased potency described herein correlates to a lower $IC_{50}$ value.

Figure 2:
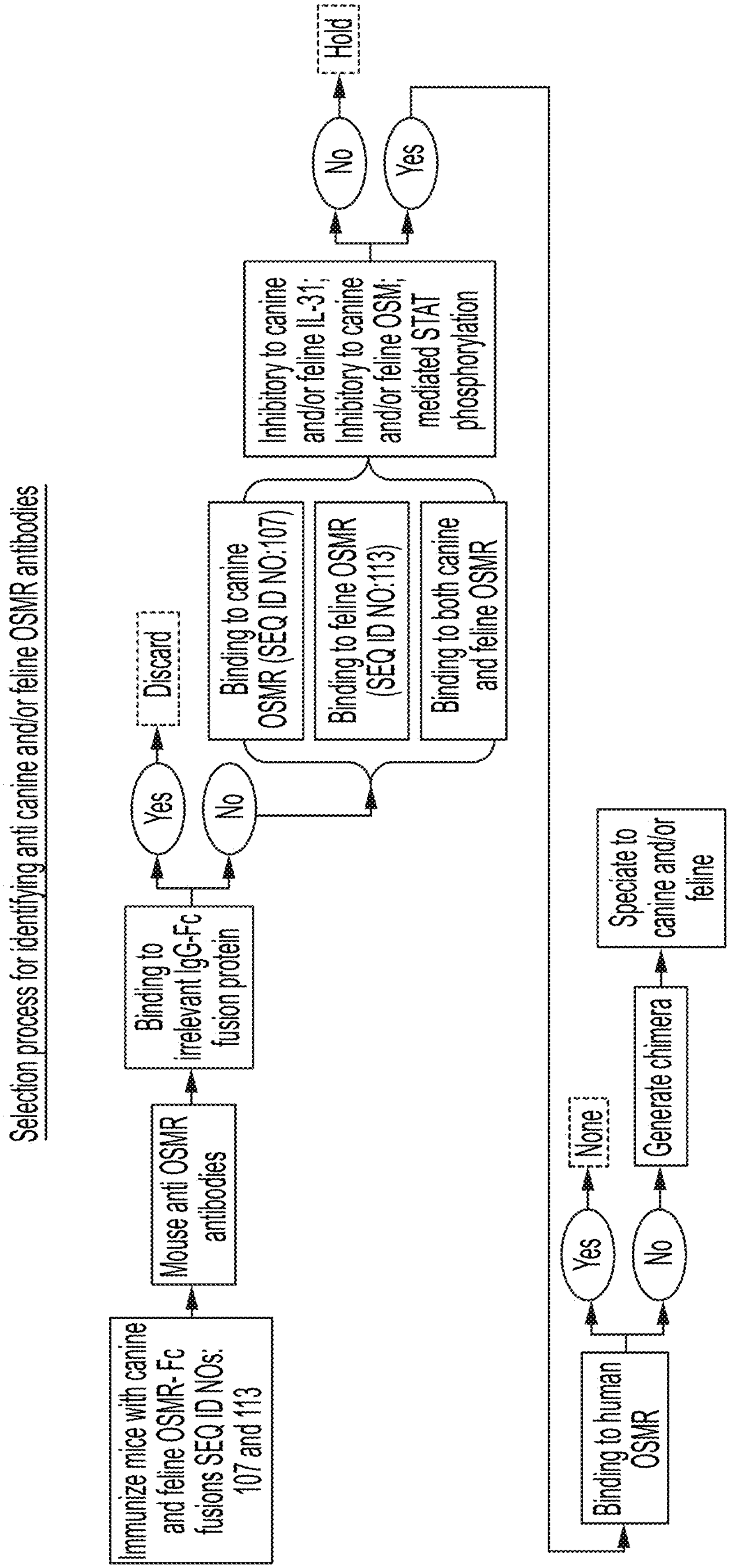
FIG. 2 is a flow chart showing the steps used to select the anti-OSMR antibodies described in this application.

Example 6. Selection of Anti-OSMR Monoclonal Antibodies Capable of Neutralizing IL-31 and OSM Mediated STAT Phosphorylation in Canine and Feline Cells Mouse anti-OSMR antibodies were selected based on the criteria outline in FIG. 2. Mice were immunized with a combination of canine and feline OSMR proteins which contain the three cytokine binding domains and a single fibronectin III domain fused to a human IgG1 Fc to facilitate expression and purification. Antibodies produced from the hybridomas were screened for binding by ELISA to canine and feline OSMR and counter screened against an unrelated human IgG. Hybridomas producing antibodies which bound to canine and/or feline OSMR and did not bind to human IgG were selected for further analysis. Exhausted hybridoma supernatants were generated from these initial hits and antibody was purified for further analysis. Antibodies from these non-clonal hybridomas were initially assayed for binding to canine and feline OSMR using Biacore to confirm results from the ELISA screen. These hybridoma candidates were further tested for their ability to inhibit IL-31 and OSM mediated STAT phosphorylation in canine DH82 and feline Fcwf-4 cells. Hybridoma candidates that bound to canine and/or feline OSMR and had some inhibitory activity in one of the IL-31 and OSM cell based assayed were selected for subcloning. Subcloning of hybridoma candidates was performed by limiting dilution of cells and monoclonality was confirmed. Supernatants these cells producing monoclonal antibodies were confirmed for binding to canine and/or feline OSMR protein by ELISA and cells producing these antibodies were used to isolated RNA for sequence analysis of the variable heavy and variable light IgG chains. Purified monoclonal antibodies from these cultures were also tested for binding to human OSMR. None of the antibody candidates described herein bound to human OSMR.

This hybridoma campaign initially produced five monoclonal antibodies with unique variable heavy and variable light combinations. These mouse anti-OSMR antibodies are 02D09 with the variable heavy chain sequence (SEQ ID NO: 31; MU_02D09_VH) the corresponding nucleotide sequence for which is (SEQ ID NO: 32; MU_02D09_VH) and a variable light chain sequence (SEQ ID NO: 33; MU_02D09_VL) the corresponding nucleotide sequence for which is (SEQ ID NO: 34; MU_02D09_VL); 09E09 with the variable heavy chain sequence (SEQ ID NO: 35; MU_09E09_VH) the corresponding nucleotide sequence for which is (SEQ ID NO: 36; MU_09E09_VH) and a variable light chain sequence (SEQ ID NO: 37; MU_09E09_VL) the corresponding nucleotide sequence for which is (SEQ ID NO: 38; MU_09E09_VL); 10F07 with the variable heavy chain sequence (SEQ ID NO: 39; MU_10F07_VH) the corresponding nucleotide sequence for which is (SEQ ID NO: 40; MU_10F07_VH) and a variable light chain sequence (SEQ ID NO: 41; MU_10F07_VL) the corresponding nucleotide sequence for which is (SEQ ID NO: 42; MU_10F07_VL); 14C04 with the variable heavy chain sequence (SEQ ID NO: 43; MU_14C04_VH) the corresponding nucleotide sequence for which is (SEQ ID NO: 44; MU_14C04_VH) and a variable light chain sequence (SEQ ID NO: 45; MU_14C04_VL) the corresponding nucleotide sequence for which is (SEQ ID NO: 46; MU_14C04_VL); and 19F07 with the variable heavy chain sequence (SEQ ID NO: 47; MU_19F07_VH) the corresponding nucleotide sequence for which is (SEQ ID NO: 48; MU_19F07_VH) and a variable light chain sequence (SEQ ID NO: 49; MU_19F07_VL) the corresponding nucleotide sequence for which is (SEQ ID NO: 50; MU_19F07_VL). FIG. 3 shows the clustalW alignment of these variable heavy and light chains with the CDRs highlighted in black boxes.

TABLE 1

Affinity (KD) of mouse anti-OSMR antibodies to the human, canine, and feline OSMR proteins using Biacore.

| | | KD (M) | | |
|---|---|---|---|---|
| Antibody ID | Type | Human OSMR (SEQ ID NO: 122) | Canine OSMR (SEQ ID NO: 107) | Feline OSMR (SEQ ID NO: 112) |
| Mu_02D09 | Mouse | no binding | no binding | 8.96E−09 |
| Mu_09E09 | Mouse | no binding | 7.87E−09 | 3.75E−09 |
| Mu_10F07 | Mouse | no binding | 2.03E−09 | 1.59E−09 |
| Mu_14C04 | Mouse | no binding | 1.42E−08 | no binding |
| Mu_19F07 | Mouse | no binding | 9.51E−10 | 2.07E−11 |

TABLE 2

Inhibition of IL-31 and OSM mediated pSTAT3 signaling in canine DH82 and feline Fcwf-4 cells with anti-canine and/or anti-feline OSMR antibodies.

| | | Inhibition of IL-31 and OSM pSTAT3 Signaling | | | |
|---|---|---|---|---|---|
| | | Cell type used: | | | |
| | | Canine DH82 | Feline IL-31 Fcwf-4 | Canine DH82 | |
| | | Cytokine used: | | | |
| Antibody ID | Antibody type | Canine IL-31 (SEQ ID NO: 123) % inh | Feline IL-31 (SEQ ID NO: 125) % inh | Canine OSM (SEQ ID NO: 109) $IC_{50}$ (μg/ml) | Feline OSM (SEQ ID NO: 110) % inh |
| Mu_02D09 | Mouse | 0 | 67 | >50 | nt |
| Mu_09E09 | Mouse | 80 | 63 | >50, 14 | nt |
| Mu_10F07 | Mouse | 93 | 91 | 0.04 | nt |
| Mu_14C04 | Mouse | 72 | 0 | 0.73 | nt |
| Mu_19F07 | Mouse | 87 | 90 | 0.27 | nt |

nt = not tested

Example 7. Generation of Chimeric Antibodies

Antibody variable domains are responsible for antigen binding. Grafting of the full variable domain onto respective constant region is expected to have little or no impact on the antibody's ability to bind the OSMR immunogen. To simultaneously confirm that the correct sequence of the heavy and light chain variable regions was identified and to produce homogenous material, expression vectors were designed to produce recombinant chimeric antibodies in mammalian expression systems. Chimeric antibodies described here consist of the variable sequence (both CDR and framework) from the host species antibody grafted onto the respective heavy and light constant regions of a canine or feline IgG molecule (for example; mouse variable: canine constant is referred to as mouse: canine chimera). Synthetic DNA sequences were constructed for the variable heavy (VH) and variable light (VL) sequences of selected antibodies.

For mouse: canine chimeras, each mouse variable region was cloned into a mammalian expression plasmid containing either the canine IgG heavy (SEQ ID NO: 114;

Canine_HC_65_1) the corresponding nucleotide sequence for which is (SEQ ID NO: 115; Canine_HC_65_1) or light chain (SEQ ID NO: 116; Canine_LC_Kappa) the corresponding nucleotide sequence for which is (SEQ ID NO: 117; Canine_LC_Kappa) constant regions. For mouse: feline chimeras, each respective variable region was cloned into a mammalian expression plasmid containing either the feline IgG heavy (SEQ ID NO: 118; Feline_HC_AlleleA_1) the corresponding nucleotide sequence for which is (SEQ ID NO: 119; Feline_HC_AlleleA_1) or light chain (SEQ ID NO: 120; Feline_LC_Kappa_G_minus) the corresponding nucleotide sequence for which is (SEQ ID NO: 121; Feline_LC_Kappa_G_minus) constant regions. These antibodies are mouse: canine 02D09 chimera with the variable heavy chain sequence (SEQ ID NO: 31; MU_02D09_VH) the corresponding nucleotide sequence for which is (SEQ ID NO: 32; MU_02D09_VH) and a variable light chain sequence (SEQ ID NO: 33; MU_02D09_VL) the corresponding nucleotide sequence for which is (SEQ ID NO: 34; MU_02D09_VL); mouse: canine 09E09 chimera with the variable heavy chain sequence (SEQ ID NO: 35; MU_09E09_VH) the corresponding nucleotide sequence for which is (SEQ ID NO: 36; MU_09E09_VH) and a variable light chain sequence (SEQ ID NO: 37; MU_09E09_VL) the corresponding nucleotide sequence for which is (SEQ ID NO: 38; MU_09E09_VL); mouse: canine 10F07 chimera with the variable heavy chain sequence (SEQ ID NO: 39; MU_10F07_VH) the corresponding nucleotide sequence for which is (SEQ ID NO: 40; MU_10F07_VH) and a variable light chain sequence (SEQ ID NO: 41; MU_10F07_VL) the corresponding nucleotide sequence for which is (SEQ ID NO: 42; MU_10F07_VL); mouse: canine 14C04 chimera with the variable heavy chain sequence (SEQ ID NO: 43; MU_14C04_VH) the corresponding nucleotide sequence for which is (SEQ ID NO: 44; MU_14C04_VH) and a variable light chain sequence (SEQ ID NO: 45; MU_10F07_VL) the corresponding nucleotide sequence for which is (SEQ ID NO: 46; MU_10F07_VL); mouse: canine 19F07 chimera with the variable heavy chain sequence (SEQ ID NO: 47; MU_19F07_VH) the corresponding nucleotide sequence for which is (SEQ ID NO: 48; MU_19F07_VH) and a variable light chain sequence (SEQ ID NO: 49; MU_19F07_VL) the corresponding nucleotide sequence for which is (SEQ ID NO: 50; MU_19F07_VL); mouse: feline 02D09 chimera with the variable heavy chain sequence (SEQ ID NO: 31; MU_02D09_VH) the corresponding nucleotide sequence for which is (SEQ ID NO: 32; MU_02D09_VH) and a variable light chain sequence (SEQ ID NO: 33; MU_02D09_VL) the corresponding nucleotide sequence for which is (SEQ ID NO: 34; MU_02D09_VL); mouse: feline 09E09 chimera with the variable heavy chain sequence (SEQ ID NO: 35; MU_09E09_VH) the corresponding nucleotide sequence for which is (SEQ ID NO: 36; MU_09E09_VH) and a variable light chain sequence (SEQ ID NO: 37; MU_09E09_VL) the corresponding nucleotide sequence for which is (SEQ ID NO: 38; MU_09E09_VL); mouse: feline 10F07 chimera with the variable heavy chain sequence (SEQ ID NO: 39; MU_10F07_VH) the corresponding nucleotide sequence for which is (SEQ ID NO: 40; MU_10F07_VH) and a variable light chain sequence (SEQ ID NO: 41; MU_10F07_VL) the corresponding nucleotide sequence for which is (SEQ ID NO: 42; MU_10F07_VL); mouse: feline 14C04 chimera with the variable heavy chain sequence (SEQ ID NO: 43; MU_14C04_VH) the corresponding nucleotide sequence for which is (SEQ ID NO: 44; MU_14C04_VH) and a variable light chain sequence (SEQ ID NO: 45; MU_14C04_VL) the corresponding nucleotide sequence for which is (SEQ ID NO: 46; MU_14C04_VL); and mouse: feline 19F07 chimera with the variable heavy chain sequence (SEQ ID NO: 47; MU_19F07_VH) the corresponding nucleotide sequence for which is (SEQ ID NO: 48; MU_19F07_VH) and a variable light chain sequence (SEQ ID NO: 49; MU_19F07_VL) the corresponding nucleotide sequence for which is (SEQ ID NO: 50; MU_19F07_VL)_These sequences contain unique restriction endonuclease sites, a Kozak consensus sequence and, an N-terminal secretion leader to facilitate expression and secretion of the chimeric recombinant antibody from a mammalian cell line. The plasmids encoding each heavy and light chain, under the control of the CMV promoter, were co-transfected into host cells and purified as described herein.

TABLE 3

Affinity (KD) of mouse: canine anti-OSMR chimeric antibodies to the human, canine, and feline OSMR proteins using Biacore.

| | | KD (M) | | | | | | | | |
|---|---|---|---|---|---|---|---|---|---|---|
| | | Human OSMR (SEQ ID NO: 122) | | | Canine OSMR (SEQ ID NO: 107) | | | Feline OSMR (SEQ ID NO: 112) | | |
| Antibody ID | Chimera type | ka ($M^{-1}$ $s^{-1}$) | kd ($s^{-1}$) | KD (M) | ka ($M^{-1}$ $s^{-1}$) | kd ($s^{-1}$) | KD (M) | ka ($M^{-1}$ $s^{-1}$) | kd ($s^{-1}$) | KD (M) |
| 02D09 * | Mouse:Canine | | no binding | | 2.56E+05 | 3.28E−03 | 1.28E−08 | 1.42E+05 | 9.42E−04 | 6.65E−09 |
| 09E09 | Mouse:Canine | | no binding | | 1.96E+05 | 1.04E−03 | 5.29E−09 | 2.94E+05 | 6.97E−04 | 2.37E−09 |
| 10F07 | Mouse:Canine | | no binding | | 1.61E+05 | 2.22E−04 | 1.38E−09 | 2.00E+04 | 4.40E−07 | 2.20E−11 |
| 14C04 | Mouse:Canine | | nt | | | nt | | | nt | |
| 19F07 | Mouse:Canine | | no binding | | 1.90E+03 | 8.40E−04 | 4.42E−07 | 4.51E+04 | 2.00E−03 | 4.45E−08 |

nt = not tested

* chimeric 02D09 showed weak binding to canine OSMR with fast off rate

TABLE 4

Inhibition of IL-31 and OSM mediated pSTAT3 signaling in canine DH82 and feline Fcwf-4 cells with anti-canine and/or anti-feline mouse: canine anti-OSMR chimeric antibodies.

| | | Inhibition of IL-31 and OSM pSTAT3 Signaling | | | |
|---|---|---|---|---|---|
| | | Cell type used: | | | |
| | | Canine DH82 | Feline IL-31 Fcwf-4 | Canine DH82 | Feline IL-31 Fcwf-4 |
| | | Cytokine used: | | | |
| Antibody ID | Chimera type | Canine IL-31 (SEQ ID NO: 123) $IC_{50}$ (μg/ml) | Feline IL-31 (SEQ ID NO: 125) $IC_{50}$ (μg/ml) | Canine OSM (SEQ ID NO: 109) $IC_{50}$ (μg/ml) | Canine OSM (SEQ ID NO: 109) $IC_{50}$ (μg/ml) |
| 02D09 | Mouse:Canine | 97.70 | IC | IC | IC |
| 09E09 | Mouse:Canine | 47.52 | IC | IC | IC |
| 10F07 | Mouse:Canine | 0.03 | 0.05 | 0.20 | 0.28 |
| 14C04 | Mouse:Canine | nt | nt | nt | nt |
| 19F07 | Mouse:Canine | nt | nt | nt | nt |

IC = incomplete curve
nt = not tested

Example 8. Design and Expression of Speciated Anti OSMR Antibodies

The generation of anti-drug antibodies (ADAs) can been associated with loss of efficacy for any biotherapeutic protein including monoclonal antibodies. Comprehensive evaluation of the literature has shown that speciation of monoclonal antibodies can reduce the propensity for mAbs to be immunogenic although examples of immunogenic fully human mAbs and non-immunogenic chimeric mAbs can be found. We describe herein two methods of speciation; caninization meaning grafting of mouse CDRs onto frameworks of a *Canis* species (example, *Canis lupus* familiaris or dog) and felinization meaning grafting of mouse CDRs onto frameworks of a *Felis* species (example, *Felis catus* or cat). To help mitigate risks associated with ADA formation for the anti-OSMR monoclonal antibodies provided herein, a caninization and felinization strategy was employed. The caninization and felinization strategy was based on identifying the most appropriate canine or feline germline antibody sequence for CDR grafting. Following extensive analysis of all available germline sequences for both the variable heavy and light chain, germline candidates were selected based on their homology to the mouse anti-OSMR mAbs, and the CDRs from these mouse progenitor mAbs were used to replace native canine or feline CDRs. The objective was to retain high affinity and cell-based activity using canine or feline antibody frameworks to minimize the potential of immunogenicity in vivo.

Caninized and felinized mAbs are expressed and characterized for their affinity to canine and feline OSMR and their potency in cell-based assays. In the event that a caninized or felinized antibody loses its ability to bind canine or feline OSMR, a systematic dissection is undertaken to identify; 1) the chain responsible for the loss of function, 2) the framework responsible for the loss of function and 3) the amino acid(s) responsible for the loss function. Speciated antibodies described here consist of the variable sequence (both CDR and framework) expressed with the respective heavy and light constant regions of a canine or feline IgG molecule. Synthetic DNA sequences are constructed for the variable heavy (VH) and variable light (VL) sequences of selected antibodies. These sequences contain unique restriction endonuclease sites, a Kozak consensus sequence and, an N-terminal secretion leader to facilitate expression and secretion of the recombinant antibody from a mammalian cell line. For caninized antibodies, each caninized variable region are cloned into a mammalian expression plasmid containing either the canine IgG heavy (SEQ ID NO: 114; Canine_HC_65_1) the corresponding nucleotide sequence for which is (SEQ ID NO: 115; Canine_HC_65_1) or light chain (SEQ ID NO: 116; Canine_LC_Kappa) the corresponding nucleotide sequence for which is (SEQ ID NO: 117; Canine_LC_Kappa) constant regions. For felinized antibodies, each respective variable region are cloned into a mammalian expression plasmid containing either the feline IgG heavy (SEQ ID NO: 118; Feline_HC_AlleleA_1) the corresponding nucleotide sequence for which is (SEQ ID NO: 119; Feline_HC_AlleleA_1) or light chain (SEQ ID NO: 120; Feline_LC_Kappa_G_minus) the corresponding nucleotide sequence for which is (SEQ ID NO: 121; Feline_LC_Kappa_G_minus) constant regions. The plasmids encoding each heavy and light chain, under the control of the CMV promoter, are co-transfected into host cells, expressed, and purified as described herein.

Feline 02D09 1.1 is the variable heavy chain sequence (SEQ ID NO: 51; FEL_02D09_VH1) the corresponding nucleotide sequence for which is (SEQ ID NO: 52; FEL_02D09_VH1) and a variable light chain sequence (SEQ ID NO: 55; FEL_02D09_VL1) the corresponding nucleotide sequence for which is (SEQ ID NO: 56; FEL_02D09_VL1); Feline 02D09 2.1 is the variable heavy chain sequence (SEQ ID NO: 53; FEL_02D09_VH2) the corresponding nucleotide sequence for which is (SEQ ID NO: 54; FEL_02D09_VH2) and a variable light chain sequence (SEQ ID NO: 55; FEL_02D09_VL1) the corresponding nucleotide sequence for which is (SEQ ID NO: 56; FEL_02D09_VL1); Feline 02D09 1.2 is the variable heavy chain sequence (SEQ ID NO: 51; FEL_02D09_VH1) the corresponding nucleotide sequence for which is (SEQ ID NO: 52; FEL_02D09_VH1) and a variable light chain sequence (SEQ ID NO: 57; FEL_02D09_VL2) the corresponding nucleotide sequence for which is (SEQ ID NO: 58; FEL_02D09_VL2); Feline 02D09 2.2 is the variable heavy chain sequence (SEQ ID NO: 53; FEL_02D09_VH2) the corresponding nucleotide sequence for which is (SEQ ID NO: 54; FEL_02D09_VH2) and a variable light chain sequence (SEQ ID NO: 57; FEL_02D09_VL2) the corresponding nucleotide sequence for which is (SEQ ID NO: 58; FEL_02D09_VL2).

Canine 09E09 1.1 is the variable heavy chain sequence (SEQ ID NO: 59; CAN_09E09_VH1) the corresponding nucleotide sequence for which is (SEQ ID NO: 60; CAN_09E09_VH1) and a variable light chain sequence (SEQ ID NO: 63; CAN_09E09_VL1) the corresponding nucleotide sequence for which is (SEQ ID NO: 64; CAN_09E09_VL1); Canine 09E09 2.1 is the variable heavy chain sequence (SEQ ID NO: 61; CAN_09E09_VH2) the corresponding nucleotide sequence for which is (SEQ ID NO: 62; CAN_09E09_VH2) and a variable light chain sequence (SEQ ID NO: 63; CAN_09E09_VL1) the corresponding nucleotide sequence for which is (SEQ ID NO: 64; CAN_09E09_VL1); Canine 09E09 1.2 is the variable heavy chain sequence (SEQ ID NO: 59; CAN_09E09_VH1) the corresponding nucleotide sequence for which is (SEQ ID NO: 60; CAN_09E09_VH1) and a variable light chain sequence (SEQ ID NO: 65; CAN_09E09_VL2) the corresponding nucleotide sequence for which is (SEQ ID NO: 66; CAN_09E09_VL2); Canine 09E09 2.2 is the variable heavy chain sequence (SEQ ID NO: 61; CAN_09E09_VH2) the corresponding nucleotide sequence for which is (SEQ ID NO: 62; CAN_09E09_VH2) and a variable light chain sequence (SEQ ID NO: 65; CAN_09E09_VL2) the corresponding nucleotide sequence for which is (SEQ ID NO: 66; CAN_09E09_VL2). Feline 09E09 1.1 is the variable heavy chain sequence (SEQ ID NO: 67; FEL_09E09_VH1) the corresponding nucleotide sequence for which is (SEQ ID NO: 68; FEL_09E09_VH1) and a variable light chain sequence (SEQ ID NO: 71; FEL_09E09_VL1) the corresponding nucleotide sequence for which is (SEQ ID NO: 72; FEL_09E09_VL1); Feline 09E09 2.1 is the variable heavy chain sequence (SEQ ID NO: 69; FEL_09E09_VH2) the corresponding nucleotide sequence for which is (SEQ ID NO: 70; FEL_09E09_VH2) and a variable light chain sequence (SEQ ID NO: 71; FEL_09E09_VL1) the corresponding nucleotide sequence for which is (SEQ ID NO: 72; FEL_09E09_VL1); Feline 09E09 1.2 is the variable heavy chain sequence (SEQ ID NO: 67; FEL_09E09_VH1) the corresponding nucleotide sequence for which is (SEQ ID NO: 68; FEL_09E09_VH1) and a variable light chain sequence (SEQ ID NO: 73; FEL_09E09_VL2) the corresponding nucleotide sequence for which is (SEQ ID NO: 74; FEL_09E09_VL2); Feline 09E09 2.2 is the variable heavy chain sequence (SEQ ID NO: 69; FEL_09E09_VH2) the corresponding nucleotide sequence for which is (SEQ ID NO: 70; FEL_09E09_VH2) and a variable light chain sequence (SEQ ID NO: 73; FEL_09E09_VL2) the corresponding nucleotide sequence for which is (SEQ ID NO: 74; FEL_09E09_VL2).

Canine 10F07 1.1 is the variable heavy chain sequence (SEQ ID NO: 75; CAN_10F07_VH1) the corresponding nucleotide sequence for which is (SEQ ID NO: 76; CAN_10F07_VH1) and a variable light chain sequence (SEQ ID NO: 77; CAN_10F07_VL1) the corresponding nucleotide sequence for which is (SEQ ID NO: 78; CAN_10F07_VL1); Canine 10F07 2.1 is the variable heavy chain sequence (SEQ ID NO: 79; CAN_10F07_VH2) the corresponding nucleotide sequence for which is (SEQ ID NO: 80; CAN_10F07_VH2) and a variable light chain sequence (SEQ ID NO: 77; CAN_10F07_VL1) the corresponding nucleotide sequence for which is (SEQ ID NO: 78; CAN_10F07_VL1); Canine 10F07 1.2 is the variable heavy chain sequence (SEQ ID NO: 75; CAN_10F07_VH1) the corresponding nucleotide sequence for which is (SEQ ID NO: 76; CAN_10F07_VH1) and a variable light chain sequence (SEQ ID NO: 81; CAN_10F07_VL2) the corresponding nucleotide sequence for which is (SEQ ID NO: 82; CAN_10F07_VL2); Canine 10F07 2.2 is the variable heavy chain sequence (SEQ ID NO: 79; CAN_10F07_VH2) the corresponding nucleotide sequence for which is (SEQ ID NO: 80; CAN_10F07_VH2) and a variable light chain sequence (SEQ ID NO: 81; CAN_10F07_VL2) the corresponding nucleotide sequence for which is (SEQ ID NO: 82; CAN_10F07_VL2). Feline 10F07 1.1 is the variable heavy chain sequence (SEQ ID NO: 83; FEL_10F07_VH1) the corresponding nucleotide sequence for which is (SEQ ID NO: 84; FEL_10F07_VH1) and a variable light chain sequence (SEQ ID NO: 85; FEL_10F07_VL1) the corresponding nucleotide sequence for which is (SEQ ID NO: 86; FEL_10F07_VL1); Feline 10F07 2.1 is the variable heavy chain sequence (SEQ ID NO: 87; FEL_10F07_VH2) the corresponding nucleotide sequence for which is (SEQ ID NO: 88; FEL_10F07_VH2) and a variable light chain sequence (SEQ ID NO: 85; FEL_10F07_VL1) the corresponding nucleotide sequence for which is (SEQ ID NO: 86; FEL_10F07_VL1); Feline 10F07 1.2 is the variable heavy chain sequence (SEQ ID NO: 83; FEL_10F07_VH1) the corresponding nucleotide sequence for which is (SEQ ID NO: 84; FEL_10F07_VH1) and a variable light chain sequence (SEQ ID NO: 89; FEL_10F07_VL2) the corresponding nucleotide sequence for which is (SEQ ID NO: 90; FEL_10F07_VL2); Feline 10F07 2.2 is the variable heavy chain sequence (SEQ ID NO: 87; FEL_10F07_VH2) the corresponding nucleotide sequence for which is (SEQ ID NO: 88; FEL_10F07_VH2) and a variable light chain sequence (SEQ ID NO: 89; FEL_10F07_VL2) the corresponding nucleotide sequence for which is (SEQ ID NO: 90; FEL_10F07_VL2).

Canine 19F07 1.1 is the variable heavy chain sequence (SEQ ID NO: 91; CAN_19F07_VH1) the corresponding nucleotide sequence for which is (SEQ ID NO: 92; CAN_19F07_VH1) and a variable light chain sequence (SEQ ID NO: 93; CAN_19F07_VL1) the corresponding nucleotide sequence for which is (SEQ ID NO: 94; CAN_19F07_VL1); Canine 19F07 2.1 is the variable heavy chain sequence (SEQ ID NO: 95; CAN_19F07_VH2) the corresponding nucleotide sequence for which is (SEQ ID NO: 96; CAN_19F07_VH2) and a variable light chain sequence (SEQ ID NO: 93; CAN_19F07_VL1) the corresponding nucleotide sequence for which is (SEQ ID NO: 94; CAN_19F07_VL1); Canine 19F07 1.2 is the variable heavy chain sequence (SEQ ID NO: 91; CAN_19F07_VH1) the corresponding nucleotide sequence for which is (SEQ ID NO: 92; CAN_19F07_VH1) and a variable light chain sequence (SEQ ID NO: 97; CAN_19F07_VL2) the corresponding nucleotide sequence for which is (SEQ ID NO: 98; CAN_19F07_VL2); Canine 19F07 2.2 is the variable heavy chain sequence (SEQ ID NO: 95; CAN_19F07_VH2) the corresponding nucleotide sequence for which is (SEQ ID NO: 96; CAN_19F07_VH2) and a variable light chain sequence (SEQ ID NO: 97; CAN_19F07_VL2) the corresponding nucleotide sequence for which is (SEQ ID NO: 98; CAN_19F07_VL2). Feline 19F07 1.1 is the variable heavy chain sequence (SEQ ID NO: 99; FEL_19F07_VH1) the corresponding nucleotide sequence for which is (SEQ ID NO: 100; FEL_19F07_VH1) and a variable light chain sequence (SEQ ID NO: 101; FEL_19F07_VL1) the corresponding nucleotide sequence for which is (SEQ ID NO: 102; FEL_19F07_VL1); Feline 19F07 2.1 is the variable heavy chain sequence (SEQ ID NO: 103; FEL_19F07_VH2) the corresponding nucleotide sequence for which is (SEQ ID NO: 104; FEL_19F07_VH2) and a variable light chain sequence (SEQ ID NO: 101; FEL_19F07_VL1) the corresponding nucleotide sequence for which is (SEQ ID NO: 102; FEL_19F07_VL1); Feline 19F07 1.2 is the variable heavy chain sequence (SEQ ID NO: 99; FEL_19F07_VH1)

the corresponding nucleotide sequence for which is (SEQ ID NO: 100; FEL_19F07_VH1) and a variable light chain sequence (SEQ ID NO: 105; FEL_19F07_VL2) the corresponding nucleotide sequence for which is (SEQ ID NO: 106; FEL_19F07_VL2); Feline 19F07 2.2 is the variable heavy chain sequence (SEQ ID NO: 103; FEL_19F07_VH2) the corresponding nucleotide sequence for which is (SEQ ID NO: 104; FEL_19F07_VH2) and a variable light chain sequence (SEQ ID NO: 105; FEL_19F07_VL2) the corresponding nucleotide sequence for which is (SEQ ID NO: 106; FEL_19F07_VL2).

Canine 14C04 1.1 is the variable heavy chain sequence (SEQ ID NO: 127; CAN_14C04_VH1) the corresponding nucleotide sequence for which is (SEQ ID NO: 128; CAN_14C04_VH1) and a variable light chain sequence (SEQ ID NO: 131; CAN_14C04_VL1) the corresponding nucleotide sequence for which is (SEQ ID NO: 132; CAN_14C04_VL1); Canine 14C04 2.1 is the variable heavy chain sequence (SEQ ID NO: 129; CAN_14C04_VH2) the corresponding nucleotide sequence for which is (SEQ ID NO: 130; CAN_14C04_VH2) and a variable light chain sequence (SEQ ID NO: 131; CAN_14C04_VL1) the corresponding nucleotide sequence for which is (SEQ ID NO: 132; CAN_14C04_VL1); Canine 14C04 1.2 is the variable heavy chain sequence (SEQ ID NO: 127; CAN_14C04_VH1) the corresponding nucleotide sequence for which is (SEQ ID NO: 128; CAN_14C04_VH1) and a variable light chain sequence (SEQ ID NO: 133; CAN_14C04_VL2) the corresponding nucleotide sequence for which is (SEQ ID NO: 134; CAN_14C04_VL2); Canine 14C04 2.2 is the variable heavy chain sequence (SEQ ID NO: 129; CAN_14C04_VH2) the corresponding nucleotide sequence for which is (SEQ ID NO: 130; CAN_14C04_VH2) and a variable light chain sequence (SEQ ID NO: 133; CAN_14C04_VL2) the corresponding nucleotide sequence for which is (SEQ ID NO: 134; CAN_14C04_VL2).

Example 9. Homology Modeling of Candidate Anti-OSMR Antibodies and Comparison of Structural Variances Between CDRs Generation of homology models based on known protein structures is useful in understanding the three-dimensional structure of antibodies. Overlaying these protein models through superposition allows direct comparison of the areas where antibodies are alike and different from one another in three-dimensional space. These methods overcome the limitations of comparing proteins as strings of linear amino acid sequences which does not account for the collective representation of each amino acid's physicochemical property with respect to its surroundings. Antibody models of the 5 mouse anti-OSMR antibodies described herein were generated using the Molecular Operating Environment (MOE™) software (Chemical Computing Group, Montreal, Canada) which is capable of creating such models similar to other software that is available. See, for example, Almagro et al.; Antibody Modeling Assessment; *Proteins: Struct. Func. Bioinf.* 79 (2011) 3050-3066, of record.

Figure 3B:
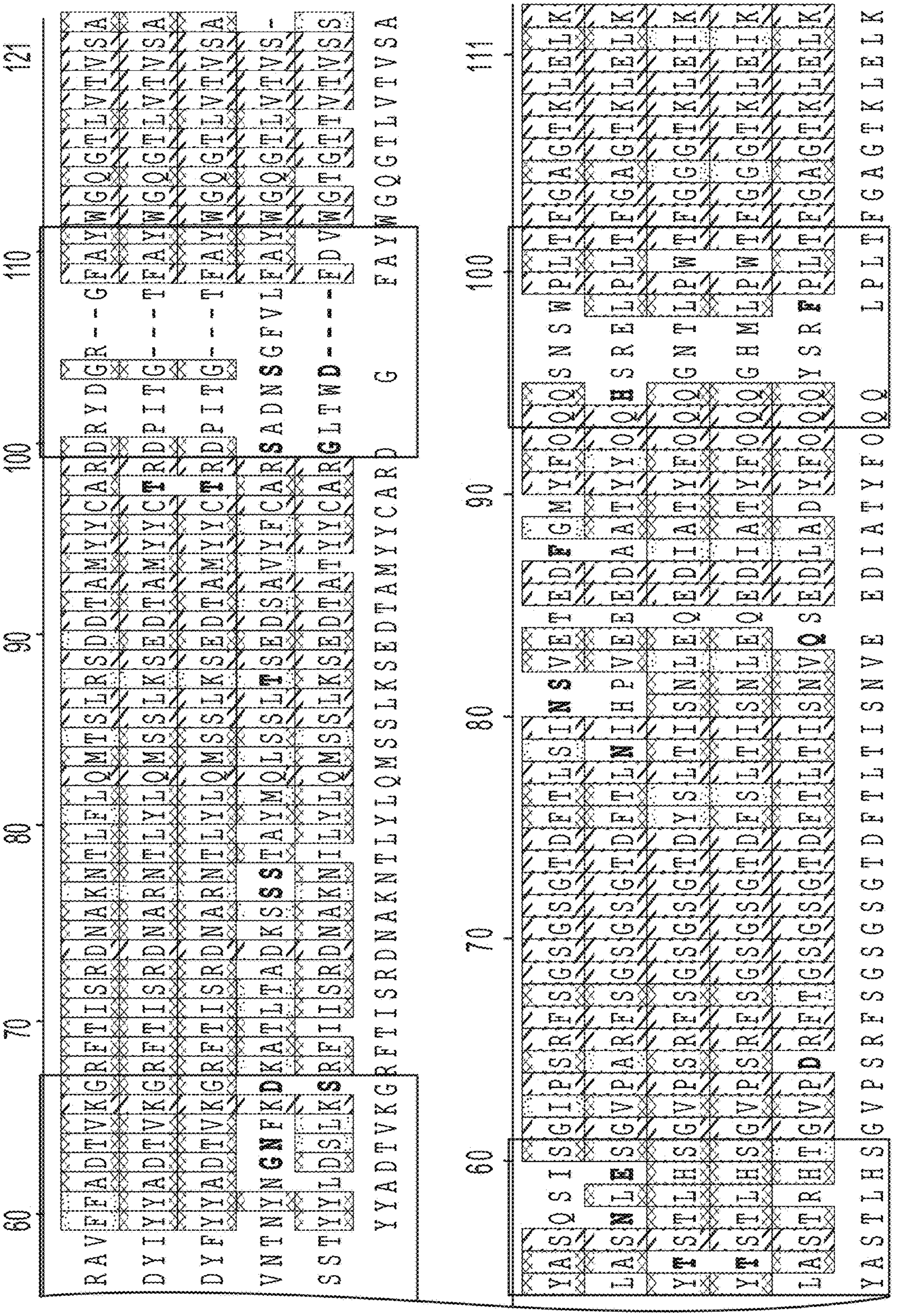

To compare the structure of the 5 mouse anti-OSMR antibody models, the root-mean-square deviation (RMSD) value was determined from pairwise comparison between each antibodies CDRs which are considered the most critical for antigen binding. The RMSD value is known metric in the art used to determine the likeness of structures in three-dimensional space by comparing the coordinates of their alpha carbon atoms which act as the backbone scaffold of the protein. When calculating RMSD, the MOE software uses a comparison of each alpha carbon to the respectively aligned alpha carbons on the other structures to generate a root mean square deviation which represents the overall difference in the structures for the selected area of interest. We describe herein the comparison of only the CDR regions between each antibody and not the entire variable domains. When calculating the RMSD value between the three antibody structures the sequence alignment is done considering structural overlap and areas where gaps are introduced to optimize the alignment. In some circumstances this results in an overestimation of RMSD similarity (lower RMSD value) due to variation in loop length not being considered. This is the case when considering CDRH3 and CDRL1 from the 5 mouse anti-OSMR antibody candidates where CDR lengths are different (FIGS. 3A and 3B). An RMSD greater than or equal to 2 angstroms represents a significant separation in three-dimensional space.

Figure 4:
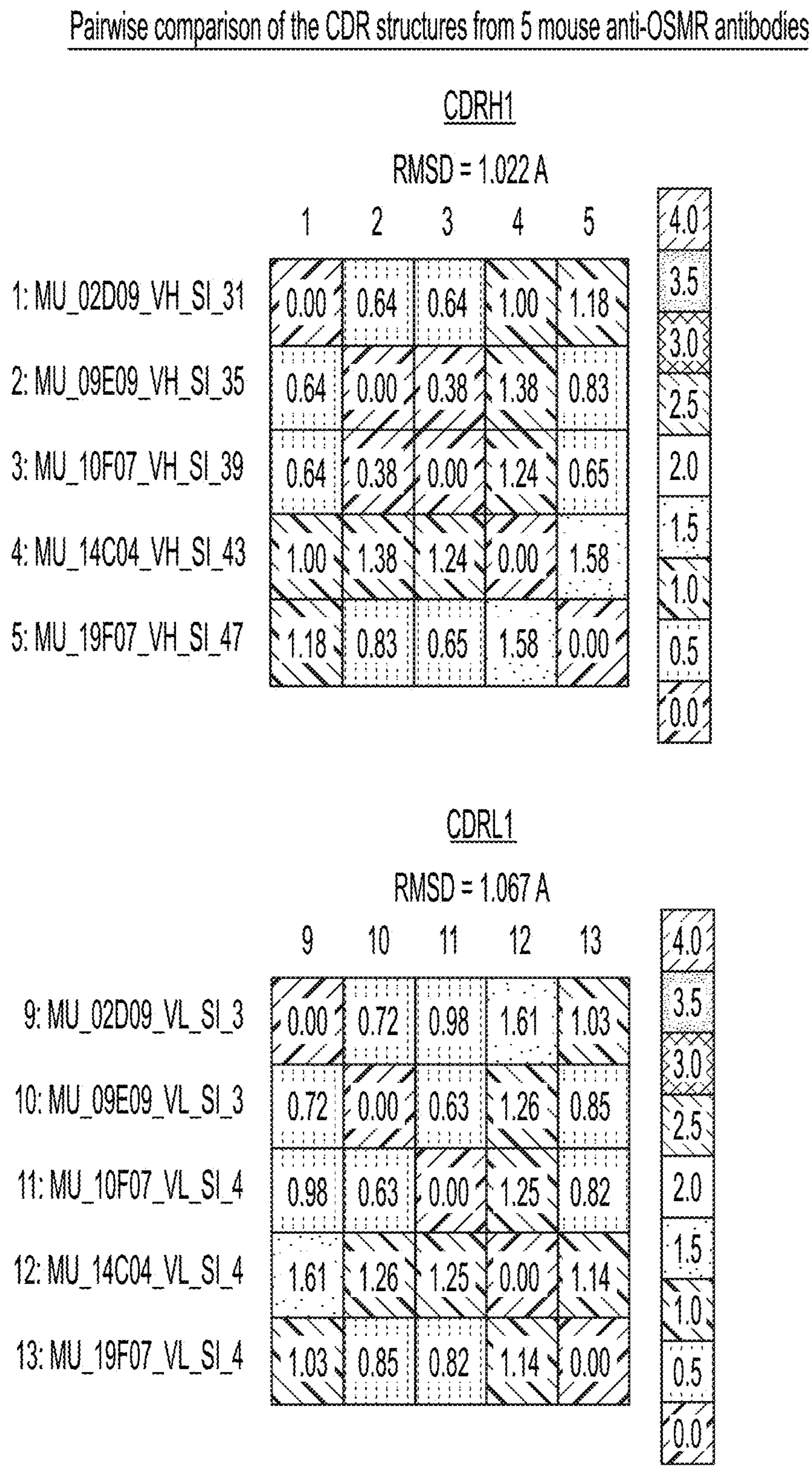
FIG. 4 are matrices showing the RMSD values of the CDRs following pairwise comparison of the structures of homology models generated for the 5 anti-OSMR antibodies described in this application.

FIG. 4 shows six matrices with the RMSD resulting from pairwise comparison of each CDR from the 5 mouse anti-OSMR antibodies described herein. Comparison of CDRH1 from these structural models indicates that these antibodies have a general structural similarity in this loop to one another with none of the RMSD values exceeding 2 angstroms. Mouse antibody 14C04 with the variable heavy chain sequence (SEQ ID NO: 43; MU_14C04_VH) the corresponding nucleotide sequence for which is (SEQ ID NO: 44; MU_14C04_VH) and a variable light chain sequence (SEQ ID NO: 45; MU_14C04_VL) the corresponding nucleotide sequence for which is (SEQ ID NO: 46; MU_14C04_VL); has the most distinct CDRH1 structure (largest RMSD compared to other antibodies) and is of interest to note this antibody is the only one which is specific for canine OSMR only. The RMSD difference between murine anti-OSMR antibody 14C04 and the others is more pronounced when comparing CDRH2 with RMSD values exceeding 2 for each comparison.

The RMSD results from comparing CDRH3 structures from the 5 mouse anti-OSMR antibodies highlights another important consideration of the structure function relationship with the antibodies and their target, OSMR. Mouse anti-OSMR antibody 14C04 is highly structurally distinct from the others in this CDR with RMSD values exceeding 2 angstroms in 3 of the 4 comparisons and as previously mentioned, 14C04 is canine OSMR specific (see Table 1 for affinity data). The other antibody having a high structural distinction from the other 4 in mouse anti-OSMR 02D09 with the variable heavy chain sequence (SEQ ID NO: 31; MU_02D09_VH) the corresponding nucleotide sequence for which is (SEQ ID NO: 32; MU_02D09_VH) and a variable light chain sequence (SEQ ID NO: 33; MU_02D09_VL) the corresponding nucleotide sequence for which is (SEQ ID NO: 34; MU_02D09_VL). Mouse anti-OSMR 02D09 is interesting in that this antibody shows specificity for binding to feline OSMR (see Table 1 and Table 3). Table 3 supports higher affinity of the chimeric 02D09 antibody to feline OSMR (compared to canine OSMR) as well as a slower off rate supporting its preferential specificity to the feline OSMR protein). To reiterate a point previously made, antibodies 02D09 and 14C04 also have longer CDRH3s and these additional amino acids are not considered in the direct structural comparison however they do highly impact the distinct structures of these two CDRH3 loops when compared to the other 3 antibodies which bind to both [emphasis added] canine and feline OSMR.

Continuing with the comparison of the light chain CDR structures, the FIG. 4 CDRL1 matrix shows the RMSD comparison of the 5 anti OSMR antibodies do not exceed the 2-angstrom difference. Again, the canine OSMR antibody 14C04 has higher RMSD values indicating a trend towards structural distinction without consideration of the 4 additional amino acids in this CDR. The additional 4 amino acids in this CDR loop represent a significant structural difference compared to the other 4 antibodies and further support a unique structural composition of the binding paratope for this antibody. Antibodies 02D09 and 14C04 have the greatest structural variance in the CDRL2 loop with the most significant (RMSD greater than 2 angstroms) existing in the comparison between them.

It is of interest to point out that the amino acid sequences of the CDRL2s from antibodies 09E09 and 10F07 are identical however the RMSD comparison between them is not zero (value is 0.31). An RMSD value of 0.31 represents structures that are highly similar to one another. Differences arise from the fact that antibodies 09E09 and 10F07 do not have identical variable light chains and therefore are not identical to one another. Structural changes introduced in other areas of the protein chain can be responsible for differences occurring distally and are reflected in subtle differences in the RMSD value.

Comparison of light chain CDRL3 reveals again that there is a significant structural difference between antibodies 02D09 and 09E09 and a trend towards these two species specific anti-OSMR mAbs to show greater structural variation when compared to those have dual specificity for canine and feline OSMR. While not wishing to be bound to one particular hypothesis we present evidence supporting a link between the structure of CDR loops of these anti-OSMR antibodies and their functionality of specifically binding to, and blocking, a canine and/or feline OSMR whereby this binding inhibits the ability of pSTAT3 signaling induced by IL-31 or OSM proteins.

Example 10. Homology Modeling of the Canine and Feline OSM: OSMR Receptors

The OSMR receptor has been characterized in the context of the cytokines to which is binds resulting in a cellular signaling response. These cytokines (including OSM) are members of the gp130 family of cytokines which elicit pleiotropic responses in the context of different cellular and tissue distributions including cellular differentiation, proliferation, hematopoiesis, immunologic, and inflammatory responses (Richards CD; The Enigmatic Cytokine Oncostatin M and Roles in Disease; *ISRN Inflammation.* 2013: 512103 (2013)). The OSMR protein shares similar structural architecture to LIFR which, in humans, forms a heterodimeric receptor complex with gp130 to signal in response to both LIF and OSM. Overlap in such functional characteristics allows for comparison of these receptors structure within and between species. A protein structure for OSMR is not presently available however a crystal structure (PDB ID: 2Q7N, 4 angstroms) of Leukemia inhibitory factor (LIF) in complex with LIF receptor (LIFR) is available (Huyton T et al.; An unusual cytokine: Ig-domain interaction revealed in the crystal structure of leukemia inhibitory factor (LIF) in complex with the LIF receptor. Proc Natl Acad Sci USA. 2007 Jul. 31; 104(31):12737-42). While not wishing to be bound to one hypothesis we present herein structural homology data using this LIF: LIFR co-crystal structure as a template to guide the understanding of the interactions between IL-31, OSM and OSMR. These structural data in combination with reports of functional mapping of amino acid residues involved in the interaction of human OSM with human OSMR allow inference to the homologous regions in canine and feline OSMR and support the understanding of the epitopes to which inhibitory anti-OSMR antibodies bind.

Figure 5B:
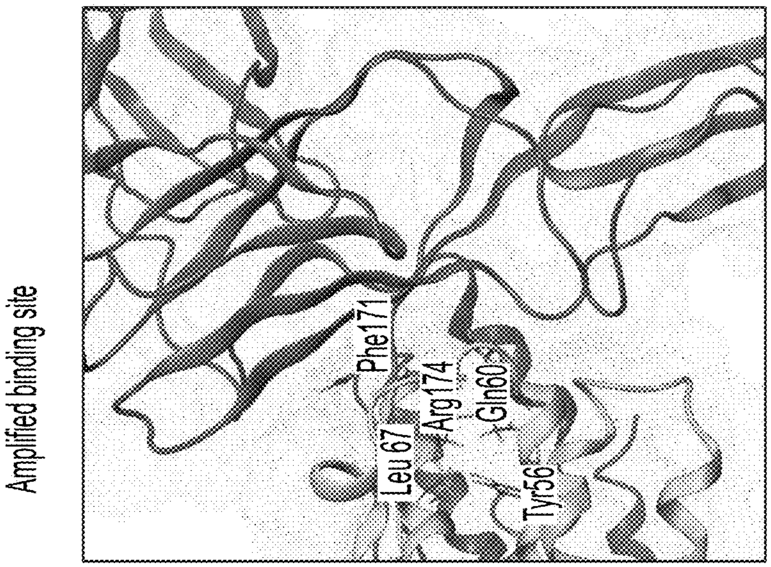
FIG. 5B shows an enlarged region of the binding interface highlighting amino acids known to be important in the human OSM: OSMR interaction.
Figure 5A:
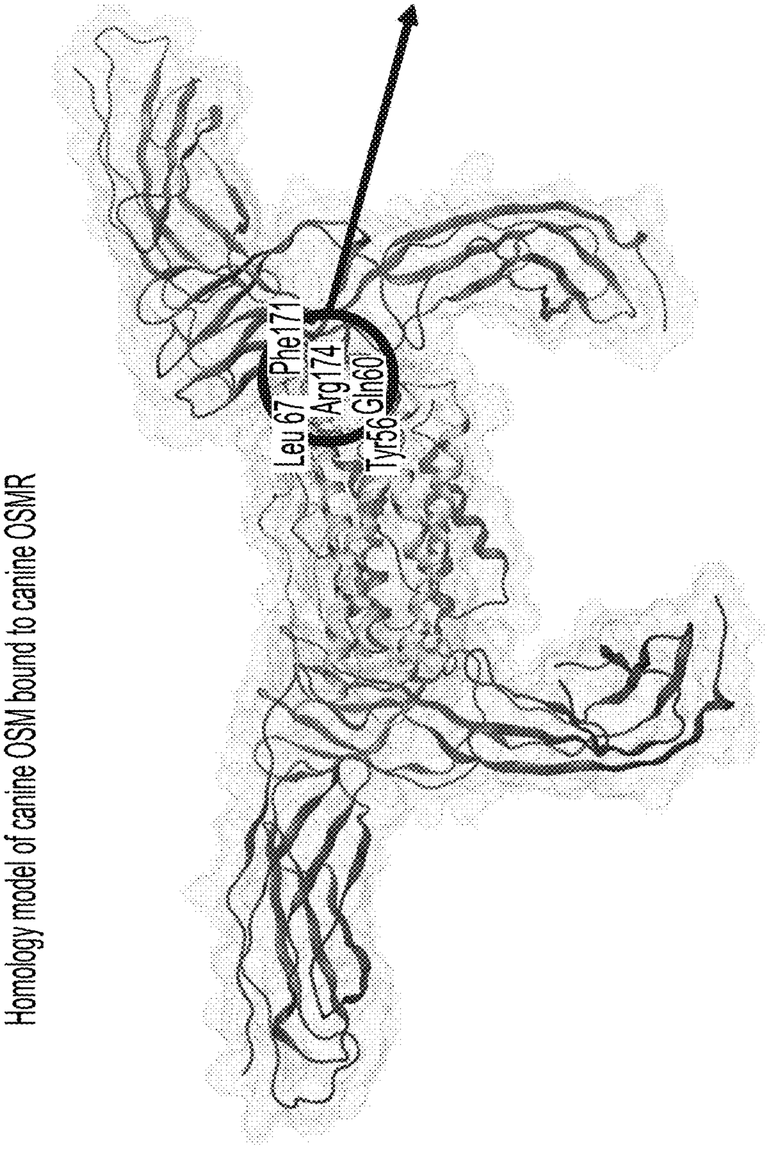
FIG. 5A is a homology model showing a dimer of canine OSM bound to a dimer of the canine OSMR protein. A black circle highlights the binding interface of OSM and OSMR.

FIG. 5A shows a representative homology model generated using amino acids 28-329 of (SEQ ID NO: 107; Canine_OSMR_hlgG1_Fc) the corresponding nucleotide sequence for which is (SEQ ID NO: 108; Canine_OSMR_hlgG1_Fc) (the extracellular domain of canine OSMR) on the template structure 2Q7N of human LIFR (SEQ ID NO: 135; Human_LIFR). A similar homology model was generated using amino acids 28-329 of (SEQ ID NO: 112; Feline_OSMR_hIgG1_Fc) the corresponding nucleotide sequence for which is (SEQ ID NO: 113; Feline_OSMR_hlgG1_Fc) (the extracellular domain of feline OSMR) on the template structure 2Q7N of human LIFR (SEQ ID NO: 135; Human_LIFR). FIG. 5A shows the homology model generated using canine OSM (SEQ ID NO: 109; Canine_OSM) on the template structure 2Q7N of human LIF (SEQ ID NO: 136; Human_LIF). A similar homology model was generated using amino acids 23-234 of feline OSM (SEQ ID NO: 110; Feline_OSM_hlgG1_Fc) the corresponding nucleotide sequence for which is (SEQ ID NO: 111; Feline_OSM_hlgG1_Fc) on the template structure 2Q7N human LIF (SEQ ID NO: 136; Human_LIF).

FIG. 5A shows the binding interface of the canine OSM homology model near the canine OSMR protein, based on the LIF: LIFR co-crystal template. FIG. 5B shows an enlarged picture of an area contained within the highlighted circle. In this enlarged representation are amino acids labeled that were identified from a previous study defining relevant amino acids involved with the human OSM: OSMR interaction (Adrian-Segarra J M et al.; The AB loop of Oncostatin M (OSM) determines species-specific signaling in humans and mice. J Biol Chem. 2018 Dec. 28; 293(52): 20181-20199). It is important to note that while this publication used the human proteins to assess the functionality of important amino acid residues involved with OSM binding to OSMR, the homologous amino acids labeled on this canine OSM:OSMR homology model are indeed positioned in this binding interface and therefore provide supporting evidence that inference from the human protein structures is supportive of the canine and feline receptor systems.

Figure 6:
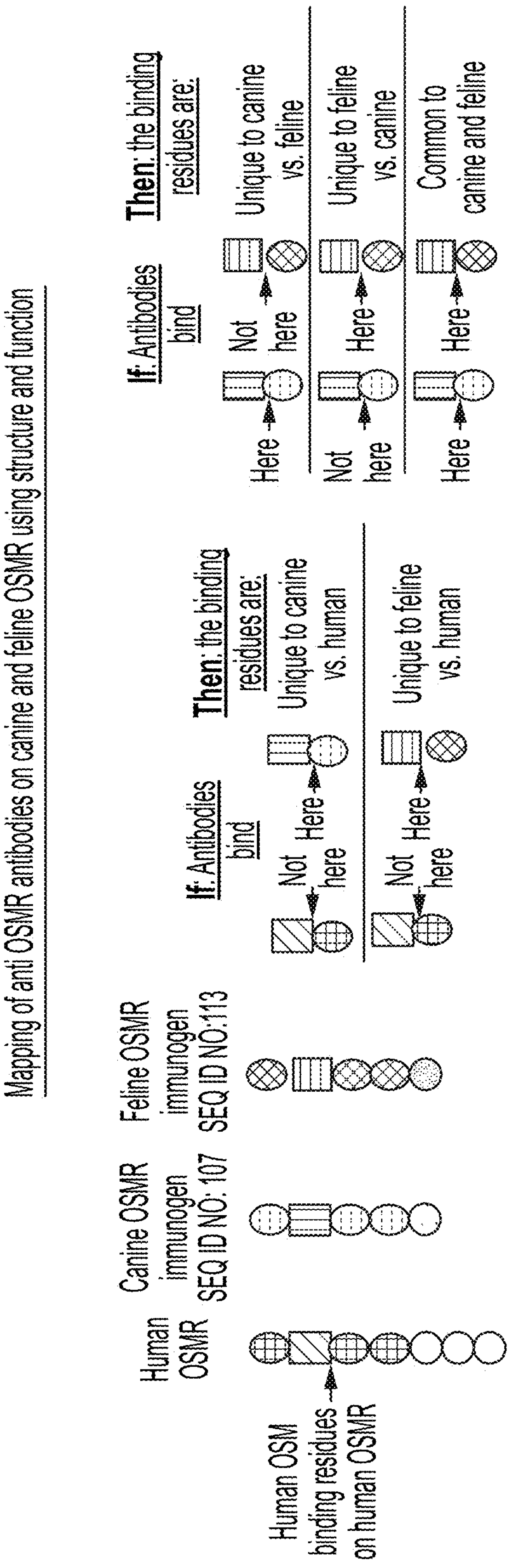
FIG. 6 shows the epitope binding sites of the antibodies described herein based on the logical location of where OSM binds to OSMR and the sequence diversity between human, canine, and feline OSMR protein.

Example 11. Determination of Anti-OSMR Binding Region on Canine and Feline OSMR Based on Homology to Known OSM Binding Domain and Amino Acid Sequence Variation Between Species FIG. 6 shows a drawing to logically define the binding region(s) of the 5 mouse anti-OSMR antibodies on canine and/or feline OSMR. That is to say, because of the narrow number of amino acid residues defining the OSM (and presumably the IL-31) binding sites on OSMR, coupled to the sequence divergence in the human OSMR protein and limited divergence between canine and feline OSMR, there are only a few places where these antibodies can specifically bind and elicit the functional activity described herein. In FIG. 6, the extracellular domains of human OSMR are represented with filled in black ovals and a hatched square which represents the cytokine binding domain and open circles which represents the fibronectin III domains. Mapping studies like those described herein define a specific area (key individual amino acid contacts) that are responsible for binding of human OSM to OSMR. Depicted here are also the homologous canine and feline OSMR protein regions that were used to immunize mice for the purpose of generating anti-OSMR antibodies. None of the antibodies selected for binding to canine and/or feline OSMR described herein bind to human OSMR indicating that the binding occurs in an area on canine and/or feline OSMR that is divergent from human. That is to say that the amino acids in these areas of canine and feline OSMR are different from human. Knowing that these antibodies bind to canine and/or feline OSMR and inhibit pSTAT3 mediated signaling induced by canine and/or feline OSM (and/or IL-31), means they bind in the discrete area where OSM and/or IL-31 bind to OSMR to activate the receptor and this area is a different amino acid sequence in canine and feline versus human OSMR.

There are 3 types of mouse anti-OSMR antibodies described herein, 1) an antibody that preferentially binds to feline OSMR 2) an antibody that specifically binds to canine OSMR and 3) 3 antibodies that bind to canine and feline OSMR. Based on these 3 binding phenotypes, an antibody that specifically binds to canine OSMR must bind in a region of OSMR near the binding sire of OSM (and IL-31) where the amino acid sequence is unique to canine versus feline OSMR. An antibody that binds preferentially to feline OSMR over canine OSMR will bind to an area that is unique to feline OSMR and near the binding site of OSM (and IL-31). Antibodies that bind both canine and feline OSMR, inhibit OSM (and/or) IL-31 mediated signaling, will bind to an area on OSMR where the amino acid sequence in conserved between canine and feline OSMR. Based on the modelling descried herein and functional data that has been determined for these antibodies, these data define the epitope of the anti-OSMR antibodies described herein.

Example 12. Docking of Anti-OSMR Antibodies on the OSMR Receptor Model

Described herein are homology models generated for the 5-candidate mouse anti-OSMR antibodies selected that bind to canine and/or feline OSMR. Also describe are the variation in the structure: function relationship between these antibodies with respect to CDR structures and differential binding and potency against neutralizing canine and/or feline IL-31 and/or OSM pSTAT3 signaling in canine and/or feline cells. Additionally, homology models of the OSM: OSMR binding interface are described which defines the regions on the OSM cytokine and receptor which are important for receptor activation. Use of these models and knowledge of the specific amino acid residues involved in these interactions can be translated to the homologous regions in the canine and feline OSM and OSMR proteins.

Docking of a protein onto another protein (or protein complex) is performed using software like MOE or related software currently available. An antibody homology model (or solved structure of an antibody) is docked onto a receptor using input from the user to define areas on the protein (example, specific amino acid residues) to guide the software. These areas are defined from knowledge of experimental data defining residues that are important for contact between a cytokine and the receptor to which it binds. These data can be derived from homologous protein structures and/or structures of proteins with similar functional characteristics and similar architecture (and not necessarily similar amino acid sequence). Docking of an anti-OSMR antibody onto the OSMR structure is performed in the MOE software with knowledge of the human OSM: OSMR interactions coupled with knowledge of which mouse anti canine and/or feline CDRs are important for species specificity. Placement of the antibody model on the relevant area of OSM:OSMR interaction is also supported by the fact that a) the mouse anti-OSMR antibodies described herein do bind to canine and/or feline OSMR and b) these antibodies block the ability of IL-31 and/or OSM to induce pSTAT3 signaling in canine and/or feline cells. These facts define a discrete area of the OSMR protein to which these antibodies can logically bind and limit the area to define where docking of the CDRs should take place.

Example 13. Analysis of OSMR Gene Expression in Skin Tissue Biopsies from Felines with Allergic Dermatitis Using In Situ Hybridization (ISH)

Twenty skin biopsies from felines with allergic skin disease were formalin-fixed and paraffin-embedded (FFPE) prior to sectioning for ISH analysis. Nineteen biopsies from normal feline skin without signs of allergic disease were subjected to FFPE and sectioned for comparative analysis. Automated single chromogenic ISH protocol from Advanced Cell Diagnostics, RNAscope 2.5 LS Reagent Kit-Red (ACD, 322750-USM) was performed using the Leica Bond-RX system. Prior to probe hybridization, tissue samples were subjected to heat and enzymatic epitope retrieval using the ACD proprietary protease reagent. Positive control staining was performed on each sample to determine the RNA integrity using a probe to the Cyclophilin B (PPIB) gene (Advanced Cell Diagnostics, Inc., Newark, CA). A custom probe was designed to detect the expression of the feline OSMR gene (Advanced Cell Diagnostics, Inc., Newark, CA). Each slide was visualized and quantified on Leica Aperio ImageScope 12.3.2.8013. Each image was annotated, and RNA expression was analyzed with the macro algorithm Leica RNA ISH v2 embedded in the ImageScope software. Data was extracted from the ImageScope software and reported as ratio of RNA signal to analyzed tissue area. Student one-tailed test was used to determine signal significance.

Figure 7:
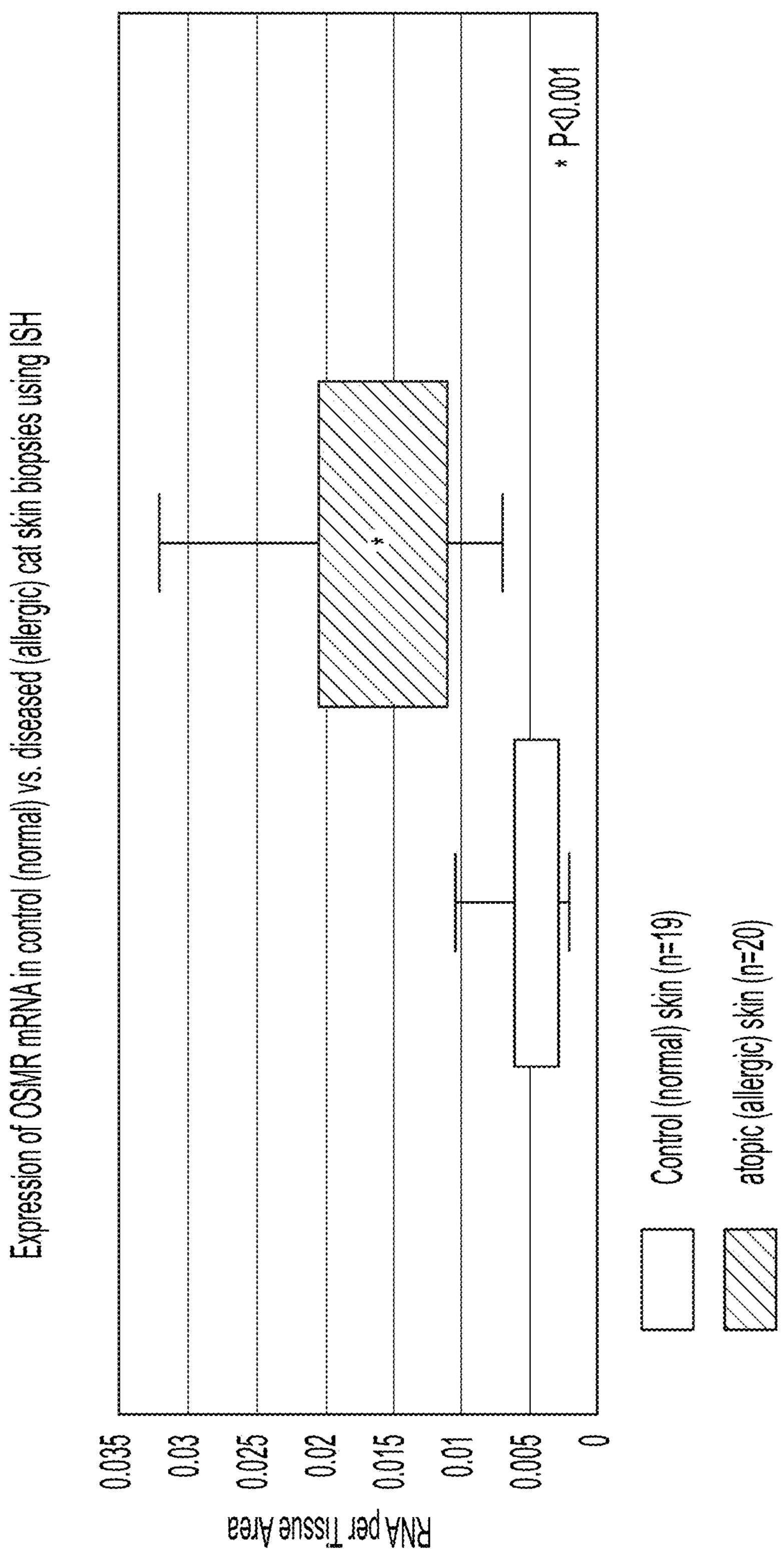
FIG. 7 shows the quantitation of OSMR mRNA in feline skin using and RNAscope ISH probe. Control tissues are from normal feline skin biopsies and diseased tissues are from skin biopsies from felines with allergic skin disease.

FIG. 7 shows the quantitative results following imaging of OSMR mRNA using ISH from normal and allergic feline skin biopsies. ISH of mRNA using RNAScope is highly specific for detection of the targeted transcript, in this case feline OSMR mRNA. There is a clear, significant overexpression of OSMR mRNA in the skin of felines with allergic disease. These results indicate a correlation between a clinically relevant diagnosis of allergic skin disease in felines and the overexpression of the OSMR gene representing a link between OSMR and the disease pathophysiology. These results support the hypothesis that OSMR is involved in feline skin disorders and targeting OSMR with an antibody capable of blocking cytokine-mediated signaling through the receptor may be useful in treating such disorders including, but not limited to, allergic and atopic dermatitis.

Example 14. Analysis of OSMR Protein in Skin Tissue Biopsies from Feline with Allergic Dermatitis Using Immunohistochemistry (IHC)

Five skin biopsies from felines with allergic skin disease were formalin-fixed and paraffin-embedded (FFPE) prior to sectioning for IHC analysis. Five biopsies from normal feline skin without signs of allergic disease were subjected to FFPE and sectioned for comparative analysis. Automated single chromogenic IHC refine red protocol was performed using the Leica Bond-RX system (Leica Biosystems, Buffalo Grove, IL). Prior to antibody staining, sample epitopes were exposed by heat induced epitope retrieval in EDTA buffer. Expression of the feline OSMR protein was carried out using a polyclonal rabbit anti-OSMR antibody (LSBio LS-B11477, Seattle, WA) and detected with Leica Bond refine red AP linked polymer and fast red chromogen (Leica Biosystems, Buffalo Grove, IL). Qualitative analysis was performed by inspection of each image for red staining indicating expression of the OSMR protein.

Figure 8:
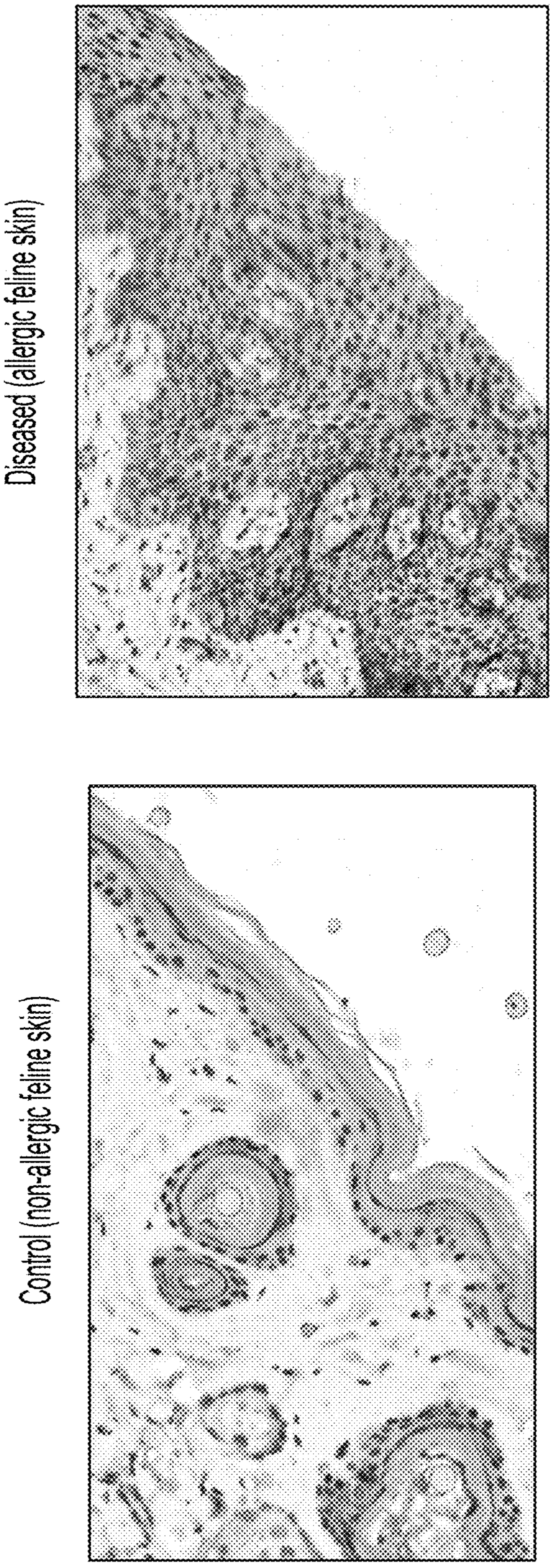
FIG. 8 shows a single representative image from IHC staining of the OSMR protein from control (non-allergic) versus diseased (allergic) skin tissue.

FIG. 8 shows a representative image comparing a normal feline skin section to a skin section from a feline with allergic disease. Colored slide images of skin contain light brown epidermal regions, punctate dark purple spots which are Dapi staining of the nuclei, and red which is the colorimetric staining of the OSMR protein following development of the alkaline phosphatase (AP) labeled secondary antibody. FIG. 8 shows staining of the feline OSMR protein in a control skin tissue image and an allergic skin tissue image following conversion of the colored images to a grayscale format. In the control (non-allergic) skin sample there is minor expression of the OSMR protein in the sub-epidermal space and an ordinary distribution of cells near the epidermal layer. The image from the allergic skin sample clearly shows the elevated expression of the OSMR protein throughout the sub-epidermal space with a large infiltration of cells with minimal distinction between the epidermal and sub-epidermal spaces. The OSMR protein is visual in these images as a gray to black shading of space outside of the black defined staining of the nuclei. It is of interest to note that although the cellular boundaries in these images are not annotated there is an appearance of staining in interstitial areas which are presumably away from the cell indicating that there may be secreted soluble forms of the OSMR receptor present. While not wishing to be bound to one hypothesis, it is conceivable that such secreted receptors may have a regulatory role by acting as an antagonist or carrier protein for the proteins which OSMR interacts with. If these soluble forms have the same amino acid sequence and structure as the cell-associated form of the receptor then an anti-OSMR antibody like the ones described herein would also bind to the soluble form. Visual examination of the five control feline skin slides and five allergic skin slides indicate a similar pattern for OSMR staining as what is described here for the two representative images. The results support the quantitative results described herein showing overexpression of OSMR in the skin of felines with allergic disease when compared to feline skin samples without allergic disease. These results provide evidence of a role for the OSMR protein in the skin of felines with skin disorders including, but not limited to, allergic and atopic dermatitis.

Example 15. An IL-31 Induced Itch Model in Dogs and Cats to Determine In Vivo Efficacy of Anti OSMR Antibodies While not wishing to be bound to one particular hypothesis we present evidence that binding of selected antibodies to canine and/or feline OSMR, that are capable of blocking (or neutralizing) the biological activity of pSTAT3 induced signaling by IL-31 and/or OSM and that such IL-31 and/or OSM inhibition at the level of the OSMR receptor, may be beneficial as a therapeutic against atopic, allergic, inflammatory and other disorders described herein for canines and felines. The ability of an antibody to effectively neutralize its target can be assessed in vivo using an appropriate model for efficacy in a host species. Such a model to determine in vivo efficacy is described.

To determine in vivo efficacy in the dog, subcutaneous (SC) administration of an anti-canine OSMR antibody is given to laboratory dogs. Baseline responses are performed with all dogs and dogs are randomized into groups and housed based on their pruritic score index (PSI). The dogs are then administered an anti-canine OSMR antibody on day 7 and IL-31 challenges are performed at day 8, 14 and 22. Reduction in mean PSI for day 8 and 14, relative to day 1, in antibody treated animals is considered for an efficacy endpoint when comparing the PSI scores for untreated animals. Assessing the PSI day to day variation associated with dogs' pruritic behaviors is controlled for variation with a 30-minute baseline PSI determined for each dog, on each day prior to IL-31 challenge. Such in vivo model data may provide evidence that; 1) anti-canine OSMR monoclonal antibodies can neutralize the ability of IL-31 to induce pruritus in dogs, 2) inhibition of IL-31 mediated signaling by blocking OSMR in a cell based assay correlates with in vivo efficacy and 3) the parameters necessary to utilize an IL-31 model for antibody evaluation are established for the evaluation of other candidate antibodies.

The efficacy of anti-feline OSMR is assessed in an IL-31 induced in vivo cat model. Pre-challenge pruritic behavior for the vehicle placebo and antibody groups is assessed from day−7 through day 28 with day zero being the day of antibody administration. On day zero cats are dosed with an anti-OSMR antibody subcutaneously which is seven days prior to the first feline IL-31 challenge. Pruritic behavior is assessed on days 7, 21, and 28 for 1 hour following an intravenous challenge of the IL-31 protein. Reduction in pruritus observed on days 7, 21 or 28 following IL-31 challenge, when compared to vehicle placebo control, is considered for efficacy. These data support the ability of an anti-OSMR antibody to neutralize pruritus induced by feline IL-31 in vivo and suggest the antibody may serve as a therapeutic in the treatment of IL-31 mediated disease in cats including, but not limited to, atopic dermatitis.

Example 16. Additional Cell-Based Data with Mouse and Mouse:Canine Chimeric Anti-OSMR Antibodies Additional cell-based experiments were performed to assess the potency of anti-OSMR antibodies in cell challenge assays for IL-31 and OSM-mediated pSTAT3 signaling. These data were generated in support of previous work described in Examples 6 and 7. The sequence of mouse and mouse:dog chimeric antibodies are described in Examples 6 and 7 respectively. These data demonstrate that both antibodies 10F07 and 19F07 possess superior potency towards inhibiting canine and feline IL-31 and OSM mediated pSTAT3 signaling in both canine and feline cells. Also of interest is the selective potency of antibody 14C04 towards inhibition of canine mediated signaling and 02D09 for feline indicating the potential for structural variance on the OSMR receptor which leads to differential specificity on the epitope recognized by these two antibodies.

TABLE 5

Inhibition of IL-31 and OSM mediated pSTAT3 signaling in canine DH82 and feline Fcwf-4 cells with anti-canine and/or anti-feline mouse: canine anti-OSMR chimeric antibodies.

| | | Inhibition of IL-31 and OSM pSTAT3 Signaling | | | |
|---|---|---|---|---|---|
| | | Cell type used: | | | |
| | | Canine DH82 | Feline IL-31 Fcwf-4 | Canine DH82 | Feline IL-31 Fcwf-4 |
| | | Cytokine used: | | | |
| Antibody ID | Antibody type | Canine IL-31 (SEQ ID NO: 123) $IC_{50}$ (μg/ml) | Feline IL-31 (SEQ ID NO: 125) $IC_{50}$ (μg/ml) | Canine OSM (SEQ ID NO: 109) $IC_{50}$ (μg/ml) | Canine OSM (SEQ ID NO: 109) $IC_{50}$ (μg/ml) |
| Mu_14C04 | mouse | 5.65 | 0% inh @ 75 μg/ml | 8.64 | nt |
| 14C04 | mouse:dog chimera | nt | nt | nt | nt |
| Mu_02D09 | mouse | 0% inh @ 75 μg/ml | 67% inh @ 75 μg/ml | >50 μg/ml | nt |
| 02D09 | mouse:dog chimera | 97.7 | nt | nt | nt |
| Mu_19F07 | mouse | 0.07 | 0.42 | 0.27 | 0.68 |
| 19F07 | mouse:dog chimera | 0.28 | nt | 0.26 | nt |
| Mu_09E09 | mouse | 80% inh @ 75 μg/ml | 63% inh @ 75 μg/ml | 54% @ 15 μg/ml | nt |
| 09E09 | mouse:dog chimera | 31.31 | nt | nt | nt |
| Mu_10F07 | mouse | 93% inh @ 75 μg/ml | 91% inh @ 75 μg/ml | 0.05 | 0.23 |
| 10F07 | mouse:dog chimera | 0.05 | 0.32 | 0.16 | nt |

nt = not tested

% inh @ = percent inhibition at indicated concentration

Example 17. Binding Data for Caninized and Felinized Anti-OSMR Antibodies

Caninized (canine) and felinized (feline) anti-OSMR antibodies were cloned, expressed, and purified. The sequence of each speciated antibody in Table 6 is described in Example 8. Affinity of these speciated antibodies to canine and feline OSMR was measured using Biacore. Table 5 describes results of these Biacore experiments for speciated antibodies that expressed and bound canine and/or feline OSMR. As indicated in the table, this first round of speciation produced antibodies from the 19F07, 09E09, and 10F07 lineage that expressed and bound to their protein target. For comparison to the mouse and mouse:canine chimeras having the same CDRs as these speciated versions, see Tables 1 and 3 respectively. The highest affinity speciation for each of these three series antibodies are Fel_09E09_1.1 binding to feline OSMR with a KD of 7.73E-9 M, Fel_10F07_2.2 binding to feline OSMR with a KD of 1.21E-9 M, Can_19F07_2.1 binding to canine OSMR with a KD of 8.30E-9 M, and Fel_19F07_2.2 binding to feline OSMR with a KD of 3.32E-12 M. The objective during the speciation process is maintain affinity of the speciated antibody form to its respective target protein, in this case to canine and/or feline OSMR. Detailed here are the binding kinetics for antibodies that exemplify this goal.

TABLE 6

Biacore binding data for caninized and felinized anti-OSMR antibodies to canine and feline OSMR. Experimental controls show binding of an anti-human OSMR antibody to human OSMR only. None of the mouse progenitor mAbs with these CDRs showed binding to human OSMR (see Table 1). Non-transfected controls were grown and purified identically to these speciated recombinant mAbs without a plasmid to express a functional antibody. cOSM binding shows these three OSMR receptor forms are capable of binding to the canine form of the OSM protein. Ctrl-HBS-EP is a buffer control for the Biacore instrument.

| | | Canine OSMR (SEQ ID NO: 107) | | | Feline OSMR (SEQ ID NO: 112) | | |
|---|---|---|---|---|---|---|---|
| Antibody ID | Antibody type | ka ($M^{-1} s^{-1}$) | kd ($s^{-1}$) | KD (M) | ka ($M^{-1} s^{-1}$) | kd ($s^{-1}$) | KD (M) |
| CAN_19F07_1.1 | caninized | 3.66E+04 | 3.34E−04 | 9.13E−09 | 1.11E+05 | 3.55E−05 | 3.20E−10 |
| CAN_19F07_2.1 | caninized | 2.64E+04 | 2.20E−04 | 8.30E−09 | 5.67E+04 | 1.12E−05 | 1.98E−10 |
| CAN_19F07_2.2 | caninized | | No binding | | 4.70E+04 | 1.13E−03 | 2.40E−08 |
| FEL_19F07_1.1 | felinized | 2.85E+04 | 2.94E−04 | 1.03E−08 | 8.13E+04 | 6.37E−05 | 7.83E−10 |
| FEL_19F07_1.2 | felinized | 1.05E+04 | 3.27E−04 | 3.10E−08 | 4.47E+04 | 1.95E−05 | 4.35E−10 |
| FEL_19F07_2.1 | felinized | | No binding | | 3.79E+03 | 4.07E−07 | 1.08E−10 |
| FEL_19F07_2.2 | felinized | 4.88E+04 | 2.15E−04 | 4.40E−09 | 1.69E+05 | 5.62E−07 | 3.32E−12 |
| CAN_09E09_1.2 | caninized | 2.86E+04 | 1.08E−03 | 3.77E−08 | 1.67E+05 | 1.84E−03 | 1.10E−08 |
| FEL_09E09_1.1 | felinized | 5.75E+04 | 1.05E−03 | 1.82E−08 | 1.27E+05 | 9.79E−04 | 7.73E−09 |
| FEL_10F07_1.2 | felinized | 6.65E+04 | 8.85E−04 | 1.33E−08 | 1.28E+05 | 6.10E−04 | 4.75E−09 |
| FEL_10F07_2.1 | felinized | 8.50E+04 | 8.51E−04 | 1.00E−08 | 1.91E+05 | 4.20E−04 | 2.20E−09 |
| FEL_10F07_2.2 | felinized | 1.81E+05 | 9.03E−04 | 4.99E−09 | 3.76E+05 | 4.57E−04 | 1.21E−09 |

TABLE 6-continued

Biacore binding data for caninized and felinized anti-OSMR antibodies to canine and feline OSMR. Experimental controls show binding of an anti-human OSMR antibody to human OSMR only. None of the mouse progenitor mAbs with these CDRs showed binding to human OSMR (see Table 1). Non-transfected controls were grown and purified identically to these speciated recombinant mAbs without a plasmid to express a functional antibody. cOSM binding shows these three OSMR receptor forms are capable of binding to the canine form of the OSM protein. Ctrl-HBS-EP is a buffer control for the Biacore instrument.

| | | Canine OSMR (SEQ ID NO: 107) | | | Feline OSMR (SEQ ID NO: 112) | | | Human OSMR (SEQ ID NO: 122) | | |
|---|---|---|---|---|---|---|---|---|---|---|
| Sample ID | Sample type | ka ($M^{-1} s^{-1}$) | kd ($s^{-1}$) | KD (M) | ka ($M^{-1} s^{-1}$) | kd ($s^{-1}$) | KD (M) | ka ($M^{-1} s^{-1}$) | kd ($s^{-1}$) | KD (M) |
| anti-hOSMR | control antibody | | No binding | | | No binding | | 2.15E+05 | 2.03E−05 | 9.42E−11 |
| Not Transfected | control | | No binding | | | No binding | | | No binding | |
| cOSM | SEQ ID NO: 109 | 6.87E+04 | 3.00E−03 | 4.36E−08 | 1.03E+05 | 4.23E−03 | 4.11E−08 | 1.02E+05 | 3.90E−03 | 3.81E−08 |
| Ctrl-HBS-EP | control | | No binding | | | No binding | | | No binding | |

Example 18. Mutational Analysis of Anti-OSMR CDRs Using Alanine Substitution To establish a functional relationship between each amino acid residue on an antibodies CDR and the involvement of that residue in binding of the antibody to its target protein, an alanine replacement mutational analysis was performed. Individual mammalian expression plasmids containing the heavy and light chain mouse variable sequence were synthesized for four of the five anti-OSMR antibodies described in Table 1 (alanine replacement for antibody Mu_14C04 was not done). The variable heavy and variable light chains were cloned with the heavy and light chain canine constant regions respectively as described herein for the generation of chimeric antibodies (Example 7). Expression and purification of these chimeric antibodies was carried out according to the procedures descried herein (Example 1). For comparative analysis, each chimera was made without any changes from the initial mouse variable heavy and variable light chain sequence (wildtype). For each mutant, an individual plasmid was generated substituting alanine for each non-alanine residue of each heavy and light variable chain CDR position. Each plasmid containing a single alanine substitution at a single position of each CDR was paired with the wildtype plasmid of the corresponding heavy or light chain and expressed using a transient CHO cell system.

Example 19. ELISA and Biacore Binding Results for Alanine Mutants of Anti-OSMR Antibodies The objective of alanine replacement mutational analysis is to further understand the involvement of individual CDR amino acid residues in binding to the OSMR target protein. A single substitution in a CDR amino acid residue to alanine may result in a functional change whereby the binding of the antibody to its target is negatively impacted (meaning there is less binding, or lower binding affinity, or lower ELISA signal, to the antibodies protein target compared to that of the wildtype antibody which contains no CDR substitutions). An assessment of binding for each alanine mutant was performed using an indirect ELISA where the feline OSMR protein (SEQ ID NO: 112) was passively immobilized to a polystyrene ELISA plate. The ELISAs were performed according to standard procedures of blocking and washing with one hour incubation times between steps. To determine binding, each wildtype or mutant antibody was added to individual wells of the ELISA plate as a purified antibody (pure antibody) or cell culture supernatant (supernatant) where indicated. As these antibodies were constructed as mouse:canine chimeras, a goat anti-canine HRP labeled secondary antibody was used to detect the amount of antibody bound to the feline OSMR protein after development using an HRP substrate. To determine whether antibody was produced from the transient CHO cultures a separate ELISA was performed using a mouse anti-canine antibody as a capture reagent on the ELISA plate. Each supernatant or pure antibody prep was added to an individual well and allowed to bind. The presence of antibody was determined using an HRP labeled goat anti-dog detection mAb (antibody expression control). The colorimetric signal produced by each ELISA plate was normalized to a background control which lacked the presence of the analyte. The data were expressed as a ratio of optical density (OD) from the ELISA with binding to feline OSMR (ELISA signal) to the OD from the antibody control plate (antibody expression control). The alanine mutations resulting in an OD ratio (ELISA signal/mAb control) less than or equal to 1.3 were considered to negatively impact binding. The OD ratio for each wildtype expression control was greater than 1.6. In general, most mutations that negatively impacted binding resulted in a OD ratio of less than 0.5 (Table A).

TABLE A

Summarizes the results from the ELISA and Biacore with the alanine replacement mutations on each CDR position for the four anti-OSMR chimeric antibodies described. The alanine replacement mutations indicated in the description column are numbered based on the position in the entire variable region which falls within the recited CDR (CDR column). The ELISA data are the ratio of signal produced by binding of alanine replacement mutants to feline OSMR. This ratio is the signal produced from binding to feline OSMR divided by the signal from the the antibody expression control (which indicates that recombinant antibody is present). Also shown here are Biacore binding kinetics to canine and feline OSMR with the corresponding signal from the expression control. The data shown in this table are from experiments using the same preparation of antibody (supernatant or pure antibody) and are only from those alanine replacement mutants where binding was binding was negatively impacted in the ELISA assay.

| | | ELISA RATIO BINDING TO: | ANTIBODY BINDING AFFINITY USING BIACORE, AFFINITY MEASURED TO: | | | |
|---|---|---|---|---|---|---|
| | | FELINE OSMR | cOSMR (SEQ ID NO: 107) | | | fOSMR (SEQ ID NO: 112) |
| DESCRIPTION | CDR | (SEQ ID NO: 112) | ka (1/Ms) | kd (1/s) | KD (M) | ka (1/Ms) |
| Mu_02D09_VH (SEQ ID NO: 31)_D31A | H1 | 0.159 | 9.08E+05 | 3.56E−03 | 3.92E−09 | 1.14E+06 |
| Mu_02D09_VH (SEQ ID NO: 31)_Y32A | H1 | 0.991 | 7.07E+05 | 2.46E−02 | 3.48E−08 | 1.20E+05 |
| Mu_02D09_VH (SEQ ID NO: 31)_G33A | H1 | 0.158 | | no binding | | 2.29E+05 |
| Mu_02D09_VH (SEQ ID NO: 31)_H35A | H1 | 0.030 | | no binding | | 1.34E+05 |
| Mu_02D09_VH (SEQ ID NO: 31)_Y50A | H2 | 0.009 | | no binding | | 1.00E+05 |
| Mu_02D09_VH (SEQ ID NO: 31)_S52A | H2 | 0.001 | | no binding | | 6.56E+05 |
| Mu_02D09_VH (SEQ ID NO: 31)_D62A | H2 | 0.010 | | no binding | | 1.09E+05 |
| Mu_02D09_VH (SEQ ID NO: 31)_D99A | H3 | 0.000 | | no binding | | 4.08E+05 |
| Mu_02D09_VH (SEQ ID NO: 31)_D100A | H3 | 0.009 | | no binding | | 1.40E+05 |
| Mu_02D09_VH (SEQ ID NO: 31)_Y101A | H3 | 0.320 | | no binding | | 1.69E+05 |
| Mu_02D09_VH (SEQ ID NO: 31)_D102A | H3 | 0.058 | | no binding | | 1.25E+05 |
| Mu_02D09_VH (SEQ ID NO: 31)_R104A | H3 | 0.000 | | no binding | | 1.29E+05 |
| Mu_02D09_VL (SEQ ID NO: 33)_Q27A | L1 | 0.025 | 1.26E+05 | 4.41E−03 | 3.50E−08 | 1.44E+05 |
| Mu_02D09_VL (SEQ ID NO: 33)_I29A | L1 | 0.377 | | no binding | | 1.55E+05 |
| Mu_02D09_VL (SEQ ID NO: 33)_S56A | L2 | 0.000 | 4.12E+04 | 6.53E−03 | 1.59E−07 | 1.16E+05 |
| Mu_02D09_VL (SEQ ID NO: 33)_W94A | L3 | 0.000 | | no binding | | 1.04E+05 |
| Mu_02D09_VL (SEQ ID NO: 33)_L96A | L3 | 1.267 | | no binding | | 4.40E+05 |
| Mu_02D09_wildtype | | 1.615 | 2.09E+04 | 1.18E−02 | 2.74E−06 | 1.31E+05 |
| Mu_09E09_VH (SEQ ID NO: 35)_S35A | H1 | 1.049 | | no binding | | 7.56E+05 |
| Mu_09E09_VH (SEQ ID NO: 35)_Y50A | H2 | 0.310 | | no binding | | 6.22E+05 |
| Mu_09E09_VH (SEQ ID NO: 35)_Y57A | H2 | 0.052 | | no binding | | 9.43E+05 |
| Mu_09E09_VH (SEQ ID NO: 35)_Y59A | H2 | 0.011 | | no binding | | no binding |
| Mu_09E09_VH (SEQ ID NO: 35)_D99A | H3 | 0.908 | | no binding | | 6.12E+05 |
| Mu_09E09_VH (SEQ ID NO: 35)_P100A | H3 | 0.946 | | no binding | | 7.29E+05 |
| Mu_09E09_VH (SEQ ID NO: 35)_I101A | H3 | 0.000 | | no binding | | no binding |
| Mu_09E09_VH (SEQ ID NO: 35)_T102A | H3 | 0.388 | | no binding | | 9.64E+05 |
| Mu_09E09_VH (SEQ ID NO: 35)_F105A | H3 | 0.256 | | no binding | | 7.72E+05 |
| Mu_09E09_VL (SEQ ID NO: 37)_Y32A | L1 | 0.092 | | no binding | | 2.51E+06 |
| Mu_09E09_VL (SEQ ID NO: 37)_N34A | L1 | 0.023 | | no binding | | 3.21E+05 |
| Mu_09E09_VL (SEQ ID NO: 37)_Y50A | L2 | 0.000 | | no binding | | no binding |

TABLE A-continued

Summarizes the results from the ELISA and Biacore with the alanine replacement mutations on each CDR position for the four anti-OSMR chimeric antibodies described. The alanine replacement mutations indicated in the description column are numbered based on the position in the entire variable region which falls within the recited CDR (CDR column). The ELISA data are the ratio of signal produced by binding of alanine replacement mutants to feline OSMR. This ratio is the signal produced from binding to feline OSMR divided by the signal from the the antibody expression control (which indicates that recombinant antibody is present). Also shown here are Biacore binding kinetics to canine and feline OSMR with the corresponding signal from the expression control. The data shown in this table are from experiments using the same preparation of antibody (supernatant or pure antibody) and are only from those alanine replacement mutants where binding was binding was negatively impacted in the ELISA assay.

| | | | | | | |
|---|---|---|---|---|---|---|
| Mu_09E09_VL (SEQ ID NO: 37)_Q90A | L3 | 0.183 | | no binding | | no binding |
| Mu_09E09_VL (SEQ ID NO: 37)_691A | L3 | 0.136 | | no binding | | 9.18E+05 |
| Mu_09E09_VL (SEQ ID NO: 37)_N92A | L3 | 0.015 | | no binding | | no binding |
| Mu_09E09_VL (SEQ ID NO: 37)_L94A | L3 | 0.055 | | no binding | | 2.68E+06 |
| Mu_09E09_VL (SEQ ID NO: 37)_W96A | L3 | 0.000 | | no binding | | no binding |
| Mu_09E09_wildtype | | 1.613 | 5.72E+05 | 2.10E−03 | 3.83E−09 | 7.59E+05 |
| Mu_10F07_VH (SEQ ID NO: 39)_D99A | H3 | 0.545 | 5.16E+04 | 5.76E−04 | 1.12E−08 | 2.21E+05 |
| Mu_10F07_VH (SEQ ID NO: 39)_I101A | H3 | 0.000 | | no binding | | 1.02E+05 |
| Mu_10F07_VH (SEQ ID NO: 39)_Y107A | H3 | 0.375 | 4.01E+04 | 6.76E−05 | 1.69E−09 | 1.73E+05 |
| Mu_10F07_VL (SEQ ID NO: 41)_L33A | L1 | 0.150 | 4.05E+04 | 2.22E−04 | 5.48E−09 | 1.79E+05 |
| Mu_10F07_VL (SEQ ID NO: 41)_Y50A | L2 | 0.000 | | no binding | | 2.42E+05 |
| Mu_10F07_VL (SEQ ID NO: 41)_T53A | L2 | 0.217 | 6.50E+04 | 2.56E−04 | 3.94E−09 | 2.55E+05 |
| Mu_10F07_VL (SEQ ID NO: 41)_W96A | L3 | 0.134 | 2.16E+08 | 8.63E+00 | 4.00E−08 | 2.25E+05 |
| Mu_10F07_VL (SEQ ID NO: 41)_T97A | L3 | 0.298 | 4.12E+04 | 2.19E−04 | 5.32E−09 | 1.72E+05 |
| Mu_10F07_wildtype | | 1.763 | 4.94E+04 | 3.02E−04 | 6.13E−09 | 2.20E+05 |
| Mu_19F07_VH (SEQ ID NO: 47)_Y33A | H1 | 1.058 | | no binding | | 2.66E+05 |
| Mu_19F07_VH (SEQ ID NO: 47)_S56A | H2 | 0.277 | | no binding | | no binding |
| Mu_19F07_VH (SEQ ID NO: 47)_Y59A | H2 | 0.740 | | no binding | | 3.51E+05 |
| Mu_19F07_VH (SEQ ID NO: 47)_Y60A | H2 | 0.479 | | no binding | | no binding |
| Mu_19F07_VH (SEQ ID NO: 47)_W102A | H3 | 0.057 | | no binding | | no binding |
| Mu_19F07_VH (SEQ ID NO: 47)_F104A | H3 | 0.982 | | no binding | | 1.44E+05 |
| Mu_19F07_VL (SEQ ID NO: 49)_L50A | L2 | 1.106 | | no binding | | 4.11E+04 |
| Mu_19F07_VL (SEQ ID NO: 49)_T53A | L2 | 0.821 | | no binding | | 1.69E+05 |
| Mu_19F07_VL (SEQ ID NO: 49)_Q89A | L3 | 0.985 | | no binding | | 4.65E+04 |
| Mu_19F07_VL (SEQ ID NO: 49)_Q90A | L3 | 1.084 | | no binding | | 2.73E+05 |
| Mu_19F07_VL (SEQ ID NO: 49)_F94A | L3 | 1.090 | | no binding | | 9.04E+04 |
| Mu_19F07_wildtype | | 1.724 | 8.84E+04 | 7.75E−04 | 7.49E−09 | 2.42E+05 |

| | fOSMR (SEQ ID NO: 112) | | ANTIBODY EXPRESSION CONTROL | | |
|---|---|---|---|---|---|
| DESCRIPTION | kd (1/s) | KD (M) | ka (1/Ms) | kd (1/s) | KD (M) |
| Mu_02D09_VH (SEQ ID NO: 31)_D31A | 8.72E−04 | 7.67E−10 | 1.21E+06 | 8.32E−05 | 6.85E−11 |
| Mu_02D09_VH (SEQ ID NO: 31)_Y32A | 7.65E−04 | 6.39E−09 | 1.21E+05 | 4.43E−05 | 3.66E−10 |
| Mu_02D09_VH (SEQ ID NO: 31)_G33A | 1.40E−03 | 6.13E−09 | 3.27E+05 | 7.35E−06 | 2.25E−11 |
| Mu_02D09_VH (SEQ ID NO: 31)_H35A | 1.08E−03 | 8.05E−09 | 1.39E+05 | 1.12E−04 | 8.03E−10 |
| Mu_02D09_VH (SEQ ID NO: 31)_Y50A | 1.20E−07 | 1.19E−12 | 1.42E+05 | 3.68E−07 | 2.59E−12 |
| Mu_02D09_VH (SEQ ID NO: 31)_S52A | 4.83E−04 | 7.36E−10 | 3.23E+05 | 7.55E−06 | 2.33E−11 |

TABLE A-continued

Summarizes the results from the ELISA and Biacore with the alanine replacement mutations on each CDR position for the four anti-OSMR chimeric antibodies described. The alanine replacement mutations indicated in the description column are numbered based on the position in the entire variable region which falls within the recited CDR (CDR column). The ELISA data are the ratio of signal produced by binding of alanine replacement mutants to feline OSMR. This ratio is the signal produced from binding to feline OSMR divided by the signal from the the antibody expression control (which indicates that recombinant antibody is present). Also shown here are Biacore binding kinetics to canine and feline OSMR with the corresponding signal from the expression control. The data shown in this table are from experiments using the same preparation of antibody (supernatant or pure antibody) and are only from those alanine replacement mutants where binding was binding was negatively impacted in the ELISA assay.

| | | | | | |
|---|---|---|---|---|---|
| Mu_02D09_VH (SEQ ID NO: 31)_D62A | 2.31E−07 | 2.11E−12 | 1.29E+05 | 2.45E−07 | 1.90E−12 |
| Mu_02D09_VH (SEQ ID NO: 31)_D99A | 4.63E−04 | 1.13E−09 | 2.35E+05 | 3.84E−04 | 1.63E−09 |
| Mu_02D09_VH (SEQ ID NO: 31)_D100A | 1.63E−03 | 1.16E−08 | 1.01E+05 | 1.71E−05 | 1.70E−10 |
| Mu_02D09_VH (SEQ ID NO: 31)_Y101A | 1.94E−03 | 1.15E−08 | 1.47E+05 | 4.11E−05 | 2.80E−10 |
| Mu_02D09_VH (SEQ ID NO: 31)_D102A | 1.74E−03 | 1.39E−08 | 1.35E+05 | 7.40E−05 | 5.47E−10 |
| Mu_02D09_VH (SEQ ID NO: 31)_R104A | 5.79E−05 | 4.49E−10 | 1.05E+05 | 2.41E−05 | 2.29E−10 |
| Mu_02D09_VL (SEQ ID NO: 33)_Q27A | 1.09E−03 | 7.57E−09 | 1.58E+05 | 1.90E−04 | 1.20E−09 |
| Mu_02D09_VL (SEQ ID NO: 33)_I29A | 1.13E−03 | 7.26E−09 | 1.33E+05 | 9.47E−05 | 7.14E−10 |
| Mu_02D09_VL (SEQ ID NO: 33)_S56A | 1.07E−03 | 9.30E−09 | 1.32E+05 | 1.11E−04 | 8.44E−10 |
| Mu_02D09_VL (SEQ ID NO: 33)_W94A | 7.94E−08 | 7.65E−13 | 3.23E+05 | 3.16E−05 | 9.77E−11 |
| Mu_02D09_VL (SEQ ID NO: 33)_L96A | 2.85E−07 | 6.48E−13 | 3.70E+05 | 2.43E−05 | 6.59E−11 |
| Mu_02D09_wildtype | 1.19E−03 | 9.08E−09 | 1.53E+05 | 9.15E−05 | 6.00E−10 |
| Mu_09E09_VH (SEQ ID NO: 35)_S35A | 1.04E−03 | 1.37E−09 | 2.97E+05 | 5.34E−05 | 1.80E−10 |
| Mu_09E09_VH (SEQ ID NO: 35)_Y50A | 1.77E−03 | 2.85E−09 | 3.01E+05 | 5.40E−05 | 1.79E−10 |
| Mu_09E09_VH (SEQ ID NO: 35)_Y57A | 2.40E−03 | 2.54E−09 | 3.05E+05 | 6.34E−05 | 2.08E−10 |
| Mu_09E09_VH (SEQ ID NO: 35)_Y59A | no binding | | 3.07E+05 | 4.52E−05 | 1.47E−10 |
| Mu_09E09_VH (SEQ ID NO: 35)_D99A | 1.08E−03 | 1.76E−09 | 3.14E+05 | 6.88E−05 | 2.19E−10 |
| Mu_09E09_VH (SEQ ID NO: 35)_P100A | 9.26E−04 | 1.27E−09 | 3.00E+05 | 2.35E−05 | 7.86E−11 |
| Mu_09E09_VH (SEQ ID NO: 35)_I101A | no binding | | 3.14E+05 | 5.40E−05 | 1.72E−10 |
| Mu_09E09_VH (SEQ ID NO: 35)_T102A | 1.87E−03 | 1.94E−09 | 3.11E+05 | 5.33E−05 | 1.72E−10 |
| Mu_09E09_VH (SEQ ID NO: 35)_F105A | 1.86E−03 | 2.40E−09 | 3.38E+05 | 4.66E−05 | 1.38E−10 |
| Mu_09E09_VL (SEQ ID NO: 37)_Y32A | 1.58E−03 | 6.32E−10 | 2.98E+05 | 8.76E−05 | 2.94E−10 |
| Mu_09E09_VL (SEQ ID NO: 37)_N34A | 1.61E−03 | 5.02E−09 | 2.81E+05 | 8.91E−05 | 3.17E−10 |
| Mu_09E09_VL (SEQ ID NO: 37)_Y50A | no binding | | 3.10E+05 | 7.96E−05 | 2.57E−10 |
| Mu_09E09_VL (SEQ ID NO: 37)_Q90A | no binding | | 2.86E+05 | 7.12E−05 | 2.49E−10 |
| Mu_09E09_VL (SEQ ID NO: 37)_G91A | 2.03E−03 | 2.21E−09 | 2.92E+05 | 8.96E−05 | 3.06E−10 |
| Mu_09E09_VL (SEQ ID NO: 37)_N92A | no binding | | 2.96E+05 | 7.59E−05 | 2.57E−10 |
| Mu_09E09_VL (SEQ ID NO: 37)_L94A | 1.67E−03 | 6.21E−10 | 3.05E+05 | 7.63E−05 | 2.50E−10 |
| Mu_09E09_VL (SEQ ID NO: 37)_W96A | no binding | | 2.83E+05 | 9.76E−05 | 3.45E−10 |
| Mu_09E09_wildtype | 9.45E−04 | 1.24E−09 | 3.74E+05 | 8.68E−07 | 2.30E−12 |
| Mu_10F07_VH (SEQ ID NO: 39)_D99A | 7.04E−04 | 3.18E−09 | 1.17E+05 | 1.18E−04 | 1.01E−09 |
| Mu_10F07_VH (SEQ ID NO: 39)_I101A | 7.01E−04 | 6.88E−09 | 1.01E+05 | 4.49E−05 | 4.45E−10 |
| Mu_10F07_VH (SEQ ID NO: 39)_Y107A | 2.47E−04 | 1.43E−09 | 9.95E+04 | 4.44E−05 | 4.46E−10 |
| Mu_10F07_VL (SEQ ID NO: 41)_L33A | 2.74E−04 | 1.53E−09 | 1.04E+05 | 8.43E−05 | 8.12E−10 |
| Mu_10F07_VL (SEQ ID NO: 41)_Y50A | 1.73E−06 | 7.14E−12 | 1.74E+05 | 1.05E−04 | 6.00E−10 |

TABLE A-continued

Summarizes the results from the ELISA and Biacore with the alanine replacement mutations on each CDR position for the four anti-OSMR chimeric antibodies described. The alanine replacement mutations indicated in the description column are numbered based on the position in the entire variable region which falls within the recited CDR (CDR column). The ELISA data are the ratio of signal produced by binding of alanine replacement mutants to feline OSMR. This ratio is the signal produced from binding to feline OSMR divided by the signal from the the antibody expression control (which indicates that recombinant antibody is present). Also shown here are Biacore binding kinetics to canine and feline OSMR with the corresponding signal from the expression control. The data shown in this table are from experiments using the same preparation of antibody (supernatant or pure antibody) and are only from those alanine replacement mutants where binding was binding was negatively impacted in the ELISA assay.

| | | | | | |
|---|---|---|---|---|---|
| Mu_10F07_VL (SEQ ID NO: 41)_T53A | 4.68E−04 | 1.83E−09 | 1.32E+05 | 2.75E−04 | 2.07E−09 |
| Mu_10F07_VL (SEQ ID NO: 41)_W96A | 1.58E−03 | 7.03E−09 | 1.07E+05 | 9.49E−05 | 8.84E−10 |
| Mu_10F07_VL (SEQ ID NO: 41)_T97A | 2.82E−04 | 1.63E−09 | 1.00E+05 | 8.07E−05 | 8.05E−10 |
| Mu_10F07_wildtype | 3.46E−04 | 1.57E−09 | 1.34E+05 | 8.27E−05 | 6.17E−10 |
| Mu_19F07_VH (SEQ ID NO: 47)_Y33A | 1.08E−04 | 4.07E−10 | 3.01E+05 | 6.08E−05 | 2.02E−10 |
| Mu_19F07_VH (SEQ ID NO: 47)_S56A | no binding | | 1.59E+05 | 6.46E−04 | 4.08E−09 |
| Mu_19F07_VH (SEQ ID NO: 47)_Y59A | 1.41E−04 | 4.00E−10 | 3.24E+05 | 1.16E−04 | 3.59E−10 |
| Mu_19F07_VH (SEQ ID NO: 47)_Y60A | no binding | | 1.50E+05 | 6.10E−04 | 4.06E−09 |
| Mu_19F07_VH (SEQ ID NO: 47)_W102A | no binding | | 3.12E+05 | 4.35E−05 | 1.39E−10 |
| Mu_19F07_VH (SEQ ID NO: 47)_F104A | 5.10E−10 | 3.55E−15 | 3.26E+05 | 5.09E−05 | 1.56E−10 |
| Mu_19F07_VL (SEQ ID NO: 49)_L50A | 5.86E−07 | 1.43E−11 | 2.93E+05 | 4.80E−05 | 1.64E−10 |
| Mu_19F07_VL (SEQ ID NO: 49)_T53A | 9.05E−07 | 5.36E−12 | 3.05E+05 | 3.75E−05 | 1.23E−10 |
| Mu_19F07_VL (SEQ ID NO: 49)_Q89A | 2.38E−06 | 5.11E−11 | 3.19E+05 | 4.30E−05 | 1.35E−10 |
| Mu_19F07_VL (SEQ ID NO: 49)_Q90A | 1.31E−07 | 4.80E−13 | 3.29E'005 | 5.29E−05 | 1.61E−10 |
| Mu_19F07_VL (SEQ ID NO: 49)_F94A | 4.70E−07 | 5.20E−12 | 3.35E+05 | 5.35E−05 | 1.60E−10 |
| Mu_19F07_wildtype | 8.06E−05 | 3.12E−10 | 2.81E+05 | 2.29E−05 | 8.20E−11 |

The Biacore data in Table A shows kinetic binding data for each alanine replacement mutation where binding was negatively impacted in the feline OSMR ELISA experiment. Data from an ELISA represents an equilibrium state where the antibody is allowed to associate and dissociate over a one-hour period resulting in steady-state binding. Using Biacore, the target protein is immobilized to a surface and the antibody is passed over this surface in a mobile liquid phase. Protein-protein interaction is determined from changes in the surface resonance which allows for calculation of association ($k_a$), disassociation ($k_d$), and affinity constant (KD). While not wishing to be bound to one hypothesis we present data from ELISA and Biacore experiments, using the same preparation of antibody, that may result in agreement between the two methods with respect to binding but also may show contradictory results due to the nature of the binding kinetics and different assay dynamics. The data presented in Table A (in combination with experimental results from yeast display mutational analysis in Example 21) allow for the definition of a structure:function relationship to be defined between the anti-OSMR antibodies described here and their ability to bind and block IL-31 and OSM-mediated signaling through the OSMR receptor.

Example 20. Method for Using Yeast Surface Display (YSD) Coupled to Mutational Scanning to Determine Structure-Function Relationship of Anti-OSMR CDR Residues To further define the amino acid residues in the anti-OSMR antibody 19F07 that are important for interaction with the OSMR protein target, an independent experimental method was employed which uses display of an antibodies variable domain on the surface of the yeast Saccharomyces cerevisiae. A mutational tolerance epitope mapping was carried out for antibody Mu_19F07 using the approach defined by Klesmith et al. (2019) *Biochemistry* 58, 4869-4881. Heavy and light chain variable domains were purchased as gBlocks (IDT) and linked via a $(G_4S)_4$ linker to construct the 19F07 single chain variable binding fragment (scFv). Genes were cloned using HiFi assembly into a minimal bacterial plasmid containing the BbvCI nicking restriction site (New England Biolabs). Using nicking mutagenesis, two single-site saturation libraries were created using this vector with two different oligo pools (IDT) encoding NNK codons for each codon position within the VH and VL domains separately (Wrenbeck et al. (2016) *Nature Methods* 13, 928-930). For all cloning steps, sufficient numbers of transformants were present to oversample the designed library (theoretical library size of 3744 and 3424 variants for the VH and VL library respectively). The parental unmutated scFv gBlock (wildtype), and VH and VL mutant libraries were PCR amplified and electroporated into EBY100 yeast with a linearized yeast surface display vector using homologous recombination. The linearized yeast display vector is a c-terminal display vector featuring a $(PAS)_{40}$-HA tag-$(G_4S)_3$ linker 5' of the gene insert and a myc tag 3' of the gene insert. The yeast cultures were grown in 50 mL synthetic defined media with glucose and casamino acids (SDCAA) at 30° C. for a day and passaged once in SDCAA for a second day of growth. Cell pellets were then transferred to 50 mL SGCAA (galactose) cultures at 18° C. for 2-3 days.

Sortable conditions were found via titrating recombinant canine OSMR-hFc1 on yeast displaying the parental sequence and reading the bound fraction using a flow cell analyzer (BD Accuri). Yeast cells displaying the parental scFv construct were titrated using a variable volume—constant protein to display ligand approach for a sufficient number of labelling days until the expected labelling fraction was 0.9. For all concentrations the protein to display ligand ratio was at least 10:1 and kept constant between conditions. The cells were stained with a chicken anti-myc FITC antibody (ICLlab) and protein A—AlexaFlour 647 to visualize full-length display and recombinant protein binding respectively. The median 647 fluorescence of full-length displaying cells calculated via FlowJo was utilized to calculate a binding profile of the ligands versus concentration. A labelling concentration of 100 nM ligand was used for both recombinant canine and feline OSMR for the two library sorts. Sorting of libraries was performed on a SH800 (Sony Biotechnology) in purity mode with a 100 μm chip. In short, cells were gated on scatter, single cells, full-length display, and then binding versus display. Cells below the binding versus display diagonal were collected (i.e. variants with reduced binding relative to the bulk population normalized for display). The number of cells collected for all sorts was greater than 67-fold coverage of their respective theoretical library size.

Sorted and reference libraries were prepared for Illumina sequencing and sequenced to a read depth of at least 75-fold oversampling of non-synonymous variants (Kowalsky et al. (2015) *PLOS ONE* 10, e0118193). Mutational fitness z-scores of the sorted versus reference libraries were calculated using PACT using a reference library read count threshold of 12 and excluding non-designed variants from the total read count (Klesmith et al. (2019) *Bioinformatics* 35, 2707-2712). Z-scores are defined as the $\log_2$ enrichment ratio of an individual mutation relative to the wild-type $\log_2$ enrichment, normalized by the variance of wild-type synonymous codon enrichment ($[\varepsilon_i-\varepsilon_{wt}]/\sigma_{wt,synon}$). A z-score threshold of 2.0 was utilized to separate enriched mutations collected via sorting that reduced binding from mutations that were tolerated. Tolerated mutations are therefore defined as mutations with a z-score less than 2.0.

Example 21. Results from YSD to Determine Amino Acid Residues on Anti OSMR Antibodies Important for Binding to Canine and Feline OSMR The results from these yeast display experiments describe an additional approach to determine relevant amino acid residues in the CDR binding domains of antibody 19F07. As described in Example 19, each independent method of analyzing alteration in affinity of an antibody is subject to the experimental dynamics which take place during binding and disassociation events. Yeast display mutational analysis of an antibodies paratope takes place in a fluid phase environment with the binding portion of the antibody (the ScFv) displayed on the surface of the yeast cell allowing access to the target antigen protein while linking the genotypic information encoding the mutation within the cell. This allows for a link between the physical properties of the binding fragment displayed and the DNA which encodes the variable heavy and light chain fragments. This method not only allows for the coupling of an individual mutation at an individual position of the CDR with binding to the target protein but also allows for analysis of all amino acid mutations at individual positions of each CDR. These data allow for determining those mutations which are permissible (allow binding), non-permissible (negatively impact binding), or in some circumstances are advantageous to binding (gain of function mutations).

Table B describes mutations in the CDRs of antibody Mu_19F07 which are allowed according to the results of the yeast surface display experiment. Data for substitution of all amino acids at each position were derived from this experiment however this table only shows those mutations at the described positions where a smaller subset of amino acids are allowed in place of the wildtype amino acid. These amino acid positions where few (or no) amino acid substitutions are allowed indicate that (by this method of binding to the target OSMR protein) these positions are more relevant to link the structure of the antibodies CDR to the functional outcome (binding to OSMR). Taken with the results from the alanine substitution ELISA and Biacore experiments, a more complete picture of the necessary structural elements on these anti-OSMR antibodies is observed.

TABLE B

Results from yeast display mutational analysis of each CDR on antibody 19F07 showing permissible (allow binding) substitutions at each indicated position. The results described here are from those mutations at amino acids positions where a limited number of allowed substitutions occurred which impact binding and not from those positions where many allowable substitutions occur.

| SEQ ID NO: | SEQUENCE DEFINITION WITH ALLOWED SUBSTITUTIONS | DESCRIPTION WITH (BINDING TARGET PROTEIN) |
|---|---|---|
| 25 | $D_1Y_2Y_3M_4A_5$ wherein $Y_3$ is Y | CDR-H1 (canine OSMR) |
| 26 | $N_1I_2N_3Y_4D_5G_6S_7S_8T_9Y_{10}Y_{11}L_{12}D_{13}S_{14}L_{15}K_{16}S_{17}$ wherein $Y_{10}$ is Y, C, F, H, T, or W | CDR-H2 (canine OSMR) |
| 27 | $G_1L_2T_3W_4D_5F_6D_7V_8W_9$ wherein $W_4$ is W, G, or C | CDR-H3 (canine OSMR) |
| 27 | $G_1L_2T_3W_4D_5F_6D_7V_8W_9$ wherein $W_4$ is W, G, or F | CDR-H3 (feline OSMR) |
| 28 | $K_1A_2S_3Q_4D_5V_6D_7T_8A_9V_{10}A_{11}$ wherein $V_6$ is V, L, M, A, N, S, E, I, H, or C; $D_7$ is D, G, Y, N, or E; $A_9$ is A, S, or G; $V_{10}$ is V, L, L, A, D, T, M, or C; $A_{11}$ is A, S, T, G, or C | CDR-L1 (canine OSMR) |
| 28 | $K_1A_2S_3Q_4D_5V_6D_7T_8A_9V_{10}A_{11}$ wherein $V_6$ is V, L, M, A, G, N, T, S, P, I, F, or H; $D_7$ is D, G, Y, N, | CDR-L1 (feline OSMR) |

TABLE B-continued

Results from yeast display mutational analysis of each CDR on antibody 19F07 showing permissible (allow binding) substitutions at each indicated position. The results described here are from those mutations at amino acids positions where a limited number of allowed substitutions occurred which impact binding and not from those positions where many allowable substitutions occur.

| SEQ ID NO: | SEQUENCE DEFINITION WITH ALLOWED SUBSTITUTIONS | DESCRIPTION WITH (BINDING TARGET PROTEIN) |
|---|---|---|
| | E, S, R, A, L, M, H, T, Q, I, or W; $A_9$ is A, S, V, T, or G; $V_{10}$ is V, L, F, I, A, S, G, T, M, Q, N, or C; $A_{11}$ is A, S, T, V, G, C, N, or D | |
| 29 | $L_1A_2S_3T_4R_5H_6T_7$ wherein $L_1$ is L, S, F, M, A, G, or Q; $A_2$ is A, S, V, G, D, P, T, L, E, or C | CDR-L2 (canine OSMR) |
| 29 | $L_1A_2S_3T_4R_5H_6T_7$ wherein $A_2$ is A, S, V, G, D, T, L, E, R, C, Y | CDR-L2 (feline OSMR) |
| 30 | $Q_1Q_2Y_3S_4R_5F_6P_7L_8T_9F_{10}$ wherein $Q_1$ is Q, S, H, K, E, G, M, A, N, F, or Y; $Q_2$ is Q or H; $Y_3$ is Y or F; $S_4$ is S, I, N, A, or T; $F_6$ is F, L, I, V, Y, M, E, W, or D; $P_7$ is P, S, C, A, G, or D; $L_8$ is L, R, P, M, S, V, I, W, F, or E; $F_{10}$ is F, L, M, I, Y, or W | CDR-L3 (canine OSMR) |
| 30 | $Q_1Q_2Y_3S_4R_5F_6P_7L_8T_9F_{10}$ wherein $Q_1$ is Q, L, S, H, K, V, E, G, M, A, T, N, F, Y, or C; $Q_2$ is Q, M, H, S, Y, T, N, F, E, C, or A; $Y_3$ is Y, L, R, M, F, W, H, I, or N; $P_7$ is P, S, H, T, R, C, A, G, or D | CDR-L3 (feline OSMR) |

Example 22. Results from YSD to Determine Amino Acid Residues on OSMR Involved with Anti-OSMR Antibody Binding Example 20 describes the method used to determine amino acid residues on the binding paratope of antibody 19F07 that are important for interaction with canine and feline OSMR. A similar method was used to determine the amino acid residues on feline OSMR that interact with feline IL-31. Feline OSMR (SEQ ID NO: 112 (Feline_OSMR_hlgG1_Fc)) was displayed on the surface of yeast in its wildtype form and conditions of binding to feline IL-31 (SEQ ID NO:125) were optimized. A mutational library of feline OSMR was generated as described and flow cytometry sorting coupled with deep sequencing was carried out to determine mutations on feline OSMR defining relevant amino acid contacts that are made with feline IL-31. These data reveal the epitope for binding of feline IL-31 to feline OSMR is a region on feline OSMR located between Leucine 157 (L157) to Phenylalanine 229 (F229) of SEQ ID NO: 112 (data not shown). It is important to note that these data support the homology model put forth in Example 10 of this application. This homology model describes a region where canine and feline OSM interact with OSMR. Functional data from cell-based assays described herein indicate these select anti-OSMR antibodies have inhibitory properties against both IL-31 and OSM-mediated pSTAT3 signaling indicating a close proximity in the binding site of IL-31 and OSM on the OSMR protein. These mapping data do indeed support a similar binding site of feline IL-31 on feline OSMR as that proposed by the homology model of canine and feline OSM on their respective OSMR proteins. Taken together these results support knowledge of the relevant epitope space on canine and feline OSMR required for binding of an antibody to inhibit the signaling function of the OSMR in vivo.

Example 23. A Pro-Inflammatory Role of Canine OSM in Canine Synoviocytes

Figure 9A:
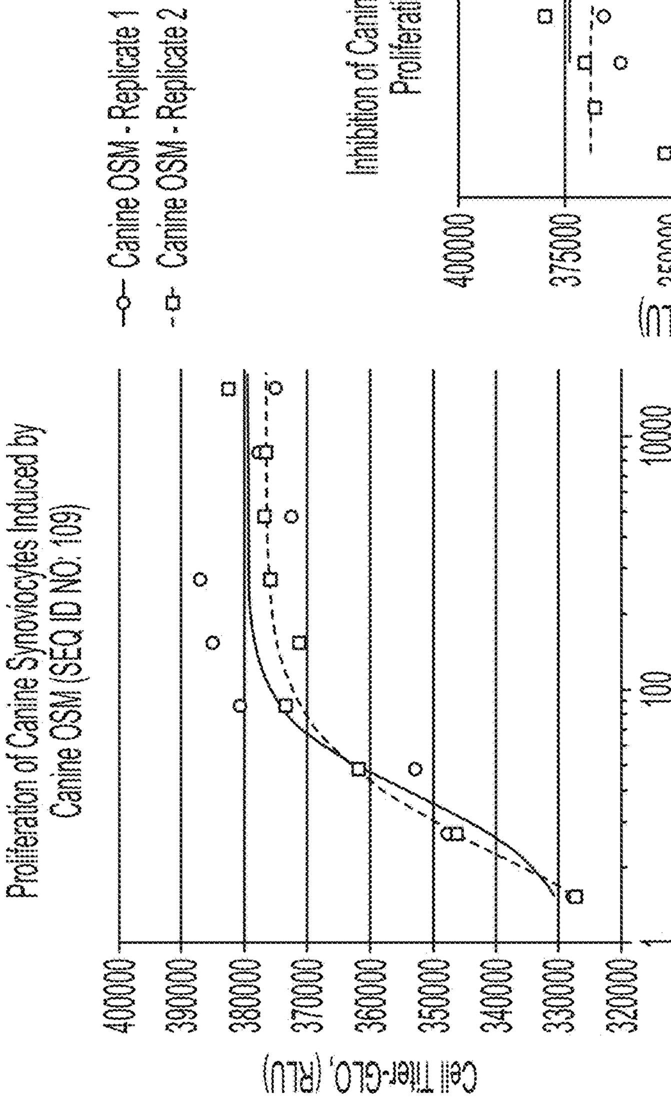
FIG. 9A shows the proliferation of canine synoviocytes in response to an increasing dose of the canine OSM protein over a 24-hour time period.
Figure 9B:
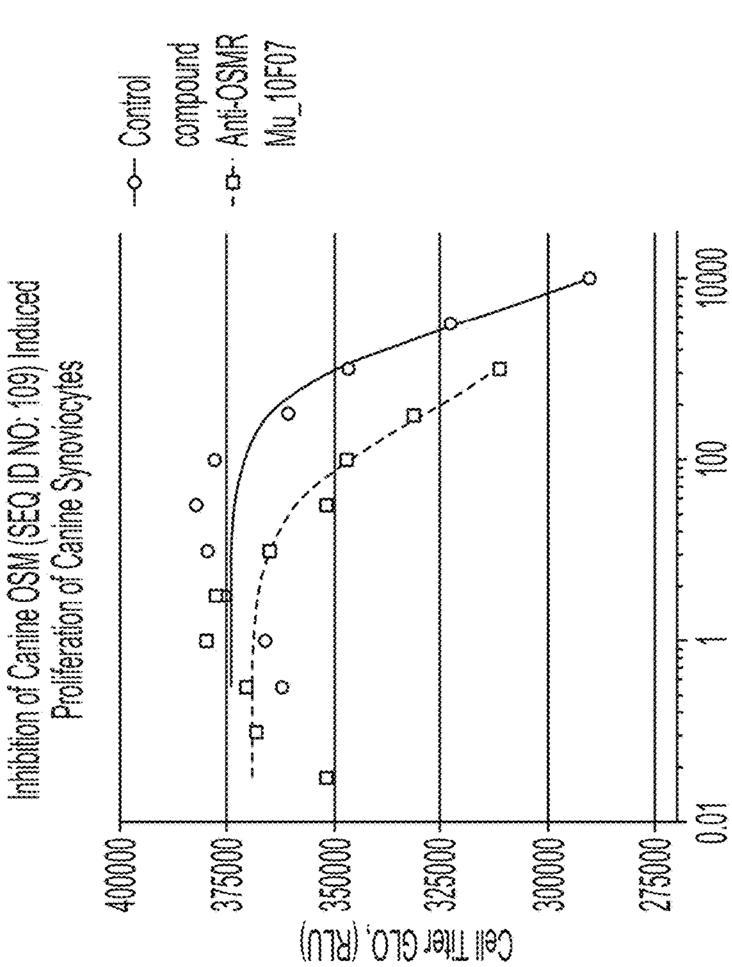
FIG. 9B shows the inhibition of OSM-induced canine synoviocyte proliferation with the anti-OSMR mouse antibody 10F07 (described herein) compared to a control antibody (also 24-hour incubation).
Figure 10A:
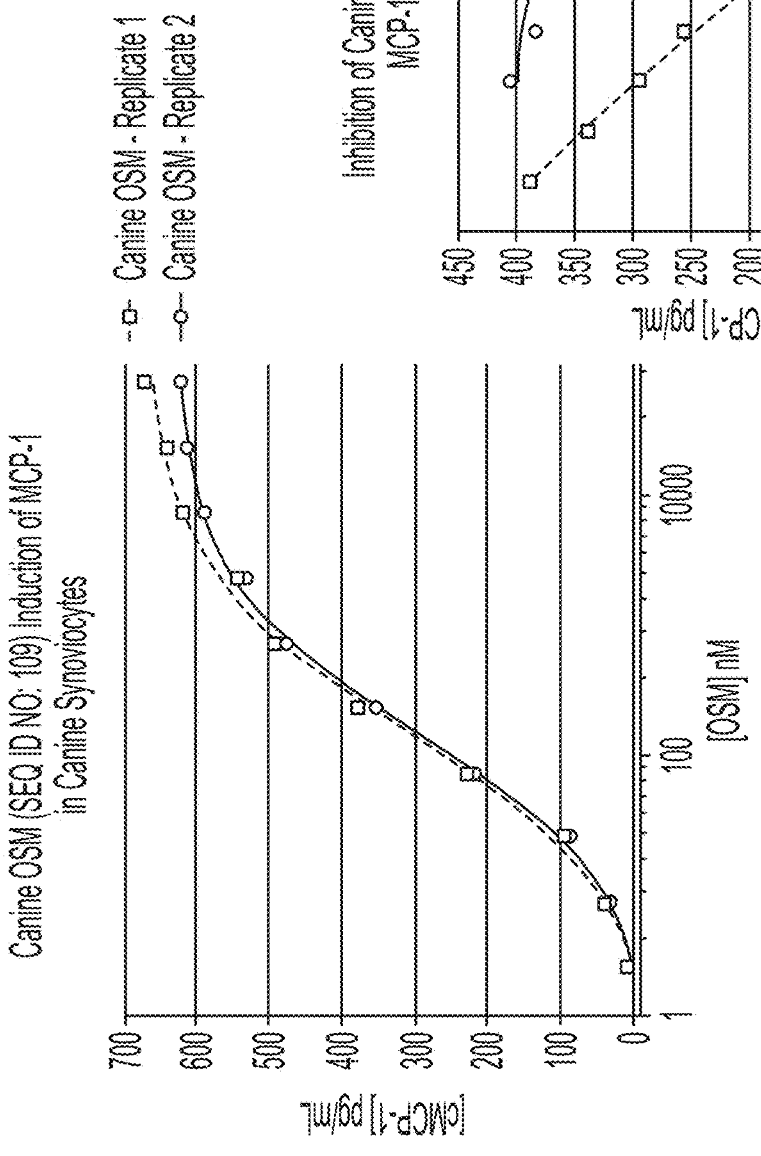
FIG. 10A shows the induction of the canine MCP-1 protein in canine synoviocytes in response to an increasing dose of the canine OSM protein over a 24-hour time period.
Figure 10B:
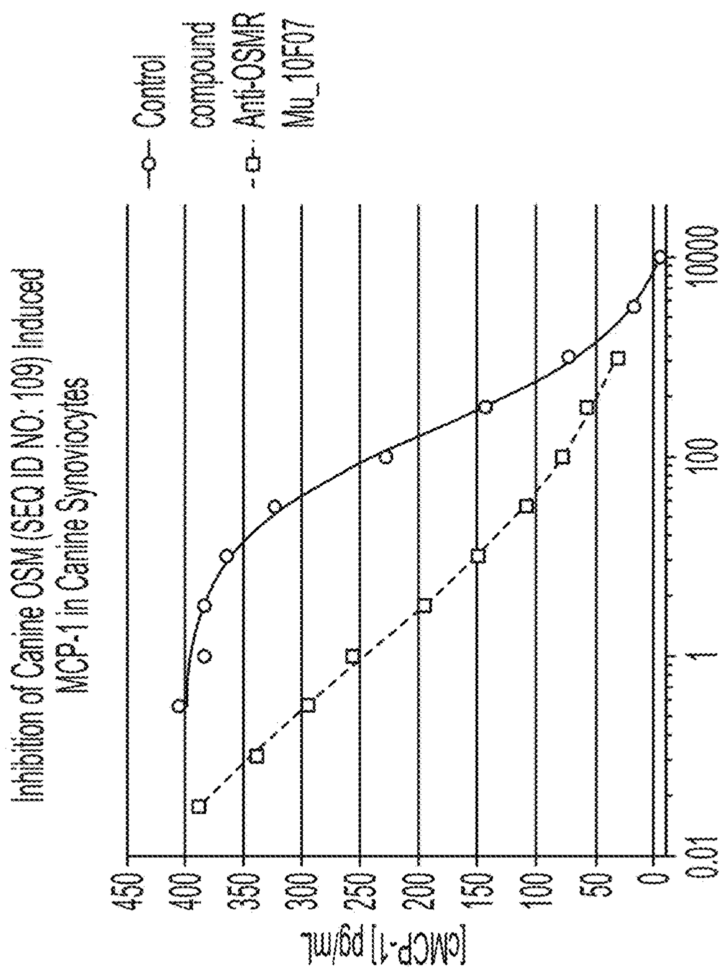
FIG. 10B shows the inhibition of OSM-induced canine synoviocyte MCP-1 production with the anti-OSMR mouse antibody 10F07 (described herein) compared to a control antibody (also 24-hour incubation).

Antagonism of OSMR signaling has proven effective at inhibiting downstream activation of Monocyte Chemoattractant Protein-1 (MCP-1) in canine chondrocytes and canine joint-derived synovial cells and significantly decreases Oncostatin M (OSM) induced cell proliferation in joint-derived synovial cells in vitro indicating a potential novel therapeutic for reduction in pain and inflammation in vivo. Anti-OSMR monoclonal antibodies represent a new class of novel therapeutics that block OSM signaling for alleviating pain and inflammation associated with canine and feline osteoarthritis (OA). For determining in vitro potency, anti-OSMR antibodies were evaluated for functional activity in joint-derived synovial cells in proliferation and inhibition cell-based assays. A CellTiter-GLO luminescent cell viability assay kit was employed to evaluate the effects of anti-OSMR mAbs on canine OSM induced cell proliferation. The primary canine joint-derived synovial cells were isolated and determined to respond to OSM stimulation by activating STAT-3 pathway and to a lesser extent STAT-5, and STAT-1. Canine joint-derived synoviocytes respond to OSM stimulation by rapid proliferation in 24 and 72 hours when plated on collagen type-1 coated plates (FIG. 9A). The anti-OSMR antibody Mu_10F07 potently inhibited OSM-induced cell proliferation in canine joint-derived synovial cells (FIG. 9B). Canine synoviocytes also respond to OSM stimulation by rapidly synthesizing MCP-1 which recruits monocytes, macrophages, dendritic cells, and T cells to sites of active inflammation (FIG. 10A). The anti-OSMR antibody 10F07 dose-dependently reduced canine OSM-induced MCP-1 synthesis. Overall, results from these in vitro studies confirm functional activity relevant to an anti-inflammatory role of blocking OSMR signaling using novel anti-OSMR antibodies.

Example 24. The Pro-Fibrotic Role of OSM

Figure 11:
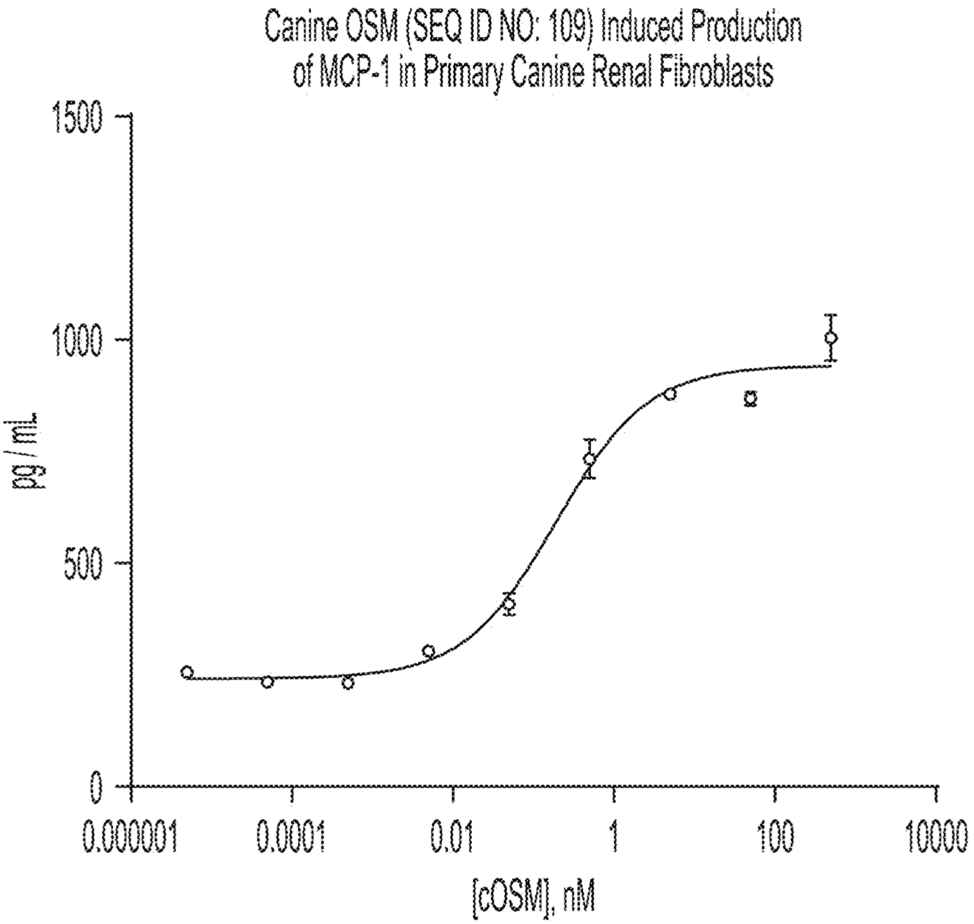
FIG. 11 shows the induction of the canine MCP-1 protein in primary canine renal fibroblasts in response to an increasing dose of the canine OSM protein over a 72-hour time period.

Activation of MCP-1 in canine primary canine renal fibroblasts was determined to investigate the role of OSM in renal fibrosis relevant to chronic kidney disease in dogs and cats. Canine OSM (SEQ ID NO:109) showed a dose dependent increase in MCP-1 levels over a 72 hour time period (FIG. 11). Blockade of this chemoattractant protein in renal fibroblasts with an anti-OSMR antibody may be beneficial in altering the progression of fibrotic disease.

Example 25. Evaluation of Anti-Canine OSMR mAbs in a Canine Model of IL-31-Induced Pruritus IL-31 challenge procedures were conducted on Days−7 to establish baseline pruritic scores and Day 7. The intravenous solution was prepared from stock concentrations of canine recombinant IL-31. Recording of pruritic activity for all dogs began after the challenge had been administered to the last dog on Study Days−7 and 7. Individuals administering the IL-31 challenge that were masked to treatment allocation could also record pruritic activity.

A pruritus score was determined for (Post Challenge Period) for each dog using the following categorical scoring system. Specifically, at consecutive 1-minute intervals, "yes"/"no" decisions were made regarding whether a pruritic behavior was displayed by each dog. Displays of the following pruritic behavior were enough to elicit a "yes" response over each discrete 1-minute time interval within an observation period. These behaviors include, licking or chewing (e.g., of paws, flank, tail, anal region), scratching (e.g., of flank or neck), headshaking or body-shaking, and rubbing any part of the body (e.g., on the cage flooring/walls). A "yes" response was indicated by marking a "1" and a "no" response was indicated by marking a "0" in the space provided for the specific 1-minute interval. The cumulative number of yes responses determined the Pruritus Score. A live feed camera located directly above each pen in the Surveillance Room allowed the scorers to observe the dogs from a separate room. Each scorer observed 4 dogs simultaneously with a real time image of each dog displayed on a single monitor. The maximum possible Post Challenge Pruritus score for an animal over the 120-minute period was 120. After completion of the observation period, the dogs were returned to their normal housing locations.

Pruritus Score for each animal was calculated as the total number of one-minute time segments pruritus behavior was observed for each time point (Days−7 and 7). A paired t-test was used to test for differences in means between Day −7 and Day 7 pruritic scores. Mouse:canine chimeric anti-OSMR antibodies 19F07 (T01) and 10F07 (T02) were administered as a single SC injection at 12.0 mg/kg and pruritic responses were observed 7 days post dosing. FIG. 12 shows the post challenge scores for the total 2-hour observation periods on Study Day −7 and Study Day 7. These results demonstrate that a single subcutaneous 12 mg/kg dose of chimeric 19F07 and 10F07 showed a significantly lower total pruritus score at Study Day 7 in a canine model of IL-31 induced pruritus compared to pruritus scores recorded on Study Day −7.

SEQUENCE LISTING

```
<160> NUMBER OF SEQ ID NOS: 136

<210> SEQ ID NO 1
<211> LENGTH: 5
<212> TYPE: PRT
<213> ORGANISM: Mus musculus

<400> SEQUENCE: 1

Asp Tyr Gly Met His
1               5


<210> SEQ ID NO 2
<211> LENGTH: 17
<212> TYPE: PRT
<213> ORGANISM: Mus musculus

<400> SEQUENCE: 2

Tyr Ile Ser Ser Gly Ser Arg Ala Val Phe Phe Ala Asp Thr Val Lys
1               5                   10                  15

Gly


<210> SEQ ID NO 3
<211> LENGTH: 10
<212> TYPE: PRT
<213> ORGANISM: Mus musculus

<400> SEQUENCE: 3

Asp Arg Tyr Asp Gly Arg Gly Phe Ala Tyr
1               5                   10


<210> SEQ ID NO 4
<211> LENGTH: 11
<212> TYPE: PRT
<213> ORGANISM: Mus musculus

<400> SEQUENCE: 4

Arg Ala Ser Gln Ser Ile Ser Asn Asn Leu His
1               5                   10
```

<210> SEQ ID NO 5
<211> LENGTH: 7
<212> TYPE: PRT
<213> ORGANISM: Mus musculus

<400> SEQUENCE: 5

Tyr Ala Ser Gln Ser Ile Ser
1 5

<210> SEQ ID NO 6
<211> LENGTH: 9
<212> TYPE: PRT
<213> ORGANISM: Mus musculus

<400> SEQUENCE: 6

Gln Gln Ser Asn Ser Trp Pro Leu Thr
1 5

<210> SEQ ID NO 7
<211> LENGTH: 5
<212> TYPE: PRT
<213> ORGANISM: Mus musculus

<400> SEQUENCE: 7

Ser Tyr Ala Met Ser
1 5

<210> SEQ ID NO 8
<211> LENGTH: 17
<212> TYPE: PRT
<213> ORGANISM: Mus musculus

<400> SEQUENCE: 8

Tyr Ile Ser Ser Gly Gly Asp Tyr Ile Tyr Tyr Ala Asp Thr Val Lys
1 5 10 15

Gly

<210> SEQ ID NO 9
<211> LENGTH: 9
<212> TYPE: PRT
<213> ORGANISM: Mus musculus

<400> SEQUENCE: 9

Asp Pro Ile Thr Gly Thr Phe Ala Tyr
1 5

<210> SEQ ID NO 10
<211> LENGTH: 11
<212> TYPE: PRT
<213> ORGANISM: Mus musculus

<400> SEQUENCE: 10

Arg Ala Ser Gln Asp Ile Asn Asn Tyr Leu Asn
1 5 10

<210> SEQ ID NO 11
<211> LENGTH: 7
<212> TYPE: PRT
<213> ORGANISM: Mus musculus

<400> SEQUENCE: 11

Tyr Thr Ser Thr Leu His Ser
1 5

<210> SEQ ID NO 12
<211> LENGTH: 9
<212> TYPE: PRT
<213> ORGANISM: Mus musculus

<400> SEQUENCE: 12

```
Gln Gln Gly Asn Thr Leu Pro Trp Thr
1               5
```

<210> SEQ ID NO 13
<211> LENGTH: 5
<212> TYPE: PRT
<213> ORGANISM: Mus musculus

<400> SEQUENCE: 13

```
Ser Tyr Ala Met Ser
1               5
```

<210> SEQ ID NO 14
<211> LENGTH: 17
<212> TYPE: PRT
<213> ORGANISM: Mus musculus

<400> SEQUENCE: 14

```
Tyr Ile Ser Ser Gly Gly Asp Tyr Phe Tyr Tyr Ala Asp Thr Val Lys
1               5                   10                  15

Gly
```

<210> SEQ ID NO 15
<211> LENGTH: 9
<212> TYPE: PRT
<213> ORGANISM: Mus musculus

<400> SEQUENCE: 15

```
Asp Pro Ile Thr Gly Thr Phe Ala Tyr
1               5
```

<210> SEQ ID NO 16
<211> LENGTH: 11
<212> TYPE: PRT
<213> ORGANISM: Mus musculus

<400> SEQUENCE: 16

```
Arg Ala Ser Gln Asp Ile Thr Asn Tyr Leu Asn
1               5                   10
```

<210> SEQ ID NO 17
<211> LENGTH: 7
<212> TYPE: PRT
<213> ORGANISM: Mus musculus

<400> SEQUENCE: 17

```
Tyr Thr Ser Thr Leu His Ser
1               5
```

<210> SEQ ID NO 18
<211> LENGTH: 9
<212> TYPE: PRT
<213> ORGANISM: Mus musculus

<400> SEQUENCE: 18

```
Gln Gln Gly His Met Leu Pro Trp Thr
1               5
```

<210> SEQ ID NO 19
<211> LENGTH: 5
<212> TYPE: PRT
<213> ORGANISM: Mus musculus

<400> SEQUENCE: 19

Asn Tyr Trp Met Asn
1               5

<210> SEQ ID NO 20
<211> LENGTH: 17
<212> TYPE: PRT
<213> ORGANISM: Mus musculus

<400> SEQUENCE: 20

Gln Ile Tyr Pro Gly His Val Asn Thr Asn Tyr Asn Gly Asn Phe Lys
1               5                   10                  15

Asp

<210> SEQ ID NO 21
<211> LENGTH: 12
<212> TYPE: PRT
<213> ORGANISM: Mus musculus

<400> SEQUENCE: 21

Ser Ala Asp Asn Ser Gly Phe Val Leu Phe Ala Tyr
1               5                   10

<210> SEQ ID NO 22
<211> LENGTH: 15
<212> TYPE: PRT
<213> ORGANISM: Mus musculus

<400> SEQUENCE: 22

Arg Ala Ser Lys Ser Val Ser Thr Ser Gly Tyr Ser Tyr Leu His
1               5                   10                  15

<210> SEQ ID NO 23
<211> LENGTH: 7
<212> TYPE: PRT
<213> ORGANISM: Mus musculus

<400> SEQUENCE: 23

Leu Ala Ser Asn Leu Glu Ser
1               5

<210> SEQ ID NO 24
<211> LENGTH: 9
<212> TYPE: PRT
<213> ORGANISM: Mus musculus

<400> SEQUENCE: 24

Gln His Ser Arg Glu Leu Pro Leu Thr
1               5

<210> SEQ ID NO 25
<211> LENGTH: 5
<212> TYPE: PRT
<213> ORGANISM: Mus musculus

<400> SEQUENCE: 25

Asp Tyr Tyr Met Ala
1               5

<210> SEQ ID NO 26
<211> LENGTH: 17
<212> TYPE: PRT
<213> ORGANISM: Mus musculus

<400> SEQUENCE: 26

Asn Ile Asn Tyr Asp Gly Ser Ser Thr Tyr Tyr Leu Asp Ser Leu Lys
1 5 10 15

Ser

<210> SEQ ID NO 27
<211> LENGTH: 8
<212> TYPE: PRT
<213> ORGANISM: Mus musculus

<400> SEQUENCE: 27

Gly Leu Thr Trp Asp Phe Asp Val
1 5

<210> SEQ ID NO 28
<211> LENGTH: 11
<212> TYPE: PRT
<213> ORGANISM: Mus musculus

<400> SEQUENCE: 28

Lys Ala Ser Gln Asp Val Asp Thr Ala Val Ala
1 5 10

<210> SEQ ID NO 29
<211> LENGTH: 7
<212> TYPE: PRT
<213> ORGANISM: Mus musculus

<400> SEQUENCE: 29

Leu Ala Ser Thr Arg His Thr
1 5

<210> SEQ ID NO 30
<211> LENGTH: 9
<212> TYPE: PRT
<213> ORGANISM: Mus musculus

<400> SEQUENCE: 30

Gln Gln Tyr Ser Arg Phe Pro Leu Thr
1 5

<210> SEQ ID NO 31
<211> LENGTH: 119
<212> TYPE: PRT
<213> ORGANISM: Mus musculus

<400> SEQUENCE: 31

Glu Val Gln Leu Val Glu Ser Gly Gly Gly Leu Val Lys Pro Gly Gly
1 5 10 15

Ser Leu Thr Leu Ser Cys Ala Ala Ser Gly Phe Thr Phe Ser Asp Tyr
20 25 30

Gly Met His Trp Leu Arg Gln Ala Pro Glu Lys Gly Leu Glu Trp Val
35 40 45

Ala Tyr Ile Ser Ser Gly Ser Arg Ala Val Phe Phe Ala Asp Thr Val
50 55 60

Lys Gly Arg Phe Thr Ile Ser Arg Asp Asn Ala Lys Asn Thr Leu Phe

```
65                  70                  75                  80

Leu Gln Met Thr Ser Leu Arg Ser Asp Asp Thr Ala Met Tyr Tyr Cys
                85                  90                  95

Ala Arg Asp Arg Tyr Asp Gly Arg Gly Phe Ala Tyr Trp Gly Gln Gly
            100                 105                 110

Thr Leu Val Thr Val Ser Ala
        115


<210> SEQ ID NO 32
<211> LENGTH: 357
<212> TYPE: DNA
<213> ORGANISM: Mus musculus

<400> SEQUENCE: 32

gaggtgcagc tggtggagtc tgggggaggc ttagtgaagc ctggagggtc cctgacactc     60

tcctgtgcag cctctggatt cactttcagt gactatggaa tgcactggct tcgtcaggct    120

ccagagaagg ggctggagtg ggtcgcatac atcagtagtg gcagtcgtgc cgtcttcttt    180

gcagacacgg tgaagggccg attcaccatc tccagagaca atgccaagaa caccctgttc    240

ctgcaaatga ccagtctgag gtctgacgac acggccatgt attactgtgc aagggacagg    300

tacgacggac gaggttttgc ttactggggc caagggactc tggtcactgt ctctgca       357


<210> SEQ ID NO 33
<211> LENGTH: 107
<212> TYPE: PRT
<213> ORGANISM: Mus musculus

<400> SEQUENCE: 33

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Thr Ser His Glu Ser Pro Arg Leu Leu Ile
        35                  40                  45

Thr Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105


<210> SEQ ID NO 34
<211> LENGTH: 321
<212> TYPE: DNA
<213> ORGANISM: Mus musculus

<400> SEQUENCE: 34

gatattgtgc taactcagtc tccagccacc ctgtctgtga ctccaggaga tagcgtcagt     60

ctttcctgca gggccagcca aagtattagc aacaacctac actggtatca acaaacatca    120

catgagtctc caaggcttct catcacgtat gcttcccagt ccatctctgg gatcccctcc    180

aggttcagtg gcagtggatc agggacagat ttcactctca gtatcaacag tgtggagact    240

gaagattttg gaatgtattt ctgtcaacag agtaacagct ggcctctcac gttcggtgct    300

gggaccaagc tggagctgaa a                                              321
```

<210> SEQ ID NO 35
<211> LENGTH: 118
<212> TYPE: PRT
<213> ORGANISM: Mus musculus

<400> SEQUENCE: 35

```
Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Tyr Ile Ser Ser Gly Gly Asp Tyr Ile Tyr Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Pro Ile Thr Gly Thr Phe Ala Tyr Trp Gly Gln Gly Thr
            100                 105                 110

Leu Val Thr Val Ser Ala
        115
```

<210> SEQ ID NO 36
<211> LENGTH: 354
<212> TYPE: DNA
<213> ORGANISM: Mus musculus

<400> SEQUENCE: 36

```
gacgtgaagc tggtggagtc tggggaaggc ttagtgaagc ctggagggtc cctgaaactc      60

tcctgtgcag cctctggatt cactttcagt agctatgcca tgtcttgggt tcgccagact     120

ccagagaaga ggctggagtg ggtcgcatac attagtagtg gtggtgatta catctactat     180

gcagacactg tgaagggccg attcaccatc tccagagaca atgccaggaa caccctgtac     240

ctgcaaatga gcagtctgaa gtctgaggac acagccatgt attactgtac aagagatccc     300

ataactggga cgtttgctta ctggggccaa gggactctgg tcactgtctc tgca           354
```

<210> SEQ ID NO 37
<211> LENGTH: 107
<212> TYPE: PRT
<213> ORGANISM: Mus musculus

<400> SEQUENCE: 37

```
Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95
```

-continued

```
Thr Phe Gly Gly Gly Thr Lys Leu Glu Ile Lys
            100                 105


<210> SEQ ID NO 38
<211> LENGTH: 321
<212> TYPE: DNA
<213> ORGANISM: Mus musculus

<400> SEQUENCE: 38

gatctccaga tgacacagac tacatcctcc ctgtctgcct ctctgggaga cagagtcacc      60

atcagttgca gggcaagtca ggacattaac aattatttaa actggtatca gcagaaacca     120

gatggaactg ttaaactcct gatctactac acatcaacat tacactcagg agtcccatca     180

aggttcagtg gcagtgggtc tggaacagat tattctctca ccattagcaa cctggagcaa     240

gaagatattg ccacttactt ttgccaacag ggtaatacgc ttccgtggac gttcggtgga     300

ggcaccaagc tggaaatcaa a                                               321


<210> SEQ ID NO 39
<211> LENGTH: 118
<212> TYPE: PRT
<213> ORGANISM: Mus musculus

<400> SEQUENCE: 39

Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Thr Tyr Ile Ser Ser Gly Gly Asp Tyr Phe Tyr Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Pro Ile Thr Gly Thr Phe Ala Tyr Trp Gly Gln Gly Thr
            100                 105                 110

Leu Val Thr Val Ser Ala
        115


<210> SEQ ID NO 40
<211> LENGTH: 354
<212> TYPE: DNA
<213> ORGANISM: Mus musculus

<400> SEQUENCE: 40

gacgtgaagc tggtggagtc tggggaaggc ttagtgaagc ctggagggtc cctgaaactc      60

tcctgtgcag cctctggatt cactttcagt agctatgcca tgtcttgggt tcgccagact     120

ccagagaaga ggctggagtg ggtcacatat attagtagtg gtggtgatta cttctactat     180

gcagacactg tgaagggccg attcaccatc tccagagaca atgccaggaa caccctgtac     240

ctgcaaatga gcagtctgaa gtctgaggac acagccatgt attactgtac aagagatccc     300

ataactggga cgtttgctta ctggggccaa gggactctgg tcactgtctc tgca           354


<210> SEQ ID NO 41
<211> LENGTH: 107
<212> TYPE: PRT
```

<213> ORGANISM: Mus musculus

<400> SEQUENCE: 41

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly His Met Leu Pro Trp
                85                  90                  95

Thr Phe Gly Gly Gly Thr Lys Leu Glu Ile Lys
            100                 105

<210> SEQ ID NO 42
<211> LENGTH: 321
<212> TYPE: DNA
<213> ORGANISM: Mus musculus

<400> SEQUENCE: 42
gatatccaga tgacacagac tacatcctcc ctgtctgcct ctctgggaga cagagtcacc        60
atcagttgca gggcaagtca ggacattacc aattatttaa actggtatca gcagaaacca      120
gatggaactg ttaaactcct gatctactac acatcaacat tacactcagg agtcccgtca      180
aggttcagtg gcagtgggtc tggaacagat ttttctctca ccattagcaa cctggagcaa      240
gaagatattg ccacttactt ttgccaacag ggtcatatgc ttccgtggac gttcggtgga      300
ggcaccaagc tggaaatcaa a                                                321

<210> SEQ ID NO 43
<211> LENGTH: 120
<212> TYPE: PRT
<213> ORGANISM: Mus musculus

<400> SEQUENCE: 43

Glu Val Gln Leu Gln Glu Ser Gly Ala Glu Leu Val Lys Pro Gly Ala
1               5                   10                  15

Ser Val Lys Ile Ser Cys Lys Ala Ser Gly Tyr Ala Phe Ser Asn Tyr
            20                  25                  30

Trp Met Asn Trp Met Lys Gln Arg Pro Gly Lys Gly Leu Glu Trp Ile
        35                  40                  45

Gly Gln Ile Tyr Pro Gly His Val Asn Thr Asn Tyr Asn Gly Asn Phe
50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Ala Asp Asn Ser Gly Phe Val Leu Phe Ala Tyr Trp Gly
            100                 105                 110

Gln Gly Thr Leu Val Thr Val Ser
        115                 120

<210> SEQ ID NO 44

<211> LENGTH: 364
<212> TYPE: DNA
<213> ORGANISM: Mus musculus

<400> SEQUENCE: 44
gaggtgcagc tgcaggagtc tggggctgag ctggtgaagc ctggggcctc agtgaagatt 60
tcctgcaaag cttctggcta cgcattcagt aactactgga tgaactggat gaagcagagg 120
cctggaaagg gtcttgagtg gattggacag atttatcctg gacatgttaa tactaactac 180
aacggaaatt tcaaggacaa ggccacactg actgcagaca aatcctccag cacagcctac 240
atgcagctca gcagcctgac ctctgaggac tctgcggtct atttctgtgc aagatcggca 300
gacaactcag gcttcgtcct ttttgcttac tggggccaag ggactctggt caccgtctct 360
ccag 364

<210> SEQ ID NO 45
<211> LENGTH: 111
<212> TYPE: PRT
<213> ORGANISM: Mus musculus

<400> SEQUENCE: 45

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Gly Tyr Ser Tyr Leu His Trp Tyr Gln Gln Lys Pro Gly Gln Pro Pro
35 40 45

Lys Leu Leu Ile Phe Leu Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ser Arg
85 90 95

Glu Leu Pro Leu Thr Phe Gly Ala Gly Thr Lys Leu Glu Leu Lys
100 105 110

<210> SEQ ID NO 46
<211> LENGTH: 334
<212> TYPE: DNA
<213> ORGANISM: Mus musculus

<400> SEQUENCE: 46
gacattgtgc tgacacagtc tcctgcttcc ttagctgtat ctctggggca gagggccacc 60
atctcatgca gggccagcaa aagtgtcagt acatctggct atagttattt gcactggtac 120
caacagaaac caggacagcc acccaaactc ctcatctttc ttgcatccaa cctagaatct 180
ggggtccctg ccaggttcag tggcagtggg tctgggacag acttcaccct caacatccat 240
cctgtggagg aggaggatgc tgcaacctat tactgtcagc acagtaggga gcttcctctc 300
acgttcggtg ctgggaccaa gctggagctg aaac 334

<210> SEQ ID NO 47
<211> LENGTH: 117
<212> TYPE: PRT
<213> ORGANISM: Mus musculus

<400> SEQUENCE: 47

Glu Val Lys Leu Val Glu Ser Glu Gly Gly Leu Val Gln Pro Gly Ser
1 5 10 15

-continued

```
Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Gly Leu Thr Trp Asp Phe Asp Val Trp Gly Thr Gly Thr Thr
            100                 105                 110

Val Thr Val Ser Ser
        115


<210> SEQ ID NO 48
<211> LENGTH: 351
<212> TYPE: DNA
<213> ORGANISM: Mus musculus

<400> SEQUENCE: 48

gaagtgaagc tggtggagtc tgagggaggc ttagtgcagc ctggaagttc catgaaactc      60

tcctgcacag cctctggatt cactttcagt gactattaca tggcttgggt ccgccaggtt     120

ccagaaaagg gtctagaatg ggttgcaaac attaattatg atggtagtag cacctactat     180

ctggactcct tgaagagccg tttcatcatc tcgagagaca atgcaaagaa cattctatac     240

ctgcaaatga gcagtctgaa gtctgaggac acagccacgt attactgtgc aagagggctt     300

acgtgggact tcgatgtctg gggcacaggg accacggtca ccgtctcctc a              351


<210> SEQ ID NO 49
<211> LENGTH: 107
<212> TYPE: PRT
<213> ORGANISM: Mus musculus

<400> SEQUENCE: 49

Asp Ile Val Met Thr Gln Ser His Lys Phe Met Ser Pro Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Leu Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Arg Phe Pro Leu
                85                  90                  95

Thr Phe Gly Ala Gly Thr Lys Leu Glu Leu Lys
            100                 105


<210> SEQ ID NO 50
<211> LENGTH: 321
<212> TYPE: DNA
<213> ORGANISM: Mus musculus

<400> SEQUENCE: 50
```

```
gacattgtga tgacccagtc tcacaaattc atgtccccat cagtaggaga cagggtcagc      60

atcacctgca aggccagtca ggatgtggat actgctgtag cctggtatca acagaaacca     120

gggcaatctc ctaaactact gatttacttg gcatccaccc ggcacactgg agtccctgat     180

cgcttcacag gcagtggatc tgggacagat ttcactctca ccattagcaa tgtgcagtct     240

gaagacttgg cagattattt ctgtcagcag tatagcaggt ttccgctcac gttcggtgct     300

gggaccaagc tggagctgaa a                                               321


<210> SEQ ID NO 51
<211> LENGTH: 119
<212> TYPE: PRT
<213> ORGANISM: Felis catus

<400> SEQUENCE: 51

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asp Tyr
            20                  25                  30

Gly Met His Trp Val Arg Gln Ala Pro Gly Lys Gly Leu Gln Trp Val
        35                  40                  45

Ala Tyr Ile Ser Ser Gly Ser Arg Ala Val Phe Phe Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Val Arg Asp Arg Tyr Asp Gly Arg Gly Phe Ala Tyr Trp Gly Gln Gly
            100                 105                 110

Thr Leu Val Thr Val Ser Ser
        115


<210> SEQ ID NO 52
<211> LENGTH: 357
<212> TYPE: DNA
<213> ORGANISM: Felis catus

<400> SEQUENCE: 52

gacgttcagc ttgtcgaatc tggcggagac ctggtaaagc cgggaggctc actccgcctt      60

acttgcgtag caagtggctt tacctacagc gattatggca tgcactgggt gaggcaggcc     120

cctggaaagg ggctccagtg ggtagcatac atatccagcg ggtcacgagc agttttcttc     180

gcggacacgg tcaaggggcg cttcacgatt agccgggaca atgcaaagaa cacactgtat     240

ttgcaaatga actctctcaa gactgaggac acagctacct attactgtgt tcgagaccgc     300

tacgacggca ggggattcgc ctattggggg caaggaactc tcgtaacggt ctcgagc        357


<210> SEQ ID NO 53
<211> LENGTH: 119
<212> TYPE: PRT
<213> ORGANISM: Felis catus

<400> SEQUENCE: 53

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Asp Tyr
            20                  25                  30

Gly Met His Trp Val Arg Gln Ala Pro Gly Lys Gly Leu Gln Trp Val
```

-continued

```
        35                  40                  45

Ala Tyr Ile Ser Ser Gly Ser Arg Ala Val Phe Phe Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Gly Leu Arg Thr Glu Asp Thr Ala Thr Tyr Tyr Cys
                85                  90                  95

Ala Arg Asp Arg Tyr Asp Gly Arg Gly Phe Ala Tyr Trp Gly Gln Gly
            100                 105                 110

Thr Leu Val Thr Val Ser Ser
        115


<210> SEQ ID NO 54
<211> LENGTH: 357
<212> TYPE: DNA
<213> ORGANISM: Felis catus

<400> SEQUENCE: 54

gatgtacagc ttgtggaaag tggcggtgat ttggtcaaac ctgggggctc cctcaggctt      60

acgtgcgttg catcaggttt tacgttctca gattacggta tgcactgggt tagacaagcg     120

cctgggaaag gcttgcagtg ggttgcttac atttcaagtg gctctcgggc tgtattcttc     180

gcggacactg tcaaggggag gtttacgatc tccagggata atgctaagaa tacactttac     240

cttcagatga acggcctgag gacggaagat acagcgacgt attattgcgc cagggataga     300

tatgacggga gaggtttcgc gtactgggga caaggtacgc ttgtcacggt ctcgagc        357


<210> SEQ ID NO 55
<211> LENGTH: 102
<212> TYPE: PRT
<213> ORGANISM: Felis catus

<400> SEQUENCE: 55

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Val Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Gln Gln Ser Asn Ser Trp Pro Leu
                85                  90                  95

Thr Phe Gly Gln Gly Thr
            100


<210> SEQ ID NO 56
<211> LENGTH: 306
<212> TYPE: DNA
<213> ORGANISM: Felis catus

<400> SEQUENCE: 56

gagatccaaa tgacacagtc cccttcttcc ttgagtgctt cacctggtga tagggtaacg      60

attacatgtc gcgcgtcaca gagcatatca aacaatcttc actggtatca gcagaaacca     120

ggaaaagttc ccaaactgtt gatctattac gcgagccagt ccattagcgg ggttccatca     180
```

```
cgcttctctg gtagtgggag cggtactgat tttactttga ccatttcctc attggaaccg      240

gaggacgctg caacgtacta ctgccagcaa agcaactcat ggcccctgac atttggacag      300

ggtacc                                                                 306
```

<210> SEQ ID NO 57
<211> LENGTH: 102
<212> TYPE: PRT
<213> ORGANISM: Felis catus

<400> SEQUENCE: 57

```
Asp Ile Val Met Thr Gln Thr Pro Leu Ser Leu Ser Val Thr Pro Gly
1               5                   10                  15

Glu Ser Ala Ser Ile Ser Cys Arg Ala Ser Gln Ser Ile Ser Asn Asn
            20                  25                  30

Leu His Trp Tyr Leu Gln Lys Ser Gly Gln Ser Pro Arg Arg Leu Ile
        35                  40                  45

Tyr Tyr Ala Ser Gln Ser Ile Ser Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Val Gly Val Tyr Tyr Cys Gln Gln Ser Asn Ser Trp Pro Leu
                85                  90                  95

Thr Phe Gly Gln Gly Thr
            100
```

<210> SEQ ID NO 58
<211> LENGTH: 306
<212> TYPE: DNA
<213> ORGANISM: Felis catus

<400> SEQUENCE: 58

```
gatattgtga tgactcagac tccactttcc cttagtgtta ctcctggtga aagtgctagt       60

atctcatgtc gggcaagcca atcaatatca aacaatctgc actggtactt gcaaaagtct      120

gggcagtctc ccagaagact catctattac gcctcacaaa gtattagtgg cgttcctgat      180

cggttctcag gcagtggctc aggaaccgat ttcaccttgc gcatcagtag agtcgaggct      240

gatgacgttg gggtttatta ctgccaacaa tctaactctt ggccgttgac gttcggccaa      300

ggtacc                                                                 306
```

<210> SEQ ID NO 59
<211> LENGTH: 118
<212> TYPE: PRT
<213> ORGANISM: Felis catus

<400> SEQUENCE: 59

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Ala Pro Gly Lys Gly Leu Gln Trp Val
        35                  40                  45

Ala Tyr Ile Ser Ser Gly Gly Asp Tyr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80
```

-continued

```
Leu Gln Met Asn Ser Leu Arg Ala Glu Asp Thr Ala Met Tyr Tyr Cys
                85                  90                  95

Val Arg Asp Pro Ile Thr Gly Thr Phe Ala Tyr Trp Gly Gln Gly Thr
            100                 105                 110

Leu Val Thr Val Ser Ser
        115
```

<210> SEQ ID NO 60
<211> LENGTH: 354
<212> TYPE: DNA
<213> ORGANISM: Canis familiaris

<400> SEQUENCE: 60

```
gaagtccagt tggtagaatc cgggggtgac cttgtcaaac cgggagggtc acttcggctc     60

agttgtgttg cttctgggtt tacattctcc tcctacgcta tgagttgggt tcgccaggca    120

ccaggcaaag gactccaatg ggttgcgtat attagcagtg gcggagatta tatctactac    180

gccgatactg tcaaagggcg atttacgata agccgagaca atgcaaaaaa caccctgtat    240

cttcagatga actcactgag ggctgaagac acggctatgt actactgtgt cagagatcca    300

ataaccggga cctttgcata ttggggacag ggacactgg tcactgtctc gagc           354
```

<210> SEQ ID NO 61
<211> LENGTH: 118
<212> TYPE: PRT
<213> ORGANISM: Canis familiaris

<400> SEQUENCE: 61

```
Glu Val Gln Leu Val Glu Ser Gly Gly Asp Leu Val Lys Pro Ala Gly
1               5                   10                  15

Ser Leu Thr Leu Ser Cys Leu Ala Ser Gly Phe Thr Phe Ser Ser Tyr
            20                  25                  30

Ala Met Ser Trp Val Arg Gln Thr Pro Glu Lys Gly Leu Gln Trp Val
        35                  40                  45

Ala Tyr Ile Ser Ser Gly Gly Asp Tyr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Pro Ile Thr Gly Thr Phe Ala Tyr Trp Gly Gln Gly Thr
            100                 105                 110

Leu Val Thr Val Ser Ser
        115
```

<210> SEQ ID NO 62
<211> LENGTH: 354
<212> TYPE: DNA
<213> ORGANISM: Canis familiaris

<400> SEQUENCE: 62

```
gaagtacaac ttgtggagag cgggggcgac ttggttaagc ctgcgggatc tttgaccttg     60

tcctgtctgg cttcaggctt tacctttagt agttacgcca tgagttgggt ccggcaaacc    120

ccggaaaagg ggctgcagtg ggtagcttat ataagttccg ggggggatta tatctactat    180

gctgacaccg tcaagggacg cttcacaata agccgagata atgcaaaaaa tacactgtac    240

ctccagatga atagcctgcg agacgaggac actgccgtct attattgtgc tcgagaccca    300
```

ataacgggaa cttttgcgta ttggggtcaa ggcacactgg ttactgtctc gagc 354

<210> SEQ ID NO 63
<211> LENGTH: 102
<212> TYPE: PRT
<213> ORGANISM: Canis familiaris

<400> SEQUENCE: 63

```
Glu Ile Val Met Thr Gln Ser Pro Ala Ser Leu Ser Leu Ser Gln Glu
1               5                   10                  15

Glu Lys Val Thr Ile Thr Cys Arg Ala Ser Gln Asp Ile Asn Asn Tyr
            20                  25                  30

Leu Asn Trp Tyr Gln Gln Lys Pro Gly Gln Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Gln Gln Gly Asn Thr Leu Pro Trp
                85                  90                  95

Thr Phe Gly Gln Gly Thr
            100
```

<210> SEQ ID NO 64
<211> LENGTH: 306
<212> TYPE: DNA
<213> ORGANISM: Canis familiaris

<400> SEQUENCE: 64

```
gagattgtta tgactcagag cccggctagc ctgtcactct cacaggagga aaaagttacc     60

atcacctgcc gggcatctca ggacataaat aactatttga actggtatca gcaaaagccc    120

ggacaagctc cgaagctgct catttactat accagcacac tgcacagcgg agtgccaagc    180

agatttagcg ggagcggaag tggaaccgac ttcagcttca ctatatcctc actcgagcct    240

gaggatgtgg ccgtttatta ctgtcaacaa gggaatacgc ttccctggac ttttgggcaa    300

ggtacc                                                               306
```

<210> SEQ ID NO 65
<211> LENGTH: 101
<212> TYPE: PRT
<213> ORGANISM: Canis familiaris

<400> SEQUENCE: 65

```
Asp Ile Val Leu Thr Gln Pro Thr Ser Val Ser Gly Ser Leu Gly Gln
1               5                   10                  15

Arg Val Thr Ile Ser Cys Arg Ala Ser Gln Asp Ile Asn Asn Tyr Leu
            20                  25                  30

Asn Trp Tyr Gln Gln Leu Pro Gly Lys Ala Pro Lys Leu Leu Val Tyr
        35                  40                  45

Tyr Thr Ser Thr Leu His Ser Gly Val Pro Asp Arg Phe Ser Gly Ser
    50                  55                  60

Asn Ser Gly Ser Ser Ala Thr Leu Thr Ile Thr Gly Leu Gln Ala Glu
65                  70                  75                  80

Asp Glu Ala Asp Tyr Tyr Cys Gln Gln Gly Asn Thr Leu Pro Trp Thr
                85                  90                  95

Phe Gly Gln Gly Thr
            100
```

<210> SEQ ID NO 66
<211> LENGTH: 303
<212> TYPE: DNA
<213> ORGANISM: Canis familiaris

<400> SEQUENCE: 66
gacattgtat tgactcagcc cacgtccgtc tctggctctt tggggcagcg ggtgaccatc 60
tcatgccgag cgtcacaaga cataaacaat tatttgaatt ggtatcagca acttccaggc 120
aaagcgccaa aacttctcgt ctattacacg tctacacttc atagcggggt ccccgataga 180
ttctccgggt caaatagtgg gagttcagct actttgacaa taacaggtct tcaggccgag 240
gacgaggcag actattactg tcagcaagga aatactctgc cttggacttt cggtcaaggt 300
acc 303

<210> SEQ ID NO 67
<211> LENGTH: 118
<212> TYPE: PRT
<213> ORGANISM: Felis catus

<400> SEQUENCE: 67

Asp Val Gln Leu Val Glu Ser Gly Gly Asp Leu Val Lys Pro Gly Gly
1 5 10 15

Ser Leu Arg Leu Thr Cys Val Ala Ser Gly Phe Thr Tyr Ser Ser Tyr
20 25 30

Ala Met Ser Trp Val Arg Gln Ala Pro Gly Lys Gly Leu Gln Trp Val
35 40 45

Ala Tyr Ile Ser Ser Gly Gly Asp Tyr Ile Tyr Tyr Ala Asp Thr Val
50 55 60

Lys Gly Arg Phe Thr Ile Ser Arg Asp Asn Ala Lys Asn Thr Leu Tyr
65 70 75 80

Leu Gln Met Asn Ser Leu Lys Thr Glu Asp Thr Ala Thr Tyr Tyr Cys
85 90 95

Val Arg Asp Pro Ile Thr Gly Thr Phe Ala Tyr Trp Gly Gln Gly Thr
100 105 110

Leu Val Thr Val Ser Ser
115

<210> SEQ ID NO 68
<211> LENGTH: 354
<212> TYPE: DNA
<213> ORGANISM: Felis catus

<400> SEQUENCE: 68
gatgttcaac ttgtcgaaag tggcggagac ctggtcaagc caggggggttc actccgactg 60 acctgcgtag cctcaggatt tacttattcc agctacgcta tgtcctgggt gaggcaagca 120
ccggggaaag ggttgcagtg ggttgcatac atttcttctg gtggagacta tatttactac 180
gcagacactg tgaaggggcg attcacaatt tcacgggata acgccaaaaa taccttgtac 240
cttcagatga actcattgaa gactgaagac acagctacct attactgtgt acgagatccg 300
attacgggaa catttgccta ttggggtcaa gggactctgg taaccgtctc gagc 354

<210> SEQ ID NO 69
<211> LENGTH: 118
<212> TYPE: PRT
<213> ORGANISM: Felis catus

<400> SEQUENCE: 69

```
Asp Val Gln Leu Val Glu Ser Gly Gly Asn Leu Val Lys Pro Gly Gly
1               5                   10                  15

Ser Leu Arg Leu Thr Cys Val Ala Ser Gly Phe Thr Phe Ser Ser Tyr
            20                  25                  30

Ala Met Ser Trp Val Arg Gln Ala Pro Gly Lys Gly Leu Gln Trp Val
        35                  40                  45

Ala Tyr Ile Ser Ser Gly Gly Asp Tyr Ile Tyr Tyr Ala Asp Thr Val
    50                  55                  60

Lys Gly Arg Phe Thr Ile Ser Lys Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Ala Arg Asp Pro Ile Thr Gly Thr Phe Ala Tyr Trp Gly Gln Gly Thr
            100                 105                 110

Leu Val Thr Val Ser Ser
        115
```

<210> SEQ ID NO 70
<211> LENGTH: 354
<212> TYPE: DNA
<213> ORGANISM: Felis catus

<400> SEQUENCE: 70

```
gacgttcagc ttgtggaaag tggagggaac ctcgtgaagc ccggtgggtc attgaggttg      60

acgtgcgtcg cgtcaggttt cacttttagc tcctatgcta tgtcatgggt tcggcaggca     120

ccagggaaag gacttcagtg ggttgcgtat ataagcagcg ggggcgacta catctactac     180

gcagacactg tcaaggggcg ctttacaatc agcaaggata atgcgaagaa cacccttttat    240

cttcaaatga acagcctgaa aactgaggac actgctacat attattgcgc cagggacccc     300

atcacgggca cttttgcgta ttgggggcaa ggtacgctgg ttactgtctc gagc           354
```

<210> SEQ ID NO 71
<211> LENGTH: 102
<212> TYPE: PRT
<213> ORGANISM: Felis catus

<400> SEQUENCE: 71

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Gln Gln Gly Asn Thr Leu Pro Trp
                85                  90                  95

Thr Phe Gly Gln Gly Thr
            100
```

<210> SEQ ID NO 72
<211> LENGTH: 306
<212> TYPE: DNA

<213> ORGANISM: Felis catus

<400> SEQUENCE: 72

```
gaaattcaga tgacgcaatc accatcctcc ttgagtgcgt cccctggaga tagagtgact      60

attacgtgtc gcgcctccca agacattaat aattacctca attggtatca gcagaagccc     120

ggaaaagtac cgaagctcct gatttattat acgagtaccc tgcactcagg ggtcccatct     180

cgattcagcg ggtcaggctc tggcactgat ttcacattga ccatcagtag tcttgaacca     240

gaggacgcag caacttatta ctgccaacaa ggcaatactc ttccctggac attcggccaa     300

ggtacc                                                                306
```

<210> SEQ ID NO 73
<211> LENGTH: 102
<212> TYPE: PRT
<213> ORGANISM: Felis catus

<400> SEQUENCE: 73

```
Asp Ile Thr Met Thr Gln Ser Pro Gly Ser Leu Ala Gly Ser Pro Gly
1               5                   10                  15

Gln Gln Val Thr Met Asn Cys Arg Ala Ser Gln Asp Ile Asn Asn Tyr
            20                  25                  30

Leu Asn Trp Tyr Gln Gln Lys Pro Gly Gln His Pro Lys Leu Leu Ile
        35                  40                  45

Tyr Tyr Thr Ser Thr Leu His Ser Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Gln Gln Gly Asn Thr Leu Pro Trp
                85                  90                  95

Thr Phe Gly Gln Gly Thr
            100
```

<210> SEQ ID NO 74
<211> LENGTH: 306
<212> TYPE: DNA
<213> ORGANISM: Felis catus

<400> SEQUENCE: 74

```
gatataacaa tgactcaatc acccggctcc ttggctgggt cccctggcca gcaagtaact      60

atgaattgcc gcgctagcca ggacattaac aactacttga actggtatca gcaaaaacca     120

ggccagcatc ccaagctgct gatttattac acatctaccc ttcacagtgg ggttcccgat     180

aggttctctg gtagcggatc aggcacggat tttacactta ccatttccaa tctccaggct     240

gaagatgtcg ccagttatta ctgtcagcag ggcaatacgc tgccctggac gtttggtcag     300

ggtacc                                                                306
```

<210> SEQ ID NO 75
<211> LENGTH: 118
<212> TYPE: PRT
<213> ORGANISM: Canis familiaris

<400> SEQUENCE: 75

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30
```

-continued

```
Ala Met Ser Trp Val Arg Gln Ala Pro Gly Lys Gly Leu Gln Trp Val
        35                  40                  45

Ala Tyr Ile Ser Ser Gly Gly Asp Tyr Phe Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Asp Pro Ile Thr Gly Thr Phe Ala Tyr Trp Gly Gln Gly Thr
            100                 105                 110

Leu Val Thr Val Ser Ser
        115


<210> SEQ ID NO 76
<211> LENGTH: 354
<212> TYPE: DNA
<213> ORGANISM: Canis familiaris

<400> SEQUENCE: 76

gaagtacaac tcgtagagtc tggcggtgac ctggtcaagc caggcggtag tctgagactc      60

tcatgtgtag cttctggttt caccttttct agctatgcaa tgtcttgggt ccgccaagca     120

cccggaaagg gtcttcaatg ggtcgcttac atttcatctg gcggggatta cttttattat     180

gctgacacag tcaagggacg cttcacgatc tcaagagaca acgctaagaa tacgctctat     240

ctccaaatga acagcctcag agctgaagat acggcaatgt attactgtgt gcgcgatcca     300

ataaccggaa cctttgctta ctgggggcaa ggcaccctcg tgactgtctc gagc           354


<210> SEQ ID NO 77
<211> LENGTH: 102
<212> TYPE: PRT
<213> ORGANISM: Canis familiaris

<400> SEQUENCE: 77

Glu Ile Val Met Thr Gln Ser Pro Ala Ser Leu Ser Leu Ser Gln Glu
1               5                   10                  15

Glu Lys Val Thr Ile Thr Cys Arg Ala Ser Gln Asp Ile Thr Asn Tyr
            20                  25                  30

Leu Asn Trp Tyr Gln Gln Lys Pro Gly Gln Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Gln Gln Gly His Met Leu Pro Trp
                85                  90                  95

Thr Phe Gly Gln Gly Thr
            100


<210> SEQ ID NO 78
<211> LENGTH: 306
<212> TYPE: DNA
<213> ORGANISM: Canis familiaris

<400> SEQUENCE: 78

gagattgtaa tgacgcagtc acccgcatcc ttgtctttga gccaagagga aaaagttact      60

atcacatgca gagcgagcca agacatcacg aattatctga actggtatca gcagaagcct     120
```

-continued

```
ggtcaggcac cgaaattgct tatttattat accagcaccc ttcactcagg agtaccttca    180

agattcagcg gttccggctc tggaacagac ttttcattta ccattagttc actcgagccc    240

gaggacgtag ccgtatatta ctgccagcag ggacatatgt tgccctggac atttgggcaa    300

ggtacc                                                               306
```

<210> SEQ ID NO 79
<211> LENGTH: 118
<212> TYPE: PRT
<213> ORGANISM: Canis familiaris

<400> SEQUENCE: 79

```
Glu Val Gln Leu Val Glu Ser Gly Gly Asp Leu Val Lys Pro Ala Gly
1               5                   10                  15

Ser Leu Thr Leu Ser Cys Leu Ala Ser Gly Phe Thr Phe Ser Ser Tyr
            20                  25                  30

Ala Met Ser Trp Val Arg Gln Thr Pro Glu Lys Gly Leu Gln Trp Val
        35                  40                  45

Ala Tyr Ile Ser Ser Gly Gly Asp Tyr Phe Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Pro Ile Thr Gly Thr Phe Ala Tyr Trp Gly Gln Gly Thr
            100                 105                 110

Leu Val Thr Val Ser Ser
        115
```

<210> SEQ ID NO 80
<211> LENGTH: 354
<212> TYPE: DNA
<213> ORGANISM: Canis familiaris

<400> SEQUENCE: 80

```
gaagtgcaac ttgtggaatc tgggggtgat ctcgtcaagc cagcagggtc attgaccttg     60

tcttgcctgg caagcggatt cactttctct tcctatgcaa tgtcctgggt gcggcagaca    120

ccggagaagg ggcttcagtg ggttgcttat attagtagtg gtggcgacta cttctattat    180

gccgatactg tgaaggggcg cttcacaatt tccagagaca atgcgaagaa cacattgtat    240

ctgcaaatga acagcttgcg cgatgaagat accgcggttt attactgtgc gcgcgaccct    300

ataacgggca cctttgccta ttggggccaa ggaacgcttg tgactgtctc gagc          354
```

<210> SEQ ID NO 81
<211> LENGTH: 101
<212> TYPE: PRT
<213> ORGANISM: Canis familiaris

<400> SEQUENCE: 81

```
Asp Ile Val Leu Thr Gln Pro Thr Ser Val Ser Gly Ser Leu Gly Gln
1               5                   10                  15

Arg Val Thr Ile Ser Cys Arg Ala Ser Gln Asp Ile Thr Asn Tyr Leu
            20                  25                  30

Asn Trp Tyr Gln Gln Leu Pro Gly Lys Ala Pro Lys Leu Leu Val Tyr
        35                  40                  45

Tyr Thr Ser Thr Leu His Ser Gly Val Pro Asp Arg Phe Ser Gly Ser
    50                  55                  60
```

```
Asn Ser Gly Ser Ser Ala Thr Leu Thr Ile Thr Gly Leu Gln Ala Glu
65                  70                  75                  80

Asp Glu Ala Asp Tyr Tyr Cys Gln Gln Gly His Met Leu Pro Trp Thr
                85                  90                  95

Phe Gly Gln Gly Thr
            100


<210> SEQ ID NO 82
<211> LENGTH: 303
<212> TYPE: DNA
<213> ORGANISM: Canis familiaris

<400> SEQUENCE: 82

gacatcgtcc tcactcaacc cacctcagtg tctgggtctc ttggtcaacg agttaccatt      60

tcatgcaggg catctcagga cattacgaat tatcttaact ggtatcaaca actcccaggt     120

aaagcgccaa aattgctcgt atactacacg tcaacattgc attctggtgt accagatagg     180

ttctctggaa gcaactcagg aagctccgcc accctcacga tcacgggtct ccaggcggag     240

gacgaggcag attactactg ccagcagggg catatgttgc cttggacctt tgggcaaggt     300

acc                                                                   303


<210> SEQ ID NO 83
<211> LENGTH: 118
<212> TYPE: PRT
<213> ORGANISM: Felis catus

<400> SEQUENCE: 83

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Ser Tyr
            20                  25                  30

Ala Met Ser Trp Val Arg Gln Ala Pro Gly Lys Gly Leu Gln Trp Val
        35                  40                  45

Ala Tyr Ile Ser Ser Gly Gly Asp Tyr Phe Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Val Arg Asp Pro Ile Thr Gly Thr Phe Ala Tyr Trp Gly Gln Gly Thr
            100                 105                 110

Leu Val Thr Val Ser Ser
        115


<210> SEQ ID NO 84
<211> LENGTH: 354
<212> TYPE: DNA
<213> ORGANISM: Felis catus

<400> SEQUENCE: 84

gacgtgcagc ttgtagagtc cggtggcgac ctcgttaaac ctggcgggag tctgaggctt      60

acctgcgtag ccagcggatt cacatatagt tcatacgcga tgtcttgggt caggcaagct     120

ccaggaaaag gactccaatg ggtcgcttac atttcttctg gtggggacta cttttattac     180

gcagatacag tcaagggacg ctttacgatc tcccgcgata acgccaaaaa tactctttac     240

ctccaaatga actctctgaa aaccgaagac actgctacat actattgtgt gagggacccg     300
```

-continued atcacaggga cctttgcata ttgggggcaa ggaactctgg ttacggtctc gagc 354

<210> SEQ ID NO 85
<211> LENGTH: 102
<212> TYPE: PRT
<213> ORGANISM: Felis catus

<400> SEQUENCE: 85

Glu Ile Gln Met Thr Gln Ser Pro Ser Ser Leu Ser Ala Ser Pro Gly
1 5 10 15

Asp Arg Val Thr Ile Thr Cys Arg Ala Ser Gln Asp Ile Thr Asn Tyr
20 25 30

Leu Asn Trp Tyr Gln Gln Lys Pro Gly Lys Val Pro Lys Leu Leu Ile
35 40 45

Tyr Tyr Thr Ser Thr Leu His Ser Gly Val Pro Ser Arg Phe Ser Gly
50 55 60

Ser Gly Ser Gly Thr Asp Phe Thr Leu Thr Ile Ser Ser Leu Glu Pro
65 70 75 80

Glu Asp Ala Ala Thr Tyr Tyr Cys Gln Gln Gly His Met Leu Pro Trp
85 90 95

Thr Phe Gly Gln Gly Thr
100

<210> SEQ ID NO 86
<211> LENGTH: 306
<212> TYPE: DNA
<213> ORGANISM: Felis catus

<400> SEQUENCE: 86
gaaatacaaa tgacacagtc accatctagt ttgtcagcct ccccaggcga ccgggtaaca 60
atcacctgca gagccagcca ggacataacc aactacctga attggtatca gcaaaaaccc 120
ggcaaagtgc caaaactcct catctactac acttccacac tgcattctgg tgttccgtcc 180
cgattttctg gatcaggatc aggaaccgac tttacactta cgatttcaag tttggagccg 240
gaagacgcag caacttatta ctgtcaacaa gggcacatgc tcccctggac ctttggtcaa 300
ggtacc 306

<210> SEQ ID NO 87
<211> LENGTH: 118
<212> TYPE: PRT
<213> ORGANISM: Felis catus

<400> SEQUENCE: 87

Asp Val Gln Leu Val Glu Ser Gly Gly Asp Leu Val Lys Pro Gly Gly
1 5 10 15

Ser Leu Arg Leu Thr Cys Val Ala Ser Gly Phe Thr Phe Ser Ser Tyr
20 25 30

Ala Met Ser Trp Val Arg Gln Ala Pro Gly Lys Gly Leu Gln Trp Val
35 40 45

Ala Tyr Ile Ser Ser Gly Gly Asp Tyr Phe Tyr Tyr Ala Asp Thr Val
50 55 60

Lys Gly Arg Phe Thr Ile Ser Arg Asp Asp Ala Lys Asn Thr Leu Tyr
65 70 75 80

Leu Gln Met Ser Ser Leu Lys Thr Glu Asp Thr Ala Thr Tyr Tyr Cys
85 90 95

Thr Gly Asp Pro Ile Thr Gly Thr Phe Ala Tyr Trp Gly Gln Gly Thr

```
            100                 105                 110

Leu Val Thr Val Ser Ser
        115


<210> SEQ ID NO 88
<211> LENGTH: 354
<212> TYPE: DNA
<213> ORGANISM: Felis catus

<400> SEQUENCE: 88

gacgtacagc ttgtagagag cggggggat cttgttaagc cgggtggttc tctccgactt      60

acttgtgtag catctggctt cactttcagc tcttatgcga tgtcatgggt ccggcaagct    120

ccgggtaagg gtctccagtg ggtggcctac ataagctcag gaggtgacta tttctactat    180

gctgacaccg ttaagggacg cttcacaatc tctagagatg atgcgaaaaa tacgctctac    240

ctgcaaatga gcagcctcaa aacagaagac acggccacct attattgtac tggagatccc    300

ataacaggta cgtttgcgta ctgggggcag gggaccctgg tcactgtctc gagc          354


<210> SEQ ID NO 89
<211> LENGTH: 102
<212> TYPE: PRT
<213> ORGANISM: Felis catus

<400> SEQUENCE: 89

Asp Ile Thr Met Thr Gln Ser Pro Gly Ser Leu Ala Gly Ser Pro Gly
1               5                   10                  15

Gln Gln Val Thr Met Asn Cys Arg Ala Ser Gln Asp Ile Thr Asn Tyr
            20                  25                  30

Leu Asn Trp Tyr Gln Gln Lys Pro Gly Gln His Pro Lys Leu Leu Ile
        35                  40                  45

Tyr Tyr Thr Ser Thr Leu His Ser Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Gln Gln Gly His Met Leu Pro Trp
                85                  90                  95

Thr Phe Gly Gln Gly Thr
            100


<210> SEQ ID NO 90
<211> LENGTH: 306
<212> TYPE: DNA
<213> ORGANISM: Felis catus

<400> SEQUENCE: 90

gacataacta tgactcagtc ccctggttcc ttggccgggt ctccggggca gcaggtgaca      60

atgaattgca gagcgtccca ggacattact aattatctca actggtatca gcagaagcct    120

ggtcagcacc caaagctgct gatttattac acgtcaacgc ttcactcagg ggttccagac    180

aggttctcag gctctggctc aggaactgat tttaccctga cgatatctaa tctccaagcg    240

gaggatgtgg ctagttacta ttgccaacaa gggcacatgc ttccctggac atttggccag    300

ggtacc                                                               306


<210> SEQ ID NO 91
<211> LENGTH: 117
<212> TYPE: PRT
<213> ORGANISM: Canis familiaris
```

<400> SEQUENCE: 91

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ala Trp Val Arg Gln Ala Pro Gly Lys Gly Leu Gln Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Gly Leu Thr Trp Asp Phe Asp Val Trp Gly Gln Gly Thr Leu
            100                 105                 110

Val Thr Val Ser Ser
        115

<210> SEQ ID NO 92
<211> LENGTH: 351
<212> TYPE: DNA
<213> ORGANISM: Canis familiaris

<400> SEQUENCE: 92
gaggtacagc ttgtggaatc tggggggat ttggtaaagc ctggcggttc cctgcgcctc 60
tcctgtgtgg cctcaggttt caccttttca gactactaca tggcgtgggt gcgccaggca 120
cccggaaaag gtctccaatg ggttgcaaat atcaattatg acggttcttc aacatactac 180
ttggactcac ttaagtctcg gtttactatt agtcgggaca atgctaaaaa taccttgtat 240
ttgcagatga actcactccg ggcggaggac acggcgatgt attactgtgt tcgcggtctt 300
acatgggact tcgatgtttg gggcagggt acactcgtta cagtctcgag c 351

<210> SEQ ID NO 93
<211> LENGTH: 102
<212> TYPE: PRT
<213> ORGANISM: Canis familiaris

<400> SEQUENCE: 93

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asp Val Asp Thr Ala
            20                  25                  30

Val Ala Trp Tyr Gln Gln Lys Pro Gly Gln Ala Pro Lys Leu Leu Ile
        35                  40                  45

Tyr Leu Ala Ser Thr Arg His Thr Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Gln Gln Tyr Ser Arg Phe Pro Leu
                85                  90                  95

Thr Phe Gly Gln Gly Thr
            100

<210> SEQ ID NO 94
<211> LENGTH: 306

```
<212> TYPE: DNA
<213> ORGANISM: Canis familiaris

<400> SEQUENCE: 94

gagatagtga tgacccagtc tccagctagc ctgtctttgt cccaggaaga gaaggtgacc     60

atcacatgca aagcgagtca agatgtagat acagcggttg cgtggtatca acaaaaaccc    120

ggacaggcac ctaaattgct gatttatctc gccagtacga ggcacactgg ggtcccatcc    180

cgctttagtg ggtcaggatc agggacggat tttctttta ccataagtag tcttgaacct    240

gaagacgtgg ctgtttatta ttgccaacaa tactcaaggt tccctttgac tttcgggcaa    300

ggtacc                                                               306


<210> SEQ ID NO 95
<211> LENGTH: 117
<212> TYPE: PRT
<213> ORGANISM: Canis familiaris

<400> SEQUENCE: 95

Glu Val Gln Leu Val Glu Ser Gly Gly Asp Leu Val Lys Pro Ala Gly
1               5                   10                  15

Ser Leu Thr Leu Ser Cys Leu Ala Ser Gly Phe Thr Phe Ser Asp Tyr
            20                  25                  30

Tyr Met Ala Trp Val Arg Gln Thr Pro Glu Lys Gly Leu Gln Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Gly Leu Thr Trp Asp Phe Asp Val Trp Gly Gln Gly Thr Leu
            100                 105                 110

Val Thr Val Ser Ser
        115


<210> SEQ ID NO 96
<211> LENGTH: 351
<212> TYPE: DNA
<213> ORGANISM: Canis familiaris

<400> SEQUENCE: 96

gaagtacaac tcgtggagag tgggggtgat ctcgtaaaac cagcggggtc tttgactctc     60

tcttgtttgg ccagtggctt tacgttctca gattattata tggcttgggt tcgacaaaca    120

cccgaaaagg gtttgcagtg ggtagcaaac attaactacg acgggagtag cacgtattac    180

ctcgactctc tgaagagtag atttacaatt agtcgcgata acgctaaaaa cacgctctac    240

cttcaaatga atagcctcag ggatgaggac acagcagtct attattgtgc cagaggtttg    300

acatgggatt tcgacgtatg gggtcaaggg actctcgtca ccgtctcgag c             351


<210> SEQ ID NO 97
<211> LENGTH: 102
<212> TYPE: PRT
<213> ORGANISM: Canis familiaris

<400> SEQUENCE: 97

Asp Ile Val Met Thr Gln Thr Pro Leu Ser Leu Ser Val Ser Pro Gly
1               5                   10                  15
```

```
Glu Thr Ala Ser Ile Ser Cys Lys Ala Ser Gln Asp Val Asp Thr Ala
            20                  25                  30

Val Ala Trp Phe Arg Gln Lys Pro Gly Gln Ser Pro Gln Arg Leu Ile
        35                  40                  45

Tyr Leu Ala Ser Thr Arg His Thr Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Thr Gly Val Tyr Tyr Cys Gln Gln Tyr Ser Arg Phe Pro Leu
                85                  90                  95

Thr Phe Gly Gln Gly Thr
            100
```

<210> SEQ ID NO 98
<211> LENGTH: 306
<212> TYPE: DNA
<213> ORGANISM: Canis familiaris

<400> SEQUENCE: 98

```
gatatagtga tgacccagac tccacttagc ctttccgtca gtccgggcga gacggcgagt      60

atctcttgta aagcctcaca ggacgtagac accgctgtgg cgtggtttcg acaaaagccg     120

ggtcagtctc cgcaacgcct gatttacttg gcctcaacgc gccacaccgg cgttcctgac     180

aggtttagtg gaagcgggag cggaactgac ttcacacttc gaatctccag agtagaagct     240

gatgatactg gcgtgtatta ttgccagcag tattcccggt ttccactgac ctttgggcag     300

ggtacc                                                                306
```

<210> SEQ ID NO 99
<211> LENGTH: 117
<212> TYPE: PRT
<213> ORGANISM: Felis catus

<400> SEQUENCE: 99

```
Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asp Tyr
            20                  25                  30

Tyr Met Ala Trp Val Arg Gln Ala Pro Gly Lys Gly Leu Gln Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Val Arg Gly Leu Thr Trp Asp Phe Asp Val Trp Gly Gln Gly Thr Leu
            100                 105                 110

Val Thr Val Ser Ser
        115
```

<210> SEQ ID NO 100
<211> LENGTH: 351
<212> TYPE: DNA
<213> ORGANISM: Felis catus

<400> SEQUENCE: 100

```
gacgtgcaac ttgtcgagtc tggtggggat ttggttaagc cgggaggatc tcttaggctg     60

acatgtgtgg catcaggttt tacatatagt gattactaca tggcatgggt ccgacaagcg    120

cccggtaaag gactccagtg ggttgcgaat ataaattatg atggtagttc aacctactat    180

ttggatagct tgaaatctag gttcaccatt tcacgcgata acgcgaagaa tacgctgtac    240

ctgcaaatga acagccttaa gacagaagat accgctactt actactgcgt aaggggactg    300

acgtgggact ttgatgtgtg ggggcaaggg acacttgtaa cggtctcgag c             351


<210> SEQ ID NO 101
<211> LENGTH: 102
<212> TYPE: PRT
<213> ORGANISM: Felis catus

<400> SEQUENCE: 101

Glu Ile Gln Met Thr Gln Ser Pro Ser Ser Leu Ser Ala Ser Pro Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Val Pro Lys Leu Leu Ile
        35                  40                  45

Tyr Leu Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Gln Gln Tyr Ser Arg Phe Pro Leu
                85                  90                  95

Thr Phe Gly Gln Gly Thr
            100


<210> SEQ ID NO 102
<211> LENGTH: 306
<212> TYPE: DNA
<213> ORGANISM: Felis catus

<400> SEQUENCE: 102

gaaattcaaa tgactcaatc accgtcatcc ttgtccgcca gccccggcga cagggtaaca     60

ataacttgta aggccagcca agatgtagat acggcggtag cgtggtatca acagaagccg    120

ggtaaggttc caaagctgct gatctatctc gcatccacca gacatacagg tgttccatcc    180

cgctttagcg ggtccggttc cggcactgat ttcaccctta ccatttccag tctggagccg    240

gaggacgctg ctacctatta ttgtcaacag tattcccgct tccccttac ctttggacag     300

ggtacc                                                               306


<210> SEQ ID NO 103
<211> LENGTH: 117
<212> TYPE: PRT
<213> ORGANISM: Felis catus

<400> SEQUENCE: 103

Asp Val Gln Leu Val Glu Ser Gly Gly Asn Leu Val Lys Pro Gly Gly
1               5                   10                  15

Ser Leu Arg Leu Thr Cys Val Ala Ser Gly Phe Thr Phe Ser Asp Tyr
            20                  25                  30

Tyr Met Ala Trp Val Arg Gln Ala Pro Gly Lys Gly Leu Gln Trp Val
        35                  40                  45

Ala Asn Ile Asn Tyr Asp Gly Ser Ser Thr Tyr Tyr Leu Asp Ser Leu
```

```
    50                  55                  60

Lys Ser Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Ala Arg Gly Leu Thr Trp Asp Phe Asp Val Trp Gly Gln Gly Thr Leu
            100                 105                 110

Val Thr Val Ser Ser
        115


<210> SEQ ID NO 104
<211> LENGTH: 351
<212> TYPE: DNA
<213> ORGANISM: Felis catus

<400> SEQUENCE: 104

gatgtgcaac tggttgagtc tggtgggaat ctggttaagc caggcggttc cctgagactt     60

acctgcgttg cgagtggctt tacctttagt gattattaca tggcatgggt acggcaagcg    120

ccaggaaaag gtctccaatg ggtagcaaac ataaattatg atggcagctc tacctactac    180

cttgacagcc ttaaatccag attcacgatt agtcgagata acgctaaaaa tactctctac    240

ttgcaaatga atagtctcaa aacggaagac accgcgacat actactgcgc tcgcggcctg    300

acttgggact tcgacgtgtg ggggcagggg acccttgtta ccgtctcgag c             351


<210> SEQ ID NO 105
<211> LENGTH: 102
<212> TYPE: PRT
<213> ORGANISM: Felis catus

<400> SEQUENCE: 105

Asp Ile Thr Met Thr Gln Ser Pro Gly Ser Leu Ala Gly Ser Pro Gly
1               5                   10                  15

Gln Gln Val Thr Met Asn Cys Lys Ala Ser Gln Asp Val Asp Thr Ala
            20                  25                  30

Val Ala Trp Tyr Gln Gln Lys Pro Gly Gln His Pro Lys Leu Leu Ile
        35                  40                  45

Tyr Leu Ala Ser Thr Arg His Thr Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Gln Gln Tyr Ser Arg Phe Pro Leu
                85                  90                  95

Thr Phe Gly Gln Gly Thr
            100


<210> SEQ ID NO 106
<211> LENGTH: 306
<212> TYPE: DNA
<213> ORGANISM: Felis catus

<400> SEQUENCE: 106

gacataacga tgactcagtc ccccggatct cttgcaggct ctcccggcca gcaagtgacg     60

atgaactgca aggcgagcca agatgtagat accgccgtcg catggtatca gcagaaacca    120

ggccaacatc cgaaactcct catctatctg gcaagtacac gccacaccgg ggtccctgat    180

aggttttccg ggtctgggtc cggaacggac ttcacactga ctatatccaa cctgcaagca    240
```

```
gaagatgtag caagttacta ttgtcagcag tactcacgct tccccctcac tttcggacag    300

ggtacc                                                               306


<210> SEQ ID NO 107
<211> LENGTH: 652
<212> TYPE: PRT
<213> ORGANISM: Canis familiaris

<400> SEQUENCE: 107

Met Ala Val Phe Ser Val Phe Gln Thr Thr Phe Phe Leu Ala Leu Leu
1               5                   10                  15

Ser Leu Arg Thr Leu Gln Ser Glu Val Leu Ser Glu Pro Leu Pro Trp
            20                  25                  30

Ala Pro Glu Ser Leu Lys Val Ser Ile Asn Ser Thr His Gln Cys Leu
        35                  40                  45

His Leu Gln Trp Ser Val His Asn Leu Ala Tyr His Gln Glu Leu Lys
    50                  55                  60

Met Val Phe Gln Ile Glu Ile Ser Arg Ile Lys Thr Ser Asn Val Ile
65                  70                  75                  80

Trp Val Glu Asn Tyr Ser Thr Thr Val Lys Gly Asn Gln Leu Leu His
                85                  90                  95

Trp Ser Trp Glu Ser Gln Leu Pro Leu Glu Cys Ala Lys His Phe Ile
            100                 105                 110

Arg Met Arg Ser Ala Val Asp Asp Ala Thr Thr Pro Glu Gln Arg Phe
        115                 120                 125

Trp Ser Asn Trp Ser Ser Trp Glu Glu Val Asp Val Gln Asn Ser Leu
    130                 135                 140

Gly His Glu Pro Leu Phe Val Phe Pro Lys Asp Lys Leu Val Glu Glu
145                 150                 155                 160

Gly Ser Asn Val Thr Ile Cys Tyr Val Ser Arg Ser Gln Gln Asn Asn
                165                 170                 175

Ile Ser Cys Tyr Leu Glu Gly Val Arg Met Gln Gly Gln Gln Leu Asp
            180                 185                 190

Pro Asn Val Ser Met Phe Asn Leu His Asn Val Ala Phe Ile Arg Glu
        195                 200                 205

Thr Gly Thr Asn Ile Tyr Cys Lys Val Asp Arg Gly Asp Asp Ile Lys
    210                 215                 220

Gly Ile Val Leu Phe Val Ser Lys Ile Leu Glu Glu Pro Lys Asp Phe
225                 230                 235                 240

Ser Cys Glu Thr Arg Asp Phe Gln Thr Leu Ser Cys Thr Trp Asp Pro
                245                 250                 255

Gly Arg Asp Thr Gly Leu Leu Lys Gln Leu Pro Gln Ser Tyr Thr Leu
            260                 265                 270

Phe Glu Ser Phe Ser Gly Lys Lys Thr Leu Cys Lys His Lys Ser Trp
        275                 280                 285

Cys Asn Trp Gln Val Ala Ser Glu Ser Gln Glu Met Tyr Asn Phe Thr
    290                 295                 300

Leu Thr Ala Glu Asn Tyr Leu Arg Lys Arg Ser Val His Ile Leu Phe
305                 310                 315                 320

Asn Leu Thr His Arg Val His Pro Met Ala Pro Phe Asn Val Leu Phe
                325                 330                 335

Lys Asp Val Ser Val Thr Asn Ala Thr Met Thr Trp Lys Val His Ser
            340                 345                 350

Thr Gly Asn Tyr Tyr Thr Leu Leu Cys Gln Val Glu Leu Tyr Gly Glu
```

-continued

```
        355                 360                 365

Gly Lys Val Ile Gln Lys His Asn Val Ser Val Lys Val Asn Gly Glu
    370                 375                 380

Leu Val Leu Ser Gly Leu Glu Pro Asp Thr Glu Tyr Ser Ala Gln Val
385                 390                 395                 400

Arg Cys Ala Asn Ala Asn His Phe Trp Lys Trp Ser Glu Trp Thr Arg
                405                 410                 415

Gln Asn Phe Thr Thr Val Glu Ala Ala Asp Lys Thr His Thr Cys Pro
            420                 425                 430

Pro Cys Pro Ala Pro Glu Leu Leu Gly Gly Pro Ser Val Phe Leu Phe
        435                 440                 445

Pro Pro Lys Pro Lys Asp Thr Leu Met Ile Ser Arg Thr Pro Glu Val
    450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Ala Leu Pro Ala Pro Ile Glu Lys Thr Ile Ser Lys Ala
    530                 535                 540

Lys Gly Gln Pro Arg Glu Pro Gln Val Tyr Thr Leu Pro Pro Ser Arg
545                 550                 555                 560

Glu Glu Met Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650


<210> SEQ ID NO 108
<211> LENGTH: 1956
<212> TYPE: DNA
<213> ORGANISM: Canis familiaris

<400> SEQUENCE: 108

atggccgtgt tctccgtgtt tcagaccaca ttctttctgg ctctgctgag cctgaggacc      60

ctgcagagcg aggtgctgtc tgagccactg ccatgggctc ctgagtccct gaaggtgagc     120

atcaactcta cacaccagtg cctgcatctg cagtggagcg tgcacaatct ggcttaccat     180

caggagctga agatggtgtt ccagatcgag atctcccgga tcaagaccag caacgtgatc     240

tgggtggaga attatagcac cacagtgaag ggcaaccagc tgctgcactg gtcctgggag     300

agccagctgc ctctggagtg tgccaagcat ttcatcagga tgcggtctgc cgtggacgat     360

gctaccacac cagagcagag attttggagc aactggtcca gctgggagga ggtggacgtg     420

cagaattctc tgggccacga gcccctgttc gtgtttccta aggataagct ggtcgaggag     480
```

```
ggcagcaacg tgaccatctg ctacgtgtct aggtcccagc agaacaatat ctcttgttat    540
ctggagggcg tgcggatgca gggacagcag ctggacccca acgtgtccat gttcaacctg    600
cataatgtgg cttttatcag ggagaccggc acaaatatct actgcaaggt ggatcggggc    660
gacgacatca agggcatcgt gctgtttgtg agcaagatcc tggaggagcc taaggacttc    720
tcttgcgaga ccagagattt tcagaccctg tcctgtacat gggaccctgg ccgcgataca    780
ggcctgctga agcagctgcc acagtcttat accctgttcg agagcttttc tggcaagaag    840
acactgtgca agcacaagtc ctggtgtaac tggcaggtgg cctccgagag ccaggagatg    900
tacaacttca ccctgacagc tgagaattat ctgagaaaga ggtccgtgca tatcctgttt    960
aatctgaccc accgcgtgca tccaatggcc cccttcaacg tgctgtttaa ggacgtgtct   1020
gtgacaaatg ctaccatgac atggaaggtg cactccaccg gcaactacta tacactgctg   1080
tgccaggtgg agctgtacgg cgagggcaaa gtgatccaga agcataacgt gtccgtgaaa   1140
gtgaatggcg agctggtgct gtctggcctg gagccagata ccgagtattc cgcccaggtg   1200
agatgtgcca acgctaatca cttctggaag tggtccgagt ggacacgcca gaacttcacc   1260
acagtggagg ccgctgacaa gacccataca tgccccccct gtcctgctcc agagctgctg   1320
ggaggaccaa gcgtgttcct gtttccaccc aagcccaagg ataccctgat gatctccagg   1380
accccagagg tgacatgcgt ggtggtggac gtgagccacg aggatcccga ggtgaagttc   1440
aactggtacg tggacggcgt ggaggtgcat aatgccaaga ccaagcccag ggaggagcag   1500
tacaactcta cctatcgggt ggtgtccgtg ctgacagtgc tgcaccagga ttggctgaac   1560
ggcaaggagt ataagtgcaa ggtgtctaat aaggccctgc ccgctcctat cgagaagacc   1620
atctccaagg ccaagggcca gcctagagag ccacaggtgt acacactgcc tccaagccgc   1680
gaggagatga ccaagaacca ggtgtctctg acatgtctgg tgaagggctt ctatccctcc   1740
gacatcgctg tggagtggga gagcaatggc cagcctgaga acaattacaa gaccacaccc   1800
cctgtgctgg actctgatgg ctccttcttt ctgtatagca agctgaccgt ggataagtct   1860
aggtggcagc agggcaacgt gttttcttgt tccgtgatgc acgaggctct gcacaatcat   1920
tacacacaga agagcctgtc tctgtcccca ggcaag                              1956
```

<210> SEQ ID NO 109
<211> LENGTH: 181
<212> TYPE: PRT
<213> ORGANISM: Canis familiaris

<400> SEQUENCE: 109

```
Ser Cys Ser Asp Lys Tyr Pro Glu Leu Leu Gly Gln Leu Gln Lys Gln
1               5                   10                  15

Ala Asp Phe Met Gln His Thr Asn Thr Leu Leu Asp Leu Tyr Ile Arg
            20                  25                  30

Ser Gln Gly Leu Asp Lys Asn Gly Leu Lys Glu His Cys Arg Glu Arg
        35                  40                  45

Pro Gly Ala Phe Pro Ser Lys Asp Ala Leu Gln Arg Leu Ser Arg Arg
    50                  55                  60

Val Phe Leu Arg Thr Leu Asp Thr Thr Leu Gly Gln Val Leu Leu Arg
65                  70                  75                  80

Leu Ala Ala Leu Glu Gln Asp Ile Pro Lys Ala Gln Asp Leu Glu Met
                85                  90                  95

Leu Ser Gly Val Lys Leu Asn Ile Arg Gly Phe Lys Asn Asn Ile His
            100                 105                 110
```

```
Cys Met Ala Gln Leu Leu Pro Gly Ser Ser Glu Thr Thr Glu Pro Thr
        115                 120                 125

Pro Thr Ser Pro Gly Ala Ser Pro Ser Pro Thr Pro Thr Leu Asp Thr
    130                 135                 140

Phe Gln Arg Arg Leu Glu Gly Cys Arg Phe Leu His Gly Tyr His Arg
145                 150                 155                 160

Phe Met Arg Ser Val Gly Gln Val Phe Arg Glu Trp Gly Lys Ser Leu
                165                 170                 175

Ser Arg Ser Arg Arg
            180


<210> SEQ ID NO 110
<211> LENGTH: 461
<212> TYPE: PRT
<213> ORGANISM: Felis catus

<400> SEQUENCE: 110

Met Gly Trp Ser Cys Ile Ile Leu Phe Leu Val Ala Thr Ala Thr Gly
1               5                   10                  15

Val His Ser Ala Met Gly Ser Cys Leu Asp Asn Tyr Gln Glu Leu Leu
            20                  25                  30

Gly Gln Leu Gln Lys Gln Ala Asp Phe Met Gln His Thr Ser Met Leu
        35                  40                  45

Leu Asp Pro Tyr Ile Ser Ile Gln Gly Leu Asp Lys Asp Gly Leu Lys
    50                  55                  60

Glu His Cys Arg Glu Arg Pro Gly Val Phe Pro Ser Lys Asp Ala Leu
65                  70                  75                  80

Gln Arg Leu Ser Arg Gln Glu Phe Leu Gln Ile Leu Asn Thr Thr Leu
                85                  90                  95

Gly His Val Leu His Arg Leu Arg Thr Leu Gln Lys Asp Ile Pro Lys
            100                 105                 110

Ala Gln Asp Leu Glu Lys Leu Asn Ile Ala Lys Leu Asn Ile Arg Gly
        115                 120                 125

Phe Lys Asn Asn Ile His Cys Met Ala Gln Leu Leu Pro Gly Ser Leu
    130                 135                 140

Glu Lys Thr Glu Pro Thr Pro Thr Gly Pro Gly Ala Ser Pro Ser Pro
145                 150                 155                 160

Thr Pro Ile Ser Asp Ala Phe Gln Arg Arg Leu Glu Gly Cys Arg Phe
                165                 170                 175

Leu His Gly Tyr His Arg Phe Met His Ser Val Gly Gln Val Phe Arg
            180                 185                 190

Glu Trp Gly Gln Ser Pro Ser Arg Ser Arg Arg His Ser Pro Arg Arg
        195                 200                 205

Gly Leu Arg Lys Gly Thr His Arg Thr His Leu Ser Ser Arg Asn Lys
    210                 215                 220

Arg Leu Met Pro Arg Gly Trp Leu Pro Arg Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
```

-continued

```
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

<210> SEQ ID NO 111
<211> LENGTH: 1383
<212> TYPE: DNA
<213> ORGANISM: Felis catus

<400> SEQUENCE: 111

```
atgggctggt cctgcatcat cctgttcctg gtggccaccg ctacaggcgt gcactctgcc     60

atgggctcct gtctggacaa ctaccaggag ctgctgggcc agctgcagaa gcaggctgac    120

tttatgcagc acacctctat gctgctggat ccctatatct ccatccaggg cctggacaag    180

gatggcctga aggagcattg cagagagcgc cctggcgtgt tcccaagcaa ggatgccctg    240

cagagactgt ctcgccagga gtttctgcag atcctgaata ccacactggg ccacgtgctg    300

cataggctgc ggaccctgca gaaggacatc cctaaggccc aggatctgga gaagctgaac    360

atcgctaagc tgaatatcag aggcttcaag aacaatatcc attgcatggc tcagctgctg    420

ccaggaagcc tggagaagac cgagccaacc ccaacaggcc ctggagcttc tccttcccca    480

acacccatct ctgacgcttt ccagaggcgg ctggagggct gtagattcct gcacggctac    540

catcgcttta tgcactctgt gggccaggtg tttagggagt ggggacagag cccatctcgg    600

tccagacgcc attccccaag gaggggactg agaaagggaa cccaccgcac acatctgtcc    660

agcaggaaca agcggctgat gccaagggga tggctgccta gggacaagac ccacacatgc    720

ccccccttgtc ctgctccaga gctgctggga ggacctagcg tgttcctgtt tccacccaag    780

ccaaaggata ccctgatgat cagccgcacc cctgaggtga catgcgtggt ggtggacgtg    840

tctcacgagg atccagaggt gaagtttaac tggtacgtgg acggcgtgga ggtgcataat    900

gctaagacaa agccaagaga ggagcagtac aatagcacct atcgcgtggt gtctgtgctg    960

acagtgctgc atcaggattg gctgaacggc aaggagtata agtgcaaggt gtccaataag   1020

gccctgcccg ctcctatcga gaagaccatc agcaaggcta agggacagcc aagggagcca   1080

caggtgtaca cactgcctcc atctcgggag gagatgacca agaaccaggt gtccctgaca   1140

tgtctggtga agggcttcta tccatccgac atcgctgtgg agtgggagag caatggccag   1200
```

-continued cccgagaaca attacaagac cacaccccct gtgctggact ccgatggcag cttctttctg 1260
tattccaagc tgaccgtgga taagagccgg tggcagcagg gcaacgtgtt tagctgttct 1320
gtgatgcacg aggccctgca caatcattat acacagaagt ccctgagcct gtctcccggc 1380
aag 1383

<210> SEQ ID NO 112
<211> LENGTH: 652
<212> TYPE: PRT
<213> ORGANISM: Felis catus

<400> SEQUENCE: 112

Met Ala Leu Phe Ser Ala Phe Gln Thr Thr Phe Leu Leu Ala Leu Leu
1 5 10 15

Ser Leu Lys Thr Tyr Gln Ser Glu Val Leu Ser Glu Pro Leu Ser Leu
20 25 30

Ala Pro Glu Ser Leu Glu Val Ser Ile Asp Ser Ala Arg Gln Cys Leu
35 40 45

His Leu Lys Trp Ser Val His Asn Leu Ala Tyr His Gln Glu Leu Lys
50 55 60

Met Val Phe Gln Ile Glu Ile Ser Arg Ile Lys Thr Ser Asn Val Ile
65 70 75 80

Trp Val Glu Asn Tyr Ser Thr Thr Val Lys Arg Asn Gln Val Leu Arg
85 90 95

Trp Ser Trp Glu Ser Lys Leu Pro Leu Glu Cys Ala Lys His Ser Val
100 105 110

Arg Met Arg Gly Ala Val Asp Asp Ala Gln Val Pro Glu Leu Arg Phe
115 120 125

Trp Ser Asn Trp Thr Ser Trp Glu Glu Val Asp Val Gln Ser Ser Leu
130 135 140

Gly His Asp Pro Leu Phe Val Phe Pro Lys Asp Lys Leu Val Glu Glu
145 150 155 160

Gly Ser Asn Val Thr Ile Cys Tyr Val Ser Arg Ser His Gln Asn Asn
165 170 175

Ile Ser Cys Tyr Leu Glu Gly Val Arg Met His Gly Glu Gln Leu Asp
180 185 190

Pro Asn Val Cys Val Phe His Leu Lys Asn Val Pro Phe Ile Arg Glu
195 200 205

Thr Gly Thr Asn Ile Tyr Cys Lys Ala Asp Gln Gly Asp Val Ile Lys
210 215 220

Gly Ile Val Leu Phe Val Ser Lys Val Phe Glu Glu Pro Lys Asp Phe
225 230 235 240

Ser Cys Glu Thr Arg Asp Leu Lys Thr Leu Asn Cys Thr Trp Ala Pro
245 250 255

Gly Ser Asp Ala Gly Leu Leu Thr Gln Leu Ser Gln Ser Tyr Thr Leu
260 265 270

Phe Glu Ser Phe Ser Gly Lys Lys Thr Leu Cys Lys His Lys Ser Trp
275 280 285

Cys Asn Trp Gln Val Ser Pro Asp Ser Gln Glu Met Tyr Asn Phe Thr
290 295 300

Leu Thr Ala Glu Asn Tyr Leu Arg Lys Arg Ser Val His Leu Leu Phe
305 310 315 320

Asn Leu Thr His Arg Val His Pro Met Ala Pro Phe Asn Val Phe Val
325 330 335

```
Lys Asn Val Ser Ala Thr Asn Ala Thr Met Thr Trp Lys Val His Ser
            340                 345                 350

Ile Gly Asn Tyr Ser Thr Leu Leu Cys Gln Ile Glu Leu Asp Gly Glu
        355                 360                 365

Gly Lys Val Ile Gln Lys Gln Asn Val Ser Val Lys Val Asn Gly Lys
    370                 375                 380

His Leu Met Lys Lys Leu Glu Pro Ser Thr Glu Tyr Ala Ala Gln Val
385                 390                 395                 400

Arg Cys Ala Asn Ala Asn His Phe Trp Lys Trp Ser Glu Trp Thr Arg
                405                 410                 415

Arg Asn Phe Thr Thr Ala Glu Ala Ala Asp Lys Thr His Thr Cys Pro
            420                 425                 430

Pro Cys Pro Ala Pro Glu Leu Leu Gly Gly Pro Ser Val Phe Leu Phe
        435                 440                 445

Pro Pro Lys Pro Lys Asp Thr Leu Met Ile Ser Arg Thr Pro Glu Val
    450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Ala Leu Pro Ala Pro Ile Glu Lys Thr Ile Ser Lys Ala
    530                 535                 540

Lys Gly Gln Pro Arg Glu Pro Gln Val Tyr Thr Leu Pro Pro Ser Arg
545                 550                 555                 560

Glu Glu Met Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650
```

<210> SEQ ID NO 113
<211> LENGTH: 2076
<212> TYPE: DNA
<213> ORGANISM: Felis catus

<400> SEQUENCE: 113

```
atggccctgt tcagcgcctt ccagaccacc ttcctgctgg ccctgctgag cctgaaaacc      60

taccagagcg aggtgctgag cgagcccctg tctctggccc ctgagagcct ggaagtgtcc     120

atcgacagcg ccagacagtg cctgcacctg aagtggagcg tgcacaacct ggcctaccac     180

caggaactga agatggtgtt ccagatcgag atcagccgga tcaagaccag caacgtgatc     240

tgggtggaaa actacagcac caccgtgaag cggaaccagg tgctgcggtg gtcctgggag     300
```

-continued

```
tctaagctgc ctctggaatg cgccaagcac agcgtgcgga tgagaggcgc cgtggatgat    360

gcccaggtgc ccgagctgag attctggtcc aactggacct cctgggaaga ggtggacgtg    420

cagtctagcc tgggccacga ccccctgttc gtgttcccca aggacaagct ggtggaagag    480

ggctccaacg tgaccatctg ctacgtgtcc agaagccacc agaacaacat cagctgctac    540

ctggaaggcg tgcgcatgca cggcgagcag ctggacccta acgtgtgcgt gttccacctg    600

aagaacgtgc ccttcatcag agagacaggc accaacatct actgcaaggc cgaccagggc    660

gacgtgatca agggcatcgt gctgtttgtg tccaaggtgt tcgaggaacc caaggacttc    720

agctgcgaga cacgggatct gaaaaccctg aactgtacct gggcccctgg ctccgatgcc    780

ggactgctga ctcagctgtc ccagagctac accctgttcg agagcttcag cggcaaaaag    840

accctgtgca agcacaagag ctggtgcaac tggcaagtgt cccccgatag ccaggaaatg    900

tacaacttca ccctgaccgc cgagaactac ctgcggaaga gatccgtgca tctgctgttc    960

aacctgaccc acagagtgca ccccatggcc cccttcaacg tgttcgtgaa gaatgtgtcc   1020

gccaccaacg ccaccatgac atggaaggtg cacagcatcg gcaactactc caccctgctg   1080

tgtcagatcg agctggacgg cgagggcaaa gtgatccaga aacagaacgt gtcagtgaaa   1140

gtgaacggca agcacctgat gaagaagctg gaacccagca ccgagtacgc cgcccaggtg   1200

cgctgtgcca acgccaacca cttctggaag tggagtgaat ggacccggcg gaacttcacc   1260

acagccgaag ccgccgctga gaacgaggtg tccacaccta tgcaggccct gaccaccaac   1320

aaggacgacg acaacatcct gttccgggac tccgccaatg ccaccagcct gcctgtgcag   1380

gatagcagct ctgtgctgcc cgccaagccc gagaacatct cctgcgtgtt ctactacgag   1440

gaaaacttca cttgcacctg gtcccccgag aaagaggcca gctacacctg gtacaaagtg   1500

aagagaacct acagctacgg ctacaagagc gacatctgcc ccagcgacaa cagcaccaga   1560

ggcaaccaca ccttctgcag ctttctgccc cccaccatca ccaaccccga caactacacc   1620

atccaggtgg aagcccagaa cgccgacggc atcatcaagt ccgacatcac ccactggtcc   1680

ctggacgcca tcacaaagat cgagcccccc gagatcttct ccgtgaagcc tgtgctgggc   1740

gtgaagagga tggtgcagat caagtggatc cggcccgtgc tggccccagt gtctagcacc   1800

ctgaagtaca ccctgcggtt caagaccgtg aacagcgcct actggatgga agtgaatttc   1860

accaaagagg acatcgaccg ggacgagaca tacaatctga ccggactgca ggccttcaca   1920

gagtacgtgc tggctctgag atgcgccacc aaagaatcca tgttttggag cggctggtcc   1980

caggaaaaga tgggcaccac cgaagagggt aagcctatcc ctaaccctct cctcggtctc   2040

gattctacgc gtaccggtca tcatcaccat caccat                             2076
```

<210> SEQ ID NO 114
<211> LENGTH: 335
<212> TYPE: PRT
<213> ORGANISM: Canis familiaris

<400> SEQUENCE: 114

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60
```

```
Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

<210> SEQ ID NO 115
<211> LENGTH: 1005
<212> TYPE: DNA
<213> ORGANISM: Canis familiaris

<400> SEQUENCE: 115

```
gcctcaacaa ctgctcctag cgtgtttccc ctggccccta gctgcggaag tacctcaggc      60

agcacagtgg ccctggcttg tctggtgtct ggatatttcc ctgagccagt gaccgtgagt     120

tggaacagcg gctctctgac ctccggggtg cacacatttc catctgtgct gcagtctagt     180

ggcctgtact ccctgtcaag catggtgact gtgccttcct ctaggtggcc atcagaaact     240

ttcacctgca acgtggccca tcccgccagc aagaccaaag tggacaagcc cgtgcctaaa     300

agggagaatg gaagggtgcc aagaccacct gattgcccta agtgtccagc tccagaagcg     360

gcgggagcac caagcgtgtt catctttcca cccaagccca aagacacact gctgattgct     420

agaactcccg aggtgacctg cgtggtggtg gacctggatc cagaggaccc cgaagtgcag     480

atctcctggt tcgtggatgg gaagcagatg cagacagcca aaactcagcc tcgggaggaa     540

cagtttaacg gaacctatag agtggtgtct gtgctgccaa ttggacacca ggactggctg     600
```

aagggcaaac agtttacatg caaggtgaac aacaaggccc tgcctagtcc aatcgagagg 660
actatttcaa aagctagggg acaggctcat cagccttccg tgtatgtgct gcctccatcc 720
cgggaggaac tgtctaagaa cacagtgagt ctgacttgtc tgatcaaaga tttctttccc 780
cctgacattg atgtggagtg gcagagcaat gggcagcagg agccagaatc caagtacaga 840
accacaccac cccagctgga cgaagatggc tcctatttcc tgtacagtaa gctgtcagtg 900
gacaaatcta ggtggcagcg cggggatacc tttatctgcg ccgtgatgca cgaggctctg 960
cacaatcatt acacacaaga aagtctgtca catagccccg gcaag 1005

<210> SEQ ID NO 116
<211> LENGTH: 106
<212> TYPE: PRT
<213> ORGANISM: Canis familiaris

<400> SEQUENCE: 116

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105

<210> SEQ ID NO 117
<211> LENGTH: 318
<212> TYPE: DNA
<213> ORGANISM: Canis familiaris

<400> SEQUENCE: 117
aggaacgacg cccagcctgc tgtgtatctg tttcagccct cccctgatca gctgcacact 60
ggctctgcta gtgtggtgtg tctgctgaac agcttctacc caaaggatat caatgtgaag 120
tggaaagtgg acggcgtgat ccaggatact gggattcagg agtccgtgac cgaacaggac 180
aaagattcaa catatagcct gagctccact ctgaccatgt ctagtaccga gtacctgagc 240
cacgaactgt attcctgcga gatcactcat aagtccctgc cctctaccct gatcaagagc 300
ttccagagat cagagtgt 318

<210> SEQ ID NO 118
<211> LENGTH: 335
<212> TYPE: PRT
<213> ORGANISM: Felis catus

<400> SEQUENCE: 118

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser

-continued

```
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Ala Ala Gly Ala Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335


<210> SEQ ID NO 119
<211> LENGTH: 1005
<212> TYPE: DNA
<213> ORGANISM: Felis catus

<400> SEQUENCE: 119

gcctccacca cggccccatc ggtgttccca ctggccccca gctgcgggac cacatctggc      60

gccaccgtgg ccctggcctg cctggtgtta ggctacttcc ctgagccggt gaccgtgtcc     120

tggaactccg gcgccctgac cagcggtgtg cacaccttcc cggccgtcct gcaggcctcg     180

gggctgtact ctctcagcag catggtgaca gtgccctcca gcaggtggct cagtgacacc     240

ttcacctgca acgtggccca cccgcccagc aacaccaagg tggacaagac cgtgcgcaaa     300

acagaccacc caccgggacc caaaccctgc gactgtccca aatgcccacc ccctgaggcg     360

gctggagcac cgtccatctt catcttcccc ccaaaaccca aggacaccct ctcgatttcc     420

cggacgcccg aggtcacatg cttggtggtg gacttgggcc cagatgactc cgatgtccag     480
```

-continued

```
atcacatggt ttgtggataa cacccaggtg tacacagcca agacgagtcc gcgtgaggag    540

cagttcaaca gcacctaccg tgtggtcagt gtcctcccca tcctacacca ggactggctc    600

aaggggaagg agttcaagtg caaggtcaac agcaaatccc tcccctcccc catcgagagg    660

accatctcca aggccaaagg acagccccac gagccccagg tgtacgtcct gcctccagcc    720

caggaggagc tcagcaggaa caaagtcagt gtgacctgcc tgatcaaatc cttccacccg    780

cctgacattg ccgtcgagtg ggagatcacc ggacagccgg agccagagaa caactaccgg    840

acgaccccgc cccagctgga cagcgacggg acctacttcg tgtacagcaa gctctcggtg    900

gacaggtccc actggcagag gggaaacacc tacacctgct cggtgtcaca cgaagctctg    960

cacagccacc acacacagaa atccctcacc cagtctccgg gtaaa                   1005


<210> SEQ ID NO 120
<211> LENGTH: 110
<212> TYPE: PRT
<213> ORGANISM: Felis catus

<400> SEQUENCE: 120

Arg Ser Asp Ala Gln Pro Ser Val Phe Leu Phe Gln Pro Ser Leu Asp
1               5                   10                  15

Glu Leu His Thr Gly Ser Ala Ser Ile Val Cys Ile Leu Asn Asp Phe
            20                  25                  30

Tyr Pro Lys Glu Val Asn Val Lys Trp Lys Val Asp Gly Val Val Gln
        35                  40                  45

Asn Lys Gly Ile Gln Glu Ser Thr Thr Glu Gln Asn Ser Lys Asp Ser
    50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                85                  90                  95

Thr Leu Val Lys Ser Phe Gln Arg Ser Glu Cys Gln Arg Glu
            100                 105                 110


<210> SEQ ID NO 121
<211> LENGTH: 330
<212> TYPE: DNA
<213> ORGANISM: Felis catus

<400> SEQUENCE: 121

cggagtgatg ctcagccatc tgtctttctc ttccaaccat ctctggacga gttacataca     60

ggaagtgcct ctatcgtgtg catattgaat gacttctacc ccaaagaggt caatgtcaag    120

tggaaagtgg atggcgtagt ccaaaacaaa ggcatccagg agagcaccac agagcagaac    180

agcaaggaca gcacctacag cctcagcagc accctgacga tgtccagtac ggagtaccaa    240

agtcatgaaa agttctcctg cgaggtcact cacaagagcc tggcctccac cctcgtcaag    300

agcttccaga ggagcgagtg tcagagagag                                     330


<210> SEQ ID NO 122
<211> LENGTH: 739
<212> TYPE: PRT
<213> ORGANISM: Homo sapiens

<400> SEQUENCE: 122

Met Ala Leu Phe Ala Val Phe Gln Thr Thr Phe Phe Leu Thr Leu Leu
1               5                   10                  15
```

-continued

```
Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
```

```
        435                 440                 445

Val Thr Leu Phe Trp Lys Pro Leu Ser Lys Leu His Ala Asn Gly Lys
    450                 455                 460

Ile Leu Phe Tyr Asn Val Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
        595                 600                 605

Ile Ala Cys Leu Leu Glu Lys Lys Thr Gly Tyr Ser Gln Glu Leu Ala
    610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
        675                 680                 685

Tyr Lys Ile Asp Asn Pro Glu Glu Lys Ala Leu Ile Val Asp Asn Leu
    690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser


<210> SEQ ID NO 123
<211> LENGTH: 159
<212> TYPE: PRT
<213> ORGANISM: Canis familiaris

<400> SEQUENCE: 123

Met Leu Ser His Thr Gly Pro Ser Arg Phe Ala Leu Phe Leu Leu Cys
1               5                   10                  15

Ser Met Glu Thr Leu Leu Ser Ser His Met Ala Pro Thr His Gln Leu
            20                  25                  30

Pro Pro Ser Asp Val Arg Lys Ile Ile Leu Glu Leu Gln Pro Leu Ser
        35                  40                  45

Arg Gly Leu Leu Glu Asp Tyr Gln Lys Lys Glu Thr Gly Val Pro Glu
    50                  55                  60

Ser Asn Arg Thr Leu Leu Leu Cys Leu Thr Ser Asp Ser Gln Pro Pro
```

```
65                  70                  75                  80

Arg Leu Asn Ser Ser Ala Ile Leu Pro Tyr Phe Arg Ala Ile Arg Pro
                85                  90                  95

Leu Ser Asp Lys Asn Ile Ile Asp Lys Ile Ile Glu Gln Leu Asp Lys
            100                 105                 110

Leu Lys Phe Gln His Glu Pro Glu Thr Glu Ile Ser Val Pro Ala Asp
        115                 120                 125

Thr Phe Glu Cys Lys Ser Phe Ile Leu Thr Ile Leu Gln Gln Phe Ser
    130                 135                 140

Ala Cys Leu Glu Ser Val Phe Lys Ser Leu Asn Ser Gly Pro Gln
145                 150                 155
```

<210> SEQ ID NO 124
<211> LENGTH: 477
<212> TYPE: DNA
<213> ORGANISM: Canis familiaris

<400> SEQUENCE: 124

```
atgctctccc acacaggacc atccaggttt gccctgttcc tgctctgctc tatggaaacc     60

ttgctgtcct cccatatggc acccacccat cagctaccac caagtgatgt acgaaaaatc    120

atcttggaat tacagccctt gtcgaggggga cttttggaag actatcagaa gaaagagaca    180

ggggtgccag aatccaaccg taccttgctg ctgtgtctca cctctgattc ccaaccacca    240

cgcctcaaca gctcagccat cttgccttat ttcagggcaa tcagaccatt atcagataag    300

aacattattg ataaaatcat agaacagctt gacaaactca aatttcaaca tgaaccagaa    360

acagaaattt ctgtgcctgc agatactttt gaatgtaaaa gcttcatctt gacgatttta    420

cagcagttct cggcgtgcct ggaaagtgtg tttaagtcac taaactctgg acctcag       477
```

<210> SEQ ID NO 125
<211> LENGTH: 165
<212> TYPE: PRT
<213> ORGANISM: Felis catus

<400> SEQUENCE: 125

```
Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Pro Ala Asp
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln His
145                 150                 155                 160
```

His His His His His
165

<210> SEQ ID NO 126
<211> LENGTH: 495
<212> TYPE: DNA
<213> ORGANISM: Felis catus

<400> SEQUENCE: 126
atgctttcac acgctggacc agcccgattc gccctcttcc tcctctgctg tatggagact 60
ctgttgccgt cccacatggc cccggcacat aggctgcagc cgtctgacat ccggaagatc 120
attctcgaac ttcgccccat gtcgaagggg ttgctgcaag actacctgaa gaaggagatc 180
ggcctgcccg aaagcaacca ctcctcgctg ccttgcctgt caagcgattc ccagctgccc 240
cacattaacg gttccgccat cctcccgtac ttccgggcca tcagaccact gtcggacaag 300
aacaccatcg acaagatcat tgaacagctg gacaagctga agtttcagcg cgagcctgaa 360
gccaaagtgt ccatgcccgc cgataacttc gagcggaaga atttcattct cgcggtgctg 420
cagcagttct ccgcgtgcct ggagcacgtc ctgcaatccc tgaacagcgg acctcagcac 480
caccatcacc accat 495

<210> SEQ ID NO 127
<211> LENGTH: 121
<212> TYPE: PRT
<213> ORGANISM: Canis familiaris

<400> SEQUENCE: 127

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Asn Tyr
20 25 30

Trp Met Asn Trp Val Arg Gln Ala Pro Gly Lys Gly Leu Gln Trp Val
35 40 45

Ala Gln Ile Tyr Pro Gly His Val Asn Thr Asn Tyr Asn Gly Asn Phe
50 55 60

Lys Asp Arg Phe Thr Ile Ser Arg Asp Asn Ala Arg Asn Thr Val Tyr
65 70 75 80

Leu Gln Met Asn Ser Leu Arg Ala Glu Asp Thr Ala Val Tyr Tyr Cys
85 90 95

Ala Arg Ser Ala Asp Asn Ser Gly Phe Val Leu Phe Ala Tyr Trp Gly
100 105 110

Gln Gly Thr Leu Val Thr Val Ser Ser
115 120

<210> SEQ ID NO 128
<211> LENGTH: 363
<212> TYPE: DNA
<213> ORGANISM: Canis familiaris

<400> SEQUENCE: 128
gaggtgcagc ttgtagagag tgggggcgac ttggttaagc caggcgggag tttgcgcttg 60
agctgcgtag cgagcggctt cacctttagt aattattgga tgaactgggt gaggcaggcc 120
ccaggaaaag gtctgcagtg ggtcgcccaa atatacccag gccatgtgaa cacaaattat 180
aacggtaatt tcaaagatag gtttacaata tctcgggaca atgcccgcaa cacggtttat 240
ctgcaaatga atagcctgag ggccgaagac acggcggttt attattgtgc taggagcgct 300
gacaacagcg gcttcgtgct gtttgcctac tggggacaag gcactctcgt gaccgtctcg 360
agc 363

<210> SEQ ID NO 129
<211> LENGTH: 121
<212> TYPE: PRT
<213> ORGANISM: Canis familiaris

<400> SEQUENCE: 129

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Asn Tyr
20 25 30

Trp Met Asn Trp Val Arg Gln Ser Pro Gly Lys Gly Leu Gln Trp Val
35 40 45

Ala Gln Ile Tyr Pro Gly His Val Asn Thr Asn Tyr Asn Gly Asn Phe
50 55 60

Lys Asp Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Phe Cys
85 90 95

Ala Arg Ser Ala Asp Asn Ser Gly Phe Val Leu Phe Ala Tyr Trp Gly
100 105 110

Gln Gly Thr Leu Val Thr Val Ser Ser
115 120

<210> SEQ ID NO 130
<211> LENGTH: 363
<212> TYPE: DNA
<213> ORGANISM: Canis familiaris

<400> SEQUENCE: 130
gaagtccagt tggtcgaatc aggcggggac cttgtcaaac caggtggtag cttgcgcctc 60
tcatgcgtgg cgtccggttt tactttttcc aattactgga tgaactgggt ccgacagtcc 120
cccggcaaag ggttgcaatg ggtagcacaa atatatccag ggcacgtaaa caccaactat 180
aatggcaact tcaaggatag gtttactatt agcagggaca acgccaaaaa cacactgtat 240
ctgcaaatga actctcttcg cgctgaagac accgccgttt atttttgtgc gcggagcgcc 300
gacaattccg gctttgtcct tttcgcttat tggggtcagg gtacattggt gacagtctcg 360
agc 363

<210> SEQ ID NO 131
<211> LENGTH: 106
<212> TYPE: PRT
<213> ORGANISM: Canis familiaris

<400> SEQUENCE: 131

Glu Ile Val Met Thr Gln Ser Pro Ala Ser Leu Ser Leu Ser Gln Glu
1 5 10 15

Glu Lys Val Thr Ile Thr Cys Arg Ala Ser Lys Ser Val Ser Thr Ser
20 25 30

Gly Tyr Ser Tyr Leu His Trp Tyr Gln Gln Lys Pro Gly Gln Ala Pro
35 40 45

Lys Leu Leu Ile Tyr Leu Ala Ser Asn Leu Glu Ser Gly Val Pro Ser
50 55 60

Arg Phe Ser Gly Ser Gly Ser Gly Thr Asp Phe Ser Phe Thr Ile Ser

```
65                  70                  75                  80

Ser Leu Glu Pro Glu Asp Val Ala Val Tyr Tyr Cys Gln His Ser Arg
                85                  90                  95

Glu Leu Pro Leu Thr Phe Gly Gln Gly Thr
            100                 105


<210> SEQ ID NO 132
<211> LENGTH: 318
<212> TYPE: DNA
<213> ORGANISM: Canis familiaris

<400> SEQUENCE: 132

gaaatagtga tgactcagag ccctgctagt ctctctttgt cacaagagga aaaggtaact      60

attacgtgtc gggcaagtaa gagtgtttcc acaagcggtt actcttattt gcattggtat     120

caacaaaaac ctggacaggc acctaagctg cttatctatc tggccagcaa cttggagtca     180

ggcgtcccgt cccgcttctc aggaagcggc agtggcactg acttttcctt caccatctct     240

tcccttgaac ctgaggacgt ggcggtgtac tactgtcagc attcacggga gctgccactg     300

acattcggcc aaggtacc                                                   318


<210> SEQ ID NO 133
<211> LENGTH: 106
<212> TYPE: PRT
<213> ORGANISM: Canis familiaris

<400> SEQUENCE: 133

Asp Ile Val Met Thr Gln Thr Pro Leu Ser Leu Ser Val Ser Pro Gly
1               5                   10                  15

Glu Thr Ala Ser Ile Ser Cys Arg Ala Ser Lys Ser Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Asn Leu Glu Ser Gly Val Ser Lys
    50                  55                  60

Arg Phe Ser Gly Ser Gly Ser Gly Thr Asp Phe Thr Leu Arg Ile Ser
65                  70                  75                  80

Arg Val Glu Ala Asp Asp Thr Gly Ile Tyr Tyr Cys Gln His Ser Arg
                85                  90                  95

Glu Leu Pro Leu Thr Phe Gly Gln Gly Thr
            100                 105


<210> SEQ ID NO 134
<211> LENGTH: 318
<212> TYPE: DNA
<213> ORGANISM: Canis familiaris

<400> SEQUENCE: 134

gatatagtta tgacacagac tccgctctcc ctcagtgtga gccctgggga aaccgccagt      60

atatcatgcc gggcatccaa aagtgtcagc acttcaggct acagttattt gcattggtat     120

cttcagaaac cgggacagag cccgcagctc ttgatctatt tggcttccaa cctggaaagc     180

ggagtttcta agcgcttttc aggttccggg agcgggacgg atttcacact tcggatctct     240

agagtggaag ccgatgatac tggaatctat tactgtcagc acagtagaga actccctctc     300

acattcgggc agggtacc                                                   318


<210> SEQ ID NO 135
```

<211> LENGTH: 789
<212> TYPE: PRT
<213> ORGANISM: Homo sapiens

<400> SEQUENCE: 135

Gln Lys Lys Gly Ala Pro His Asp Leu Lys Cys Val Thr Asn Asn Leu
1               5                   10                  15

Gln Val Trp Asn Cys Ser Trp Lys Ala Pro Ser Gly Thr Gly Arg Gly
            20                  25                  30

Thr Asp Tyr Glu Val Cys Ile Glu Asn Arg Ser Arg Ser Cys Tyr Gln
        35                  40                  45

Leu Glu Lys Thr Ser Ile Lys Ile Pro Ala Leu Ser His Gly Asp Tyr
    50                  55                  60

Glu Ile Thr Ile Asn Ser Leu His Asp Phe Gly Ser Ser Thr Ser Lys
65                  70                  75                  80

Phe Thr Leu Asn Glu Gln Asn Val Ser Leu Ile Pro Asp Thr Pro Glu
                85                  90                  95

Ile Leu Asn Leu Ser Ala Asp Phe Ser Thr Ser Thr Leu Tyr Leu Lys
            100                 105                 110

Trp Asn Asp Arg Gly Ser Val Phe Pro His Arg Ser Asn Val Ile Trp
        115                 120                 125

Glu Ile Lys Val Leu Arg Lys Glu Ser Met Glu Leu Val Lys Leu Val
    130                 135                 140

Thr His Asn Thr Thr Leu Asn Gly Lys Asp Thr Leu His His Trp Ser
145                 150                 155                 160

Trp Ala Ser Asp Met Pro Leu Glu Cys Ala Ile His Phe Val Glu Ile
                165                 170                 175

Arg Cys Tyr Ile Asp Asn Leu His Phe Ser Gly Leu Glu Glu Trp Ser
            180                 185                 190

Asp Trp Ser Pro Val Lys Asn Ile Ser Trp Ile Pro Asp Ser Gln Thr
        195                 200                 205

Lys Val Phe Pro Gln Asp Lys Val Ile Leu Val Gly Ser Asp Ile Thr
    210                 215                 220

Phe Cys Cys Val Ser Gln Glu Lys Val Leu Ser Ala Leu Ile Gly His
225                 230                 235                 240

Thr Asn Cys Pro Leu Ile His Leu Asp Gly Glu Asn Val Ala Ile Lys
                245                 250                 255

Ile Arg Asn Ile Ser Val Ser Ala Ser Ser Gly Thr Asn Val Val Phe
            260                 265                 270

Thr Thr Glu Asp Asn Ile Phe Gly Thr Val Ile Phe Ala Gly Tyr Pro
        275                 280                 285

Pro Asp Thr Pro Gln Gln Leu Asn Cys Glu Thr His Asp Leu Lys Glu
    290                 295                 300

Ile Ile Cys Ser Trp Asn Pro Gly Arg Val Thr Ala Leu Val Gly Pro
305                 310                 315                 320

Arg Ala Thr Ser Tyr Thr Leu Val Glu Ser Phe Ser Gly Lys Tyr Val
                325                 330                 335

Arg Leu Lys Arg Ala Glu Ala Pro Thr Asn Glu Ser Tyr Gln Leu Leu
            340                 345                 350

Phe Gln Met Leu Pro Asn Gln Glu Ile Tyr Asn Phe Thr Leu Asn Ala
        355                 360                 365

His Asn Pro Leu Gly Arg Ser Gln Ser Thr Ile Leu Val Asn Ile Thr
    370                 375                 380

Glu Lys Val Tyr Pro His Thr Pro Thr Ser Phe Lys Val Lys Asp Ile

-continued

```
385                 390                 395                 400

Asn Ser Thr Ala Val Lys Leu Ser Trp His Leu Pro Gly Asn Phe Ala
                405                 410                 415

Lys Ile Asn Phe Leu Cys Glu Ile Glu Ile Lys Lys Ser Asn Ser Val
            420                 425                 430

Gln Glu Gln Arg Asn Val Thr Ile Lys Gly Val Glu Asn Ser Ser Tyr
        435                 440                 445

Leu Val Ala Leu Asp Lys Leu Asn Pro Tyr Thr Leu Tyr Thr Phe Arg
    450                 455                 460

Ile Arg Cys Ser Thr Glu Thr Phe Trp Lys Trp Ser Lys Trp Ser Asn
465                 470                 475                 480

Lys Lys Gln His Leu Thr Thr Glu Ala Ser Pro Ser Lys Gly Pro Asp
                485                 490                 495

Thr Trp Arg Glu Trp Ser Ser Asp Gly Lys Asn Leu Ile Ile Tyr Trp
            500                 505                 510

Lys Pro Leu Pro Ile Asn Glu Ala Asn Gly Lys Ile Leu Ser Tyr Asn
        515                 520                 525

Val Ser Cys Ser Ser Asp Glu Glu Thr Gln Ser Leu Ser Glu Ile Pro
    530                 535                 540

Asp Pro Gln His Lys Ala Glu Ile Arg Leu Asp Lys Asn Asp Tyr Ile
545                 550                 555                 560

Ile Ser Val Val Ala Lys Asn Ser Val Gly Ser Ser Pro Pro Ser Lys
                565                 570                 575

Ile Ala Ser Met Glu Ile Pro Asn Asp Asp Leu Lys Ile Glu Gln Val
            580                 585                 590

Val Gly Met Gly Lys Gly Ile Leu Leu Thr Trp His Tyr Asp Pro Asn
        595                 600                 605

Met Thr Cys Asp Tyr Val Ile Lys Trp Cys Asn Ser Ser Arg Ser Glu
    610                 615                 620

Pro Cys Leu Met Asp Trp Arg Lys Val Pro Ser Asn Ser Thr Glu Thr
625                 630                 635                 640

Val Ile Glu Ser Asp Glu Phe Arg Pro Gly Ile Arg Tyr Asn Phe Phe
                645                 650                 655

Leu Tyr Gly Cys Arg Asn Gln Gly Tyr Gln Leu Leu Arg Ser Met Ile
            660                 665                 670

Gly Tyr Ile Glu Glu Leu Ala Pro Ile Val Ala Pro Asn Phe Thr Val
        675                 680                 685

Glu Asp Thr Ser Ala Asp Ser Ile Leu Val Lys Trp Glu Asp Ile Pro
    690                 695                 700

Val Glu Glu Leu Arg Gly Phe Leu Arg Gly Tyr Leu Phe Tyr Phe Gly
705                 710                 715                 720

Lys Gly Glu Arg Asp Thr Ser Lys Met Arg Val Leu Glu Ser Gly Arg
                725                 730                 735

Ser Asp Ile Lys Val Lys Asn Ile Thr Asp Ile Ser Gln Lys Thr Leu
            740                 745                 750

Arg Ile Ala Asp Leu Gln Gly Lys Thr Ser Tyr His Leu Val Leu Arg
        755                 760                 765

Ala Tyr Thr Asp Gly Gly Val Gly Pro Glu Lys Ser Met Tyr Val Val
    770                 775                 780

Thr Lys Glu Asn Ser
785
```

<210> SEQ ID NO 136

-continued

```
<211> LENGTH: 180
<212> TYPE: PRT
<213> ORGANISM: Homo sapiens

<400> SEQUENCE: 136

Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180
```

What is claimed is:

1. An isolated antibody, or antigen-binding portion thereof that specifically binds to canine or feline Oncostatin M receptor Beta (OSMR-β) or both, comprising a combination of complementary determining region (CDR) sequences selected from the group consisting of:

1) 02D09: variable heavy (VH)-CDR1 of SEQ ID NO: 1 (DYGMH),
VH-CDR2 of SEQ ID NO: 2 (YISSGSRAVFFADTVKG),
VH-CDR3 of SEQ ID NO: 3 (DRYDGRGFAY),
variable light (VL)-CDR1 of SEQ ID NO: 4 (RASQSISNNLH),
VL-CDR2 of SEQ NO: 5 (YASQSIS), and
VL-CDR3 of SEQ ID NO: 6 (QQSNSWPLT);

2) 09E09: VH-CDR1 of SEQ ID NO: 7 (SYAMS),
VH-CDR2 of SEQ ID NO: 8 (YISSGGDYIYYADTVKG),
VH-CDR3 of SEQ ID NO: 9 (DPITGTFAY),
VL-CDR1 of SEQ ID NO: 10 (RASQDINNYLN),
VL-CDR2 of SEQ ID NO: 11 (YTSTLHS), and
VL-CDR3 of SEQ ID NO: 12 (QQGNTLPWT);

3) 10F07: VH-CDR1 of SEQ ID NO: 13 (SYAMS),
VH-CDR2 of SEQ ID NO: 14 (YISSGGDYFYYADTVKG),
VH-CDR3 of SEQ ID NO: 15 (DPITGTFAY),
VL-CDR1 of SEQ ID NO: 16 (RASQDITNYLN),
VL-CDR2 of SEQ ID NO: 17 (YTSTLHS), and
VL-CDR3 of SEQ ID NO: 18 (QQGHMLPWT);

-continued 4) 14C04: VH-CDR1 of SEQ ID NO: 19 (NYWMN),
VH-CDR2 of SEQ ID NO: 20 (QIYPGHVNTNYNGNFKD),
VH-CDR3 of SEQ ID NO: 21 (SADNSGFVLFAY),
VL-CDR1 of SEQ ID NO: 22 (RASKSVSTSGYSYLH),
VL-CDR2 of SEQ ID NO: 23 (LASNLES), and
VL-CDR3 of SEQ ID NO: 24 (QHSRELPLT);

5) 19F07: VH-CDR1 of SEQ ID NO: 25 (DYYMA),
VH-CDR2 of SEQ ID NO: 26 (NINYDGSSTYYLDSLKS),
VH-CDR3 of SEQ ID NO: 27 (GLTWDFDV),
VL-CDR1 of SEQ ID NO: 28 (KASQDVDTAVA),
VL-CDR2 of SEQ ID NO: 29 (LASTRHT), and
VL-CDR3 of SEQ ID NO: 30 (QQYSRFPLT);
or 6) CDR variants of 1, 2, 3, 4, or 5.

2. The antibody, or antigen-binding portion thereof of claim 1, wherein the antibody antagonizes IL-31-mediated signaling or OSM-mediated signaling or both in a canine and/or feline cell.

3. The antibody, or antigen-binding portion thereof of claim 2, wherein the antibody antagonizes both IL-31-mediated signaling and OSM-mediated signaling in a canine and/or feline cell.

4. The antibody of claim 1, comprising at least one of the group consisting of:

(a) a variable heavy chain comprising
(MU_02D09_VH)
SEQ ID NO: 31
EVQLVESGGGLVKPGGSLTLSCAASGFTFSDYGMHWLRQAPEKGLEWVAYISSGSRAVFFAD

TVKGRFTISRDNAKNTLFLQMTSLRSDDTAMYYCARDRYDGRGFAYWGQGTLVTVSA, (MU_09E09_VH)
SEQ ID NO: 35
DVKLVESGEGLVKPGGSLKLSCAASGFTFSSYAMSWVRQTPEKRLEWVAYISSGGDYIYYADT

VKGRFTISRDNARNTLYLQMSSLKSEDTAMYYCTRDPITGTFAYWGQGTLVTVSA, (MU_10F07_VH)
SEQ ID NO: 39
DVKLVESGEGLVKPGGSLKLSCAASGFTFSSYAMSWVRQTPEKRLEWVTYISSGGDYFYYAD

TVKGRFTISRDNARNTLYLQMSSLKSEDTAMYYCTRDPITGTFAYWGQGTLVTVSA, (MU_14C04_VH)
SEQ ID NO: 43
EVQLQESGAELVKPGASVKISCKASGYAFSNYWMNWMKQRPGKGLEWIGQIYPGHVNTNYN

GNFKDKATLTADKSSSTAYMQLSSLTSEDSAVYFCARSADNSGFVLFAYWGQGTLVTVS, (MU_19F07_VH)
SEQ ID NO: 47
EVKLVESEGGLVQPGSSMKLSCTASGFTFSDYYMAWVRQVPEKGLEWVANINYDGSSTYYLD

SLKSRFIISRDNAKNILYLQMSSLKSEDTATYYCARGLTWDFDVWGTGTTVTVSS, (FEL_02D09_VH1)
SEQ ID NO: 51
DVQLVESGGDLVKPGGSLRLTCVASGFTYSDYGMHWVRQAPGKGLQWVAYISSGSRAVFFA

DTVKGRFTISRDNAKNTLYLQMNSLKTEDTATYYCVRDRYDGRGFAYWGQGTLVTVSS, (FEL_02D09_VH2)
SEQ ID NO: 53
DVQLVESGGDLVKPGGSLRLTCVASGFTFSDYGMHWVRQAPGKGLQWVAYISSGSRAVFFA

DTVKGRFTISRDNAKNTLYLQMNGLRTEDTATYYCARDRYDGRGFAYWGQGTLVTVSS, (CAN_09E09_VH1)
SEQ ID NO: 59
EVQLVESGGDLVKPGGSLRLSCVASGFTFSSYAMSWVRQAPGKGLQWVAYISSGGDYIYYAD

TVKGRFTISRDNAKNTLYLQMNSLRAEDTAMYYCVRDPITGTFAYWGQGTLVTVSS, (CAN_09E09_VH2)
SEQ ID NO: 61
EVQLVESGGDLVKPAGSLTLSCLASGFTFSSYAMSWVRQTPEKGLQWVAYISSGGDYIYYADT

VKGRFTISRDNAKNTLYLQMNSLRDEDTAVYYCARDPITGTFAYWGQGTLVTVSS, (FEL_09E09_VH1)
SEQ ID NO: 67
DVQLVESGGDLVKPGGSLRLTCVASGFTYSSYAMSWVRQAPGKGLQWVAYISSGGDYIYYAD

TVKGRFTISRDNAKNTLYLQMNSLKTEDTATYYCVRDPITGTFAYWGQGTLVTVSS, (FEL_09E09_VH2)
SEQ ID NO: 69
DVQLVESGGNLVKPGGSLRLTCVASGFTFSSYAMSWVRQAPGKGLQWVAYISSGGDYIYYAD

TVKGRFTISKDNAKNTLYLQMNSLKTEDTATYYCARDPITGTFAYWGQGTLVTVSS, (CAN_10F07_VH1)
SEQ ID NO: 75
EVQLVESGGDLVKPGGSLRLSCVASGFTFSSYAMSWVRQAPGKGLQWVAYISSGGDYFYYA

DTVKGRFTISRDNAKNTLYLQMNSLRAEDTAMYYCVRDPITGTFAYWGQGTLVTVSS, (CAN_10F07_VH2)
SEQ ID NO: 79
EVQLVESGGDLVKPAGSLTLSCLASGFTFSSYAMSWVRQTPEKGLQWVAYISSGGDYFYYAD

TVKGRFTISRDNAKNTLYLQMNSLRDEDTAVYYCARDPITGTFAYWGQGTLVTVSS, (FEL_10F07_VH1)
SEQ ID NO: 83

-continued

DVQLVESGGDLVKPGGSLRLTCVASGFTYSSYAMSWVRQAPGKGLQWVAYISSGGDYFYYA

DTVKGRFTISRDNAKNTLYLQMNSLKTEDTATYYCVRDPITGTFAYWGQGTLVTVSS, (FEL_10F07_VH2)

SEQ ID NO: 87

DVQLVESGGDLVKPGGSLRLTCVASGFTFSSYAMSWVRQAPGKGLQWVAYISSGGDYFYYA

DTVKGRFTISRDDAKNTLYLQMSSLKTEDTATYYCTGDPITGTFAYWGQGTLVTVSS, (CAN_19F07_VH1)

SEQ ID NO: 91

EVQLVESGGDLVKPGGSLRLSCVASGFTFSDYYMAWVRQAPGKGLQWVANINYDGSSTYYLD

SLKSRFTISRDNAKNTLYLQMNSLRAEDTAMYYCVRGLTWDFDVWGQGTLVTVSS, (CAN_19F07_VH2)

SEQ ID NO: 95

EVQLVESGGDLVKPAGSLTLSCLASGFTFSDYYMAWVRQTPEKGLQWVANINYDGSSTYYLD

SLKSRFTISRDNAKNTLYLQMNSLRDEDTAVYYCARGLTWDFDVWGQGTLVTVSS, (FEL_19F07_VH1)

SEQ ID NO: 99

DVQLVESGGDLVKPGGSLRLTCVASGFTYSDYYMAWVRQAPGKGLQWVANINYDGSSTYYL

DSLKSRFTISRDNAKNTLYLQMNSLKTEDTATYYCVRGLTWDFDVWGQGTLVTVSS, (FEL_19F07_VH2)

SEQ ID NO: 103

DVQLVESGGNLVKPGGSLRLTCVASGFTFSDYYMAWVRQAPGKGLQWVANINYDGSSTYYLD

SLKSRFTISRDNAKNTLYLQMNSLKTEDTATYYCARGLTWDFDVWGQGTLVTVSS, (CAN_14C04_VH1)

SEQ ID NO: 127

EVQLVESGGDLVKPGGSLRLSCVASGFTFSNYWMNWVRQAPGKGLQWVAQIYPGHVNTNYN

GNFKDRFTISRDNARNTVYLQMNSLRAEDTAVYYCARSADNSGFVLFAYWGQGTLVTVSS,
or (CAN_14C04_VH2)

SEQ ID NO: 129

EVQLVESGGDLVKPGGSLRLSCVASGFTFSNYWMNWVRQSPGKGLQWVAQIYPGHVNTNYN

GNFKDRFTISRDNAKNTLYLQMNSLRAEDTAVYFCARSADNSGFVLFAYWGQGTLVTVSS;
and (b) a variable light chain comprising
(MU_02D09_VL)

SEQ ID NO: 33

DIVLTQSPATLSVTPGDSVSLSCRASQSISNNLHWYQQTSHESPRLLITYASQSISGIPSRFSGS

GSGTDFTLSINSVETEDFGMYFCQQSNSWPLTFGAGTKLELK, (MU_09E09_VL)

SEQ ID NO: 37

DLQMTQTTSSLSASLGDRVTISCRASQDINNYLNWYQQKPDGTVKLLIYYTSTLHSGVPSRFSG

SGSGTDYSLTISNLEQEDIATYFCQQGNTLPWTFGGGTKLEIK, (MU_10F07_VL)

SEQ ID NO: 41

DIQMTQTTSSLSASLGDRVTISCRASQDITNYLNWYQQKPDGTVKLLIYYTSTLHSGVPSRFSG

SGSGTDFSLTISNLEQEDIATYFCQQGHMLPWTFGGGTKLEIK, (MU_14C04_VL)

SEQ ID NO: 45

DIVLTQSPASLAVSLGQRATISCRASKSVSTSGYSYLHWYQQKPGQPPKLLIFLASNLESGVPA

RFSGSGSGTDFTLNIHPVEEEDAATYYCQHSRELPLTFGAGTKLELK, (MU_19F07_VL)

SEQ ID NO: 49

DIVMTQSHKFMSPSVGDRVSITCKASQDVDTAVAWYQQKPGQSPKWYLASTRHTGVPDRFT

GSGSGTDFTLTISNVQSEDLADYFCQQYSRFPLTFGAGTKLELK, (FEL_02D09_VL1)

SEQ ID NO: 55

-continued

EIQMTQSPSSLSASPGDRVTITCRASQSISNNLHWYQQKPGKVPKLLIYYASQSISGVPSRFSG

SGSGTDFTLTISSLEPEDAATYYCQQSNSWPLTFGQGT, (FEL_02D09_VL2)

SEQ ID NO: 57

DIVMTQTPLSLSVTPGESASISCRASQSISNNLHWYLQKSGQSPRRLIYYASQSISGVPDRFSG

SGSGTDFTLRISRVEADDVGVYYCQQSNSWPLTFGQGT, (CAN_09E09_VL1)

SEQ ID NO: 63

EIVMTQSPASLSLSQEEKVTITCRASQDINNYLNWYQQKPGQAPKLLIYYTSTLHSGVPSRFSG

SGSGTDFSFTISSLEPEDVAVYYCQQGNTLPWTFGQGT, (CAN_09E09_VL2)

SEQ ID NO: 65

DIVLTQPTSVSGSLGQRVTISCRASQDINNYLNWYQQLPGKAPKLLVYYTSTLHSGVPDRFSGS

NSGSSATLTITGLQAEDEADYYCQQGNTLPWTFGQGT, (FEL_09E09_VL1)

SEQ ID NO: 71

EIQMTQSPSSLSASPGDRVTITCRASQDINNYLNWYQQKPGKVPKLLIYYTSTLHSGVPSRFSG

SGSGTDFTLTISSLEPEDAATYYCQQGNTLPWTFGQGT, (FEL_09E09_VL2)

SEQ ID NO: 73

DITMTQSPGSLAGSPGQQVTMNCRASQDINNYLNWYQQKPGQHPKLLIYYTSTLHSGVPDRF

SGSGSGTDFTLTISNLQAEDVASYYCQQGNTLPWTFGQGT, (CAN_10F07_VL1)

SEQ ID NO: 77

EIVMTQSPASLSLSQEEKVTITCRASQDITNYLNWYQQKPGQAPKLLIYYTSTLHSGVPSRFSG

SGSGTDFSFTISSLEPEDVAVYYCQQGHMLPWTFGQGT, (CAN_10F07_VL2)

SEQ ID NO: 81

DIVLTQPTSVSGSLGQRVTISCRASQDITNYLNWYQQLPGKAPKLLVYYTSTLHSGVPDRFSGS

NSGSSATLTITGLQAEDEADYYCQQGHMLPWTFGQGT, (FEL_10F07_VL1)

SEQ ID NO: 85

EIQMTQSPSSLSASPGDRVTITCRASQDITNYLNWYQQKPGKVPKLLIYYTSTLHSGVPSRFSG

SGSGTDFTLTISSLEPEDAATYYCQQGHMLPWTFGQGT, (FEL_10F07_VL2)

SEQ ID NO: 89

DITMTQSPGSLAGSPGQQVTMNCRASQDITNYLNWYQQKPGQHPKLLIYYTSTLHSGVPDRFS

GSGSGTDFTLTISNLQAEDVASYYCQQGHMLPWTFGQGT, (CAN_19F07_VL1)

SEQ ID NO: 93

EIVMTQSPASLSLSQEEKVTITCKASQDVDTAVAWYQQKPGQAPKWYLASTRHTGVPSRFSG

SGSGTDFSFTISSLEPEDVAVYYCQQYSRFPLTFGQGT, (CAN_19F07_VL2)

SEQ ID NO: 97

DIVMTQTPLSLSVSPGETASISCKASQDVDTAVAWFRQKPGQSPQRLIYLASTRHTGVPDRFS

GSGSGTDFTLRISRVEADDTGVYYCQQYSRFPLTFGQGT, (FEL_19F07_VL1)

SEQ ID NO: 101

EIQMTQSPSSLSASPGDRVTITCKASQDVDTAVAWYQQKPGKVPKLLIYLASTRHTGVPSRFS

GSGSGTDFTLTISSLEPEDAATYYCQQYSRFPLTFGQGT, (FEL_19F07_VL2)

SEQ ID NO: 105

DITMTQSPGSLAGSPGQQVTMNCKASQDVDTAVAWYQQKPGQHPKWYLASTRHTGVPDRF

SGSGSGTDFTLTISNLQAEDVASYYCQQYSRFPLTFGQGT,

-continued (CAN_14C04_VL1)

SEQ ID NO: 131

EIVMTQSPASLSLSQEEKVTITCRASKSVSTSGYSYLHWYQQKPGQAPKLLIYLASNLESGVPS

RFSGSGSGTDFSFTISSLEPEDVAVYYCQHSRELPLTFGQGT,
or (CAN_14C04_VL2)

SEQ ID NO: 133

DIVMTQTPLSLSVSPGETASISCRASKSVSTSGYSYLHWYLQKPGQSPQLLIYLASNLESGVSK

RFSGSGSGTDFTLRISRVEADDTGIYYCQHSRELPLTFGQGT.

5. The antibody of claim 1, wherein the antibody is chimeric.

6. The antibody of claim 1, wherein the antibody is caninized or felinized.

7. The antibody of claim 1, wherein the antibody inhibits or neutralizes an IL-31-mediated or OSM-mediated pruritic or allergic condition in a dog or cat, wherein the IL-31-mediated or OSM-mediated pruritic or allergic condition is selected from the group consisting of atopic dermatitis, allergic dermatitis, and pruritis.

8. The antibody of claim 7, wherein the IL-31-mediated or OSM-mediated pruritic condition is selected from the group consisting of atopic dermatitis and pruritis.

9. A veterinary composition comprising a therapeutically effective amount of the antibody of claim 1.

* * * * *

UNITED STATES PATENT AND TRADEMARK OFFICE

CERTIFICATE OF CORRECTION

PATENT NO. : 12,180,290 B2
APPLICATION NO. : 17/503592
DATED : December 31, 2024
INVENTOR(S) : Gary Francis Bammert and Andrea Joy Gonzales It is certified that error appears in the above-identified patent and that said Letters Patent is hereby corrected as shown below:

In the Claims

In Claim 1, at Column 194, Line 45, add "or" after the text "(QHSRELPLT);"
In Claim 1, at Column 194, Lines 51, 52 and 54, remove the text "; or 6) CDR variants of 1, 2, 3, 4 or 5"
In Claim 4, at Columns 194 to 201, delete the entire text and replace with the following text:
The antibody of claim 1, comprising at least one of the group consisting of:
a) a variable heavy chain comprising
SEQ ID NO: 31 (MU_02D09_VH)
EVQLVESGGGLVKPGGSLTLSCAASGFTFSDYGMHWLRQAPEKGLEWVAYISSGSRAVFFAD
TVKGRFTISRDNAKNTLFLQMTSLRSDDTAMYYCARDRYDGRGFAYWGQGTLVTVSA, and
a variable light chain comprising
SEQ ID NO: 33 (MU_02D09_VL)
DIVLTQSPATLSVTPGDSVSLSCRASQSISNNLHWYQQTSHESPRLLITYASQSISGIPSRFSGSG
SGTDFTLSINSVETEDFGMYFCQQSNSWPLTFGAGTKLELK,
b) a variable heavy chain comprising
SEQ ID NO: 35 (MU_09E09_VH)
DVKLVESGEGLVKPGGSLKLSCAASGFTFSSYAMSWVRQTPEKRLEWVAYISSGGDYIYYAD
TVKGRFTISRDNARNTLYLQMSSLKSEDTAMYYCTRDPITGTFAYWGQGTLVTVSA, and
a variable light chain comprising
SEQ ID NO: 37 (MU_09E09_VL)
DLQMTQTTSSLSASLGDRVTISCRASQDINNYLNWYQQKPDGTVKLLIYYTSTLHSGVPSRFS
GSGSGTDYSLTISNLEQEDIATYFCQQGNTLPWTFGGGTKLEIK,
c) a variable heavy chain comprising
SEQ ID NO: 39 (MU_10F07_VH)
DVKLVESGEGLVKPGGSLKLSCAASGFTFSSYAMSWVRQTPEKRLEWVTYISSGGDYFYYAD
TVKGRFTISRDNARNTLYLQMSSLKSEDTAMYYCTRDPITGTFAYWGQGTLVTVSA, and
a variable light chain comprising
SEQ ID NO: 41 (MU_10F07_VL)

Signed and Sealed this
Twenty-seventh Day of May, 2025

Coke Morgan Stewart
*Acting Director of the United States Patent and Trademark Office*

DIQMTQTTSSLSASLGDRVTISCRASQDITNYLNWYQQKPDGTVKLLIYYTSTLHSGVPSRFSG
SGSGTDFSLTISNLEQEDIATYFCQQGHMLPWTFGGGTKLEIK,
d) a variable heavy chain comprising
SEQ ID NO: 43 (MU_14C04_VH)
EVQLQESGAELVKPGASVKISCKASGYAFSNYWMNWMKQRPGKGLEWIGQIYPGHVNTNY
NGNFKDKATLTADK
SSSTAYMQLSSLTSEDSAVYFCARSADNSGFVLFAYWGQGTLVTVS, and
a variable light chain comprising
SEQ ID NO: 45 (MU_14C04_VL)
DIVLTQSPASLAVSLGQRATISCRASKSVSTSGYSYLHWYQQKPGQPPKLLIFLASNLESGVPA
RFSGSGSGTDFTLNIHPVEEEDAATYYCQHSRELPLTFGAGTKLELK,
e) a variable heavy chain comprising
SEQ ID NO: 47 (MU_19F07_VH)
EVKLVESEGGLVQPGSSMKLSCTASGFTFSDYYMAWVRQVPEKGLEWVANINYDGSSTYYL
DSLKSRFIISRDNAKNILYLQMSSLKSEDTATYYCARGLTWDFDVWGTGTTVTVSS, and
a variable light chain comprising
SEQ ID NO: 49 (MU_19F07_VL)
DIVMTQSHKFMSPSVGDRVSITCKASQDVDTAVAWYQQKPGQSPKLLIYLASTRHTGVPDRF
TGSGSGTDFTLTISNVQSEDLADYFCQQYSRFPLTFGAGTKLELK,
f) a variable heavy chain comprising
SEQ ID NO: 51 (FEL_02D09_VH1)
DVQLVESGGDLVKPGGSLRLTCVASGFTYSDYGMHWVRQAPGKGLQWVAYISSGSRAVFFA
DTVKGRFTISRDNAKNTLYLQMNSLKTEDTATYYCVRDRYDGRGFAYWGQGTLVTVSS, and
a variable light chain comprising
SEQ ID NO: 55 (FEL_02D09_VL1)
EIQMTQSPSSLSASPGDRVTITCRASQSISNNLHWYQQKPGKVPKLLIYYASQSISGVPSRFSGS
GSGTDFTLTISSLEPEDAATYYCQQSNSWPLTFGQGT,
g) a variable heavy chain comprising
SEQ ID NO: 53 (FEL_02D09_VH2)
DVQLVESGGDLVKPGGSLRLTCVASGFTFSDYGMHWVRQAPGKGLQWVAYISSGSRAVFFA
DTVKGRFTISRDNAKNTLYLQMNGLRTEDTATYYCARDRYDGRGFAYWGQGTLVTVSS, and
a variable light chain comprising
SEQ ID NO: 57 (FEL_02D09_VL2)
DIVMTQTPLSLSVTPGESASISCRASQSISNNLHWYLQKSGQSPRRLIYYASQSISGVPDRFSGS
GSGTDFTLRISRVEADDVGVYYCQQSNSWPLTFGQGT,
h) a variable heavy chain comprising
SEQ ID NO: 59 (CAN_09E09_VH1)
EVQLVESGGDLVKPGGSLRLSCVASGFTFSSYAMSWVRQAPGKGLQWVAYISSGGDYIYYA
DTVKGRFTISRDNAKNTLYLQMNSLRAEDTAMYYCVRDPITGTFAYWGQGTLVTVSS, and
a variable light chain comprising
SEQ ID NO: 63 (CAN_09E09_VL1)
EIVMTQSPASLSLSQEEKVTITCRASQDINNYLNWYQQKPGQAPKLLIYYTSTLHSGVPSRFSG
SGSGTDFSFTISSLEPEDVAVYYCQQGNTLPWTFGQGT,
i) a variable heavy chain comprising
SEQ ID NO: 61 (CAN_09E09_VH2)

EVQLVESGGDLVKPAGSLTLSCLASGFTFSSYAMSWVRQTPEKGLQWVAYISSGGDYIYYAD
TVKGRFTISRDNAKNTLYLQMNSLRDEDTAVYYCARDPITGTFAYWGQGTLVTVSS, and
a variable light chain comprising
SEQ ID NO: 65 (CAN_09E09_VL2)
DIVLTQPTSVSGSLGQRVTISCRASQDINNYLNWYQQLPGKAPKLLVYYTSTLHSGVPDRFSG
SNSGSSATLTITGLQAEDEADYYCQQGNTLPWTFGQGT,
j) a variable heavy chain comprising
SEQ ID NO: 67 (FEL_09E09_VH1)
DVQLVESGGDLVKPGGSLRLTCVASGFTYSSYAMSWVRQAPGKGLQWVAYISSGGDYIYYA
DTVKGRFTISRDNAKNTLYLQMNSLKTEDTATYYCVRDPITGTFAYWGQGTLVTVSS, and
a variable light chain comprising
SEQ ID NO: 71 (FEL_09E09_VL1)
EIQMTQSPSSLSASPGDRVTITCRASQDINNYLNWYQQKPGKVPKLLIYYTSTLHSGVPSRFSG
SGSGTDFTLTISSLEPEDAATYYCQQGNTLPWTFGQGT,
k) a variable heavy chain comprising
SEQ ID NO: 69 (FEL_09E09_VH2)
DVQLVESGGNLVKPGGSLRLTCVASGFTFSSYAMSWVRQAPGKGLQWVAYISSGGDYIYYA
DTVKGRFTISKDNAKNTLYLQMNSLKTEDTATYYCARDPITGTFAYWGQGTLVTVSS, and
a variable light chain comprising
SEQ ID NO: 73 (FEL_09E09_VL2)
DITMTQSPGSLAGSPGQQVTMNCRASQDINNYLNWYQQKPGQHPKLLIYYTSTLHSGVPDRF
SGSGSGTDFTLTISNLQAEDVASYYCQQGNTLPWTFGQGT,
l) a variable heavy chain comprising
SEQ ID NO: 75 (CAN_10F07_VH1)
EVQLVESGGDLVKPGGSLRLSCVASGFTFSSYAMSWVRQAPGKGLQWVAYISSGGDYFYYA
DTVKGRFTISRDNAKNTLYLQMNSLRAEDTAMYYCVRDPITGTFAYWGQGTLVTVSS, and
a variable light chain comprising
SEQ ID NO: 77 (CAN_10F07_VL1)
EIVMTQSPASLSLSQEEKVTITCRASQDITNYLNWYQQKPGQAPKLLIYYTSTLHSGVPSRFSG
SGSGTDFSFTISSLEPEDVAVYYCQQGHMLPWTFGQGT,
m) a variable heavy chain comprising
SEQ ID NO: 79 (CAN_10F07_VH2)
EVQLVESGGDLVKPAGSLTLSCLASGFTFSSYAMSWVRQTPEKGLQWVAYISSGGDYFYYAD
TVKGRFTISRDNAKNTLYLQMNSLRDEDTAVYYCARDPITGTFAYWGQGTLVTVSS, and
a variable light chain comprising
SEQ ID NO: 81 (CAN_10F07_VL2)
DIVLTQPTSVSGSLGQRVTISCRASQDITNYLNWYQQLPGKAPKLLVYYTSTLHSGVPDRFSG
SNSGSSATLTITGLQAEDEADYYCQQGHMLPWTFGQGT,
n) a variable heavy chain comprising
a variable light chain comprising
SEQ ID NO: 83 (FEL_10F07_VH1)
DVQLVESGGDLVKPGGSLRLTCVASGFTYSSYAMSWVRQAPGKGLQWVAYISSGGDYFYYA
DTVKGRFTISRDNAKNTLYLQMNSLKTEDTATYYCVRDPITGTFAYWGQGTLVTVSS, and
SEQ ID NO: 85 (FEL_10F07_VL1)

EIQMTQSPSSLSASPGDRVTITCRASQDITNYLNWYQQKPGKVPKLLIYYTSTLHSGVPSRFSG
SGSGTDFTLTISSLEPEDAATYYCQQGHMLPWTFGQGT,
o) a variable heavy chain comprising
SEQ ID NO: 87 (FEL_10F07_VH2)
DVQLVESGGDLVKPGGSLRLTCVASGFTFSSYAMSWVRQAPGKGLQWVAYISSGGDYFYYA
DTVKGRFTISRDDAKNTLYLQMSSLKTEDTATYYCTGDPITGTFAYWGQGTLVTVSS, and
a variable light chain comprising
SEQ ID NO: 89 (FEL_10F07_VL2)
DITMTQSPGSLAGSPGQQVTMNCRASQDITNYLNWYQQKPGQHPKLLIYYTSTLHSGVPDRF
SGSGSGTDFTLTISNLQAEDVASYYCQQGHMLPWTFGQGT,
p) a variable heavy chain comprising
SEQ ID NO: 91 (CAN_19F07_VH1)
EVQLVESGGDLVKPGGSLRLSCVASGFTFSDYYMAWVRQAPGKGLQWVANINYDGSSTYYL
DSLKSRFTISRDNAKNTLYLQMNSLRAEDTAMYYCVRGLTWDFDVWGQGTLVTVSS, and
a variable light chain comprising
SEQ ID NO: 93 (CAN_19F07_VL1)
EIVMTQSPASLSLSQEEKVTITCKASQDVDTAVAWYQQKPGQAPKLLIYLASTRHTGVPSRFS
GSGSGTDFSFTISSLEPEDVAVYYCQQYSRFPLTFGQGT,
q) a variable heavy chain comprising
SEQ ID NO: 95 (CAN_19F07_VH2)
EVQLVESGGDLVKPAGSLTLSCLASGFTFSDYYMAWRQTPEKGLQWVANINYDGSSTYYLD
SLKSRFTISRDNAKNTLYLQMNSLRDEDTAVYYCARGLTWDFDVWGQGTLVTVSS, and
a variable light chain comprising
SEQ ID NO: 97 (CAN_19F07_VL2)
DIVMTQTPLSLSVSPGETASISCKASQDVDTAVAWFRQKPGQSPQRLIYLASTRHTGVPDRFS
GSGSGTDFTLRISRVEADDTGVYYCQQYSRFPLTFGQGT,
r) a variable heavy chain comprising
SEQ ID NO: 99 (FEL_19F07_VH1)
DVQLVESGGDLVKPGGSLRLTCVASGFTYSDYYMAWVRQAPGKGLQWVANINYDGSSTYY
LDSLKSRFTISRDNAKNTLYLQMNSLKTEDTATYYCVRGLTWDFDVWGQGTLVTVSS, and
a variable light chain comprising
SEQ ID NO: 101 (FEL_19F07_VL1)
EIQMTQSPSSLSASPGDRVTITCKASQDVDTAVAWYQQKPGKVPKLLIYLASTRHTGVPSRFS
GSGSGTDFTLTISSLEPEDAATYYCQQYSRFPLTFGQGT,
s) a variable heavy chain comprising
SEQ ID NO: 103 (FEL_19F07_VH2)
DVQLVESGGNLVKPGGSLRLTCVASGFTFSDYYMAWVRQAPGKGLQWVANINYDGSSTYY
LDSLKSRFTISRDNAKNTLYLQMNSLKTEDTATYYCARGLTWDFDVWGQGTLVTVSS, and
a variable light chain comprising
SEQ ID NO: 105 (FEL_19F07_VL2)
DITMTQSPGSLAGSPGQQVTMNCKASQDVDTAVAWYQQKPGQHPKLLIYLASTRHTGVPDR
FSGSGSGTDFTLTISNLQAEDVASYYCQQYSRFPLTFGQGT,
t) a variable heavy chain comprising
SEQ ID NO: 127. (CAN_14C04_VH1)
EVQLVESGGDLVKPGGSLRLSCVASGFTFSNYWMNWVRQAPGKGLQWVAQIYPGHVNTNY
NGNFKDRFTISRDNARNTVYLQMNSLRAEDTAVYYCARSADNSGFVLFAYWGQGTLVTVS S, and a variable light chain comprising
SEQ ID NO: 131. (CAN_14C04_VL1)
EIVMTQSPASLSLSQEEKVTITCRASKSVSTSGYSYLHWYQQKPGQAPKLLIYLASNLESGVPS
RFSGSGSGTDFSFTISSLEPEDVAVYYCQHSRELPLTFGQGT, or u) a variable heavy chain comprising
SEQ ID NO: 129. (CAN_14C04_VH2)
EVQLVESGGDLVKPGGSLRISCVASGFTFSNYWMNWVRQSPGKGLQWVAQIYPGHVNTNYN
GNFKDRFTISRDNAKNTLYLQMNSLRAEDTAVYFCARSADNSGFVLFAYWGQGTLVTVSS,
and
a variable light chain comprising
SEQ ID NO: 133. (CAN_14C04_VL2)
DIVMTQTPLSLSVSPGETASISCRASKSVSTSGYSYLHWYLQKPGQSPQLLIYLASNLESGVSK
RFSGSGSGTDFTLRISRVEADDTGIYYCQHSRELPLTFGQGT.